(12) United States Patent
Tsao et al.

(10) Patent No.: US 10,894,975 B2
(45) Date of Patent: Jan. 19, 2021

(54) IMAGE DIFFERENTIATED MULTIPLEX ASSAYS FOR MULTIPLEX DETECTION OF DNA MUTATIONS

(71) Applicant: PLEXBIO CO., LTD., Taipei (TW)

(72) Inventors: Dean Tsao, Hillsborough, CA (US); Chin-Shiou Huang, Santa Clara, CA (US); Shian pin Hu, Taipei (TW)

(73) Assignee: PLEXBIO CO., LTD., Taipei (TW)

( * ) Notice: Subject to any disclaimer, the term of this patent is extended or adjusted under 35 U.S.C. 154(b) by 233 days.

(21) Appl. No.: 15/838,331

(22) Filed: Dec. 11, 2017

(65) Prior Publication Data

US 2018/0201983 A1    Jul. 19, 2018

Related U.S. Application Data

(63) Continuation-in-part of application No. 15/836,809, filed on Dec. 8, 2017, now abandoned.

(60) Provisional application No. 62/432,534, filed on Dec. 9, 2016.

(51) Int. Cl.

| C12Q 1/68 | (2018.01) |
| C12Q 1/6827 | (2018.01) |
| C12Q 1/6886 | (2018.01) |
| C12Q 1/6816 | (2018.01) |
| G01N 21/64 | (2006.01) |
| C12Q 1/6834 | (2018.01) |

(52) U.S. Cl.
CPC ........ *C12Q 1/6827* (2013.01); *C12Q 1/6816* (2013.01); *C12Q 1/6834* (2013.01); *C12Q 1/6886* (2013.01); *G01N 21/6428* (2013.01); *C12Q 2600/156* (2013.01); *C12Q 2600/16* (2013.01); *G01N 2021/6439* (2013.01)

(58) Field of Classification Search
None
See application file for complete search history.

(56) References Cited

U.S. PATENT DOCUMENTS

| 7,833,757 B2 | 11/2010 | Steinberg et al. |
| 7,858,307 B2 | 12/2010 | Ho |
| 7,871,770 B2 | 1/2011 | Ho |
| 8,148,139 B2 | 4/2012 | Ho |
| 8,232,092 B2 | 7/2012 | Ho et al. |
| 8,610,848 B2 | 12/2013 | Shim et al. |
| 8,939,376 B1 | 1/2015 | De Smedt et al. |
| 8,967,483 B2 | 3/2015 | De Smedt et al. |
| 9,040,463 B2 | 5/2015 | Demierre et al. |
| 9,063,044 B2 | 6/2015 | Kao et al. |
| 9,255,922 B2 | 2/2016 | Ho et al. |
| 10,019,815 B2 | 7/2018 | Chung et al. |
| 10,302,640 B2 | 5/2019 | Tsao et al. |
| 10,436,776 B2 | 10/2019 | Chung et al. |
| 10,436,778 B2 | 10/2019 | Tsao et al. |
| 2006/0097056 A1 | 5/2006 | De Smedt et al. |
| 2007/0172823 A1 | 7/2007 | Steinberg et al. |
| 2009/0201504 A1 | 8/2009 | Ho et al. |
| 2010/0075438 A1 | 3/2010 | Ho et al. |
| 2010/0081215 A1 | 4/2010 | De Geest et al. |
| 2010/0210477 A1 | 8/2010 | Ho |
| 2011/0007955 A1 | 1/2011 | Ho et al. |
| 2012/0088691 A1 | 4/2012 | Chen et al. |
| 2013/0302910 A1 | 11/2013 | Demierre |
| 2014/0242614 A1 | 8/2014 | Kao et al. |
| 2014/0274778 A1 | 9/2014 | Tsao et al. |
| 2015/0057190 A1 | 2/2015 | De Smedt et al. |
| 2017/0146545 A1 | 5/2017 | Chung et al. |
| 2017/0160272 A1 | 6/2017 | Tsao et al. |
| 2017/0270690 A1 | 9/2017 | Chung et al. |
| 2018/0195113 A1 | 7/2018 | Tsao et al. |
| 2019/0242884 A1 | 8/2019 | Tsao et al. |
| 2019/0265567 A1 | 8/2019 | Tsao et al. |
| 2019/0369091 A1 | 12/2019 | Tsao et al. |

FOREIGN PATENT DOCUMENTS

| CN | 102246037 B | 5/2014 |
| EP | 1173760 B1 | 6/2005 |
| EP | 2100143 A1 | 9/2009 |
| EP | 2179289 A1 | 4/2010 |
| EP | 2342561 A1 | 7/2011 |
| EP | 2367633 A1 | 9/2011 |

(Continued)

OTHER PUBLICATIONS

International Preliminary Report on Patentability received for PCT Patent Application No. PCT/US2017/065656, dated Jun. 20, 2019, 9 pages.
Arnason et al.., "Morphoiogy, tumor genetics, and outcomes in five cases of biliary adenofibroma", Laboratory Investigation, vol. 94, Suppl. 1, 2014, pp. 417A
Carethers, John M., "DNA Testing and Molecular Screening for Colon Cancer", Clin Gastroenterol Hepatol., vol. 12, No. 3, Mar. 2014, pp. 377-381.
Clarke et al., "braf Mutant Colorectal Cancer as a Distinct Subset of Colorectal Cancer: Clinical Characteristics, Clinical Behavior, and Response to Targeted Therapies", Journal of Gastrointestinal Oncology, vol. 6, No. 6, Dec. 2015, pp. 660-667.

(Continued)

*Primary Examiner* — James Martinell
(74) *Attorney, Agent, or Firm* — Morrison & Foerster LLP

(57) ABSTRACT

Provided herein are methods and kits for detecting the presence of DNA mutations in the KRAS, BRAF, CTNNB1, and APC genes. The methods and kits employ microcarriers, each with a probe specific for a DNA mutation in the KRAS, BRAF, CTNNB1, or APC gene and an identifier unique to the probe sequence. Upon isolation and amplification of DNA from a sample, hybridization of amplified DNA with a probe, specific for a DNA mutation, that is coupled to a microcarrier indicates the presence of the DNA mutation in the sample. Since each microcarrier can be identified through detection of the identifier, multiplex screening assays for multiple mutations in each of the KRAS, BRAF, CTNNB1, and APC genes are provided.

17 Claims, 30 Drawing Sheets

Specification includes a Sequence Listing.

(56) References Cited

FOREIGN PATENT DOCUMENTS

| | | | |
|---|---|---|---|
| EP | 2484447 | A1 | 8/2012 |
| EP | 2673086 | A1 | 12/2013 |
| EP | 2774997 | A1 | 9/2014 |
| EP | 1903337 | B1 | 7/2015 |
| WO | 2009/128938 | A1 | 10/2009 |
| WO | 2010/042745 | A1 | 4/2010 |
| WO | WO-2013-123031 | A2 * | 8/2013 |
| WO | 2014/144016 | A1 | 9/2014 |
| WO | 2016/198954 | A1 | 12/2016 |
| WO | 2018/107183 | A1 | 6/2018 |

OTHER PUBLICATIONS

Davies et al., "Mutations of the BRAF Gene in Human Cancer", Nature, vol. 417, Jun. 27, 2002, pp. 949-954.

Fearon et al., "A Genetic Model for Colorectal Tumorigenesis", Cell, vol. 61, Jun. 1, 1990, pp. 759-767.

Friedman et al., "A rapid multiplex mass spectrometry assay for mutational profiling of colorectal cancer", Laboratory Investigation, vol. 95, Suppl. 1, 2015, pp. 514A.

Garnett et al., "Guilty as Charged: B-RAF is a Human Oncogene", Cancer Cell, vol. 6, Oct. 2004, pp. 313-319.

Gibriel, Abdullah A., "Options Available for Labelling Nucleic Acid Samples in DNA Microarray-Based Detection Methods", Briefings in Functional Genomics, vol. 11, No. 4, 2012, pp. 311-318.

Imperiale et al., "Multitarget Stool DNA Testing for Colorectal-Cancer Screening", The New England Journal of Medicine, vol. 370, No. 14, Apr. 3, 2014, pp. 1287-1297.

International Search Report and Written Opinion received for PCT Application No. PCT/US2017/065656, dated Jan. 23, 2018, 13 pages.

Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition", Tetrahedron, vol. 54, 1998, pp. 3607-3630.

Lüchtenborg et al., "APC Mutations in Sporadic Colorectal Carcinomas from the Netherlands Cohort Study", Carcinogenesis, vol. 25, No. 7, 2004, pp. 1219-1226.

Miyoshi et al., "Somatic Mutations of the APC Gene in Colorectal Tumors: Mutation Cluster Region in the APC Gene", Human Molecular Genetics, vol. 1, No. 4, 1992, pp. 229-233.

Morin et al., "Activation of β-Catenin-Tcf Signaling in Colon Cancer by Mutations in β-Catenin or APC", Science, vol. 275, Mar. 21, 1997, pp. 1787-1790.

Mundade et al., "Genetic Pathways, Prevention, and Treatment of Sporadic Colorectal Cancer", Oncoscience, vol. 1, No. 6, 2014, pp. 400-406.

Polakis, Paul, "Wnt Signaling and Cancer", Genes and Development, vol. 14, 2000, pp. 1837-1851.

Prior et al., "A Comprehensive Survey of Ras Mutations in Cancer", Cancer Research, vol. 72, No. 10, 2012, pp. 2457-2467.

Schmidt, Markus,"Xenobiology: A New Form of Life as the Ultimate Biosafety Tool", BioEssays, vol. 32, 2010, pp. 322-331.

Schneider et al., "Detection of up to 65% of Precancerous Lesions of the Human Colon and Rectum by Mutation Analysis of APC, K-Ras, B-Raf and CTNNB1", Cancers, vol. 3, 2011, pp. 91-105.

Segditsas et al., "Colorectal Cancer and Genetic Alterations in the Wnt Pathway", Oncogene, vol. 25, 2006, pp. 7531-7537.

Shiina et al., "The HLA Genomic Loci Map: Expression, Interaction, Diversity and Disease", Journal of Human Genetics, vol. 54, 2009, pp. 15-39.

Smith et al., "Mutations in APC, Kirsten-Ras, and P53—Alternative Genetic Pathways to Colorectal Cancer", Proceedings of the National Academy of Sciences, vol. 99, No. 14, Jul. 9, 2002, pp. 9433-9438.

Tsao et al., U.S. Appl. No. 15/836,809, filed Dec. 8, 2017, titled "Image Differentiated Multiplex Assays for Multiplex Detection of DNA Mutations". (U.S. Patent Application is not submitted herewith pursuant to the waiver of 37 C.F.R. § 1.98(a)(2)(iii) issued by the Office on Sep. 21, 2004.).

Voorham et al., "Comprehensive Mutation Analysis in Colorectai Flat Adenomas", PLoS One, vol. 7, Jul. 2012, pp. 1-8.

Angeloni et al., (2016). "Xmap Cookbook," available online at <http://www.komabiotech.co.kr/www/techniques/pdf/Luminex_cookbook_3rd.pdf>, retrieved on Jun. 24, 2020, 148 pages.

Braeckmans et al., (2003). "Encoding microcarriers by spatial selective photobleaching," Nature Materials, 2(3):169-173.

Derveaux et al., (2008). "Layer-by-layer coated digitally encoded microcarriers for quantification of proteins in serum and plasma," Analytical chemistry, 80(1):85-94.

Extended European Search Report and Opinion received for EP Application No. 17877986.4, dated Jul. 3, 2020, 12 pages.

Herzig et al., (2015). "Molecular markers for colon diagnosis, prognosis and targeted therapy: Molecular Markers for Colon Diagnosis," Journal of Surgical Oncology, 111(1):96-102.

Ivanova et al., (2011). "Novel multiplex bead-based assay with LNA-modified probes for detection of MPL exon 10 mutations," Leukemia Research, 35(8):1120-3.

Li et al., (2011). "A novel liquidchip platform for simultaneous detection of 70 alleles of DNA somatic mutations on EGFR, KRAS, BRAF, and PIK3CA from formalin-fixed and paraffin-embedded slides containing tumor tissues," Clinical Chemistry and Laboratory Medicine, 49(2):191-5.

* cited by examiner

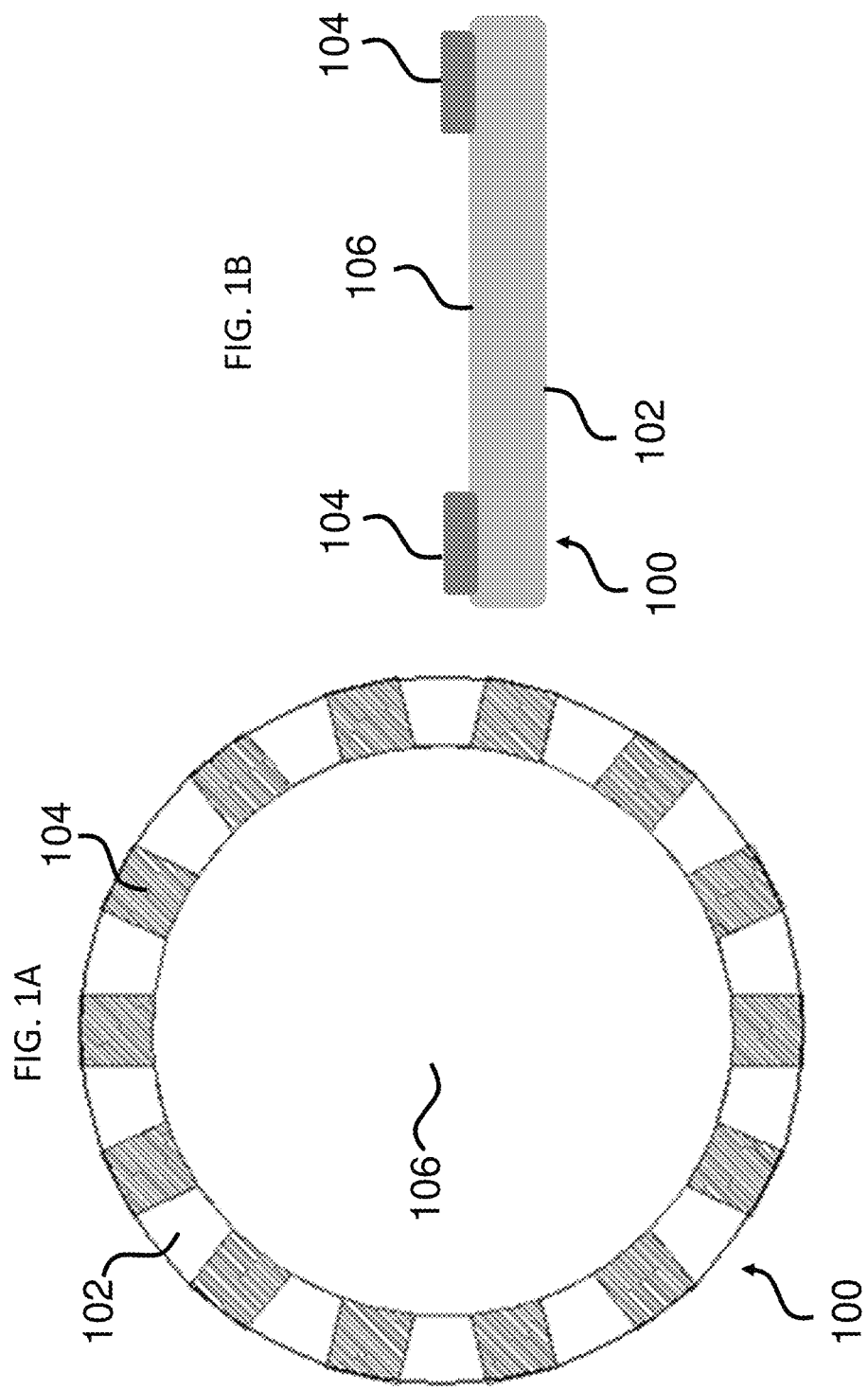

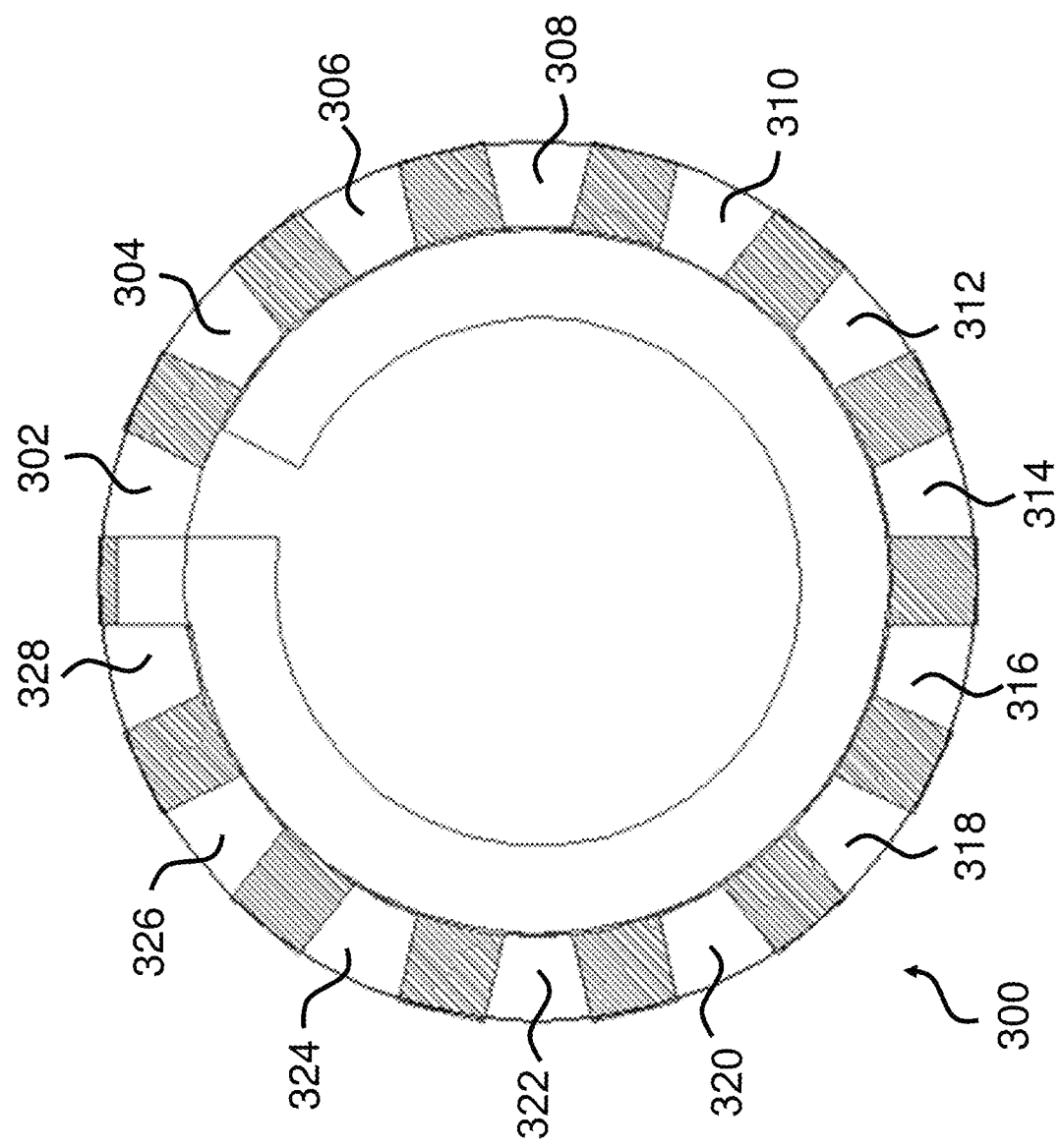

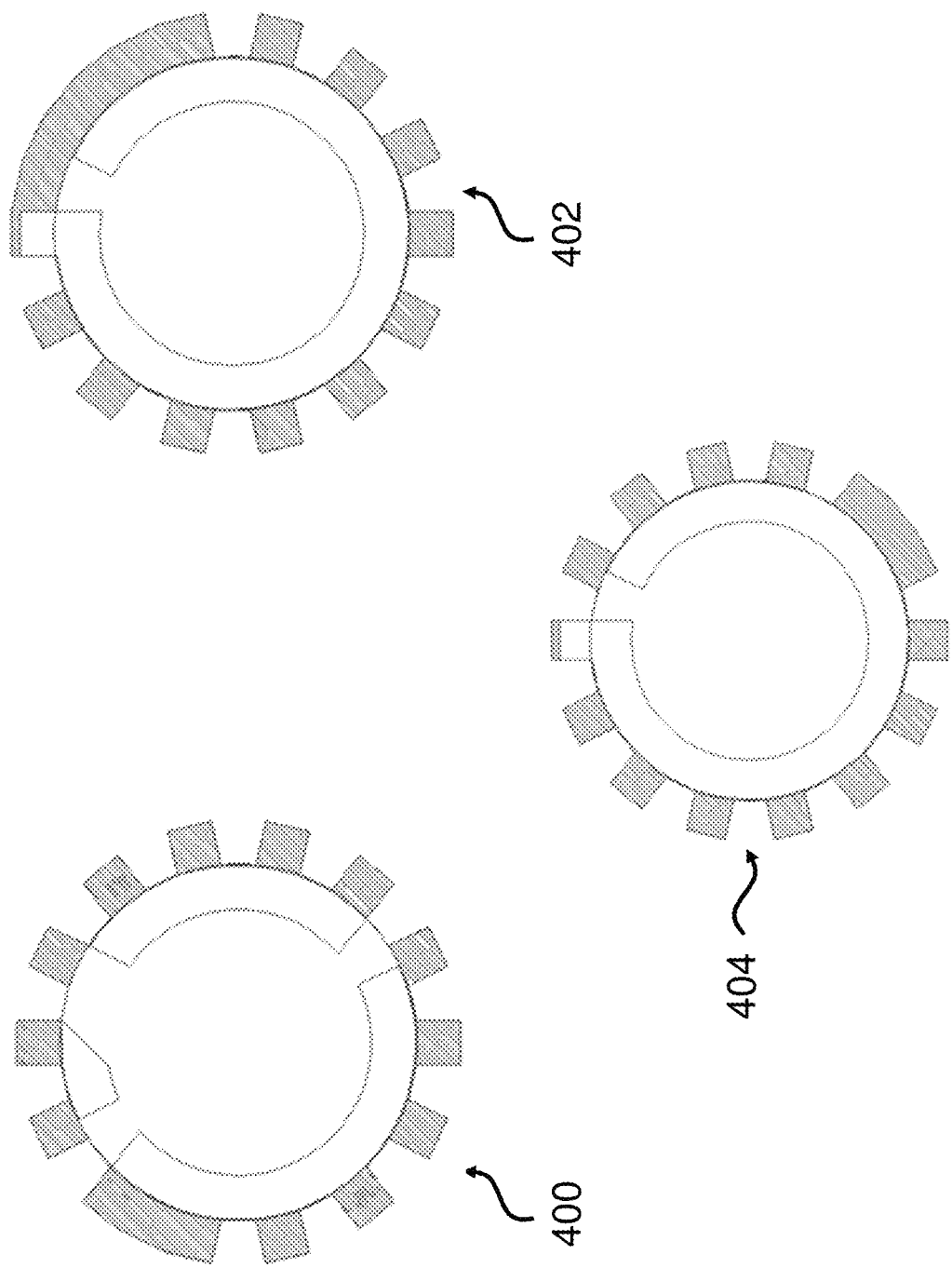

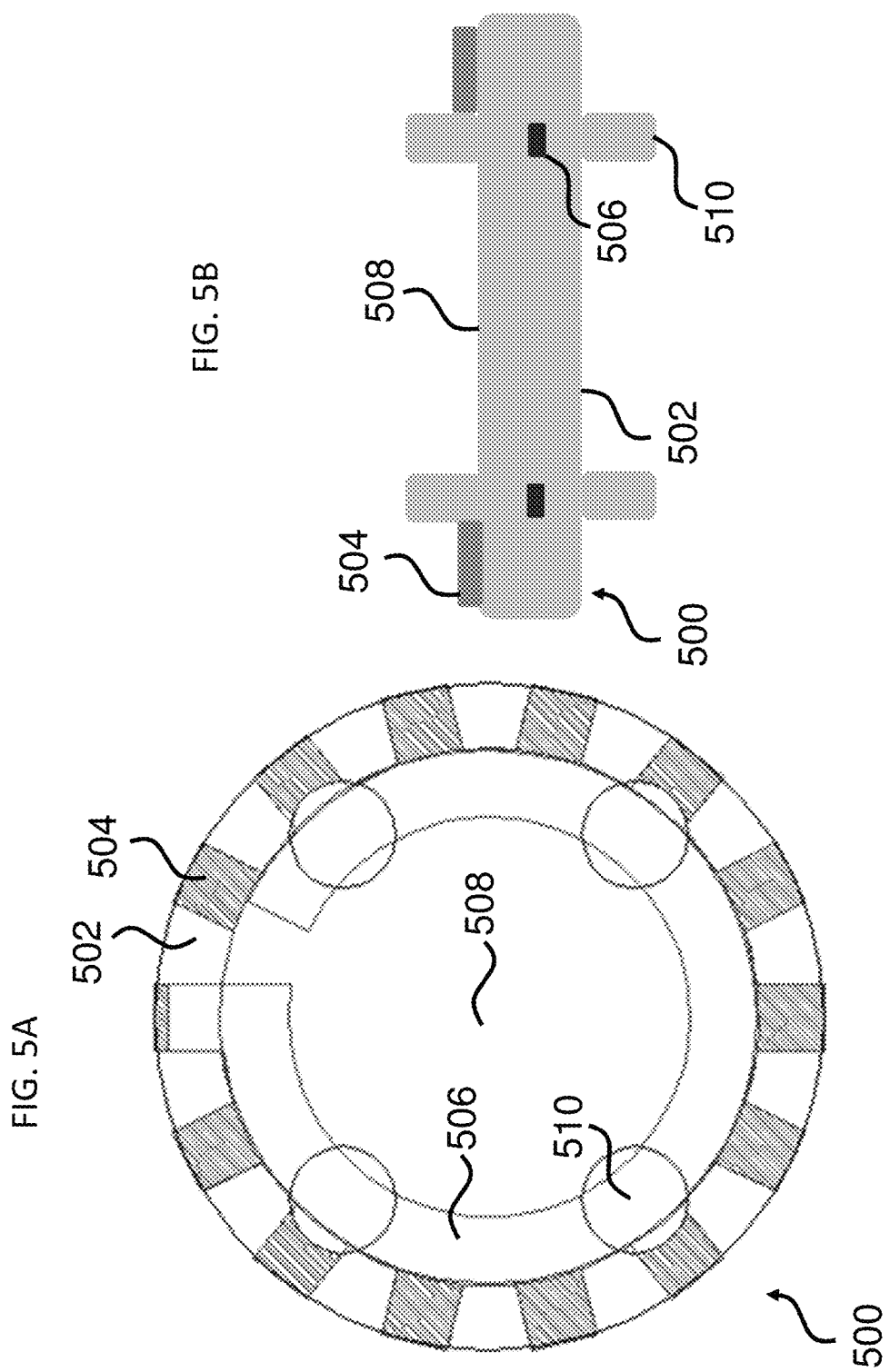

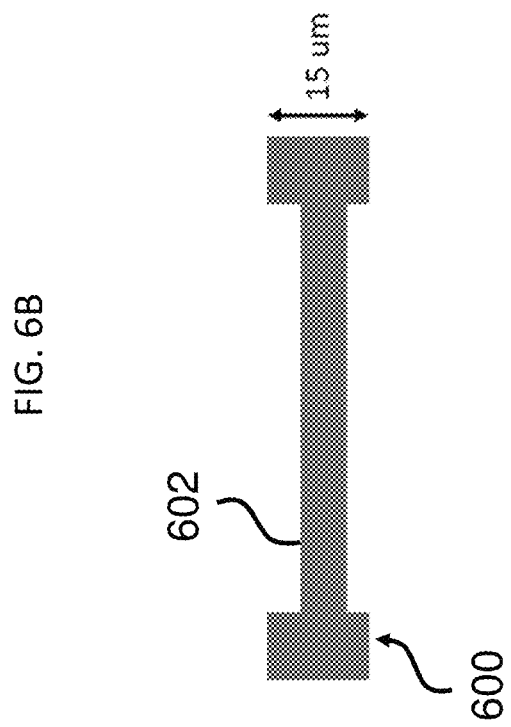
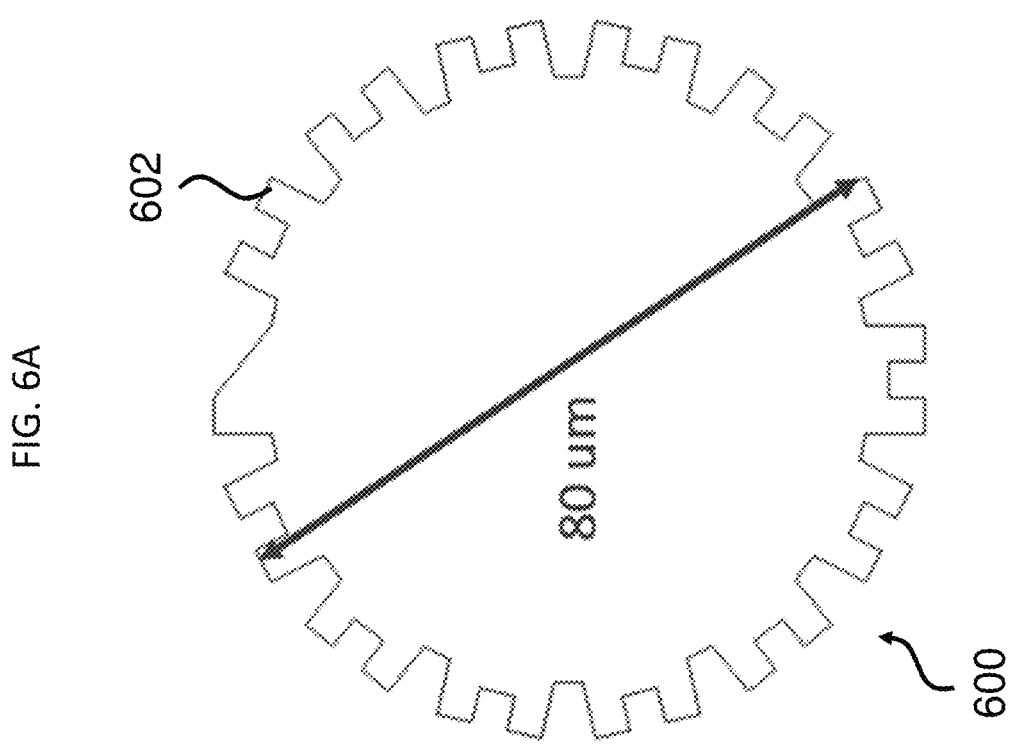
FIG. 6B
FIG. 6A

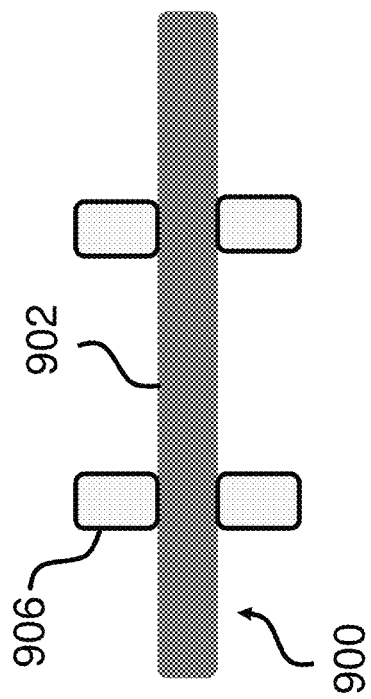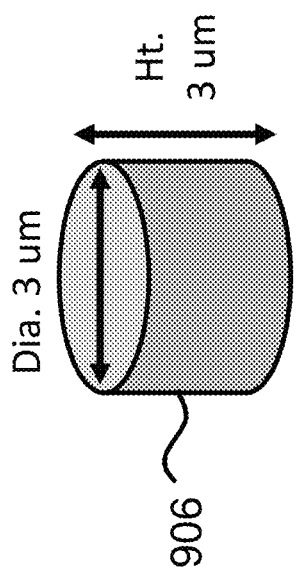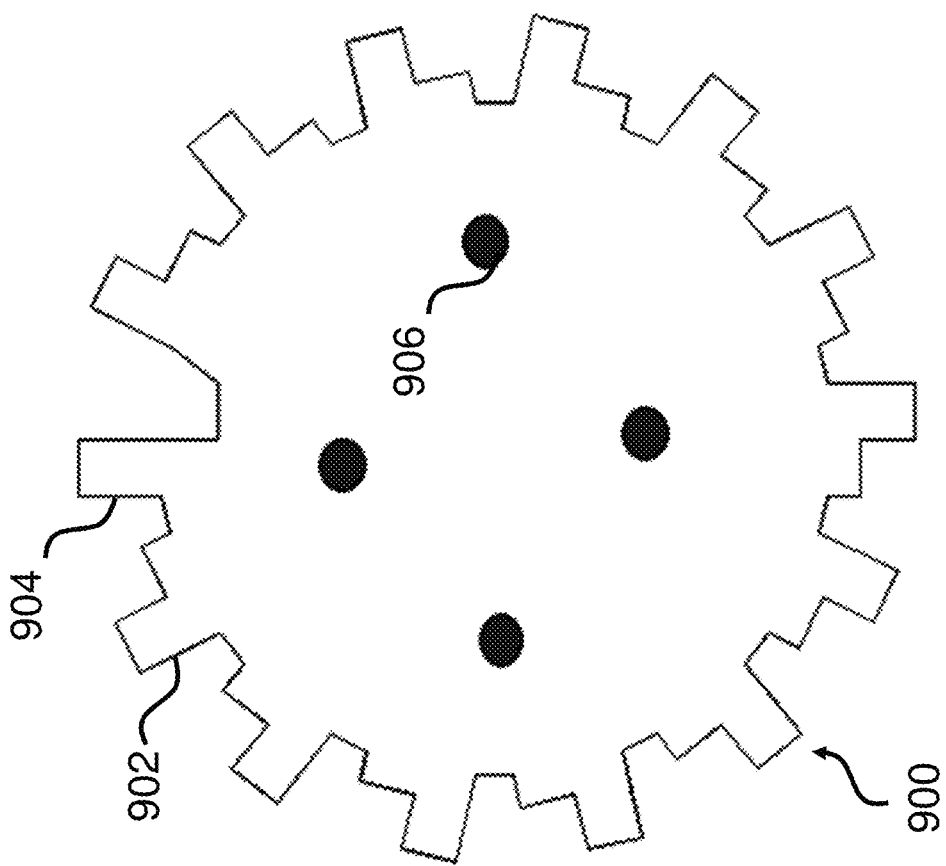

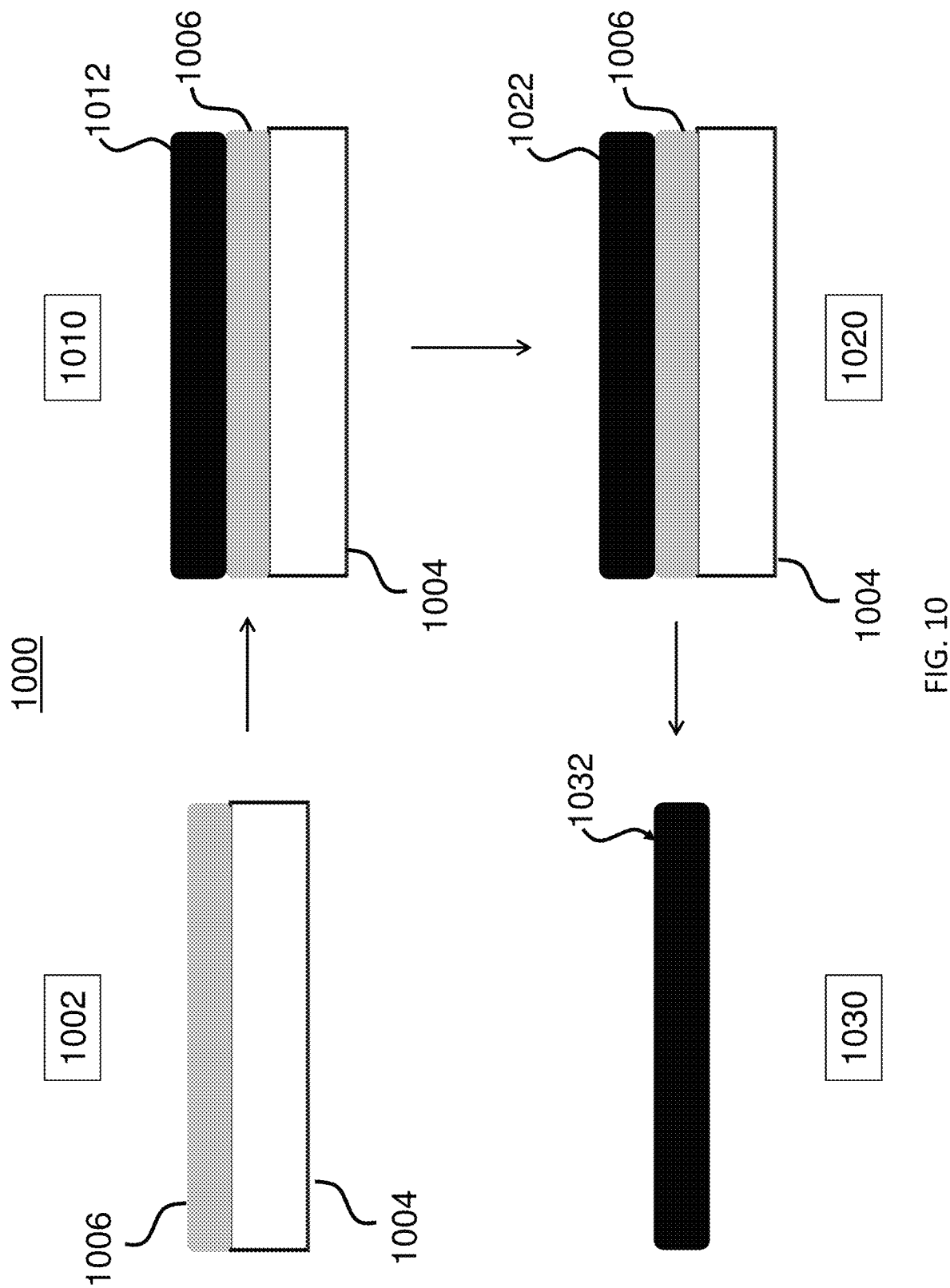

| | KRAS | | | | BRAF | | CTNNB1 | | | APC | | | |
|---|---|---|---|---|---|---|---|---|---|---|---|---|---|
| Mutations\Probe | G12D | G12V | G12S | G13D | V600E1 | V600E2 | T41A | T41I | E1309 | Q1367 | R1450 | T1556 | WT |
| G12D | 1259 | 0 | 0 | 0 | 0 | 0 | 0 | 0 | 0 | 0 | 0 | 0 | 0 |
| G12V | 0 | 28435 | 0 | 0 | 0 | 0 | 0 | 0 | 0 | 0 | 0 | 0 | 0 |
| G12S | 0 | 0 | 17717 | 0 | 0 | 0 | 0 | 0 | 0 | 0 | 0 | 0 | 0 |
| G13D | 0 | 0 | 0 | 2372 | 0 | 0 | 0 | 0 | 0 | 0 | 0 | 0 | 0 |
| V600E1 | 0 | 0 | 2440 | 0 | 8679 | 0 | 0 | 0 | 0 | 0 | 0 | 0 | 0 |
| V600E2 | 0 | 0 | 2075 | 0 | 0 | 4752 | 0 | 0 | 0 | 0 | 0 | 0 | 0 |
| T41A | 0 | 0 | 0 | 0 | 0 | 0 | 4127 | 0 | 0 | 0 | 0 | 0 | 0 |
| T41I | 0 | 0 | 0 | 0 | 0 | 0 | 0 | 7412 | 0 | 0 | 0 | 0 | 0 |
| E1309 | 0 | 0 | 0 | 0 | 0 | 0 | 0 | 0 | 8909 | 0 | 0 | 0 | 0 |
| Q1367 | 0 | 0 | 0 | 0 | 0 | 0 | 0 | 0 | 0 | 3736 | 0 | 0 | 0 |
| R1450 | 0 | 0 | 0 | 0 | 0 | 0 | 0 | 0 | 0 | 0 | 4937 | 0 | 0 |
| T1556 | 0 | 0 | 0 | 0 | 0 | 0 | 0 | 0 | 0 | 0 | 0 | 1330 | 0 |
| Ref | 14575 | 14382 | 13352 | 14724 | 14485 | 14292 | 16264 | 13668 | 14228 | 15020 | 13387 | 15633 | 14604 |
| blank | 0 | 0 | 0 | 0 | 0 | 0 | 0 | 0 | 0 | 0 | 0 | 0 | 0 |
| Sensitivity | 0.10% | 0.10% | 0.10% | 0.10% | 0.10% | 0.10% | 1% | 0.10% | 0.10% | 0.10% | 0.10% | 1% | 0% |

FIG. 18A

SEQUENCE LISTING

<160> NUMBER OF SEQ ID NOS: 246

<210> SEQ ID NO 1
<211> LENGTH: 24
<212> TYPE: DNA
<213> ORGANISM: Artificial Sequence
<220> FEATURE:
<223> OTHER INFORMATION: Synthetic Construct

<400> SEQUENCE: 1
gtactggtgg agtatttgat agtg                                      24

<210> SEQ ID NO 2
<211> LENGTH: 23
<212> TYPE: DNA
<213> ORGANISM: Artificial Sequence
<220> FEATURE:
<223> OTHER INFORMATION: Synthetic Construct

<400> SEQUENCE: 2
atcgtcaagg cactcttgcc tac                                          23

<210> SEQ ID NO 3
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 3, 5, 6, 8, 9, 11
<223> OTHER INFORMATION: Locked nucleic acid
<220> FEATURE:
<221> NAME/KEY: misc_feature
<222> LOCATION: 14
<223> OTHER INFORMATION: Inverted deoxythymidine
<220> FEATURE:
<221> NAME/KEY: misc_feature
<222> LOCATION: 14
<223> OTHER INFORMATION: Can be present in repeat of up to 3 times

<400> SEQUENCE: 3
tacgccacca gctt                                                    14

<210> SEQ ID NO 4
<211> LENGTH: 11
<212> TYPE: DNA
<213> ORGANISM: Artificial Sequence
<220> FEATURE:
<223> OTHER INFORMATION: Synthetic Construct

<400> SEQUENCE: 4
ggagctgatg g                                                       11

<210> SEQ ID NO 5
<211> LENGTH: 11
<212> TYPE: DNA
<213> ORGANISM: Artificial Sequence
<220> FEATURE:
<223> OTHER INFORMATION: Synthetic Construct

<400> SEQUENCE: 5
ggagctgttg g                                                       11

<210> SEQ ID NO 6
<211> LENGTH: 12
<212> TYPE: DNA
<213> ORGANISM: Artificial Sequence
<220> FEATURE:
<223> OTHER INFORMATION: Synthetic Construct

<400> SEQUENCE: 6
tggagctagt gg                                                      12

<210> SEQ ID NO 7
<211> LENGTH: 15
<212> TYPE: DNA
<213> ORGANISM: Artificial Sequence
<220> FEATURE:
<223> OTHER INFORMATION: Synthetic Construct

<400> SEQUENCE: 7
tggagctggt gacgt                                                   15

<210> SEQ ID NO 8
<211> LENGTH: 21
<212> TYPE: DNA
<213> ORGANISM: Artificial Sequence

```
<220> FEATURE:
<223> OTHER INFORMATION: Synthetic Construct

<400> SEQUENCE: 8
ggacccactc catcgagatt t                                              21

<210> SEQ ID NO 9
<211> LENGTH: 33
<212> TYPE: DNA
<213> ORGANISM: Artificial Sequence
<220> FEATURE:
<223> OTHER INFORMATION: Synthetic Construct

<400> SEQUENCE: 9
cagatatatt tcttcatgaa gacctcacag taa                                 33

<210> SEQ ID NO 10
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 3, 4, 5, 7, 8, 9, 10, 12, 13, 14, 15, 16
<223> OTHER INFORMATION: Locked nucleic acid
<220> FEATURE:
<221> NAME/KEY: misc_feature
<222> LOCATION: 17
<223> OTHER INFORMATION: Inverted deoxythymidine
<220> FEATURE:
<221> NAME/KEY: misc_feature
<222> LOCATION: 17
<223> OTHER INFORMATION: Can be present in repeat of up to 3 times

<400> SEQUENCE: 10
gagatttcac tgtagct                                                   17

<210> SEQ ID NO 11
<211> LENGTH: 17
<212> TYPE: DNA
<213> ORGANISM: Artificial Sequence
<220> FEATURE:
<223> OTHER INFORMATION: Synthetic Construct

<400> SEQUENCE: 11
tctagctaca gagaaat                                                   17

<210> SEQ ID NO 12
<211> LENGTH: 18
<212> TYPE: DNA
<213> ORGANISM: Artificial Sequence
<220> FEATURE:
<223> OTHER INFORMATION: Synthetic Construct

<400> SEQUENCE: 12
gtctagctac agaaaaat                                                  18

<210> SEQ ID NO 13
<211> LENGTH: 21
<212> TYPE: DNA
<213> ORGANISM: Artificial Sequence
<220> FEATURE:
<223> OTHER INFORMATION: Synthetic Construct

<400> SEQUENCE: 13
ggaatccatt ctggtgccac t                                              21
```

```
<210> SEQ ID NO 14
<211> LENGTH: 24
<212> TYPE: DNA
<213> ORGANISM: Artificial Sequence
<220> FEATURE:
<223> OTHER INFORMATION: Synthetic Construct

<400> SEQUENCE: 14
agaaaatccc tgttcccact cata                                          24

<210> SEQ ID NO 15
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 3, 4, 5, 6, 7, 8, 9, 10, 11, 12, 13
<223> OTHER INFORMATION: Locked nucleic acid
<220> FEATURE:
<221> NAME/KEY: misc_feature
<222> LOCATION: 16
<223> OTHER INFORMATION: Inverted deoxythymidine
<220> FEATURE:
<221> NAME/KEY: misc_feature
<222> LOCATION: 16
<223> OTHER INFORMATION: Can be present in repeat of up to 3 times

<400> SEQUENCE: 15
gccactacca cagctt                                                   16

<210> SEQ ID NO 16
<211> LENGTH: 14
<212> TYPE: DNA
<213> ORGANISM: Artificial Sequence
<220> FEATURE:
<223> OTHER INFORMATION: Synthetic Construct

<400> SEQUENCE: 16
aggagctgtg gcag                                                     14

<210> SEQ ID NO 17
<211> LENGTH: 12
<212> TYPE: DNA
<213> ORGANISM: Artificial Sequence
<220> FEATURE:
<223> OTHER INFORMATION: Synthetic Construct

<400> SEQUENCE: 17
ggagctgtga ta                                                       12

<210> SEQ ID NO 18
<211> LENGTH: 21
<212> TYPE: DNA
<213> ORGANISM: Artificial Sequence
<220> FEATURE:
<223> OTHER INFORMATION: Synthetic Construct

<400> SEQUENCE: 18
ggtgccacta ccacagctcc t                                             21

<210> SEQ ID NO 19
<211> LENGTH: 25
<212> TYPE: DNA
<213> ORGANISM: Artificial Sequence
<220> FEATURE:
<223> OTHER INFORMATION: Synthetic Construct
```

<400> SEQUENCE: 19
tctcaaaact gcattctgac tttca    25

<210> SEQ ID NO 20
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 3, 4, 5, 6, 7, 8, 9, 10, 11, 12
<223> OTHER INFORMATION: Locked nucleic acid
<220> FEATURE:
<221> NAME/KEY: misc_feature
<222> LOCATION: 16
<223> OTHER INFORMATION: Inverted deoxythymidine
<220> FEATURE:
<221> NAME/KEY: misc_feature
<222> LOCATION: 16
<223> OTHER INFORMATION: Can be present in repeat of up to 3 times

<400> SEQUENCE: 20
gctccttctc tgagtt    16

<210> SEQ ID NO 21
<211> LENGTH: 17
<212> TYPE: DNA
<213> ORGANISM: Artificial Sequence
<220> FEATURE:
<223> OTHER INFORMATION: Synthetic Construct

<400> SEQUENCE: 21
tttaccactc agaaaag    17

<210> SEQ ID NO 22
<211> LENGTH: 15
<212> TYPE: DNA
<213> ORGANISM: Artificial Sequence
<220> FEATURE:
<223> OTHER INFORMATION: Synthetic Construct

<400> SEQUENCE: 22
taccactcag aggag    15

<210> SEQ ID NO 23
<211> LENGTH: 26
<212> TYPE: DNA
<213> ORGANISM: Artificial Sequence
<220> FEATURE:
<223> OTHER INFORMATION: Synthetic Construct

<400> SEQUENCE: 23
taaaaataaa gcacctactg ctgaaa    26

<210> SEQ ID NO 24
<211> LENGTH: 24
<212> TYPE: DNA
<213> ORGANISM: Artificial Sequence
<220> FEATURE:
<223> OTHER INFORMATION: Synthetic Construct

<400> SEQUENCE: 24
agcttgctta ggtccactct ctct    24

<210> SEQ ID NO 25

```
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 3, 5, 6, 12, 14, 15, 17, 18, 19, 20
<223> OTHER INFORMATION: Locked nucleic acid
<220> FEATURE:
<221> NAME/KEY: misc_feature
<222> LOCATION: 21
<223> OTHER INFORMATION: Inverted deoxythymidine
<220> FEATURE:
<221> NAME/KEY: misc_feature
<222> LOCATION: 21
<223> OTHER INFORMATION: Can be present in repeat of up to 3 times

<400> SEQUENCE: 25
ccactctctc tcttttcagc t                                      21

<210> SEQ ID NO 26
<211> LENGTH: 19
<212> TYPE: DNA
<213> ORGANISM: Artificial Sequence
<220> FEATURE:
<223> OTHER INFORMATION: Synthetic Construct

<400> SEQUENCE: 26
actgctgaaa agagagagt                                         19

<210> SEQ ID NO 27
<211> LENGTH: 25
<212> TYPE: DNA
<213> ORGANISM: Artificial Sequence
<220> FEATURE:
<223> OTHER INFORMATION: Synthetic Construct

<400> SEQUENCE: 27
taggatgtaa tcagacgaca cagga                                  25

<210> SEQ ID NO 28
<211> LENGTH: 25
<212> TYPE: DNA
<213> ORGANISM: Artificial Sequence
<220> FEATURE:
<223> OTHER INFORMATION: Synthetic Construct

<400> SEQUENCE: 28
cagctgacct agttccaatc tttta                                  25

<210> SEQ ID NO 29
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 3, 4, 5, 6, 7, 8, 9, 10, 11, 12, 15, 17, 18
<223> OTHER INFORMATION: Locked nucleic acid
<220> FEATURE:
<221> NAME/KEY: misc_feature
<222> LOCATION: 19
<223> OTHER INFORMATION: Inverted deoxythymidine
<220> FEATURE:
<221> NAME/KEY: misc_feature
<222> LOCATION: 19
<223> OTHER INFORMATION: Can be present in repeat of up to 3 times

<400> SEQUENCE: 29
```

-continued

```
cttttcttttt atttctgct                                              19

<210> SEQ ID NO 30
<211> LENGTH: 15
<212> TYPE: DNA
<213> ORGANISM: Artificial Sequence
<220> FEATURE:
<223> OTHER INFORMATION: Synthetic Construct

<400> SEQUENCE: 30
gaaataaaag attgg                                                   15

<210> SEQ ID NO 31
<211> LENGTH: 21
<212> TYPE: DNA
<213> ORGANISM: Artificial Sequence
<220> FEATURE:
<223> OTHER INFORMATION: Synthetic Construct

<400> SEQUENCE: 31
tctccctcca aaagtggtgc t                                            21

<210> SEQ ID NO 32
<211> LENGTH: 21
<212> TYPE: DNA
<213> ORGANISM: Artificial Sequence
<220> FEATURE:
<223> OTHER INFORMATION: Synthetic Construct

<400> SEQUENCE: 32
tggcaatcga acgactctca a                                            21

<210> SEQ ID NO 33
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 4, 5, 6, 7, 9, 10, 11, 12
<223> OTHER INFORMATION: Locked nucleic acid
<220> FEATURE:
<221> NAME/KEY: misc_feature
<222> LOCATION: 14
<223> OTHER INFORMATION: Inverted deoxythymidine
<220> FEATURE:
<221> NAME/KEY: misc_feature
<222> LOCATION: 14
<223> OTHER INFORMATION: Can be present in repeat of up to 3 times

<400> SEQUENCE: 33
gtgctcagac acct                                                    14

<210> SEQ ID NO 34
<211> LENGTH: 15
<212> TYPE: DNA
<213> ORGANISM: Artificial Sequence
<220> FEATURE:
<223> OTHER INFORMATION: Synthetic Construct

<400> SEQUENCE: 34
ttttgggtgt ctaag                                                   15

<210> SEQ ID NO 35
<211> LENGTH: 23
<212> TYPE: DNA
```

```
<213> ORGANISM: Artificial Sequence
<220> FEATURE:
<223> OTHER INFORMATION: Synthetic Construct

<400> SEQUENCE: 35
gcagaagtaa aacacctcca cca                                            23

<210> SEQ ID NO 36
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 16, 17
<223> OTHER INFORMATION: Locked nucleic acid

<400> SEQUENCE: 36
ggtgctttat ttttaggtac ttc                                            23

<210> SEQ ID NO 37
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 3, 4, 6, 7, 8, 9, 11, 12, 13
<223> OTHER INFORMATION: Locked nucleic acid
<220> FEATURE:
<221> NAME/KEY: misc_feature
<222> LOCATION: 15
<223> OTHER INFORMATION: Inverted deoxythymidine
<220> FEATURE:
<221> NAME/KEY: misc_feature
<222> LOCATION: 15
<223> OTHER INFORMATION: Can be present in repeat of up to 3 times

<400> SEQUENCE: 37
cttctcgctt ggttt                                                     15

<210> SEQ ID NO 38
<211> LENGTH: 15
<212> TYPE: DNA
<213> ORGANISM: Artificial Sequence
<220> FEATURE:
<223> OTHER INFORMATION: Synthetic Construct

<400> SEQUENCE: 38
caaaccaagt gagaa                                                     15

<210> SEQ ID NO 39
<211> LENGTH: 22
<212> TYPE: DNA
<213> ORGANISM: Artificial Sequence
<220> FEATURE:
<223> OTHER INFORMATION: Synthetic Construct

<400> SEQUENCE: 39
caggaaaatg acaatgggaa tg                                             22

<210> SEQ ID NO 40
<211> LENGTH: 29
<212> TYPE: DNA
<213> ORGANISM: Artificial Sequence
<220> FEATURE:
<223> OTHER INFORMATION: Synthetic Construct
```

```
<400> SEQUENCE: 40
atctaatagg tccttttcag aatcaatag                                    29

<210> SEQ ID NO 41
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 3, 4, 5, 6, 8, 9, 10, 11, 13, 14, 15, 16
<223> OTHER INFORMATION: Locked nucleic acid
<220> FEATURE:
<221> NAME/KEY: misc_feature
<222> LOCATION: 18
<223> OTHER INFORMATION: Inverted deoxythymidine
<220> FEATURE:
<221> NAME/KEY: misc_feature
<222> LOCATION: 18
<223> OTHER INFORMATION: Can be present in repeat of up to 3 times

<400> SEQUENCE: 41
caatagtttt ttctgcct                                                18

<210> SEQ ID NO 42
<211> LENGTH: 17
<212> TYPE: DNA
<213> ORGANISM: Artificial Sequence
<220> FEATURE:
<223> OTHER INFORMATION: Synthetic Construct

<400> SEQUENCE: 42
agaggcagaa aaaaact                                                 17

<210> SEQ ID NO 43
<211> LENGTH: 24
<212> TYPE: DNA
<213> ORGANISM: Artificial Sequence
<220> FEATURE:
<223> OTHER INFORMATION: Synthetic Construct

<400> SEQUENCE: 43
tgagtgttac ttcttcccac actc                                         24

<210> SEQ ID NO 44
<211> LENGTH: 20
<212> TYPE: DNA
<213> ORGANISM: Artificial Sequence
<220> FEATURE:
<223> OTHER INFORMATION: Synthetic Construct

<400> SEQUENCE: 44
attgcttttg cgcaatccct                                              20

<210> SEQ ID NO 45
<211> LENGTH: 24
<212> TYPE: DNA
<213> ORGANISM: Artificial Sequence
<220> FEATURE:
<223> OTHER INFORMATION: Synthetic Construct

<400> SEQUENCE: 45
tttttttttt ttggagacgg tctg                                         24

<210> SEQ ID NO 46
```

```
<211> LENGTH: 15
<212> TYPE: DNA
<213> ORGANISM: Artificial Sequence
<220> FEATURE:
<223> OTHER INFORMATION: Synthetic Construct

<400> SEQUENCE: 46
aatataatat attat                                                      15

<210> SEQ ID NO 47
<211> LENGTH: 25
<212> TYPE: DNA
<213> ORGANISM: Artificial Sequence
<220> FEATURE:
<223> OTHER INFORMATION: Synthetic Construct

<400> SEQUENCE: 47 ttttttttttt ttaaggagct gatgg                                          25

<210> SEQ ID NO 48
<211> LENGTH: 25
<212> TYPE: DNA
<213> ORGANISM: Artificial Sequence
<220> FEATURE:
<223> OTHER INFORMATION: Synthetic Construct

<400> SEQUENCE: 48 ttttttttttt ttaaggagct gttgg                                          25

<210> SEQ ID NO 49
<211> LENGTH: 24
<212> TYPE: DNA
<213> ORGANISM: Artificial Sequence
<220> FEATURE:
<223> OTHER INFORMATION: Synthetic Construct

<400> SEQUENCE: 49
tttttttttt tatggagcta gtgg                                            24

<210> SEQ ID NO 50
<211> LENGTH: 25
<212> TYPE: DNA
<213> ORGANISM: Artificial Sequence
<220> FEATURE:
<223> OTHER INFORMATION: Synthetic Construct

<400> SEQUENCE: 50 tttttttta tggagctggt gacgt                                            25

<210> SEQ ID NO 51
<211> LENGTH: 27
<212> TYPE: DNA
<213> ORGANISM: Artificial Sequence
<220> FEATURE:
<223> OTHER INFORMATION: Synthetic Construct

<400> SEQUENCE: 51 tttttttaatt tctagctaca gagaaat                                        27

<210> SEQ ID NO 52
<211> LENGTH: 27
<212> TYPE: DNA
<213> ORGANISM: Artificial Sequence
<220> FEATURE:
<223> OTHER INFORMATION: Synthetic Construct

<400> SEQUENCE: 52
```
tttttttatg tctagctaca gaaaaat            27

<210> SEQ ID NO 53
<211> LENGTH: 25
<212> TYPE: DNA
<213> ORGANISM: Artificial Sequence
<220> FEATURE:
<223> OTHER INFORMATION: Synthetic Construct

<400> SEQUENCE: 53
tttttttttt taggagctgt ggcag            25

<210> SEQ ID NO 54
<211> LENGTH: 25
<212> TYPE: DNA
<213> ORGANISM: Artificial Sequence
<220> FEATURE:
<223> OTHER INFORMATION: Synthetic Construct

<400> SEQUENCE: 54
tttttttttt tttggagctg tgata            25

<210> SEQ ID NO 55
<211> LENGTH: 25
<212> TYPE: DNA
<213> ORGANISM: Artificial Sequence
<220> FEATURE:
<223> OTHER INFORMATION: Synthetic Construct

<400> SEQUENCE: 55
tttttttttt taccactcag aaaag            25

<210> SEQ ID NO 56
<211> LENGTH: 26
<212> TYPE: DNA
<213> ORGANISM: Artificial Sequence
<220> FEATURE:
<223> OTHER INFORMATION: Synthetic Construct

<400> SEQUENCE: 56
ttttttttta ataccactca gaggag            26

<210> SEQ ID NO 57
<211> LENGTH: 27
<212> TYPE: DNA
<213> ORGANISM: Artificial Sequence
<220> FEATURE:
<223> OTHER INFORMATION: Synthetic Construct

<400> SEQUENCE: 57 tttttttac tgctgaaaag agagagt            27

<210> SEQ ID NO 58
<211> LENGTH: 28
<212> TYPE: DNA
<213> ORGANISM: Artificial Sequence
<220> FEATURE:
<223> OTHER INFORMATION: Synthetic Construct

<400> SEQUENCE: 58
tttttttttt tttgaaataa aagattgg            28

<210> SEQ ID NO 59
<211> LENGTH: 24
<212> TYPE: DNA

```
<213> ORGANISM: Artificial Sequence
<220> FEATURE:
<223> OTHER INFORMATION: Synthetic Construct

<400> SEQUENCE: 59
tttttttttt tttgggtgtc taag                                           24

<210> SEQ ID NO 60
<211> LENGTH: 25
<212> TYPE: DNA
<213> ORGANISM: Artificial Sequence
<220> FEATURE:
<223> OTHER INFORMATION: Synthetic Construct

<400> SEQUENCE: 60 tttttttttta caaccaagt gagaa                                          25

<210> SEQ ID NO 61
<211> LENGTH: 27
<212> TYPE: DNA
<213> ORGANISM: Artificial Sequence
<220> FEATURE:
<223> OTHER INFORMATION: Synthetic Construct

<400> SEQUENCE: 61
tttttttttt agaggcagaa aaaaact                                        27

<210> SEQ ID NO 62
<211> LENGTH: 188
<212> TYPE: PRT
<213> ORGANISM: Artificial Sequence
<220> FEATURE:
<223> OTHER INFORMATION: Synthetic Construct

<400> SEQUENCE: 62

Met Thr Glu Tyr Lys Leu Val Val Val Gly Ala Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185
```

-continued

```
<210> SEQ ID NO 63
<211> LENGTH: 766
<212> TYPE: PRT
<213> ORGANISM: Artificial Sequence
<220> FEATURE:
<223> OTHER INFORMATION: Synthetic Construct

<400> SEQUENCE: 63
```

Met Ala Ala Leu Ser Gly Gly Gly Gly Ala Glu Pro Gly Gln
1               5                   10                  15

Ala Leu Phe Asn Gly Asp Met Glu Pro Glu Ala Gly Ala Gly Ala Gly
            20                  25                  30

Ala Ala Ala Ser Ser Ala Ala Asp Pro Ala Ile Pro Glu Glu Val Trp
        35                  40                  45

Asn Ile Lys Gln Met Ile Lys Leu Thr Gln Glu His Ile Glu Ala Leu
50                  55                  60

Leu Asp Lys Phe Gly Gly Glu His Asn Pro Pro Ser Ile Tyr Leu Glu
65                  70                  75                  80

Ala Tyr Glu Glu Tyr Thr Ser Lys Leu Asp Ala Leu Gln Gln Arg Glu
                85                  90                  95

Gln Gln Leu Leu Glu Ser Leu Gly Asn Gly Thr Asp Phe Ser Val Ser
            100                 105                 110

Ser Ser Ala Ser Met Asp Thr Val Thr Ser Ser Ser Ser Ser Ser Leu
        115                 120                 125

Ser Val Leu Pro Ser Ser Leu Ser Val Phe Gln Asn Pro Thr Asp Val
130                 135                 140

Ala Arg Ser Asn Pro Lys Ser Pro Gln Lys Pro Ile Val Arg Val Phe
145                 150                 155                 160

Leu Pro Asn Lys Gln Arg Thr Val Val Pro Ala Arg Cys Gly Val Thr
                165                 170                 175

Val Arg Asp Ser Leu Lys Lys Ala Leu Met Met Arg Gly Leu Ile Pro
            180                 185                 190

Glu Cys Cys Ala Val Tyr Arg Ile Gln Asp Gly Glu Lys Lys Pro Ile
        195                 200                 205

Gly Trp Asp Thr Asp Ile Ser Trp Leu Thr Gly Glu Glu Leu His Val
210                 215                 220

Glu Val Leu Glu Asn Val Pro Leu Thr Thr His Asn Phe Val Arg Lys
225                 230                 235                 240

Thr Phe Phe Thr Leu Ala Phe Cys Asp Phe Cys Arg Lys Leu Leu Phe
                245                 250                 255

Gln Gly Phe Arg Cys Gln Thr Cys Gly Tyr Lys Phe His Gln Arg Cys
            260                 265                 270

Ser Thr Glu Val Pro Leu Met Cys Val Asn Tyr Asp Gln Leu Asp Leu
        275                 280                 285

Leu Phe Val Ser Lys Phe Phe Glu His His Pro Ile Pro Gln Glu Glu
290                 295                 300

Ala Ser Leu Ala Glu Thr Ala Leu Thr Ser Gly Ser Ser Pro Ser Ala
305                 310                 315                 320

Pro Ala Ser Asp Ser Ile Gly Pro Gln Ile Leu Thr Ser Pro Ser Pro
                325                 330                 335

Ser Lys Ser Ile Pro Ile Pro Gln Pro Phe Arg Pro Ala Asp Glu Asp
            340                 345                 350

His Arg Asn Gln Phe Gly Gln Arg Asp Arg Ser Ser Ser Ala Pro Asn
        355                 360                 365

Val His Ile Asn Thr Ile Glu Pro Val Asn Ile Asp Asp Leu Ile Arg

```
            370                 375                 380
Asp Gln Gly Phe Arg Gly Asp Gly Gly Ser Thr Thr Gly Leu Ser Ala
385                 390                 395                 400

Thr Pro Pro Ala Ser Leu Pro Gly Ser Leu Thr Asn Val Lys Ala Leu
                405                 410                 415

Gln Lys Ser Pro Gly Pro Gln Arg Glu Arg Lys Ser Ser Ser Ser Ser
            420                 425                 430

Glu Asp Arg Asn Arg Met Lys Thr Leu Gly Arg Arg Asp Ser Ser Asp
        435                 440                 445

Asp Trp Glu Ile Pro Asp Gly Gln Ile Thr Val Gly Gln Arg Ile Gly
    450                 455                 460

Ser Gly Ser Phe Gly Thr Val Tyr Lys Gly Lys Trp His Gly Asp Val
465                 470                 475                 480

Ala Val Lys Met Leu Asn Val Thr Ala Pro Thr Pro Gln Gln Leu Gln
                485                 490                 495

Ala Phe Lys Asn Glu Val Gly Val Leu Arg Lys Thr Arg His Val Asn
            500                 505                 510

Ile Leu Leu Phe Met Gly Tyr Ser Thr Lys Pro Gln Leu Ala Ile Val
        515                 520                 525

Thr Gln Trp Cys Glu Gly Ser Ser Leu Tyr His His Leu His Ile Ile
    530                 535                 540

Glu Thr Lys Phe Glu Met Ile Lys Leu Ile Asp Ile Ala Arg Gln Thr
545                 550                 555                 560

Ala Gln Gly Met Asp Tyr Leu His Ala Lys Ser Ile Ile His Arg Asp
                565                 570                 575

Leu Lys Ser Asn Asn Ile Phe Leu His Glu Asp Leu Thr Val Lys Ile
            580                 585                 590

Gly Asp Phe Gly Leu Ala Thr Val Lys Ser Arg Trp Ser Gly Ser His
        595                 600                 605

Gln Phe Glu Gln Leu Ser Gly Ser Ile Leu Trp Met Ala Pro Glu Val
    610                 615                 620

Ile Arg Met Gln Asp Lys Asn Pro Tyr Ser Phe Gln Ser Asp Val Tyr
625                 630                 635                 640

Ala Phe Gly Ile Val Leu Tyr Glu Leu Met Thr Gly Gln Leu Pro Tyr
                645                 650                 655

Ser Asn Ile Asn Asn Arg Asp Gln Ile Ile Phe Met Val Gly Arg Gly
            660                 665                 670

Tyr Leu Ser Pro Asp Leu Ser Lys Val Arg Ser Asn Cys Pro Lys Ala
        675                 680                 685

Met Lys Arg Leu Met Ala Glu Cys Leu Lys Lys Arg Asp Glu Arg
    690                 695                 700

Pro Leu Phe Pro Gln Ile Leu Ala Ser Ile Glu Leu Leu Ala Arg Ser
705                 710                 715                 720

Leu Pro Lys Ile His Arg Ser Ala Ser Glu Pro Ser Leu Asn Arg Ala
                725                 730                 735

Gly Phe Gln Thr Glu Asp Phe Ser Leu Tyr Ala Cys Ala Ser Pro Lys
            740                 745                 750

Thr Pro Ile Gln Ala Gly Gly Tyr Gly Ala Phe Pro Val His
        755                 760                 765

<210> SEQ ID NO 64
<211> LENGTH: 781
<212> TYPE: PRT
<213> ORGANISM: Artificial Sequence
```

<220> FEATURE:
<223> OTHER INFORMATION: Synthetic Construct

<400> SEQUENCE: 64

```
Met Ala Thr Gln Ala Asp Leu Met Glu Leu Asp Met Ala Met Glu Pro
1               5                   10                  15

Asp Arg Lys Ala Ala Val Ser His Trp Gln Gln Ser Tyr Leu Asp
            20                  25                  30

Ser Gly Ile His Ser Gly Ala Thr Thr Thr Ala Pro Ser Leu Ser Gly
                35                  40                  45

Lys Gly Asn Pro Glu Glu Asp Val Asp Thr Ser Gln Val Leu Tyr
            50                  55                  60

Glu Trp Glu Gln Gly Phe Ser Gln Ser Phe Thr Gln Glu Gln Val Ala
65                      70                  75                  80

Asp Ile Asp Gly Gln Tyr Ala Met Thr Arg Ala Gln Arg Val Arg Ala
                    85                  90                  95

Ala Met Phe Pro Glu Thr Leu Asp Glu Gly Met Gln Ile Pro Ser Thr
                100                 105                 110

Gln Phe Asp Ala Ala His Pro Thr Asn Val Gln Arg Leu Ala Glu Pro
            115                 120                 125

Ser Gln Met Leu Lys His Ala Val Val Asn Leu Ile Asn Tyr Gln Asp
            130                 135                 140

Asp Ala Glu Leu Ala Thr Arg Ala Ile Pro Glu Leu Thr Lys Leu Leu
145                 150                 155                 160

Asn Asp Glu Asp Gln Val Val Val Asn Lys Ala Ala Val Met Val His
                    165                 170                 175

Gln Leu Ser Lys Lys Glu Ala Ser Arg His Ala Ile Met Arg Ser Pro
                180                 185                 190

Gln Met Val Ser Ala Ile Val Arg Thr Met Gln Asn Thr Asn Asp Val
            195                 200                 205

Glu Thr Ala Arg Cys Thr Ala Gly Thr Leu His Asn Leu Ser His His
            210                 215                 220

Arg Glu Gly Leu Leu Ala Ile Phe Lys Ser Gly Gly Ile Pro Ala Leu
225                 230                 235                 240

Val Lys Met Leu Gly Ser Pro Val Asp Ser Val Leu Phe Tyr Ala Ile
                245                 250                 255

Thr Thr Leu His Asn Leu Leu Leu His Gln Glu Gly Ala Lys Met Ala
            260                 265                 270

Val Arg Leu Ala Gly Gly Leu Gln Lys Met Val Ala Leu Leu Asn Lys
            275                 280                 285

Thr Asn Val Lys Phe Leu Ala Ile Thr Thr Asp Cys Leu Gln Ile Leu
    290                 295                 300

Ala Tyr Gly Asn Gln Glu Ser Lys Leu Ile Ile Leu Ala Ser Gly Gly
305                 310                 315                 320

Pro Gln Ala Leu Val Asn Ile Met Arg Thr Tyr Thr Tyr Glu Lys Leu
                325                 330                 335

Leu Trp Thr Thr Ser Arg Val Leu Lys Val Leu Ser Val Cys Ser Ser
            340                 345                 350

Asn Lys Pro Ala Ile Val Glu Ala Gly Gly Met Gln Ala Leu Gly Leu
            355                 360                 365

His Leu Thr Asp Pro Ser Gln Arg Leu Val Gln Asn Cys Leu Trp Thr
    370                 375                 380

Leu Arg Asn Leu Ser Asp Ala Ala Thr Lys Gln Glu Gly Met Glu Gly
385                 390                 395                 400
```

```
Leu Leu Gly Thr Leu Val Gln Leu Leu Gly Ser Asp Asp Ile Asn Val
            405                 410                 415

Val Thr Cys Ala Ala Gly Ile Leu Ser Asn Leu Thr Cys Asn Asn Tyr
        420                 425                 430

Lys Asn Lys Met Met Val Cys Gln Val Gly Gly Ile Glu Ala Leu Val
            435                 440                 445

Arg Thr Val Leu Arg Ala Gly Asp Arg Glu Asp Ile Thr Glu Pro Ala
450                 455                 460

Ile Cys Ala Leu Arg His Leu Thr Ser Arg His Gln Glu Ala Glu Met
465                 470                 475                 480

Ala Gln Asn Ala Val Arg Leu His Tyr Gly Leu Pro Val Val Val Lys
                485                 490                 495

Leu Leu His Pro Pro Ser His Trp Pro Leu Ile Lys Ala Thr Val Gly
            500                 505                 510

Leu Ile Arg Asn Leu Ala Leu Cys Pro Ala Asn His Ala Pro Leu Arg
        515                 520                 525

Glu Gln Gly Ala Ile Pro Arg Leu Val Gln Leu Leu Val Arg Ala His
530                 535                 540

Gln Asp Thr Gln Arg Arg Thr Ser Met Gly Gly Thr Gln Gln Gln Phe
545                 550                 555                 560

Val Glu Gly Val Arg Met Glu Glu Ile Val Glu Gly Cys Thr Gly Ala
                565                 570                 575

Leu His Ile Leu Ala Arg Asp Val His Asn Arg Ile Val Ile Arg Gly
            580                 585                 590

Leu Asn Thr Ile Pro Leu Phe Val Gln Leu Leu Tyr Ser Pro Ile Glu
        595                 600                 605

Asn Ile Gln Arg Val Ala Ala Gly Val Leu Cys Glu Leu Ala Gln Asp
610                 615                 620

Lys Glu Ala Ala Glu Ala Ile Glu Ala Glu Gly Ala Thr Ala Pro Leu
625                 630                 635                 640

Thr Glu Leu Leu His Ser Arg Asn Glu Gly Val Ala Thr Tyr Ala Ala
                645                 650                 655

Ala Val Leu Phe Arg Met Ser Glu Asp Lys Pro Gln Asp Tyr Lys Lys
            660                 665                 670

Arg Leu Ser Val Glu Leu Thr Ser Ser Leu Phe Arg Thr Glu Pro Met
        675                 680                 685

Ala Trp Asn Glu Thr Ala Asp Leu Gly Leu Asp Ile Gly Ala Gln Gly
690                 695                 700

Glu Pro Leu Gly Tyr Arg Gln Asp Asp Pro Ser Tyr Arg Ser Phe His
705                 710                 715                 720

Ser Gly Gly Tyr Gly Gln Asp Ala Leu Gly Met Asp Pro Met Met Glu
                725                 730                 735

His Glu Met Gly Gly His His Pro Gly Ala Asp Tyr Pro Val Asp Gly
            740                 745                 750

Leu Pro Asp Leu Gly His Ala Gln Asp Leu Met Asp Gly Leu Pro Pro
        755                 760                 765

Gly Asp Ser Asn Gln Leu Ala Trp Phe Asp Thr Asp Leu
770                 775                 780

<210> SEQ ID NO 65
<211> LENGTH: 2843
<212> TYPE: PRT
<213> ORGANISM: Artificial Sequence
<220> FEATURE:
```

<223> OTHER INFORMATION: Synthetic Construct

<400> SEQUENCE: 65

```
Met Ala Ala Ala Ser Tyr Asp Gln Leu Leu Lys Gln Val Glu Ala Leu
1               5                   10                  15

Lys Met Glu Asn Ser Asn Leu Arg Gln Glu Leu Glu Asp Asn Ser Asn
            20                  25                  30

His Leu Thr Lys Leu Glu Thr Glu Ala Ser Asn Met Lys Glu Val Leu
        35                  40                  45

Lys Gln Leu Gln Gly Ser Ile Glu Asp Glu Ala Met Ala Ser Ser Gly
    50                  55                  60

Gln Ile Asp Leu Leu Glu Arg Leu Lys Glu Leu Asn Leu Asp Ser Ser
65                  70                  75                  80

Asn Phe Pro Gly Val Lys Leu Arg Ser Lys Met Ser Leu Arg Ser Tyr
                85                  90                  95

Gly Ser Arg Glu Gly Ser Val Ser Ser Arg Ser Gly Glu Cys Ser Pro
            100                 105                 110

Val Pro Met Gly Ser Phe Pro Arg Arg Gly Phe Val Asn Gly Ser Arg
        115                 120                 125

Glu Ser Thr Gly Tyr Leu Glu Glu Leu Glu Lys Glu Arg Ser Leu Leu
    130                 135                 140

Leu Ala Asp Leu Asp Lys Glu Glu Lys Glu Lys Asp Trp Tyr Tyr Ala
145                 150                 155                 160

Gln Leu Gln Asn Leu Thr Lys Arg Ile Asp Ser Leu Pro Leu Thr Glu
                165                 170                 175

Asn Phe Ser Leu Gln Thr Asp Met Thr Arg Arg Gln Leu Glu Tyr Glu
            180                 185                 190

Ala Arg Gln Ile Arg Val Ala Met Glu Glu Gln Leu Gly Thr Cys Gln
        195                 200                 205

Asp Met Glu Lys Arg Ala Gln Arg Arg Ile Ala Arg Ile Gln Gln Ile
    210                 215                 220

Glu Lys Asp Ile Leu Arg Ile Arg Gln Leu Leu Gln Ser Gln Ala Thr
225                 230                 235                 240

Glu Ala Glu Arg Ser Ser Gln Asn Lys His Glu Thr Gly Ser His Asp
                245                 250                 255

Ala Glu Arg Gln Asn Glu Gly Gln Gly Val Gly Glu Ile Asn Met Ala
            260                 265                 270

Thr Ser Gly Asn Gly Gln Gly Ser Thr Thr Arg Met Asp His Glu Thr
        275                 280                 285

Ala Ser Val Leu Ser Ser Ser Thr His Ser Ala Pro Arg Arg Leu
    290                 295                 300

Thr Ser His Leu Gly Thr Lys Val Glu Met Val Tyr Ser Leu Leu Ser
305                 310                 315                 320

Met Leu Gly Thr His Asp Lys Asp Met Ser Arg Thr Leu Leu Ala
                325                 330                 335

Met Ser Ser Ser Gln Asp Ser Cys Ile Ser Met Arg Gln Ser Gly Cys
            340                 345                 350

Leu Pro Leu Leu Ile Gln Leu Leu His Gly Asn Asp Lys Asp Ser Val
        355                 360                 365

Leu Leu Gly Asn Ser Arg Gly Ser Lys Glu Ala Arg Ala Arg Ala Ser
    370                 375                 380

Ala Ala Leu His Asn Ile Ile His Ser Gln Pro Asp Asp Lys Arg Gly
385                 390                 395                 400
```

```
Arg Arg Glu Ile Arg Val Leu His Leu Leu Glu Gln Ile Arg Ala Tyr
                405                 410                 415

Cys Glu Thr Cys Trp Glu Trp Gln Glu Ala His Glu Pro Gly Met Asp
            420                 425                 430

Gln Asp Lys Asn Pro Met Pro Ala Pro Val Glu His Gln Ile Cys Pro
        435                 440                 445

Ala Val Cys Val Leu Met Lys Leu Ser Phe Asp Glu His Arg His
450                 455                 460

Ala Met Asn Glu Leu Gly Gly Leu Gln Ala Ile Ala Glu Leu Leu Gln
465                 470                 475                 480

Val Asp Cys Glu Met Tyr Gly Leu Thr Asn Asp His Tyr Ser Ile Thr
                485                 490                 495

Leu Arg Arg Tyr Ala Gly Met Ala Leu Thr Asn Leu Thr Phe Gly Asp
            500                 505                 510

Val Ala Asn Lys Ala Thr Leu Cys Ser Met Lys Gly Cys Met Arg Ala
        515                 520                 525

Leu Val Ala Gln Leu Lys Ser Glu Ser Glu Asp Leu Gln Gln Val Ile
530                 535                 540

Ala Ser Val Leu Arg Asn Leu Ser Trp Arg Ala Asp Val Asn Ser Lys
545                 550                 555                 560

Lys Thr Leu Arg Glu Val Gly Ser Val Lys Ala Leu Met Glu Cys Ala
            565                 570                 575

Leu Glu Val Lys Lys Glu Ser Thr Leu Lys Ser Val Leu Ser Ala Leu
        580                 585                 590

Trp Asn Leu Ser Ala His Cys Thr Glu Asn Lys Ala Asp Ile Cys Ala
        595                 600                 605

Val Asp Gly Ala Leu Ala Phe Leu Val Gly Thr Leu Thr Tyr Arg Ser
610                 615                 620

Gln Thr Asn Thr Leu Ala Ile Ile Glu Ser Gly Gly Gly Ile Leu Arg
625                 630                 635                 640

Asn Val Ser Ser Leu Ile Ala Thr Asn Glu Asp His Arg Gln Ile Leu
            645                 650                 655

Arg Glu Asn Asn Cys Leu Gln Thr Leu Leu Gln His Leu Lys Ser His
        660                 665                 670

Ser Leu Thr Ile Val Ser Asn Ala Cys Gly Thr Leu Trp Asn Leu Ser
        675                 680                 685

Ala Arg Asn Pro Lys Asp Gln Glu Ala Leu Trp Asp Met Gly Ala Val
        690                 695                 700

Ser Met Leu Lys Asn Leu Ile His Ser Lys His Lys Met Ile Ala Met
705                 710                 715                 720

Gly Ser Ala Ala Ala Leu Arg Asn Leu Met Ala Asn Arg Pro Ala Lys
                725                 730                 735

Tyr Lys Asp Ala Asn Ile Met Ser Pro Gly Ser Ser Leu Pro Ser Leu
            740                 745                 750

His Val Arg Lys Gln Lys Ala Leu Glu Ala Glu Leu Asp Ala Gln His
        755                 760                 765

Leu Ser Glu Thr Phe Asp Asn Ile Asp Asn Leu Ser Pro Lys Ala Ser
        770                 775                 780

His Arg Ser Lys Gln Arg His Lys Gln Ser Leu Tyr Gly Asp Tyr Val
785                 790                 795                 800

Phe Asp Thr Asn Arg His Asp Asp Asn Arg Ser Asp Asn Phe Asn Thr
                805                 810                 815

Gly Asn Met Thr Val Leu Ser Pro Tyr Leu Asn Thr Thr Val Leu Pro
```

-continued

```
                820                 825                 830
Ser Ser Ser Ser Ser Arg Gly Ser Leu Asp Ser Ser Arg Ser Glu Lys
            835                 840                 845
Asp Arg Ser Leu Glu Arg Glu Arg Gly Ile Gly Leu Gly Asn Tyr His
        850                 855                 860
Pro Ala Thr Glu Asn Pro Gly Thr Ser Ser Lys Arg Gly Leu Gln Ile
865                 870                 875                 880
Ser Thr Thr Ala Ala Gln Ile Ala Lys Val Met Glu Glu Val Ser Ala
                885                 890                 895
Ile His Thr Ser Gln Glu Asp Arg Ser Ser Gly Ser Thr Thr Glu Leu
            900                 905                 910
His Cys Val Thr Asp Glu Arg Asn Ala Leu Arg Arg Ser Ser Ala Ala
        915                 920                 925
His Thr His Ser Asn Thr Tyr Asn Phe Thr Lys Ser Glu Asn Ser Asn
            930                 935                 940
Arg Thr Cys Ser Met Pro Tyr Ala Lys Leu Glu Tyr Lys Arg Ser Ser
945                 950                 955                 960
Asn Asp Ser Leu Asn Ser Val Ser Ser Asp Gly Tyr Gly Lys Arg
                965                 970                 975
Gly Gln Met Lys Pro Ser Ile Glu Ser Tyr Ser Glu Asp Glu Ser
            980                 985                 990
Lys Phe Cys Ser Tyr Gly Gln Tyr Pro Ala Asp Leu Ala His Lys Ile
        995                 1000                1005
His Ser Ala Asn His Met Asp Asp Asn Asp Gly Glu Leu Asp Thr Pro
            1010                1015                1020
Ile Asn Tyr Ser Leu Lys Tyr Ser Asp Glu Gln Leu Asn Ser Gly Arg
1025                1030                1035                1040
Gln Ser Pro Ser Gln Asn Glu Arg Trp Ala Arg Pro Lys His Ile Ile
                1045                1050                1055
Glu Asp Glu Ile Lys Gln Ser Glu Gln Arg Gln Ser Arg Asn Gln Ser
            1060                1065                1070
Thr Thr Tyr Pro Val Tyr Thr Glu Ser Thr Asp Asp Lys His Leu Lys
        1075                1080                1085
Phe Gln Pro His Phe Gly Gln Gln Glu Cys Val Ser Pro Tyr Arg Ser
        1090                1095                1100
Arg Gly Ala Asn Gly Ser Glu Thr Asn Arg Val Gly Ser Asn His Gly
1105                1110                1115                1120
Ile Asn Gln Asn Val Ser Gln Ser Leu Cys Gln Glu Asp Asp Tyr Glu
                1125                1130                1135
Asp Asp Lys Pro Thr Asn Tyr Ser Glu Arg Tyr Ser Glu Glu Glu Gln
            1140                1145                1150
His Glu Glu Glu Arg Pro Thr Asn Tyr Ser Ile Lys Tyr Asn Glu
            1155                1160                1165
Glu Lys Arg His Val Asp Gln Pro Ile Asp Tyr Ser Leu Lys Tyr Ala
        1170                1175                1180
Thr Asp Ile Pro Ser Ser Gln Lys Gln Ser Phe Ser Phe Ser Lys Ser
1185                1190                1195                1200
Ser Ser Gly Gln Ser Ser Lys Thr Glu His Met Ser Ser Ser Ser Glu
                1205                1210                1215
Asn Thr Ser Thr Pro Ser Ser Asn Ala Lys Arg Gln Asn Gln Leu His
            1220                1225                1230
Pro Ser Ser Ala Gln Ser Arg Ser Gly Gln Pro Gln Lys Ala Ala Thr
            1235                1240                1245
```

```
Cys Lys Val Ser Ser Ile Asn Gln Glu Thr Ile Gln Thr Tyr Cys Val
        1250                1255                1260

Glu Asp Thr Pro Ile Cys Phe Ser Arg Cys Ser Ser Leu Ser Ser Leu
1265                1270                1275                1280

Ser Ser Ala Glu Asp Glu Ile Gly Cys Asn Gln Thr Thr Gln Glu Ala
            1285                1290                1295

Asp Ser Ala Asn Thr Leu Gln Ile Ala Glu Ile Lys Glu Lys Ile Gly
            1300                1305                1310

Thr Arg Ser Ala Glu Asp Pro Val Ser Glu Val Pro Ala Val Ser Gln
            1315                1320                1325

His Pro Arg Thr Lys Ser Ser Arg Leu Gln Gly Ser Ser Leu Ser Ser
            1330                1335                1340

Glu Ser Ala Arg His Lys Ala Val Glu Phe Ser Ser Gly Ala Lys Ser
1345                1350                1355                1360

Pro Ser Lys Ser Gly Ala Gln Thr Pro Lys Ser Pro Pro Glu His Tyr
            1365                1370                1375

Val Gln Glu Thr Pro Leu Met Phe Ser Arg Cys Thr Ser Val Ser Ser
            1380                1385                1390

Leu Asp Ser Phe Glu Ser Arg Ser Ile Ala Ser Ser Val Gln Ser Glu
            1395                1400                1405

Pro Cys Ser Gly Met Val Ser Gly Ile Ile Ser Pro Ser Asp Leu Pro
        1410                1415                1420

Asp Ser Pro Gly Gln Thr Met Pro Pro Ser Arg Ser Lys Thr Pro Pro
1425                1430                1435                1440

Pro Pro Pro Gln Thr Ala Gln Thr Lys Arg Glu Val Pro Lys Asn Lys
            1445                1450                1455

Ala Pro Thr Ala Glu Lys Arg Glu Ser Gly Pro Lys Gln Ala Ala Val
            1460                1465                1470

Asn Ala Ala Val Gln Arg Val Gln Val Leu Pro Asp Ala Asp Thr Leu
            1475                1480                1485

Leu His Phe Ala Thr Glu Ser Thr Pro Asp Gly Phe Ser Cys Ser Ser
            1490                1495                1500

Ser Leu Ser Ala Leu Ser Leu Asp Glu Pro Phe Ile Gln Lys Asp Val
1505                1510                1515                1520

Glu Leu Arg Ile Met Pro Pro Val Gln Glu Asn Asp Asn Gly Asn Glu
            1525                1530                1535

Thr Glu Ser Glu Gln Pro Lys Glu Ser Asn Glu Asn Gln Glu Lys Glu
            1540                1545                1550

Ala Glu Lys Thr Ile Asp Ser Glu Lys Asp Leu Leu Asp Asp Ser Asp
            1555                1560                1565

Asp Asp Asp Ile Glu Ile Leu Glu Glu Cys Ile Ile Ser Ala Met Pro
            1570                1575                1580

Thr Lys Ser Ser Arg Lys Ala Lys Lys Pro Ala Gln Thr Ala Ser Lys
1585                1590                1595                1600

Leu Pro Pro Pro Val Ala Arg Lys Pro Ser Gln Leu Pro Val Tyr Lys
            1605                1610                1615

Leu Leu Pro Ser Gln Asn Arg Leu Gln Pro Gln Lys His Val Ser Phe
            1620                1625                1630

Thr Pro Gly Asp Asp Met Pro Arg Val Tyr Cys Val Glu Gly Thr Pro
            1635                1640                1645

Ile Asn Phe Ser Thr Ala Thr Ser Leu Ser Asp Leu Thr Ile Glu Ser
            1650                1655                1660
```

```
Pro Pro Asn Glu Leu Ala Ala Gly Glu Gly Val Arg Gly Gly Ala Gln
1665                1670                1675                1680

Ser Gly Glu Phe Glu Lys Arg Asp Thr Ile Pro Thr Glu Gly Arg Ser
            1685                1690                1695

Thr Asp Glu Ala Gln Gly Gly Lys Thr Ser Val Thr Ile Pro Glu
        1700                1705                1710

Leu Asp Asp Asn Lys Ala Glu Glu Gly Asp Ile Leu Ala Glu Cys Ile
    1715                1720                1725

Asn Ser Ala Met Pro Lys Gly Lys Ser His Lys Pro Phe Arg Val Lys
    1730                1735                1740

Lys Ile Met Asp Gln Val Gln Gln Ala Ser Ala Ser Ser Ser Ala Pro
1745                1750                1755                1760

Asn Lys Asn Gln Leu Asp Gly Lys Lys Lys Pro Thr Ser Pro Val
            1765                1770                1775

Lys Pro Ile Pro Gln Asn Thr Glu Tyr Arg Thr Arg Val Arg Lys Asn
            1780                1785                1790

Ala Asp Ser Lys Asn Asn Leu Asn Ala Glu Arg Val Phe Ser Asp Asn
            1795                1800                1805

Lys Asp Ser Lys Lys Gln Asn Leu Lys Asn Asn Ser Lys Val Phe Asn
    1810                1815                1820

Asp Lys Leu Pro Asn Asn Glu Asp Arg Val Arg Gly Ser Phe Ala Phe
1825                1830                1835                1840

Asp Ser Pro His His Tyr Thr Pro Ile Glu Gly Thr Pro Tyr Cys Phe
            1845                1850                1855

Ser Arg Asn Asp Ser Leu Ser Ser Leu Asp Phe Asp Asp Asp Val
            1860                1865                1870

Asp Leu Ser Arg Glu Lys Ala Glu Leu Arg Lys Ala Lys Glu Asn Lys
            1875                1880                1885

Glu Ser Glu Ala Lys Val Thr Ser His Thr Glu Leu Thr Ser Asn Gln
            1890                1895                1900

Gln Ser Ala Asn Lys Thr Gln Ala Ile Ala Lys Gln Pro Ile Asn Arg
1905                1910                1915                1920

Gly Gln Pro Lys Pro Ile Leu Gln Lys Gln Ser Thr Phe Pro Gln Ser
            1925                1930                1935

Ser Lys Asp Ile Pro Asp Arg Gly Ala Ala Thr Asp Glu Lys Leu Gln
            1940                1945                1950

Asn Phe Ala Ile Glu Asn Thr Pro Val Cys Phe Ser His Asn Ser Ser
            1955                1960                1965

Leu Ser Ser Leu Ser Asp Ile Asp Gln Glu Asn Asn Asn Lys Glu Asn
            1970                1975                1980

Glu Pro Ile Lys Glu Thr Glu Pro Pro Asp Ser Gln Gly Glu Pro Ser
1985                1990                1995                2000

Lys Pro Gln Ala Ser Gly Tyr Ala Pro Lys Ser Phe His Val Glu Asp
            2005                2010                2015

Thr Pro Val Cys Phe Ser Arg Asn Ser Ser Leu Ser Ser Leu Ser Ile
            2020                2025                2030

Asp Ser Glu Asp Asp Leu Leu Gln Glu Cys Ile Ser Ser Ala Met Pro
            2035                2040                2045

Lys Lys Lys Lys Pro Ser Arg Leu Lys Gly Asp Asn Glu Lys His Ser
            2050                2055                2060

Pro Arg Asn Met Gly Gly Ile Leu Gly Glu Asp Leu Thr Leu Asp Leu
2065                2070                2075                2080

Lys Asp Ile Gln Arg Pro Asp Ser Glu His Gly Leu Ser Pro Asp Ser
```

```
            2085                2090                2095

Glu Asn Phe Asp Trp Lys Ala Ile Gln Glu Gly Ala Asn Ser Ile Val
            2100                2105                2110

Ser Ser Leu His Gln Ala Ala Ala Ala Cys Leu Ser Arg Gln Ala
            2115                2120                2125

Ser Ser Asp Ser Asp Ser Ile Leu Ser Leu Lys Ser Gly Ile Ser Leu
            2130                2135                2140

Gly Ser Pro Phe His Leu Thr Pro Asp Gln Glu Glu Lys Pro Phe Thr
2145                2150                2155                2160

Ser Asn Lys Gly Pro Arg Ile Leu Lys Pro Gly Glu Lys Ser Thr Leu
            2165                2170                2175

Glu Thr Lys Lys Ile Glu Ser Glu Ser Lys Gly Ile Lys Gly Gly Lys
            2180                2185                2190

Lys Val Tyr Lys Ser Leu Ile Thr Gly Lys Val Arg Ser Asn Ser Glu
            2195                2200                2205

Ile Ser Gly Gln Met Lys Gln Pro Leu Gln Ala Asn Met Pro Ser Ile
            2210                2215                2220

Ser Arg Gly Arg Thr Met Ile His Ile Pro Gly Val Arg Asn Ser Ser
2225                2230                2235                2240

Ser Ser Thr Ser Pro Val Ser Lys Lys Gly Pro Pro Leu Lys Thr Pro
            2245                2250                2255

Ala Ser Lys Ser Pro Ser Glu Gly Gln Thr Ala Thr Thr Ser Pro Arg
            2260                2265                2270

Gly Ala Lys Pro Ser Val Lys Ser Glu Leu Ser Pro Val Ala Arg Gln
            2275                2280                2285

Thr Ser Gln Ile Gly Gly Ser Ser Lys Ala Pro Ser Arg Ser Gly Ser
            2290                2295                2300

Arg Asp Ser Thr Pro Ser Arg Pro Ala Gln Gln Pro Leu Ser Arg Pro
2305                2310                2315                2320

Ile Gln Ser Pro Gly Arg Asn Ser Ile Ser Pro Gly Arg Asn Gly Ile
            2325                2330                2335

Ser Pro Pro Asn Lys Leu Ser Gln Leu Pro Arg Thr Ser Ser Pro Ser
            2340                2345                2350

Thr Ala Ser Thr Lys Ser Ser Gly Ser Gly Lys Met Ser Tyr Thr Ser
            2355                2360                2365

Pro Gly Arg Gln Met Ser Gln Gln Asn Leu Thr Lys Gln Thr Gly Leu
            2370                2375                2380

Ser Lys Asn Ala Ser Ser Ile Pro Arg Ser Glu Ser Ala Ser Lys Gly
2385                2390                2395                2400

Leu Asn Gln Met Asn Asn Gly Asn Gly Ala Asn Lys Lys Val Glu Leu
            2405                2410                2415

Ser Arg Met Ser Ser Thr Lys Ser Ser Gly Ser Glu Ser Asp Arg Ser
            2420                2425                2430

Glu Arg Pro Val Leu Val Arg Gln Ser Thr Phe Ile Lys Glu Ala Pro
            2435                2440                2445

Ser Pro Thr Leu Arg Arg Lys Leu Glu Glu Ser Ala Ser Phe Glu Ser
            2450                2455                2460

Leu Ser Pro Ser Ser Arg Pro Ala Ser Pro Thr Arg Ser Gln Ala Gln
2465                2470                2475                2480

Thr Pro Val Leu Ser Pro Ser Leu Pro Asp Met Ser Leu Ser Thr His
            2485                2490                2495

Ser Ser Val Gln Ala Gly Gly Trp Arg Lys Leu Pro Pro Asn Leu Ser
            2500                2505                2510
```

-continued

Pro Thr Ile Glu Tyr Asn Asp Gly Arg Pro Ala Lys Arg His Asp Ile
        2515                2520                2525

Ala Arg Ser His Ser Glu Ser Pro Ser Arg Leu Pro Ile Asn Arg Ser
    2530                2535                2540

Gly Thr Trp Lys Arg Glu His Ser Lys His Ser Ser Leu Pro Arg
2545                2550                2555                2560

Val Ser Thr Trp Arg Arg Thr Gly Ser Ser Ser Ile Leu Ser Ala
            2565                2570                2575

Ser Ser Glu Ser Ser Glu Lys Ala Lys Ser Glu Asp Glu Lys His Val
        2580                2585                2590

Asn Ser Ile Ser Gly Thr Lys Gln Ser Lys Glu Asn Gln Val Ser Ala
        2595                2600                2605

Lys Gly Thr Trp Arg Lys Ile Lys Glu Asn Glu Phe Ser Pro Thr Asn
    2610                2615                2620

Ser Thr Ser Gln Thr Val Ser Ser Gly Ala Thr Asn Gly Ala Glu Ser
2625                2630                2635                2640

Lys Thr Leu Ile Tyr Gln Met Ala Pro Ala Val Ser Lys Thr Glu Asp
            2645                2650                2655

Val Trp Val Arg Ile Glu Asp Cys Pro Ile Asn Asn Pro Arg Ser Gly
        2660                2665                2670

Arg Ser Pro Thr Gly Asn Thr Pro Val Ile Asp Ser Val Ser Glu
    2675                2680                2685

Lys Ala Asn Pro Asn Ile Lys Asp Ser Lys Asp Asn Gln Ala Lys Gln
    2690                2695                2700

Asn Val Gly Asn Gly Ser Val Pro Met Arg Thr Val Gly Leu Glu Asn
2705                2710                2715                2720

Arg Leu Asn Ser Phe Ile Gln Val Asp Ala Pro Asp Gln Lys Gly Thr
            2725                2730                2735

Glu Ile Lys Pro Gly Gln Asn Asn Pro Val Pro Val Ser Glu Thr Asn
        2740                2745                2750

Glu Ser Ser Ile Val Glu Arg Thr Pro Phe Ser Ser Ser Ser Ser Ser
        2755                2760                2765

Lys His Ser Ser Pro Ser Gly Thr Val Ala Ala Arg Val Thr Pro Phe
    2770                2775                2780

Asn Tyr Asn Pro Ser Pro Arg Lys Ser Ser Ala Asp Ser Thr Ser Ala
2785                2790                2795                2800

Arg Pro Ser Gln Ile Pro Thr Pro Val Asn Asn Asn Thr Lys Lys Arg
            2805                2810                2815

Asp Ser Lys Thr Asp Ser Thr Glu Ser Ser Gly Thr Gln Ser Pro Lys
        2820                2825                2830

Arg His Ser Gly Ser Tyr Leu Val Thr Ser Val
    2835                2840

<210> SEQ ID NO 66
<211> LENGTH: 859
<212> TYPE: DNA
<213> ORGANISM: Artificial Sequence
<220> FEATURE:
<223> OTHER INFORMATION: Synthetic Construct

<400> SEQUENCE: 66
tgtgctcgga gctcgatttt cctaggcggc ggccgcggcg gcggaggcag cagcggcggc    60
ggcagtggcg gcggcgaagg tggcggcggc tcggccagta ctcccggccc cgccatttc   120 ggactgggag cgagcgcggc gcaggcactg aaggcggcgg cggggccaga ggctcagcgg   180

```
ctcccaggcc tgctgaaaat gactgaatat aaacttgtgg tagttggagc tggtggcgta    240
ggcaagagtg ccttgacgat acagctaatt cagaatcatt ttgtggacga atatgatcca    300
acaatagagg attcctacag gaagcaagta gtaattgatg agaaacctg tctcttggat     360 attctcgaca cagcaggtca agaggagtac agtgcaatga gggaccagta catgaggact    420
ggggagggct ttctttgtgt atttgccata aataatacta aatcatttga agatattcac    480
cattatagag aacaaattaa aagagttaag gactctgaag atgtacctat ggtcctagta    540
ggaaataaat gtgatttgcc ttctagaaca gtagacacaa acaggctca ggacttagca     600 agaagttatg gaattccttt tattgaaaca tcagcaaaga caagacagag agtggaggat    660
gctttttata cattggtgag agagatccga caatacagat tgaaaaaaat cagcaaagaa    720
gaaaagactc ctggctgtgt gaaaattaaa aaatgcatta taatgtaatc tgggtgttga    780
tgatgccttc tatacattag ttcgagaaat tcgaaaacat aaagaaaaga tgagcaaaga    840
tggtaaaaag aagaaaaag                                                859

<210> SEQ ID NO 67
<211> LENGTH: 9595
<212> TYPE: DNA
<213> ORGANISM: Artificial Sequence
<220> FEATURE:
<223> OTHER INFORMATION: Synthetic Construct

<400> SEQUENCE: 67
gttataagat ggcggcgctg agcggtggcg gtggtggcgg cgcggagccg ggccaggctc     60
tgttcaacgg ggacatggag cccgaggccg gcgccggcgc cggcgccgcg gcctcttcgg    120
ctgcggaccc tgccattccg gaggaggtgt ggaatatcaa acaaatgatt aagttgacac    180
aggaacatat agaggcccta ttggacaaat ttggtgggga gcataatcca ccatcaatat    240
atctggaggc ctatgaagaa tacaccagca agctagatgc actccaacaa agagaacaac    300
agttattgga atctctgggg aacggaactg attttttctgt ttctagctct gcatcaatgg    360
ataccgttac atcttcttcc tcttctagcc tttcagtgct accttcatct ctttcagttt    420
ttcaaaatcc cacagatgtg gcacggagca acccccaagtc accacaaaaa cctatcgtta    480
gagtcttcct gcccaacaaa cagaggacag tggtacctgc aaggtgtgga gttacagtcc    540
gagacagtct aaagaaagca ctgatgatga gaggtctaat cccagagtgc tgtgctgttt    600
acagaattca ggatggagag aagaaaccaa ttggttggga cactgatatt tcctggctta    660
ctggagaaga attgcatgtg gaagtgttgg agaatgttcc acttacaaca cacaactttg    720
tacgaaaaac gttttcacc ttagcatttt gtgactttg tcgaaagctg cttttccagg      780
gtttccgctg tcaaacatgt ggttataaat ttcaccagcg ttgtagtaca gaagttccac    840
tgatgtgtgt taattatgac caacttgatt tgctgtttgt ctccaagttc tttgaacacc    900
acccaatacc acaggaagag gcgtccttag cagagactgc cctaacatct ggatcatccc    960
cttccgcacc cgcctcggac tctattgggc cccaaattct caccagtccg tctccttcaa   1020
aatccattcc aattccacag cccttccgac cagcagatga agatcatcga aatcaatttg   1080
ggcaacgaga ccgatcctca tcagctccca atgtgcatat aaacacaata gaacctgtca   1140
atattgatga cttgattaga gaccaaggat tcgtggtga tggagcccct tgaaccagc     1200 tgatgcgctg tcttcggaaa taccaatccc ggactcccag tccctcca cattctgtcc    1260 ccagtgaaat agtgtttgat tttgagcctg gcccagtgtt cagaggatca accacaggtt   1320
```

```
tgtctgctac cccccctgcc tcattacctg gctcactaac taacgtgaaa gccttacaga   1380
aatctccagg acctcagcga gaaaggaagt catcttcatc ctcagaagac aggaatcgaa   1440
tgaaaacact tggtagacgg gactcgagtg atgattggga gattcctgat gggcagatta   1500
cagtgggaca agaattgga tctggatcat ttggaacagt ctacaaggga agtggcatg    1560 gtgatgtggc agtgaaaatg ttgaatgtga cagcacctac acctcagcag ttacaagcct   1620
tcaaaaatga gtaggagta ctcaggaaaa cacgacatgt gaatatccta ctcttcatgg    1680
gctattccac aaagccacaa ctggctattg ttacccagtg gtgtgagggc tccagcttgt   1740
atcaccatct ccatatcatt gagaccaaat ttgagatgat caaacttata gatattgcac   1800
gacagactgc acagggcatg gattacttac acgccaagtc aatcatccac agagacctca   1860
agagtaataa tatatttctt catgaagacc tcacagtaaa aataggtgat tttggtctag   1920
ctacagtgaa atctcgatgg agtgggtccc atcagtttga acagttgtct ggatccattt   1980
tgtggatggc accagaagtc atcagaatgc aagataaaaa tccatacagc tttcagtcag   2040
atgtatatgc atttggaatt gttctgtatg aattgatgac tggacagtta ccttattcaa   2100
acatcaacaa cagggaccag ataattttta tggtgggacg aggatacctg tctccagatc   2160
tcagtaaggt acggagtaac tgtccaaaag ccatgaagag attaatggca gagtgcctca   2220 aaagaaaag agatgagaga ccactctttc cccaaattct cgcctctatt gagctgctgg    2280
cccgctcatt gccaaaaatt caccgcagtg catcagaacc ctccttgaat cgggctggtt   2340
tccaaacaga ggattttagt ctatatgctt gtgcttctcc aaaaacaccc atccaggcag   2400
ggggatatgg agaatttgca gccttcaagt agccaccatc atggcagcat ctgctcttat   2460
ttcttaagtc ttgtgttcgt acaatttgtt aacatcaaaa cacagttctg ttcctcaaat   2520 cttttttaa agatacaaaa tttccaatgc ataagctgat gtggaacaga atggaatttc   2580
ccatccaaca aaagaggaaa gaatgtttta ggaaccagaa ttctctgctg ccagtgtttc   2640
ttcaacaaaa ataccacgag catacaagtc tgcccagtcc caggaagaaa gaggagagac   2700
cctgaattct gacctttga tggtcaggca tgatggaaag aaactgctgc tacagcttgg    2760
gagatttgct atggaaagtc tgccagtcaa ctttgcccctt ctaaccacca gatcaatttg   2820
tggctgatca tctgatgggg cagtttcaat caccaagcat cgttctcttt cctgttctgg   2880
aattttgttt tggagctctt tcccctagtg accaccagtt agtttctgag ggatggaaca   2940
aaaatgcagc ttgcccttc tatgtggtgc gtgttcaggc cttgacagat tttatcaaaa    3000
ggaaactatt ttatttaaat ggaggctgag tggtgagtag atgtgtcttg gtatggagga   3060
aaagggcatg ctgcatcttc ttcctgacct ccggggtctc tggccttttg tttccttgct   3120
cactgagggg tctgtctaac caagcaggct agatagtgct ggcacacatt gccttctttc   3180
tcattgggtc cagcaatgaa gataagtgtt tgggtttttt tttttcctc cacaatgtag    3240 caaattctca ggaaatacag tttatatctt cctcctatgc tcttccagtc accaactact   3300
tatgcggcta ctttgtccag ggcacaaaat gccgtggcag tatctaacta aaccccaca    3360 aaactgctta ataacagttt tgaatgtgag aaatttagat aatttaaata taaggtacag   3420
gttttaattt ctgagtttct tcttttctat ttttattaaa aagaaaataa ttttcagatt   3480
taattgaatt ggaaaaaaac aatacttccc accagaatta tatatcctga aaattgtatt   3540
tttgttatat aaacaacttt taagaaagat cattatcctt ttctctacct aaatatgagg   3600
agtcttagca taatgacaaa tatttataat ttttcaatta atggtacttg ctggatccac   3660
actaacatct ttgctaataa tctcattgtt tcttccaact gattcctaac actatatccc   3720
```

```
acatcttctt tctagtcttt tatctagaat atgcaaccta aaataaaaat ggtggcgtct    3780
ccattcattc tccttcttcc ttttttccca agcctggtct tcaaaaggtt gggcaatttg    3840
gcagctgaat tcccagacag agaatagagc aattttaggg atattaggac tgagggaggg    3900
tgtgggaaag ctgtcatcag ttgtttttat agaaagaact ggcattcatt aagaacctaa    3960
atcttatctt tgcacaaatg gaaaatataa cctagttata gcttcctttg gcctttatta    4020
aagggtaata tcaatcacag tcatagcaaa gaaagcggat gtattaatgg caaattaatg    4080
gaaaacctcc cttatcagga atctagactc agaatttagg aacacaaatc aaatcagacc    4140
aaccaagcta tagccaagga cttgaaagaa attaaacaag acccagaata aatcaaggaa    4200
ttagaaattg ttatttaaaa atttcagatt gtaactccag ccctgctgt ctatattgca     4260 gccactaaaa gctcactacc attagatttt tgctaacata catgtattca gaagaaagcc    4320
tattgaaatt ttcattgtct tgtaaaaggt tgtcctagta aaatggaaaa gatccttaag    4380
ttattaatca gtttgaaaag caaatttgtt tttaagtttt acatcagcag ggcagtgtct    4440
tacaaaattc agaaattgca aaggtggaaa taattcacgc tgatttgaag aacatcttct    4500
gtgcaataat actgcctctc ttgaaaagca ttggctgttt tttctttta aatatatctc     4560 tagatgcttt taaatgtggc tgtgttccct ttaccaagat tggcttcaag tttccgcagg    4620
tagagagacc tgggcttgaa caagaggatg tgtttcatgt cctgctgagg aggtagaaca    4680
tgtgcagcct gggtccggga ctgcctccgt ggggcagggg caggggcggt accattaggg    4740
aggaagctta gcatttcagt ttcttaaaca atattcaggg tgatacactt tttcttccct    4800
tgcattttag aataggctgg tatctcattt gaacgggga gcagacttga tctcaaatga     4860
agctgtgccc aggagccagg cttagcatat tgagattttt atagatacct taaaaaataa    4920
aatatttaaa cctctctttt cttccttttt ctatgaaata ggtttttct ctagtttaca     4980 aatgacatga aaataggttt tatttgtgtt ttatctgctt tattttttga tgcttagaca    5040
acagttagac ttactgagct cctaaaaaaa cgaggaagaa gtccttattt gtgaaaagca    5100
ctttatgagt aattgtatag acagtatgtg gctgcgtcac tgatcatctt gtaagggtgt    5160
aacagtcttg tctgtaaagt ggctgcagtg ccttctgtag tgtgttttat ttttggtagg    5220
gagaggtgaa gccttctgaa aaatttgaga gcaactacag aggattgttt gtaactgtgt    5280
agtattcctg atggacttt ttcatcgtta gagtcaagga cctagacttt tgccactgaa     5340
ataatattga ccaaaaaaat agtttataaa agggatttgt gaatagaaaa ttcagtgtga    5400
tcatttgttg ttaatgtgca ccttaaaaga agattctgtc tagctgtcaa attctggttc    5460
ccgaatatct caccctgat tgtatttgag atctagtagg gcatactggg gcattttaga    5520
agataaaatc ccatacaaat gatatatgct atatttatgt tggtgttgga gaagaaagag    5580
cagtatataa agaaataatt caagactgca gcactgtcaa cctgaaactt tgtaaatatt    5640
tcctagcttc tggtttggtg cggtgacagc actttcatca caggatgtta ccttgtattc    5700
accaggcgga gtgcgagctg ctgcacatcc tcctcagatc tcacctgtcc ccactgtaca    5760
tccacccgcc agctgcttgc aaacctcatc tctagcttta gttcgaaacc acattgcagg    5820
gttcaggtga cctctacaaa aaactacctc ttcagaatga ggtaatgaat agttatttat    5880
tttaaaatat gaaagtcag gagctctaga acatgacgat gatttaagat tttaactttt     5940
ttgtgtactt gtatttgagc actctcattt tgtcctaaag gcattatac atttaagcag     6000 taatactgta aaaaaatgtg ttgctcggaa tatctgaatg ttgttgaaag tggtgccaga    6060
```

```
accggtttag gggtacgttt cagaatctta accttgagtc aattgcatga aattaaatag    6120
ctgtggtatc acttcactaa cagtgatgta atttttaattt tcagtaggct tggcatgaca    6180
gtacatcctc ataatgagtt tgctgcagct ttgtcacatg cacaggcatt catagaaaga    6240
ccacccagct aagagggtag aatgattact ctttttgcaa gattctcttc tttgtccaag    6300
ttggcattgt tagtgctagg aataccagca ccttgagacg agcagattcc aaccattagg    6360
ctataaacac catagccaga gatggaaggt ttactgtgag tatgaacagc aaatagctta    6420
caggtcatga gttgaaatgg tgtaggtgag gctctagaaa ataccttga caatttgcca     6480
aatgatctta ctgtgccttc atgatgcaat aaaaaagcta acattttagc agaaatcagt    6540
gatttgtgaa gagagcagcc actctggttt aactcagctg tgttaataat ttttagagtg    6600
caatttagac tgcataggta aatgcactaa agagtttata gccaaaatca catttaacaa    6660
tgagaaaaca cacaggtaaa ttttcagtga acaaaattat tttttaaag cacataatcc     6720
ctagtatagt cagatatatt tatcacatag agcaactagg ttgcaaatat agttcagtga    6780
catttctaga gaaactttt ctactcccat aggctcttca aagcatggaa cttttataca     6840
acagaaatgt tgacagaaat tgctgtagtt tagggttgaa gtactgtatg atgggcagca    6900
atcatgtatt aacttagaag gggaaattga aatataggac cgaatttggt tttatcagtt    6960
tccagagtac tgctgccaac ctagacactg attttttcaga gtttgaaatg taaatttctt    7020
cccgggactt gattgcacat gaagctggac tgcgttagtc atcctgtccc aaagcgctgt    7080
gggggccagg gtggaggtct caaggcatcc tttatgacct ggccattgga tgtaaaagaa    7140
aacatattcc atgctgtggt tcttgtatct tgtttcattc ctcaccattg aaagagaaag    7200
tccatgtatt gtctccagca catccttgaa atgttatact gggatggatt actgatgccc    7260
atcggtagtt gagcccccaga agagggtagt agcatctctg cctcaggtga tgatttgtag    7320
cttggccaga ggagagcgga gtcaccagta tatctgtggt ccatgttgct agctctggta    7380
aaattaaaaa tactggtaag atgtttgttt tattagtaca ctagacagta agctctgttt    7440
tgttgttttc aaataaccta ttttcacttt tgtttgggca aagacattta aattgaaatt    7500
caattctaat ttttgttaat tgtggaaagg gtaattaaca gttcctatca ggtattttta    7560
atgtggaaaa ggacagaaac ccaactccta aaatcttaaa ttaaggtaac agtgctttaa    7620
aaaaaaaaaa tgcatggggc aattagtcgg caactcaatg agtgactaaa gtacttttat    7680
ttaacatcca caacttcaac tgttaagttt tattaattac taaatcagct ttattaaaat    7740
gttgacattt atttagctat tttgaataat tatagtgact tgacgagtgt gtatgaggac    7800
acagccaatg taagccagtg tatccatttt ttagaggtgc atttttttttt aaagaattct    7860
gtagatagaa gtgctctgaa aacaactaaa atatgtttat tcatggtagt atcaaaaaat    7920
gtttgtacaa accatctgct tctcccggcc agccgagttc attctccagc accgtgaccg    7980
ctggttctca tgtacagcac atatgcggga gagttggcag aaaatttgtg aagagatgcc    8040
gcaaaggaag ggtctgttga cgggtgggat tgggggtttt tgatgaagttg cttagtcctg    8100
gttttgtttt gaaaattact gcgttgcatt tttgtgttaa gttttttgaac ccacgtgtgt    8160
tttggtggag tatgagttgg aagtcactgc aaactagcat aaacaacaaa gctcacagag    8220
taggcacaga tgtagagaac agagaccaaa atgggtgag gtggcagtaa atctaggata     8280
gggaaaaatt aatgtgaggg tgggaaataa actgtaatta cctgaaatca aatgtaagag    8340
tgcaataagt atgctttta ttctaagctg tgaacggttc ttttaagaat cattccttcc     8400
taatacattt gtgtatgttc catagctgat taaaaccagc tatatcaaca tataatgcct    8460
```

-continued

```
tttttattcat gttaatgacc aacgtaagtg gctagccttt atgtcttatt tatcttcatg    8520
ttatgttagt ttacatacag gggtgtatgt ctctgtgctg tcccttctc ctgccttcat     8580 tttaaaatgc atccatgggt cctccgtgtt tcctttggcc atgccacata tatagactca    8640
gtttggcctt catgatatcg cctgattttt gaggactgta tcacagtgat atgtatttgt   8700
ggtaatctca tttgttggtt gtacatctga tcctttcctc aacatggcaa ttgctgcctt   8760
tcctaagata ggatcataca actgatcagg ggattgaatt tgatcattca tcaacatgtg   8820
tctctgaatt ttattcagta gttgtcattg ctctttggtt tagaccaaga aaaaggaaat   8880 ccccccttt catgtattcc ttggtttgag gacatgactc ctgtaaggga gaggaaaggg    8940
agatgcttcc tgtttgaact gcagtgaatt cacggttcct gtttcaccac tccaaacctt   9000
atggcgactc acacacacat tcctcttttc tgttactgcc aaaggttcgg gtttagtaca   9060
cttcagttcc actcaagcat tgaaaaggtt ctcgtggagt ctgggcgtg cccagtgaaa    9120 agatggggac ttttttaattg tccacagacc tctctatacc tgctttgcaa aaattacaat   9180
ggagtaacta ttttttaaagc ttattttttca attcataaaa aagacattta ttttcagtca   9240
aatggatgat gtctccctct tttcccctat tctcaatgtt tgcttgaatc ttttattatt   9300 tttttaatt ctccccata cccacttcct gatactttgg ttctctttcc tgctcaggtc     9360
ccttcatttg tactttggag ttttctcat gtaaatttgt ataacagaaa atattgttca    9420
gtttggatag aaagcatgga gaataaaaa agatagctga aattcagatt gaagaaattt    9480
atttctgtgt aaagttattt aaaaactgta ttatataaa ggcaaaaaa gttctatgta     9540 cttgatgtga atatgcgaat actgctataa taaagattga ctgcatggag aagtc         9595
```

<210> SEQ ID NO 68
<211> LENGTH: 3267
<212> TYPE: DNA
<213> ORGANISM: Artificial Sequence
<220> FEATURE:
<223> OTHER INFORMATION: Synthetic Construct

<400> SEQUENCE: 68

```
aagtcccatc agtcctgggg atcggaccag tggactttct cttaagattt cctctttcat     60
tcttaagaat agaagtgtta ttatttttttt taatgccctg gctatgtgag tttgaatcga   120
agcaacttta aacctagag caactaaact ctaagtgcag cgggtgcgat gcgtcagtag    180
ggtgagcaca taaaaaatcc atgtcttgca cctgtatttt agcgtactat gcagggtatt   240
tgaagtatac catacaactg ttttgaaaat ccagcgtgga caatggctac tcaagctgat   300
ttgatggagt tggacatggc catggaacca gacagaaaag cggctgttag tcactggcag   360
caacagtctt acctggactc tggaatccat tctggtgcca ctaccacagc tccttctctg   420
agtggtaaag gcaatcctga ggaagaggat gtggatacct cccaagtcct gtatgagtgg   480
gaacagggat tttctcagtc cttcactcaa gaacaagtag ctgatattga tggacagtat   540
gcaatgactc gagctcagag ggtacgagct gctatgttcc ctgagacatt agatgagggc   600
atgcagatcc catctacaca gtttgatgct gctcatccca ctaatgtcca gcgtttggct   660
gaaccatcac agatgctgaa acatgcagtt gtaaacttga ttaactatca agatgatgca   720
gaacttgcca cacgtgcaat ccctgaactg acaaaactgc taaatgacga ggaccaggtg   780
gtggttaata aggctgcagt tatggtccat cagctttcta aaaaggaagc ttccagacac   840
gctatcatgc gttctcctca gatggtgtct gctattgtac gtaccatgca gaatacaaat   900
```

```
gatgtagaaa cagctcgttg taccgctggg accttgcata acctttccca tcatcgtgag    960
ggcttactgg ccatctttaa gtctggaggc attcctgccc tggtgaaaat gcttggttca   1020
ccagtggatt ctgtgttgtt ttatgccatt acaactctcc acaaccttt attacatcaa    1080
gaaggagcta aaatggcagt gcgtttagct ggtgggctgc agaaaatggt tgccttgctc   1140
aacaaaacaa atgttaaatt cttggctatt acgacagact gccttcaaat tttagcttat   1200
ggcaaccaag aaagcaagct catcatactg gctagtggtg accccaagc tttagtaaat    1260
ataatgagga cctatactta cgaaaaacta ctgtggacca aagcagagt gctgaaggtg    1320
ctatctgtct gctctagtaa taagccggct attgtagaag ctggtggaat gcaagcttta   1380
ggacttcacc tgacagatcc aagtcaacgt cttgttcaga actgtctttg gactctcagg   1440
aatctttcag atgctgcaac taaacaggaa gggatggaag gtctccttgg gactcttgtt   1500
cagcttctgg gttcagatga tataaatgtg gtcacctgtg cagctggaat tctttctaac   1560
ctcacttgca ataattataa gaacaagatg atggtctgcc aagtgggtgg tatagaggct   1620
cttgtgcgta ctgtccttcg ggctggtgac agggaagaca tcactgagcc tgccatctgt   1680
gctcttcgtc atctgaccag ccgacaccaa gaagcagaga tggcccagaa tgcagttcgc   1740
cttcactatg gactaccagt tgtggttaag ctcttcacc caccatccca ctggcctctg    1800
ataaaggcta ctgttggatt gattcgaaat cttgccctt gtcccgcaaa tcatgcacct    1860
ttgcgtgagc agggtgccat tccacgacta gttcagttgc ttgttcgtgc acatcaggat   1920
acccagcgcc gtacgtccat gggtgggaca cagcagcaat tgtggaggg ggtccgcatg    1980
gaagaaatag ttgaaggttg taccggagcc cttcacatcc tagctcggga tgttcacaac   2040
cgaattgtta tcagaggact aaataccatt ccattgtttg tgcagctgct ttattctccc   2100
attgaaaaca tccaaagagt agctgcaggg gtcctctgtg aacttgctca ggacaaggaa   2160
gctgcagaag ctattgaagc tgagggagcc acagctcctc tgacagagtt acttcactct   2220
aggaatgaag gtgtggcgac atatgcagct gctgttttgt tccgaatgtc tgaggacaag   2280
ccacaagatt acaagaaacg gctttcagtt gagctgacca gctctctctt cagaacagag   2340
ccaatggctt ggaatgagac tgctgatctt ggacttgata ttggtgccca gggagaaccc   2400
cttggatatc gccaggatga tcctagctat cgttcttttc actctggtgg atatggccag   2460
gatgccttgg gtatggaccc catgatgaaa catgagatgg gtggccacca ccctggtgct   2520
gactatccag ttgatgggct gccagatctg gggcatgccc aggacctcat ggatgggctg   2580
cctccaggtg acagcaatca gctggcctgg tttgatactg acctgtaaat catcctttag   2640
gagtaacaat acaaatggat tttgggagtg actcaagaag tgaagaatgc acaagaatgg   2700
atcacaagat ggaatttatc aaaccctagc cttgcttgtt aaattttttt tttttttttt   2760
ttaagaatat ctgtaatggt actgacttg cttgctttga agtagctctt tttttttttt    2820
tttttttttt tttgcagtaa ctgtttttta agtctctcgt agtgttaagt tatagtgaat   2880
actgctacag caatttctaa tttttaagaa ttgagtaatg gtgtagaaca ctaattcata   2940
atcactctaa ttaattgtaa tctgaataaa gtgtaacaat tgtgtagcct ttttgtataa   3000
aatagacaaa tagaaaatgg tccaattagt ttccttttta atatgcttaa aataagcagg   3060
tggatctatt tcatgttttt gatcaaaaac tatttgggat atgtatgggt agggtaaatc   3120
agtaagaggt gttatttgga accttgtttt ggacagttta ccagttgcct tttatcccaa   3180
agttgttgta acctgctgtg atacgatgct tcaagagaaa atgcggttat aaaaaatggt   3240
tcagaattaa acttttaatt cattcga                                      3267
```

<210> SEQ ID NO 69
<211> LENGTH: 10740
<212> TYPE: DNA
<213> ORGANISM: Artificial Sequence
<220> FEATURE:
<223> OTHER INFORMATION: Synthetic Construct

<400> SEQUENCE: 69

| | | | | | |
|---|---|---|---|---|---|
| gtattggtgc | agcccgccag | ggtgtcactg | gagacagaat | ggaggtgctg | ccggactcgg | 60 |
| aaatggggtc | caagggtagc | caaggatggc | tgcagcttca | tatgatcagt | tgttaaagca | 120 |
| agttgaggca | ctgaagatgg | agaactcaaa | tcttcgacaa | gagctagaag | ataattccaa | 180 |
| tcatcttaca | aaactggaaa | ctgaggcatc | taatatgaag | gaagtactta | aacaactaca | 240 |
| aggaagtatt | gaagatgaag | ctatggcttc | ttctggacag | attgatttat | tagagcgtct | 300 |
| taaagagctt | aacttagata | gcagtaattt | ccctggagta | aaactgcggt | caaaaatgtc | 360 |
| cctccgttct | tatggaagcc | gggaaggatc | tgtatcaagc | cgttctggag | agtgcagtcc | 420 |
| tgttcctatg | ggttcatttc | caagaagagg | gtttgtaaat | ggaagcagag | aaagtactgg | 480 |
| atatttagaa | gaacttgaga | agagaggtc | attgcttctt | gctgatcttg | acaaagaaga | 540 |
| aaaggaaaaa | gactggtatt | acgctcaact | tcagaatctc | actaaaagaa | tagatagtct | 600 |
| tcctttaact | gaaaattttt | ccttacaaac | agatatgacc | agaaggcaat | ggaatatga | 660 |
| agcaaggcaa | atcagagttg | cgatggaaga | acaactaggt | acctgccagg | atatggaaaa | 720 |
| acgagcacag | cgaagaatag | ccagaattca | gcaaatcgaa | aaggacatac | ttcgtatacg | 780 |
| acagcttta | cagtcccaag | caacagaagc | agagaggtca | tctcagaaca | agcatgaaac | 840 |
| cggctcacat | gatgctgagc | ggcagaatga | aggtcaagga | gtgggagaaa | tcaacatggc | 900 |
| aacttctggt | aatggtcagg | gttcaactac | acgaatggac | catgaaacag | ccagtgtttt | 960 |
| gagttctagt | agcacacact | ctgcacctcg | aaggctgaca | agtcatctgg | gaaccaaggt | 1020 |
| ggaaatggtg | tattcattgt | tgtcaatgct | tggtactcat | gataaggatg | atatgtcgcg | 1080 |
| aactttgcta | gctatgtcta | gctcccaaga | cagctgtata | tccatgcgac | agtctggatg | 1140 |
| tcttcctctc | ctcatccagc | ttttacatgg | caatgacaaa | gactctgtat | tgttgggaaa | 1200 |
| ttcccggggc | agtaaagagg | ctcgggccag | ggccagtgca | gcactccaca | acatcattca | 1260 |
| ctcacagcct | gatgacaaga | gaggcaggcg | tgaaatccga | gtccttcatc | ttttggaaca | 1320 |
| gatacgcgct | tactgtgaaa | cctgttggga | gtggcaggaa | gctcatgaac | caggcatgga | 1380 |
| ccaggacaaa | aatccaatgc | cagctcctgt | gaacatcag | atctgtcctg | ctgtgtgtgt | 1440 |
| tctaatgaaa | ctttcatttg | atgaagagca | tagacatgca | atgaatgaac | taggggact | 1500 |
| acaggccatt | gcagaattat | tgcaagtgga | ctgtgaaatg | tatgggctta | ctaatgacca | 1560 |
| ctacagtatt | acactaagac | gatatgctgg | aatggctttg | acaaacttga | cttttggaga | 1620 |
| tgtagccaac | aaggctacgc | tatgctctat | gaaaggctgc | atgagagcac | ttgtgggcca | 1680 |
| actaaaatct | gaaagtgaag | acttacagca | ggttattgcg | agtgttttga | ggaatttgtc | 1740 |
| ttggcgagca | gatgtaaata | gtaaaaagac | gttgcgagaa | gttggaagtg | tgaaagcatt | 1800 |
| gatggaatgt | gctttagaag | ttaaaaagga | atcaaccctc | aaaagcgtat | tgagtgcctt | 1860 |
| atggaatttg | tcagcacatt | gcactgagaa | taaagctgat | atatgtgctg | tagatggtgc | 1920 |
| acttgcatt | ttggttggca | ctcttactta | ccggagccag | acaaacactt | tagccattat | 1980 |
| tgaaagtgga | ggtgggatat | tacggaatgt | gtccagcttg | atagctacaa | atgaggacca | 2040 |

```
caggcaaatc ctaagagaga acaactgtct acaaacttta ttacaacact taaaatctca    2100
tagtttgaca atagtcagta atgcatgtgg aactttgtgg aatctctcag caagaaatcc    2160
taaagaccag gaagcattat gggacatggg ggcagttagc atgctcaaga acctcattca    2220
ttcaaagcac aaaatgattg ctatgggaag tgctgcagct ttaaggaatc tcatggcaaa    2280
taggcctgcg aagtacaagg atgccaatat tatgtctcct ggctcaagct tgccatctct    2340
tcatgttagg aaacaaaaag ccctagaagc agaattagat gctcagcact tatcagaaac    2400
ttttgacaat atagacaatt taagtcccaa ggcatctcat cgtagtaagc agagacacaa    2460
gcaaagtctc tatggtgatt atgtttttga caccaatcga catgatgata ataggtcaga    2520
caattttaat actggcaaca tgactgtcct ttcaccatat ttgaatacta cagtgttacc    2580
cagctcctct tcatcaagag gaagcttaga tagttctcgt tctgaaaaag atagaagttt    2640
ggagagagaa cgcggaattg gtctaggcaa ctaccatcca gcaacagaaa atccaggaac    2700
ttcttcaaag cgaggtttgc agatctccac cactgcagcc cagattgcca aagtcatgga    2760
agaagtgtca gccattcata cctctcagga agacagaagt tctgggtcta ccactgaatt    2820
acattgtgtg acagatgaga gaaatgcact tagaagaagc tctgctgccc atacacattc    2880
aaacacttac aatttcacta agtcggaaaa ttcaaatagg acatgttcta tgccttatgc    2940
caaattagaa tacaagagat cttcaaatga tagtttaaat agtgtcagta gtagtgatgg    3000
ttatggtaaa agaggtcaaa tgaaaccctc gattgaatcc tattctgaag atgatgaaag    3060
taagttttgc agttatggtc aatacccagc cgacctagcc cataaaatac atagtgcaaa    3120
tcatatggat gataatgatg agaaactaga tacaccaata aattatagtc ttaaatattc    3180
agatgagcag ttgaactctg gaaggcaaag tccttcacag aatgaaagat gggcaagacc    3240
caaacacata atagaagatg aaataaaaca aagtgagcaa agacaatcaa ggaatcaaag    3300
tacaacttat cctgtttata ctgagagcac tgatgataaa cacctcaagt tccaaccaca    3360
ttttggacag caggaatgtg tttctccata caggtcacgg ggagccaatg gttcagaaac    3420
aaatcgagtg ggttctaatc atggaattaa tcaaaatgta agccagtctt tgtgtcaaga    3480
agatgactat gaagatgata gcctaccaa ttatagtgaa cgttactctg aagaagaaca    3540
gcatgaagaa gaagagagac caacaaatta tagcataaaa tataatgaag agaaacgtca    3600
tgtggatcag cctattgatt atagtttaaa atatgccaca gatattcctt catcacagaa    3660
acagtcattt tcattctcaa agagttcatc tggacaaagc agtaaaaccg aacatatgtc    3720
ttcaagcagt gagaatacgt ccacaccttc atctaatgcc aagaggcaga atcagctcca    3780
tccaagttct gcacagagta gaagtggtca gcctcaaaag gctgccactt gcaaagtttc    3840
ttctattaac caagaaacaa tacagactta ttgtgtagaa gatactccaa tatgtttttc    3900
aagatgtagt tcattatcat ctttgtcatc agctgaagat gaaataggat gtaatcagac    3960
gacacaggaa gcagattctg ctaatacct gcaaatagca gaaataaaag aaaagattgg    4020
aactaggtca gctgaagatc ctgtgagcga agttccagca gtgtcacagc ccctagaac    4080 caaatccagc agactgcagg gttctagttt atcttcagaa tcagccaggc acaaagctgt    4140
tgaattttct tcaggagcga aatctccctc caaaagtggt gctcagacac ccaaaagtcc    4200
acctgaacac tatgttcagg acccccact catgtttagc agatgtactt ctgtcagttc    4260
acttgatagt tttgagagtc gttcgattgc cagctccgtt cagagtgaac catgcagtgg    4320
aatggtaagt ggcattataa gccccagtga tcttccagat agccctgac aaaccatgcc    4380 accaagcaga agtaaaacac ctccaccacc tcctcaaaca gctcaaacca agcgagaagt    4440
```

```
acctaaaaat aaagcaccta ctgctgaaaa gagagagagt ggacctaagc aagctgcagt    4500
aaatgctgca gttcagaggg tccaggttct tccagatgct gatactttat tacattttgc    4560
cacggaaagt actccagatg gattttcttg ttcatccagc ctgagtgctc tgagcctcga    4620
tgagccattt atacagaaag atgtggaatt aagaataatg cctccagttc aggaaaatga    4680
caatgggaat gaaacagaat cagagcagcc taaagaatca aatgaaaacc aagagaaaga    4740
ggcagaaaaa actattgatt ctgaaaagga cctattagat gattcagatg atgatgatat    4800
tgaaatacta gaagaatgta ttatttctgc catgccaaca aagtcatcac gtaaagcaaa    4860
aaagccagcc cagactgctt caaaattacc tccacctgtg gcaaggaaac caagtcagct    4920
gcctgtgtac aaacttctac catcacaaaa caggttgcaa ccccaaaagc atgttagttt    4980
tacaccgggg gatgatatgc cacgggtgta ttgtgttgaa gggacaccta taaacttttc    5040
cacagctaca tctctaagtg atctaacaat cgaatcccct ccaaatgagt tagctgctgg    5100
agaaggagtt agaggagggg cacagtcagg tgaatttgaa aaacgagata ccattcctac    5160
agaaggcaga agtacagatg aggctcaagg aggaaaaacc tcatctgtaa ccatacctga    5220
attggatgac aataaagcag aggaaggtga tattcttgca gaatgcatta attctgctat    5280
gcccaagggg aaaagtcaca agcctttccg tgtgaaaaag ataatggacc aggtccagca    5340
agcatctgcg tcttcttctg cacccaacaa aaatcagtta gatggtaaga aaagaaaacc    5400
aacttcacca gtaaaaccta taccacaaaa tactgaatat aggacacgtg taagaaaaaa    5460
tgcagactca aaaaataatt taaatgctga gagagttttc tcagacaaca agattcaaa    5520 gaaacagaat ttgaaaaata attccaaggt cttcaatgat aagctcccaa ataatgaaga    5580
tagagtcaga ggaagttttg cttttgattc acctcatcat tacacgccta ttgaaggaac    5640
tccttactgt ttttcacgaa atgattcttt gagttctcta gattttgatg atgatgatgt    5700
tgacctttcc agggaaaagg ctgaattaag aaaggcaaaa gaaaataagg aatcagaggc    5760
taaagttacc agccacacag aactaacctc caaccaacaa tcagctaata agacacaagc    5820
tattgcaaag cagccaataa atcgaggtca gcctaaaccc atacttcaga acaatccac    5880 ttttccccag tcatccaaag acataccaga cagaggggca gcaactgatg aaaagttaca    5940
gaattttgct attgaaaata ctccggtttg cttttctcat aattcctctc tgagttctct    6000
cagtgacatt gaccaagaaa acaacaataa agaaaatgaa cctatcaaag agactgagcc    6060
ccctgactca cagggagaac caagtaaacc tcaagcatca ggctatgctc ctaaatcatt    6120
tcatgttgaa gataccccag tttgtttctc aagaaacagt tctctcagtt ctcttagtat    6180
tgactctgaa gatgacctgt tgcaggaatg tataagctcc gcaatgccaa aaagaaaaa    6240 gccttcaaga ctcaagggtg ataatgaaaa acatagtccc agaaatatgg gtggcatatt    6300
aggtgaagat ctgacacttg atttgaaaga tatacagaga ccagattcag aacatggtct    6360
atcccctgat tcagaaaatt ttgattggaa agctattcag gaaggtgcaa attccatagt    6420
aagtagttta catcaagctg ctgctgctgc atgtttatct agacaagctt cgtctgattc    6480
agattccatc ctttccctga aatcaggaat ctctctggga tcaccatttc atcttacacc    6540
tgatcaagaa gaaaaaccct ttacaagtaa taaggccca cgaattctaa accaggggga    6600
gaaaagtaca ttggaaacta aaagataga atctgaaagt aaaggaatca aggaggaaa    6660 aaaagtttat aaaagtttga ttactggaaa agttcgatct aattcagaaa tttcaggcca    6720
aatgaaacag ccccttcaag caaacatgcc ttcaatctct cgaggcagga caatgattca    6780
```

```
tattccagga gttcgaaata gctcctcaag tacaagtcct gtttctaaaa aaggcccacc    6840
ccttaagact ccagcctcca aaagccctag tgaaggtcaa acagccacca cttctcctag    6900
aggagccaag ccatctgtga aatcagaatt aagccctgtt gccaggcaga catcccaaat    6960
aggtgggtca agtaaagcac cttctagatc aggatctaga gattcgaccc cttcaagacc    7020
tgcccagcaa ccattaagta gacctataca gtctcctggc cgaaactcaa tttcccctgg    7080
tagaaatgga ataagtcctc ctaacaaatt atctcaactt ccaaggacat catcccctag    7140
tactgcttca actaagtcct caggttctgg aaaaatgtca tatacatctc caggtagaca    7200
gatgagccaa cagaaccttacc ccaaacaaac aggtttatcc aagaatgcca gtagtattcc    7260
aagaagtgag tctgcctcca aaggactaaa tcagatgaat aatggtaatg gagccaataa    7320
aaaggtagaa ctttctagaa tgtcttcaac taaatcaagt ggaagtgaat ctgatagatc    7380
agaaagacct gtattagtac gccagtcaac tttcatcaaa gaagctccaa gcccaacctt    7440
aagaagaaaa ttggaggaat ctgcttcatt tgaatctctt tctccatcat ctagaccagc    7500
ttctcccact aggtcccagg cacaaactcc agttttaagt ccttcccttc ctgatatgtc    7560
tctatccaca cattcgtctg ttcaggctgg tggatggcga aaactcccac ctaatctcag    7620
tcccactata gagtataatg atggaagacc agcaaagcgc catgatattg cacggtctca    7680
ttctgaaagt ccttctagac ttccaatcaa taggtcagga acctggaaac gtgagcacag    7740
caaacattca tcatcccttc ctcgagtaag cacttggaga agaactggaa gttcatcttc    7800
aattctttct gcttcatcag aatccagtga aaaagcaaaa agtgaggatg aaaaacatgt    7860
gaactctatt tcaggaacca aacaaagtaa agaaaaccaa gtatccgcaa aaggaacatg    7920
gagaaaaata aagaaaatg aattttctcc cacaaatagt acttctcaga ccgtttcctc    7980
aggtgctaca aatggtgctg aatcaaagac tctaatttat caaatggcac ctgctgtttc    8040
taaaacagag gatgtttggg tgagaattga ggactgtccc attaacaatc ctagatctgg    8100
aagatctccc acaggtaata ctcccccggt gattgacagt gtttcagaaa aggcaaatcc    8160
aaacattaaa gattcaaaag ataatcaggc aaaacaaaat gtgggtaatg gcagtgttcc    8220
catgcgtacc gtgggtttgg aaaatcgcct gaactccttt attcaggtgg atgcccctga    8280
ccaaaaagga actgagataa aaccaggaca aaataatcct gtccctgtat cagagactaa    8340
tgaaagttct atagtggaac gtaccccatt cagttctagc agctcaagca acacagttc    8400
acctagtggg actgttgctg ccagagtgac tcctttaat tacaacccaa gccctaggaa    8460
aagcagcgca gatagcactt cagctcggcc atctcgatc ccaactccag tgaataacaa    8520
cacaaagaag cgagattcca aaactgacag cacagaatcc agtggaaccc aaagtcctaa    8580
gcgccattct gggtcttacc ttgtgacatc tgtttaaaag agaggaagaa tgaaactaag    8640
aaaattctat gttaattaca actgctatat agacattttg tttcaaatga aactttaaaa    8700
gactgaaaaa ttttgtaaat aggtttgatt cttgttagag ggttttgtt ctggaagcca    8760
tatttgatag tatactttgt cttcactggt cttattttgg gaggcactct tgatggttag    8820
gaaaaaaata gtaaagccaa gtatgtttgt acagtatgtt ttacatgtat ttaaagtagc    8880
atcccatccc aacttccttt aattattgct tgtcttaaaa taatgaacac tacagataga    8940
aaatatgata tattgctgtt atcaatcatt tctagattat aaactgacta aacttacatc    9000
agggaaaaat tggtatttat gcaaaaaaaa atgttttgt ccttgtgagt ccatctaaca    9060
tcataattaa tcatgtggct gtgaaattca cagtaatatg gttcccgatg aacaagttta    9120
cccagcctgc tttgctttac tgcatgaatg aaactgatgg ttcaatttca gaagtaatga    9180
```

```
ttaacagtta tgtggtcaca tgatgtgcat agagatagct acagtgtaat aatttacact      9240
attttgtgct ccaaacaaaa caaaaatctg tgtaactgta aaacattgaa tgaaactatt      9300
ttacctgaac tagattttat ctgaaagtag gtagaatttt tgctatgctg taatttgttg      9360
tatattctgg tatttgaggt gagatggctg ctcttttatt aatgagacat gaattgtgtc      9420
tcaacagaaa ctaaatgaac atttcagaat aaattattgc tgtatgtaaa ctgttactga      9480
aattggtatt tgtttgaagg gtcttgtttc acatttgtat taataattgt ttaaaatgcc      9540
tcttttaaaa gcttatataa attttttttct tcagcttcta tgcattaaga gtaaaattcc     9600
tcttactgta ataaaaacaa ttgaagaaga ctgttgccac ttaaccattc catgcgttgg      9660
cacttatcta ttcctgaaat ttcttttatg tgattagctc atcttgattt ttaatatttt      9720
tccacttaaa ctttttttttc ttactccact ggagctcagt aaaagtaaat tcatgtaata    9780
gcaatgcaag cagcctagca cagactaagc attgagcata ataggcccac ataatttcct     9840
ctttcttaat attatagaat tctgtacttg aaattgattc ttagacattg cagtctcttc      9900
gaggctttac agtgtaaact gtcttgcccc ttcatcttct tgttgcaact gggtctgaca      9960
tgaacacttt ttatcaccct gtatgttagg gcaagatctc agcagtgaag tataatcagc     10020
actttgccat gctcagaaaa ttcaaatcac atggaacttt agaggtagat ttaatacgat     10080
taagatattc agaagtatat tttagaatcc ctgcctgtta aggaaacttt atttgtggta     10140
ggtacagttc tggggtacat gttaagtgtc cccttataca gtggagggaa gtcttccttc     10200
ctgaaggaaa ataaactgac acttattaac taagataatt tacttaatat atcttccctg    10260
atttgtttta aaagatcaga gggtgactga tgatacatgc atacatattt gttgaataaa     10320
tgaaaattta ttttttagtga taagattcat acactctgta tttggggagg gaaaaccttt    10380
ttaagcatgg tgggggcactc agataggagt gaatacacct acctggtgcc ttgaaaatca   10440
catcaagtag ttaattatct acccccttacc tgtgtttata acttccaggt aatgagaatg   10500
atttttttta aagctaaaat gccagtaaat aaaagtgcta tgacttgagc taagatattt     10560
gactccaatg cctgtactgt gtctactgca ccactttgta aacacttcaa tttactatct     10620
ttgaaatgat tgacctttaa atttttgcca aatgttatct gaaattgtct atgaatacca    10680
tctacttctg ttgttttccc aggcttccat aaacaatgga gatacatgca aaaaaaaaa    10740
```

<210> SEQ ID NO 70
<211> LENGTH: 12
<212> TYPE: DNA
<213> ORGANISM: Artificial Sequence
<220> FEATURE:
<223> OTHER INFORMATION: Synthetic Construct

<400> SEQUENCE: 70
ggagacggtc tg                                                          12

<210> SEQ ID NO 71
<211> LENGTH: 20
<212> TYPE: DNA
<213> ORGANISM: Artificial Sequence
<220> FEATURE:
<223> OTHER INFORMATION: Synthetic Construct

<400> SEQUENCE: 71
aatcccatca ccatcttcca                                                  20

<210> SEQ ID NO 72

<211> LENGTH: 20
<212> TYPE: DNA
<213> ORGANISM: Artificial Sequence
<220> FEATURE:
<223> OTHER INFORMATION: Synthetic Construct

<400> SEQUENCE: 72
tggactccac gacgtactca                                            20

<210> SEQ ID NO 73
<211> LENGTH: 18
<212> TYPE: DNA
<213> ORGANISM: Artificial Sequence
<220> FEATURE:
<223> OTHER INFORMATION: Synthetic Construct

<400> SEQUENCE: 73
ctgtcttcca ctcactcc                                              18

<210> SEQ ID NO 74
<211> LENGTH: 25
<212> TYPE: DNA
<213> ORGANISM: Artificial Sequence
<220> FEATURE:
<223> OTHER INFORMATION: Synthetic Construct

<400> SEQUENCE: 74
tttttttttt ttagctgatg gcgta                                      25

<210> SEQ ID NO 75
<211> LENGTH: 25
<212> TYPE: DNA
<213> ORGANISM: Artificial Sequence
<220> FEATURE:
<223> OTHER INFORMATION: Synthetic Construct

<400> SEQUENCE: 75
tttttttttt atggagctga tggcg                                      25

<210> SEQ ID NO 76
<211> LENGTH: 25
<212> TYPE: DNA
<213> ORGANISM: Artificial Sequence
<220> FEATURE:
<223> OTHER INFORMATION: Synthetic Construct

<400> SEQUENCE: 76
tttttttttt ttatggagct gatgg                                      25

<210> SEQ ID NO 77
<211> LENGTH: 25
<212> TYPE: DNA
<213> ORGANISM: Artificial Sequence
<220> FEATURE:
<223> OTHER INFORMATION: Synthetic Construct

<400> SEQUENCE: 77
tttttttttt tttgctgatg gcgta                                      25

<210> SEQ ID NO 78
<211> LENGTH: 25
<212> TYPE: DNA
<213> ORGANISM: Artificial Sequence
<220> FEATURE:
<223> OTHER INFORMATION: Synthetic Construct

<400> SEQUENCE: 78 tttttttttat ggagctgttg gtggc                                       25

<210> SEQ ID NO 79
<211> LENGTH: 25
<212> TYPE: DNA
<213> ORGANISM: Artificial Sequence
<220> FEATURE:
<223> OTHER INFORMATION: Synthetic Construct

<400> SEQUENCE: 79
tttttttttt aaggagctgt tggtg                                        25

<210> SEQ ID NO 80
<211> LENGTH: 25
<212> TYPE: DNA
<213> ORGANISM: Artificial Sequence
<220> FEATURE:
<223> OTHER INFORMATION: Synthetic Construct

<400> SEQUENCE: 80
tttttttttt tatggagctg ttggt                                        25

<210> SEQ ID NO 81
<211> LENGTH: 25
<212> TYPE: DNA
<213> ORGANISM: Artificial Sequence
<220> FEATURE:
<223> OTHER INFORMATION: Synthetic Construct

<400> SEQUENCE: 81 tttttttta tggagctgta ggtgg                                         25

<210> SEQ ID NO 82
<211> LENGTH: 25
<212> TYPE: DNA
<213> ORGANISM: Artificial Sequence
<220> FEATURE:
<223> OTHER INFORMATION: Synthetic Construct

<400> SEQUENCE: 82
tttttttttt ggagctagtg gcgta                                        25

<210> SEQ ID NO 83
<211> LENGTH: 25
<212> TYPE: DNA
<213> ORGANISM: Artificial Sequence
<220> FEATURE:
<223> OTHER INFORMATION: Synthetic Construct

<400> SEQUENCE: 83
tttttaattt gctagtggcg taggc                                        25

<210> SEQ ID NO 84
<211> LENGTH: 25
<212> TYPE: DNA
<213> ORGANISM: Artificial Sequence
<220> FEATURE:
<223> OTHER INFORMATION: Synthetic Construct

<400> SEQUENCE: 84
ttttttttta tttagctagt ggcgt                                        25

<210> SEQ ID NO 85
<211> LENGTH: 25
<212> TYPE: DNA

```
<213> ORGANISM: Artificial Sequence
<220> FEATURE:
<223> OTHER INFORMATION: Synthetic Construct

<400> SEQUENCE: 85
tttttttttt tgttggagct agtgg                                              25

<210> SEQ ID NO 86
<211> LENGTH: 25
<212> TYPE: DNA
<213> ORGANISM: Artificial Sequence
<220> FEATURE:
<223> OTHER INFORMATION: Synthetic Construct

<400> SEQUENCE: 86
tttttttttt ttaaggagct agtgg                                              25

<210> SEQ ID NO 87
<211> LENGTH: 25
<212> TYPE: DNA
<213> ORGANISM: Artificial Sequence
<220> FEATURE:
<223> OTHER INFORMATION: Synthetic Construct

<400> SEQUENCE: 87
ttttttttaa aggtgacgta ggcaa                                              25

<210> SEQ ID NO 88
<211> LENGTH: 25
<212> TYPE: DNA
<213> ORGANISM: Artificial Sequence
<220> FEATURE:
<223> OTHER INFORMATION: Synthetic Construct

<400> SEQUENCE: 88 tttttttta tgacgtaggc aagag                                               25

<210> SEQ ID NO 89
<211> LENGTH: 25
<212> TYPE: DNA
<213> ORGANISM: Artificial Sequence
<220> FEATURE:
<223> OTHER INFORMATION: Synthetic Construct

<400> SEQUENCE: 89
tttttttttt tgctggtgac gtagg                                              25

<210> SEQ ID NO 90
<211> LENGTH: 25
<212> TYPE: DNA
<213> ORGANISM: Artificial Sequence
<220> FEATURE:
<223> OTHER INFORMATION: Synthetic Construct

<400> SEQUENCE: 90
tttttttttt aagctggtga cgtag                                              25

<210> SEQ ID NO 91
<211> LENGTH: 25
<212> TYPE: DNA
<213> ORGANISM: Artificial Sequence
<220> FEATURE:
<223> OTHER INFORMATION: Synthetic Construct

<400> SEQUENCE: 91 tttttttta aggagctggt gacgt                                               25
```

<210> SEQ ID NO 92
<211> LENGTH: 27
<212> TYPE: DNA
<213> ORGANISM: Artificial Sequence
<220> FEATURE:
<223> OTHER INFORMATION: Synthetic Construct

<400> SEQUENCE: 92 tttttttta tacagagaaa tctcgat                                         27

<210> SEQ ID NO 93
<211> LENGTH: 27
<212> TYPE: DNA
<213> ORGANISM: Artificial Sequence
<220> FEATURE:
<223> OTHER INFORMATION: Synthetic Construct

<400> SEQUENCE: 93 tttttttta atttacagag aaatctc                                         27

<210> SEQ ID NO 94
<211> LENGTH: 27
<212> TYPE: DNA
<213> ORGANISM: Artificial Sequence
<220> FEATURE:
<223> OTHER INFORMATION: Synthetic Construct

<400> SEQUENCE: 94 tttttttaatt actagctaca gagaaat                                       27

<210> SEQ ID NO 95
<211> LENGTH: 27
<212> TYPE: DNA
<213> ORGANISM: Artificial Sequence
<220> FEATURE:
<223> OTHER INFORMATION: Synthetic Construct

<400> SEQUENCE: 95 ttttttttaat tactagctac agagaaa                                       27

<210> SEQ ID NO 96
<211> LENGTH: 27
<212> TYPE: DNA
<213> ORGANISM: Artificial Sequence
<220> FEATURE:
<223> OTHER INFORMATION: Synthetic Construct

<400> SEQUENCE: 96
tttttttttt aatttctagc tacagag                                        27

<210> SEQ ID NO 97
<211> LENGTH: 25
<212> TYPE: DNA
<213> ORGANISM: Artificial Sequence
<220> FEATURE:
<223> OTHER INFORMATION: Synthetic Construct

<400> SEQUENCE: 97
ttttatgtct agctacagaa aaatc                                          25

<210> SEQ ID NO 98
<211> LENGTH: 27
<212> TYPE: DNA
<213> ORGANISM: Artificial Sequence
<220> FEATURE:

<223> OTHER INFORMATION: Synthetic Construct

<400> SEQUENCE: 98 tttttttttat ttttagctac agaaaaa                                           27

<210> SEQ ID NO 99
<211> LENGTH: 27
<212> TYPE: DNA
<213> ORGANISM: Artificial Sequence
<220> FEATURE:
<223> OTHER INFORMATION: Synthetic Construct

<400> SEQUENCE: 99
tttttttatt tctagctaca gaaaaat                                            27

<210> SEQ ID NO 100
<211> LENGTH: 28
<212> TYPE: DNA
<213> ORGANISM: Artificial Sequence
<220> FEATURE:
<223> OTHER INFORMATION: Synthetic Construct

<400> SEQUENCE: 100 tttttttat tctagctaca gaaaaatc                                            28

<210> SEQ ID NO 101
<211> LENGTH: 27
<212> TYPE: DNA
<213> ORGANISM: Artificial Sequence
<220> FEATURE:
<223> OTHER INFORMATION: Synthetic Construct

<400> SEQUENCE: 101
tttttttttt taggagctgt ggcagtg                                            27

<210> SEQ ID NO 102
<211> LENGTH: 26
<212> TYPE: DNA
<213> ORGANISM: Artificial Sequence
<220> FEATURE:
<223> OTHER INFORMATION: Synthetic Construct

<400> SEQUENCE: 102
tttttttttt tagctgtggc agtggc                                             26

<210> SEQ ID NO 103
<211> LENGTH: 26
<212> TYPE: DNA
<213> ORGANISM: Artificial Sequence
<220> FEATURE:
<223> OTHER INFORMATION: Synthetic Construct

<400> SEQUENCE: 103
tttttttttt tgctgtggca gtggca                                             26

<210> SEQ ID NO 104
<211> LENGTH: 25
<212> TYPE: DNA
<213> ORGANISM: Artificial Sequence
<220> FEATURE:
<223> OTHER INFORMATION: Synthetic Construct

<400> SEQUENCE: 104
tttttttttt aaggagctgt ggcag                                              25

```
<210> SEQ ID NO 105
<211> LENGTH: 25
<212> TYPE: DNA
<213> ORGANISM: Artificial Sequence
<220> FEATURE:
<223> OTHER INFORMATION: Synthetic Construct

<400> SEQUENCE: 105
tttttttttg gagctgtgat agtgg                                          25

<210> SEQ ID NO 106
<211> LENGTH: 25
<212> TYPE: DNA
<213> ORGANISM: Artificial Sequence
<220> FEATURE:
<223> OTHER INFORMATION: Synthetic Construct

<400> SEQUENCE: 106
tttttttttg agctgtgata gtggc                                          25

<210> SEQ ID NO 107
<211> LENGTH: 25
<212> TYPE: DNA
<213> ORGANISM: Artificial Sequence
<220> FEATURE:
<223> OTHER INFORMATION: Synthetic Construct

<400> SEQUENCE: 107
ttttttttta gctgtgatag tggca                                          25

<210> SEQ ID NO 108
<211> LENGTH: 25
<212> TYPE: DNA
<213> ORGANISM: Artificial Sequence
<220> FEATURE:
<223> OTHER INFORMATION: Synthetic Construct

<400> SEQUENCE: 108
ttttttttta gaaggagctg tgata                                          25

<210> SEQ ID NO 109
<211> LENGTH: 25
<212> TYPE: DNA
<213> ORGANISM: Artificial Sequence
<220> FEATURE:
<223> OTHER INFORMATION: Synthetic Construct

<400> SEQUENCE: 109
tttttttttt ttttggagct gtgat                                          25

<210> SEQ ID NO 110
<211> LENGTH: 25
<212> TYPE: DNA
<213> ORGANISM: Artificial Sequence
<220> FEATURE:
<223> OTHER INFORMATION: Synthetic Construct

<400> SEQUENCE: 110
tttaatttta ctcagaaaag gagct                                          25

<210> SEQ ID NO 111
<211> LENGTH: 25
<212> TYPE: DNA
<213> ORGANISM: Artificial Sequence
<220> FEATURE:
<223> OTHER INFORMATION: Synthetic Construct
```

```
<400> SEQUENCE: 111 tttttttaata ccactcagaa aagga                                       25

<210> SEQ ID NO 112
<211> LENGTH: 25
<212> TYPE: DNA
<213> ORGANISM: Artificial Sequence
<220> FEATURE:
<223> OTHER INFORMATION: Synthetic Construct

<400> SEQUENCE: 112
ttttttttac cactcagaaa aggag                                        25

<210> SEQ ID NO 113
<211> LENGTH: 25
<212> TYPE: DNA
<213> ORGANISM: Artificial Sequence
<220> FEATURE:
<223> OTHER INFORMATION: Synthetic Construct

<400> SEQUENCE: 113
ttttttttat taccactcag aaaag                                        25

<210> SEQ ID NO 114
<211> LENGTH: 25
<212> TYPE: DNA
<213> ORGANISM: Artificial Sequence
<220> FEATURE:
<223> OTHER INFORMATION: Synthetic Construct

<400> SEQUENCE: 114 ttttttttc agaaaggag ctgtg                                          25

<210> SEQ ID NO 115
<211> LENGTH: 27
<212> TYPE: DNA
<213> ORGANISM: Artificial Sequence
<220> FEATURE:
<223> OTHER INFORMATION: Synthetic Construct

<400> SEQUENCE: 115
ttttttttta aaactcagag gaggagc                                      27

<210> SEQ ID NO 116
<211> LENGTH: 27
<212> TYPE: DNA
<213> ORGANISM: Artificial Sequence
<220> FEATURE:
<223> OTHER INFORMATION: Synthetic Construct

<400> SEQUENCE: 116
tttttttttt tattaccact cagagga                                      27

<210> SEQ ID NO 117
<211> LENGTH: 27
<212> TYPE: DNA
<213> ORGANISM: Artificial Sequence
<220> FEATURE:
<223> OTHER INFORMATION: Synthetic Construct

<400> SEQUENCE: 117
ttttttttta ttaccactca gaggagg                                      27

<210> SEQ ID NO 118
<211> LENGTH: 27
```

```
<212> TYPE: DNA
<213> ORGANISM: Artificial Sequence
<220> FEATURE:
<223> OTHER INFORMATION: Synthetic Construct

<400> SEQUENCE: 118
tttttttttt attaacactc agaggag                                              27

<210> SEQ ID NO 119
<211> LENGTH: 27
<212> TYPE: DNA
<213> ORGANISM: Artificial Sequence
<220> FEATURE:
<223> OTHER INFORMATION: Synthetic Construct

<400> SEQUENCE: 119
ttttttttta ttaccaatca gaggagg                                              27

<210> SEQ ID NO 120
<211> LENGTH: 28
<212> TYPE: DNA
<213> ORGANISM: Artificial Sequence
<220> FEATURE:
<223> OTHER INFORMATION: Synthetic Construct

<400> SEQUENCE: 120
tttttttttt aaatagcaga aataaaag                                             28

<210> SEQ ID NO 121
<211> LENGTH: 28
<212> TYPE: DNA
<213> ORGANISM: Artificial Sequence
<220> FEATURE:
<223> OTHER INFORMATION: Synthetic Construct

<400> SEQUENCE: 121
tttttttttt tgaaataaaa gattggaa                                             28

<210> SEQ ID NO 122
<211> LENGTH: 28
<212> TYPE: DNA
<213> ORGANISM: Artificial Sequence
<220> FEATURE:
<223> OTHER INFORMATION: Synthetic Construct

<400> SEQUENCE: 122
tttttttttt tttagaaata aaagattg                                             28

<210> SEQ ID NO 123
<211> LENGTH: 28
<212> TYPE: DNA
<213> ORGANISM: Artificial Sequence
<220> FEATURE:
<223> OTHER INFORMATION: Synthetic Construct

<400> SEQUENCE: 123
tttttttttt tttgaaataa atgaatgg                                             28

<210> SEQ ID NO 124
<211> LENGTH: 28
<212> TYPE: DNA
<213> ORGANISM: Artificial Sequence
<220> FEATURE:
<223> OTHER INFORMATION: Synthetic Construct

<400> SEQUENCE: 124
```

```
tttttttttt tttcagaaat aaaagatt                                      28

<210> SEQ ID NO 125
<211> LENGTH: 24
<212> TYPE: DNA
<213> ORGANISM: Artificial Sequence
<220> FEATURE:
<223> OTHER INFORMATION: Synthetic Construct

<400> SEQUENCE: 125
ttttttttta tttgggtgtc taag                                          24

<210> SEQ ID NO 126
<211> LENGTH: 24
<212> TYPE: DNA
<213> ORGANISM: Artificial Sequence
<220> FEATURE:
<223> OTHER INFORMATION: Synthetic Construct

<400> SEQUENCE: 126
tttttttggt gtctaagcac cact                                          24

<210> SEQ ID NO 127
<211> LENGTH: 24
<212> TYPE: DNA
<213> ORGANISM: Artificial Sequence
<220> FEATURE:
<223> OTHER INFORMATION: Synthetic Construct

<400> SEQUENCE: 127
tttttttttc taagcaccac tttt                                          24

<210> SEQ ID NO 128
<211> LENGTH: 24
<212> TYPE: DNA
<213> ORGANISM: Artificial Sequence
<220> FEATURE:
<223> OTHER INFORMATION: Synthetic Construct

<400> SEQUENCE: 128
tttttttttt ttttgggtgt ctaa                                          24

<210> SEQ ID NO 129
<211> LENGTH: 24
<212> TYPE: DNA
<213> ORGANISM: Artificial Sequence
<220> FEATURE:
<223> OTHER INFORMATION: Synthetic Construct

<400> SEQUENCE: 129 ttttttttttg gtgtctaagc acca                                         24

<210> SEQ ID NO 130
<211> LENGTH: 25
<212> TYPE: DNA
<213> ORGANISM: Artificial Sequence
<220> FEATURE:
<223> OTHER INFORMATION: Synthetic Construct

<400> SEQUENCE: 130
ttttttttaa gtgagaagta cctaa                                         25

<210> SEQ ID NO 131
<211> LENGTH: 25
<212> TYPE: DNA
<213> ORGANISM: Artificial Sequence
```

<220> FEATURE:
<223> OTHER INFORMATION: Synthetic Construct

<400> SEQUENCE: 131
tttttttttt ttcaaaccaa gtgag                                25

<210> SEQ ID NO 132
<211> LENGTH: 25
<212> TYPE: DNA
<213> ORGANISM: Artificial Sequence
<220> FEATURE:
<223> OTHER INFORMATION: Synthetic Construct

<400> SEQUENCE: 132
tttttttttt accaagtgag aagta                                25

<210> SEQ ID NO 133
<211> LENGTH: 25
<212> TYPE: DNA
<213> ORGANISM: Artificial Sequence
<220> FEATURE:
<223> OTHER INFORMATION: Synthetic Construct

<400> SEQUENCE: 133
ttttttttag ctcaaaccaa gtgag                                25

<210> SEQ ID NO 134
<211> LENGTH: 25
<212> TYPE: DNA
<213> ORGANISM: Artificial Sequence
<220> FEATURE:
<223> OTHER INFORMATION: Synthetic Construct

<400> SEQUENCE: 134
tttttttttt gcacctactg ctgaa                                25

<210> SEQ ID NO 135
<211> LENGTH: 25
<212> TYPE: DNA
<213> ORGANISM: Artificial Sequence
<220> FEATURE:
<223> OTHER INFORMATION: Synthetic Construct

<400> SEQUENCE: 135
ttttttttta cctactgctg aaaag                                25

<210> SEQ ID NO 136
<211> LENGTH: 25
<212> TYPE: DNA
<213> ORGANISM: Artificial Sequence
<220> FEATURE:
<223> OTHER INFORMATION: Synthetic Construct

<400> SEQUENCE: 136 ttttttttg ctgaaaagag agagt                                 25

<210> SEQ ID NO 137
<211> LENGTH: 27
<212> TYPE: DNA
<213> ORGANISM: Artificial Sequence
<220> FEATURE:
<223> OTHER INFORMATION: Synthetic Construct

<400> SEQUENCE: 137 ttttttttc ctactgctga aaagaga                               27

<210> SEQ ID NO 138
<211> LENGTH: 27
<212> TYPE: DNA
<213> ORGANISM: Artificial Sequence
<220> FEATURE:
<223> OTHER INFORMATION: Synthetic Construct

<400> SEQUENCE: 138
tttttttttt gcagaaaaaa actattg                                              27

<210> SEQ ID NO 139
<211> LENGTH: 30
<212> TYPE: DNA
<213> ORGANISM: Artificial Sequence
<220> FEATURE:
<223> OTHER INFORMATION: Synthetic Construct

<400> SEQUENCE: 139
tttttttttt tcagaaaaaa actattgatt                                           30

<210> SEQ ID NO 140
<211> LENGTH: 28
<212> TYPE: DNA
<213> ORGANISM: Artificial Sequence
<220> FEATURE:
<223> OTHER INFORMATION: Synthetic Construct

<400> SEQUENCE: 140 ttttttaga aagaggcaga aaaaaact                                              28

<210> SEQ ID NO 141
<211> LENGTH: 28
<212> TYPE: DNA
<213> ORGANISM: Artificial Sequence
<220> FEATURE:
<223> OTHER INFORMATION: Synthetic Construct

<400> SEQUENCE: 141
tttttttttt tgaggcagaa aaaaacta                                             28

<210> SEQ ID NO 142
<211> LENGTH: 18
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 3, 4, 6, 9, 10, 11, 12, 13, 14
<223> OTHER INFORMATION: Locked nucleic acid
<220> FEATURE:
<221> NAME/KEY: misc_feature
<222> LOCATION: 18
<223> OTHER INFORMATION: Inverted deoxythymidine
<220> FEATURE:
<221> NAME/KEY: misc_feature
<222> LOCATION: 18
<223> OTHER INFORMATION: Can be present in repeat of up to 3 times

<400> SEQUENCE: 142
ttggagctgg tggcgtat                                                        18

<210> SEQ ID NO 143
<211> LENGTH: 17
<212> TYPE: DNA
<213> ORGANISM: Artificial Sequence
<220> FEATURE:
<223> OTHER INFORMATION: Synthetic Construct -continued

```
<220> FEATURE:
<221> NAME/KEY: misc_feature
<222> LOCATION: 4, 5, 7, 8, 10, 13, 15
<223> OTHER INFORMATION: Locked nucleic acid
<220> FEATURE:
<221> NAME/KEY: misc_feature
<222> LOCATION: 17
<223> OTHER INFORMATION: Inverted deoxythymidine
<220> FEATURE:
<221> NAME/KEY: misc_feature
<222> LOCATION: 17
<223> OTHER INFORMATION: Can be present in repeat of up to 3 times

<400> SEQUENCE: 143
gctggtggcg taggcat                                                    17

<210> SEQ ID NO 144
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 3, 4, 5, 6, 7, 8, 9, 10, 11, 12
<223> OTHER INFORMATION: Locked nucleic acid
<220> FEATURE:
<221> NAME/KEY: misc_feature
<222> LOCATION: 16
<223> OTHER INFORMATION: Inverted deoxythymidine
<220> FEATURE:
<221> NAME/KEY: misc_feature
<222> LOCATION: 16
<223> OTHER INFORMATION: Can be present in repeat of up to 3 times

<400> SEQUENCE: 144
gctggtggcg taggct                                                     16

<210> SEQ ID NO 145
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 3, 4, 6, 9, 10, 12, 13, 15
<223> OTHER INFORMATION: Locked nucleic acid
<220> FEATURE:
<221> NAME/KEY: misc_feature
<222> LOCATION: 17
<223> OTHER INFORMATION: Inverted deoxythymidine
<220> FEATURE:
<221> NAME/KEY: misc_feature
<222> LOCATION: 17
<223> OTHER INFORMATION: Can be present in repeat of up to 3 times

<400> SEQUENCE: 145
ttggagctgg tggcgtt                                                    17

<210> SEQ ID NO 146
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 3, 6, 7, 8, 9, 10, 11, 12, 13
<223> OTHER INFORMATION: Locked nucleic acid
<220> FEATURE:
<221> NAME/KEY: misc_feature
<222> LOCATION: 17
```

```
<223> OTHER INFORMATION: Inverted deoxythymidine
<220> FEATURE:
<221> NAME/KEY: misc_feature
<222> LOCATION: 17
<223> OTHER INFORMATION: Can be present in repeat of up to 3 times

<400> SEQUENCE: 146
gagatttcac tgtagct                                                    17

<210> SEQ ID NO 147
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 3, 4, 7, 8, 11, 12, 13, 14, 15
<223> OTHER INFORMATION: Locked nucleic acid
<220> FEATURE:
<221> NAME/KEY: misc_feature
<222> LOCATION: 17
<223> OTHER INFORMATION: Inverted deoxythymidine
<220> FEATURE:
<221> NAME/KEY: misc_feature
<222> LOCATION: 17
<223> OTHER INFORMATION: Can be present in repeat of up to 3 times

<400> SEQUENCE: 147
gagatttcac tgtagct                                                    17

<210> SEQ ID NO 148
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 3, 4, 5, 7, 8, 9, 10, 11, 13, 14, 15, 16
<223> OTHER INFORMATION: Locked nucleic acid
<220> FEATURE:
<221> NAME/KEY: misc_feature
<222> LOCATION: 17
<223> OTHER INFORMATION: Inverted deoxythymidine
<220> FEATURE:
<221> NAME/KEY: misc_feature
<222> LOCATION: 17
<223> OTHER INFORMATION: Can be present in repeat of up to 3 times

<400> SEQUENCE: 148
gagatttcac tgtagct                                                    17

<210> SEQ ID NO 149
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 3, 4, 6, 7, 9, 10, 11, 13, 15, 16
<223> OTHER INFORMATION: Locked nucleic acid
<220> FEATURE:
<221> NAME/KEY: misc_feature
<222> LOCATION: 17
<223> OTHER INFORMATION: Inverted deoxythymidine
<220> FEATURE:
<221> NAME/KEY: misc_feature
<222> LOCATION: 17
<223> OTHER INFORMATION: Can be present in repeat of up to 3 times

<400> SEQUENCE: 149
```
gagatttcac tgtagct                                                  17

<210> SEQ ID NO 150
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 4, 5, 8, 9, 10, 11, 13, 14
<223> OTHER INFORMATION: Locked nucleic acid
<220> FEATURE:
<221> NAME/KEY: misc_feature
<222> LOCATION: 15
<223> OTHER INFORMATION: Inverted deoxythymidine
<220> FEATURE:
<221> NAME/KEY: misc_feature
<222> LOCATION: 15
<223> OTHER INFORMATION: Can be present in repeat of up to 3 times

<400> SEQUENCE: 150
tgccactacc acagt                                                    15

<210> SEQ ID NO 151
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 3, 5, 6, 7, 8, 10, 11, 12, 14
<223> OTHER INFORMATION: Locked nucleic acid
<220> FEATURE:
<221> NAME/KEY: misc_feature
<222> LOCATION: 16
<223> OTHER INFORMATION: Inverted deoxythymidine
<220> FEATURE:
<221> NAME/KEY: misc_feature
<222> LOCATION: 16
<223> OTHER INFORMATION: Can be present in repeat of up to 3 times

<400> SEQUENCE: 151
cactaccaca gctcct                                                   16

<210> SEQ ID NO 152
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 3, 4, 5, 6, 8, 9, 10, 12, 13, 15
<223> OTHER INFORMATION: Locked nucleic acid
<220> FEATURE:
<221> NAME/KEY: misc_feature
<222> LOCATION: 16
<223> OTHER INFORMATION: Inverted deoxythymidine
<220> FEATURE:
<221> NAME/KEY: misc_feature
<222> LOCATION: 16
<223> OTHER INFORMATION: Can be present in repeat of up to 3 times

<400> SEQUENCE: 152
gccactacca cagctt                                                   16

<210> SEQ ID NO 153
<211> LENGTH: 16
<212> TYPE: DNA

```
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 2, 4, 5, 6, 7, 11, 12, 13
<223> OTHER INFORMATION: Locked nucleic acid
<220> FEATURE:
<221> NAME/KEY: misc_feature
<222> LOCATION: 16
<223> OTHER INFORMATION: Inverted deoxythymidine
<220> FEATURE:
<221> NAME/KEY: misc_feature
<222> LOCATION: 16
<223> OTHER INFORMATION: Can be present in repeat of up to 3 times

<400> SEQUENCE: 153
gccactacca cagctt                                                    16

<210> SEQ ID NO 154
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 3, 4, 5, 6, 8, 9, 10, 11, 13, 15, 18
<223> OTHER INFORMATION: Locked nucleic acid
<220> FEATURE:
<221> NAME/KEY: misc_feature
<222> LOCATION: 19
<223> OTHER INFORMATION: Inverted deoxythymidine
<220> FEATURE:
<221> NAME/KEY: misc_feature
<222> LOCATION: 19
<223> OTHER INFORMATION: Can be present in repeat of up to 3 times

<400> SEQUENCE: 154
cttttctttt atttctgct                                                 19

<210> SEQ ID NO 155
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 5, 6, 8, 10, 11, 12, 13, 14, 15, 16, 17, 18
<223> OTHER INFORMATION: Locked nucleic acid
<220> FEATURE:
<221> NAME/KEY: misc_feature
<222> LOCATION: 19
<223> OTHER INFORMATION: Inverted deoxythymidine
<220> FEATURE:
<221> NAME/KEY: misc_feature
<222> LOCATION: 19
<223> OTHER INFORMATION: Can be present in repeat of up to 3 times

<400> SEQUENCE: 155
cttttctttt atttctgct                                                 19

<210> SEQ ID NO 156
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 3, 4, 8, 9, 10, 12, 14, 15, 17, 18
<223> OTHER INFORMATION: Locked nucleic acid
```

```
<220> FEATURE:
<221> NAME/KEY: misc_feature
<222> LOCATION: 19
<223> OTHER INFORMATION: Inverted deoxythymidine
<220> FEATURE:
<221> NAME/KEY: misc_feature
<222> LOCATION: 19
<223> OTHER INFORMATION: Can be present in repeat of up to 3 times

<400> SEQUENCE: 156
cttttctttt atttctgct                                                    19

<210> SEQ ID NO 157
<211> LENGTH: 19
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 5, 6, 7, 8, 9, 10, 11, 12, 13, 14, 15, 18
<223> OTHER INFORMATION: Locked nucleic acid
<220> FEATURE:
<221> NAME/KEY: misc_feature
<222> LOCATION: 19
<223> OTHER INFORMATION: Inverted deoxythymidine
<220> FEATURE:
<221> NAME/KEY: misc_feature
<222> LOCATION: 19
<223> OTHER INFORMATION: Can be present in repeat of up to 3 times

<400> SEQUENCE: 157
cttttctttt atttctgct                                                    19

<210> SEQ ID NO 158
<211> LENGTH: 14
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 3, 4, 7, 9, 11, 12, 13
<223> OTHER INFORMATION: Locked nucleic acid
<220> FEATURE:
<221> NAME/KEY: misc_feature
<222> LOCATION: 14
<223> OTHER INFORMATION: Inverted deoxythymidine
<220> FEATURE:
<221> NAME/KEY: misc_feature
<222> LOCATION: 14
<223> OTHER INFORMATION: Can be present in repeat of up to 3 times

<400> SEQUENCE: 158
gtgctcagac acct                                                         14

<210> SEQ ID NO 159
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 8, 9, 10, 11, 12, 13, 14
<223> OTHER INFORMATION: Locked nucleic acid
<220> FEATURE:
<221> NAME/KEY: misc_feature
<222> LOCATION: 20
<223> OTHER INFORMATION: Inverted deoxythymidine
<220> FEATURE:
<221> NAME/KEY: misc_feature
<222> LOCATION: 20
```

```
<223> OTHER INFORMATION: Can be present in repeat of up to 3 times

<400> SEQUENCE: 159
agtggtgctc agacacccat                                                  20

<210> SEQ ID NO 160
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 3, 4, 7, 9, 10, 13, 15, 16, 17, 18
<223> OTHER INFORMATION: Locked nucleic acid
<220> FEATURE:
<221> NAME/KEY: misc_feature
<222> LOCATION: 20
<223> OTHER INFORMATION: Inverted deoxythymidine
<220> FEATURE:
<221> NAME/KEY: misc_feature
<222> LOCATION: 20
<223> OTHER INFORMATION: Can be present in repeat of up to 3 times

<400> SEQUENCE: 160
agtggtgctc agacacccat                                                  20

<210> SEQ ID NO 161
<211> LENGTH: 20
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 4, 9, 10, 11, 13, 14, 16, 18
<223> OTHER INFORMATION: Locked nucleic acid
<220> FEATURE:
<221> NAME/KEY: misc_feature
<222> LOCATION: 20
<223> OTHER INFORMATION: Inverted deoxythymidine
<220> FEATURE:
<221> NAME/KEY: misc_feature
<222> LOCATION: 20
<223> OTHER INFORMATION: Can be present in repeat of up to 3 times

<400> SEQUENCE: 161
agtggtgctc agacacccat                                                  20

<210> SEQ ID NO 162
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 3, 4, 6, 8, 9, 10, 13, 14, 15
<223> OTHER INFORMATION: Locked nucleic acid
<220> FEATURE:
<221> NAME/KEY: misc_feature
<222> LOCATION: 17
<223> OTHER INFORMATION: Inverted deoxythymidine
<220> FEATURE:
<221> NAME/KEY: misc_feature
<222> LOCATION: 17
<223> OTHER INFORMATION: Can be present in repeat of up to 3 times

<400> SEQUENCE: 162
gtacttctcg cttggtt                                                     17
```

```
<210> SEQ ID NO 163
<211> LENGTH: 15
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 3, 4, 6, 7, 8, 9, 11, 12, 13
<223> OTHER INFORMATION: Locked nucleic acid
<220> FEATURE:
<221> NAME/KEY: misc_feature
<222> LOCATION: 15
<223> OTHER INFORMATION: Inverted deoxythymidine
<220> FEATURE:
<221> NAME/KEY: misc_feature
<222> LOCATION: 15
<223> OTHER INFORMATION: Can be present in repeat of up to 3 times

<400> SEQUENCE: 163
cttctcgctt ggttt                                            15

<210> SEQ ID NO 164
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 3, 4, 5, 7, 8, 9, 10, 13, 14, 15
<223> OTHER INFORMATION: Locked nucleic acid
<220> FEATURE:
<221> NAME/KEY: misc_feature
<222> LOCATION: 17
<223> OTHER INFORMATION: Inverted deoxythymidine
<220> FEATURE:
<221> NAME/KEY: misc_feature
<222> LOCATION: 17
<223> OTHER INFORMATION: Can be present in repeat of up to 3 times

<400> SEQUENCE: 164
gtacttctcg cttggtt                                          17

<210> SEQ ID NO 165
<211> LENGTH: 17
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 3, 5, 6, 7, 8, 9, 10, 11, 14, 15
<223> OTHER INFORMATION: Locked nucleic acid
<220> FEATURE:
<221> NAME/KEY: misc_feature
<222> LOCATION: 17
<223> OTHER INFORMATION: Inverted deoxythymidine
<220> FEATURE:
<221> NAME/KEY: misc_feature
<222> LOCATION: 17
<223> OTHER INFORMATION: Can be present in repeat of up to 3 times

<400> SEQUENCE: 165
gtacttctcg cttggtt                                          17

<210> SEQ ID NO 166
<211> LENGTH: 27
<212> TYPE: DNA
<213> ORGANISM: Artificial Sequence
<220> FEATURE:
<223> OTHER INFORMATION: Synthetic Construct
<220> FEATURE:
```

```
<221> NAME/KEY: misc_feature
<222> LOCATION: 3, 4, 6, 7, 19, 20, 22, 24, 25
<223> OTHER INFORMATION: Locked nucleic acid
<220> FEATURE:
<221> NAME/KEY: misc_feature
<222> LOCATION: 27
<223> OTHER INFORMATION: Inverted deoxythymidine
<220> FEATURE:
<221> NAME/KEY: misc_feature
<222> LOCATION: 27
<223> OTHER INFORMATION: Can be present in repeat of up to 3 times

<400> SEQUENCE: 166
taggtccact ctctctcttt tcagcat                                              27

<210> SEQ ID NO 167
<211> LENGTH: 27
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 3, 4, 6, 7, 8, 9, 11, 12, 13, 14, 16, 20, 23, 24
<223> OTHER INFORMATION: Locked nucleic acid
<220> FEATURE:
<221> NAME/KEY: misc_feature
<222> LOCATION: 27
<223> OTHER INFORMATION: Inverted deoxythymidine
<220> FEATURE:
<221> NAME/KEY: misc_feature
<222> LOCATION: 27
<223> OTHER INFORMATION: Can be present in repeat of up to 3 times

<400> SEQUENCE: 167
taggtccact ctctctcttt tcagcat                                              27

<210> SEQ ID NO 168
<211> LENGTH: 21
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 3, 5, 7, 9, 11, 12, 17, 19, 20
<223> OTHER INFORMATION: Locked nucleic acid
<220> FEATURE:
<221> NAME/KEY: misc_feature
<222> LOCATION: 21
<223> OTHER INFORMATION: Inverted deoxythymidine
<220> FEATURE:
<221> NAME/KEY: misc_feature
<222> LOCATION: 21
<223> OTHER INFORMATION: Can be present in repeat of up to 3 times

<400> SEQUENCE: 168
ccactctctc tcttttcagc t                                                    21

<210> SEQ ID NO 169
<211> LENGTH: 27
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 3, 6, 7, 10, 13, 17, 19, 22, 24, 25
<223> OTHER INFORMATION: Locked nucleic acid
<220> FEATURE:
<221> NAME/KEY: misc_feature
<222> LOCATION: 27
<223> OTHER INFORMATION: Inverted deoxythymidine
```

```
<220> FEATURE:
<221> NAME/KEY: misc_feature
<222> LOCATION: 27
<223> OTHER INFORMATION: Can be present in repeat of up to 3 times

<400> SEQUENCE: 169
taggtccact ctctctcttt tcagcat                                              27

<210> SEQ ID NO 170
<211> LENGTH: 24
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 3, 5, 6, 7, 8, 9, 10, 17, 18, 19, 20, 21, 22
<223> OTHER INFORMATION: Locked nucleic acid
<220> FEATURE:
<221> NAME/KEY: misc_feature
<222> LOCATION: 24
<223> OTHER INFORMATION: Inverted deoxythymidine
<220> FEATURE:
<221> NAME/KEY: misc_feature
<222> LOCATION: 24
<223> OTHER INFORMATION: Can be present in repeat of up to 3 times

<400> SEQUENCE: 170
gaatcaatag tttttctgc ctct                                                  24

<210> SEQ ID NO 171
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 3, 4, 6, 7, 8, 10, 11, 12, 13, 19, 20, 21, 22
<223> OTHER INFORMATION: Locked nucleic acid
<220> FEATURE:
<221> NAME/KEY: misc_feature
<222> LOCATION: 23
<223> OTHER INFORMATION: Inverted deoxythymidine
<220> FEATURE:
<221> NAME/KEY: misc_feature
<222> LOCATION: 23
<223> OTHER INFORMATION: Can be present in repeat of up to 3 times

<400> SEQUENCE: 171
tcagaatcaa tagtttttc tgt                                                   23

<210> SEQ ID NO 172
<211> LENGTH: 24
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 1, 3, 5, 6, 7, 8, 9, 10, 17, 18, 19, 20, 21, 22
<223> OTHER INFORMATION: Locked nucleic acid
<220> FEATURE:
<221> NAME/KEY: misc_feature
<222> LOCATION: 24
<223> OTHER INFORMATION: Inverted deoxythymidine
<220> FEATURE:
<221> NAME/KEY: misc_feature
<222> LOCATION: 24
<223> OTHER INFORMATION: Can be present in repeat of up to 3 times

<400> SEQUENCE: 172
```
gaatcaatag attttactgc ctct                                              24

<210> SEQ ID NO 173
<211> LENGTH: 23
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 4, 5, 6, 7, 8, 9, 17, 18, 19, 20, 21
<223> OTHER INFORMATION: Locked nucleic acid
<220> FEATURE:
<221> NAME/KEY: misc_feature
<222> LOCATION: 23
<223> OTHER INFORMATION: Inverted deoxythymidine
<220> FEATURE:
<221> NAME/KEY: misc_feature
<222> LOCATION: 23
<223> OTHER INFORMATION: Can be present in repeat of up to 3 times

<400> SEQUENCE: 173
aatcaatagt tttttctgcc tct                                               23

<210> SEQ ID NO 174
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 3, 5, 6, 7, 8, 10, 12, 14
<223> OTHER INFORMATION: Locked nucleic acid
<220> FEATURE:
<221> NAME/KEY: misc_feature
<222> LOCATION: 16
<223> OTHER INFORMATION: Inverted deoxythymidine
<220> FEATURE:
<221> NAME/KEY: misc_feature
<222> LOCATION: 16
<223> OTHER INFORMATION: Can be present in repeat of up to 3 times

<400> SEQUENCE: 174
tccttctctg agtggt                                                       16

<210> SEQ ID NO 175
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 4, 5, 7, 8, 11, 12, 13
<223> OTHER INFORMATION: Locked nucleic acid
<220> FEATURE:
<221> NAME/KEY: misc_feature
<222> LOCATION: 16
<223> OTHER INFORMATION: Inverted deoxythymidine
<220> FEATURE:
<221> NAME/KEY: misc_feature
<222> LOCATION: 16
<223> OTHER INFORMATION: Can be present in repeat of up to 3 times

<400> SEQUENCE: 175
gctccttctc tgagtt                                                       16

<210> SEQ ID NO 176
<211> LENGTH: 16
<212> TYPE: DNA
<213> ORGANISM: Artificial Sequence

```
<220> FEATURE:
<223> OTHER INFORMATION: Synthetic Construct
<220> FEATURE:
<221> NAME/KEY: misc_feature
<222> LOCATION: 2, 3, 6, 7, 10, 11, 12, 14
<223> OTHER INFORMATION: Locked nucleic acid
<220> FEATURE:
<221> NAME/KEY: misc_feature
<222> LOCATION: 16
<223> OTHER INFORMATION: Inverted deoxythymidine
<220> FEATURE:
<221> NAME/KEY: misc_feature
<222> LOCATION: 16
<223> OTHER INFORMATION: Can be present in repeat of up to 3 times

<400> SEQUENCE: 176
tccttctctg agtggt                                                  16

<210> SEQ ID NO 177
<211> LENGTH: 16
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: 2, 4, 5, 8, 9, 11, 12, 13, 14
<223> OTHER INFORMATION: Locked nucleic acid
<220> FEATURE:
<221> NAME/KEY: misc_feature
<222> LOCATION: 16
<223> OTHER INFORMATION: Inverted deoxythymidine
<220> FEATURE:
<221> NAME/KEY: misc_feature
<222> LOCATION: 16
<223> OTHER INFORMATION: Can be present in repeat of up to 3 times

<400> SEQUENCE: 177
gctccttctc tgagtt                                                  16

<210> SEQ ID NO 178
<211> LENGTH: 13
<212> TYPE: DNA
<213> ORGANISM: Artificial Sequence
<220> FEATURE:
<223> OTHER INFORMATION: Synthetic Construct

<400> SEQUENCE: 178
agctgatggc gta                                                     13

<210> SEQ ID NO 179
<211> LENGTH: 14
<212> TYPE: DNA
<213> ORGANISM: Artificial Sequence
<220> FEATURE:
<223> OTHER INFORMATION: Synthetic Construct

<400> SEQUENCE: 179
tggagctgat ggcg                                                    14

<210> SEQ ID NO 180
<211> LENGTH: 12
<212> TYPE: DNA
<213> ORGANISM: Artificial Sequence
<220> FEATURE:
<223> OTHER INFORMATION: Synthetic Construct

<400> SEQUENCE: 180
tggagctgat gg                                                      12
```

<210> SEQ ID NO 181
<211> LENGTH: 12
<212> TYPE: DNA
<213> ORGANISM: Artificial Sequence
<220> FEATURE:
<223> OTHER INFORMATION: Synthetic Construct

<400> SEQUENCE: 181
gctgatggcg ta                                                          12

<210> SEQ ID NO 182
<211> LENGTH: 16
<212> TYPE: DNA
<213> ORGANISM: Artificial Sequence
<220> FEATURE:
<223> OTHER INFORMATION: Synthetic Construct

<400> SEQUENCE: 182
tggagctgtt ggtggc                                                      16

<210> SEQ ID NO 183
<211> LENGTH: 13
<212> TYPE: DNA
<213> ORGANISM: Artificial Sequence
<220> FEATURE:
<223> OTHER INFORMATION: Synthetic Construct

<400> SEQUENCE: 183
ggagctgttg gtg                                                         13

<210> SEQ ID NO 184
<211> LENGTH: 13
<212> TYPE: DNA
<213> ORGANISM: Artificial Sequence
<220> FEATURE:
<223> OTHER INFORMATION: Synthetic Construct

<400> SEQUENCE: 184
tggagctgtt ggt                                                         13

<210> SEQ ID NO 185
<211> LENGTH: 15
<212> TYPE: DNA
<213> ORGANISM: Artificial Sequence
<220> FEATURE:
<223> OTHER INFORMATION: Synthetic Construct

<400> SEQUENCE: 185
tggagctgta ggtgg                                                       15

<210> SEQ ID NO 186
<211> LENGTH: 17
<212> TYPE: DNA
<213> ORGANISM: Artificial Sequence
<220> FEATURE:
<223> OTHER INFORMATION: Synthetic Construct

<400> SEQUENCE: 186
ttggagctag tggcgta                                                     17

<210> SEQ ID NO 187
<211> LENGTH: 15
<212> TYPE: DNA
<213> ORGANISM: Artificial Sequence
<220> FEATURE:
<223> OTHER INFORMATION: Synthetic Construct

```
<400> SEQUENCE: 187
gctagtggcg taggc                                             15

<210> SEQ ID NO 188
<211> LENGTH: 12
<212> TYPE: DNA
<213> ORGANISM: Artificial Sequence
<220> FEATURE:
<223> OTHER INFORMATION: Synthetic Construct

<400> SEQUENCE: 188
agctagtggc gt                                                12

<210> SEQ ID NO 189
<211> LENGTH: 14
<212> TYPE: DNA
<213> ORGANISM: Artificial Sequence
<220> FEATURE:
<223> OTHER INFORMATION: Synthetic Construct

<400> SEQUENCE: 189
gttggagcta gtgg                                              14

<210> SEQ ID NO 190
<211> LENGTH: 11
<212> TYPE: DNA
<213> ORGANISM: Artificial Sequence
<220> FEATURE:
<223> OTHER INFORMATION: Synthetic Construct

<400> SEQUENCE: 190
ggagctagtg g                                                 11

<210> SEQ ID NO 191
<211> LENGTH: 14
<212> TYPE: DNA
<213> ORGANISM: Artificial Sequence
<220> FEATURE:
<223> OTHER INFORMATION: Synthetic Construct

<400> SEQUENCE: 191
ggtgacgtag gcaa                                              14

<210> SEQ ID NO 192
<211> LENGTH: 15
<212> TYPE: DNA
<213> ORGANISM: Artificial Sequence
<220> FEATURE:
<223> OTHER INFORMATION: Synthetic Construct

<400> SEQUENCE: 192
tgacgtaggc aagag                                             15

<210> SEQ ID NO 193
<211> LENGTH: 14
<212> TYPE: DNA
<213> ORGANISM: Artificial Sequence
<220> FEATURE:
<223> OTHER INFORMATION: Synthetic Construct

<400> SEQUENCE: 193
gctggtgacg tagg                                              14

<210> SEQ ID NO 194
```

```
<211> LENGTH: 14
<212> TYPE: DNA
<213> ORGANISM: Artificial Sequence
<220> FEATURE:
<223> OTHER INFORMATION: Synthetic Construct

<400> SEQUENCE: 194
agctggtgac gtag                                                    14

<210> SEQ ID NO 195
<211> LENGTH: 14
<212> TYPE: DNA
<213> ORGANISM: Artificial Sequence
<220> FEATURE:
<223> OTHER INFORMATION: Synthetic Construct

<400> SEQUENCE: 195
ggagctggtg acgt                                                    14

<210> SEQ ID NO 196
<211> LENGTH: 17
<212> TYPE: DNA
<213> ORGANISM: Artificial Sequence
<220> FEATURE:
<223> OTHER INFORMATION: Synthetic Construct

<400> SEQUENCE: 196
tacagagaaa tctcgat                                                 17

<210> SEQ ID NO 197
<211> LENGTH: 14
<212> TYPE: DNA
<213> ORGANISM: Artificial Sequence
<220> FEATURE:
<223> OTHER INFORMATION: Synthetic Construct

<400> SEQUENCE: 197
tacagagaaa tctc                                                    14

<210> SEQ ID NO 198
<211> LENGTH: 16
<212> TYPE: DNA
<213> ORGANISM: Artificial Sequence
<220> FEATURE:
<223> OTHER INFORMATION: Synthetic Construct

<400> SEQUENCE: 198
ctagctacag agaaat                                                  16

<210> SEQ ID NO 199
<211> LENGTH: 15
<212> TYPE: DNA
<213> ORGANISM: Artificial Sequence
<220> FEATURE:
<223> OTHER INFORMATION: Synthetic Construct

<400> SEQUENCE: 199
ctagctacag agaaa                                                   15

<210> SEQ ID NO 200
<211> LENGTH: 13
<212> TYPE: DNA
<213> ORGANISM: Artificial Sequence
<220> FEATURE:
<223> OTHER INFORMATION: Synthetic Construct

<400> SEQUENCE: 200
```
tctagctaca gag                                                              13

<210> SEQ ID NO 201
<211> LENGTH: 19
<212> TYPE: DNA
<213> ORGANISM: Artificial Sequence
<220> FEATURE:
<223> OTHER INFORMATION: Synthetic Construct

<400> SEQUENCE: 201
gtctagctac agaaaaatc                                                        19

<210> SEQ ID NO 202
<211> LENGTH: 14
<212> TYPE: DNA
<213> ORGANISM: Artificial Sequence
<220> FEATURE:
<223> OTHER INFORMATION: Synthetic Construct

<400> SEQUENCE: 202
tagctacaga aaaa                                                             14

<210> SEQ ID NO 203
<211> LENGTH: 17
<212> TYPE: DNA
<213> ORGANISM: Artificial Sequence
<220> FEATURE:
<223> OTHER INFORMATION: Synthetic Construct

<400> SEQUENCE: 203
tctagctaca gaaaaat                                                          17

<210> SEQ ID NO 204
<211> LENGTH: 18
<212> TYPE: DNA
<213> ORGANISM: Artificial Sequence
<220> FEATURE:
<223> OTHER INFORMATION: Synthetic Construct

<400> SEQUENCE: 204
tctagctaca gaaaaatc                                                         18

<210> SEQ ID NO 205
<211> LENGTH: 15
<212> TYPE: DNA
<213> ORGANISM: Artificial Sequence
<220> FEATURE:
<223> OTHER INFORMATION: Synthetic Construct

<400> SEQUENCE: 205
aggagctgtg gcagt                                                            15

<210> SEQ ID NO 206
<211> LENGTH: 16
<212> TYPE: DNA
<213> ORGANISM: Artificial Sequence
<220> FEATURE:
<223> OTHER INFORMATION: Synthetic Construct

<400> SEQUENCE: 206
aggagctgtg gcagtg                                                           16

<210> SEQ ID NO 207
<211> LENGTH: 14
<212> TYPE: DNA

```
<213> ORGANISM: Artificial Sequence
<220> FEATURE:
<223> OTHER INFORMATION: Synthetic Construct

<400> SEQUENCE: 207
gctgtggcag tggc                                                        14

<210> SEQ ID NO 208
<211> LENGTH: 15
<212> TYPE: DNA
<213> ORGANISM: Artificial Sequence
<220> FEATURE:
<223> OTHER INFORMATION: Synthetic Construct

<400> SEQUENCE: 208
gctgtggcag tggca                                                       15

<210> SEQ ID NO 209
<211> LENGTH: 15
<212> TYPE: DNA
<213> ORGANISM: Artificial Sequence
<220> FEATURE:
<223> OTHER INFORMATION: Synthetic Construct

<400> SEQUENCE: 209
aaggagctgt ggcag                                                       15

<210> SEQ ID NO 210
<211> LENGTH: 16
<212> TYPE: DNA
<213> ORGANISM: Artificial Sequence
<220> FEATURE:
<223> OTHER INFORMATION: Synthetic Construct

<400> SEQUENCE: 210
ggagctgtga tagtgg                                                      16

<210> SEQ ID NO 211
<211> LENGTH: 16
<212> TYPE: DNA
<213> ORGANISM: Artificial Sequence
<220> FEATURE:
<223> OTHER INFORMATION: Synthetic Construct

<400> SEQUENCE: 211
gagctgtgat agtggc                                                      16

<210> SEQ ID NO 212
<211> LENGTH: 16
<212> TYPE: DNA
<213> ORGANISM: Artificial Sequence
<220> FEATURE:
<223> OTHER INFORMATION: Synthetic Construct

<400> SEQUENCE: 212
agctgtgata gtggca                                                      16

<210> SEQ ID NO 213
<211> LENGTH: 16
<212> TYPE: DNA
<213> ORGANISM: Artificial Sequence
<220> FEATURE:
<223> OTHER INFORMATION: Synthetic Construct

<400> SEQUENCE: 213
agaaggagct gtgata                                                      16
```

<210> SEQ ID NO 214
<211> LENGTH: 11
<212> TYPE: DNA
<213> ORGANISM: Artificial Sequence
<220> FEATURE:
<223> OTHER INFORMATION: Synthetic Construct

<400> SEQUENCE: 214
ggagctgtga t                                                        11

<210> SEQ ID NO 215
<211> LENGTH: 16
<212> TYPE: DNA
<213> ORGANISM: Artificial Sequence
<220> FEATURE:
<223> OTHER INFORMATION: Synthetic Construct

<400> SEQUENCE: 215
actcagaaaa ggagct                                                   16

<210> SEQ ID NO 216
<211> LENGTH: 17
<212> TYPE: DNA
<213> ORGANISM: Artificial Sequence
<220> FEATURE:
<223> OTHER INFORMATION: Synthetic Construct

<400> SEQUENCE: 216
taccactcag aaaagga                                                  17

<210> SEQ ID NO 217
<211> LENGTH: 20
<212> TYPE: DNA
<213> ORGANISM: Artificial Sequence
<220> FEATURE:
<223> OTHER INFORMATION: Synthetic Construct

<400> SEQUENCE: 217
tttaccactc agaaaaggag                                               20

<210> SEQ ID NO 218
<211> LENGTH: 16
<212> TYPE: DNA
<213> ORGANISM: Artificial Sequence
<220> FEATURE:
<223> OTHER INFORMATION: Synthetic Construct

<400> SEQUENCE: 218
ttaccactca gaaaag                                                   16

<210> SEQ ID NO 219
<211> LENGTH: 16
<212> TYPE: DNA
<213> ORGANISM: Artificial Sequence
<220> FEATURE:
<223> OTHER INFORMATION: Synthetic Construct

<400> SEQUENCE: 219
cagaaaagga gctgtg                                                   16

<210> SEQ ID NO 220
<211> LENGTH: 15
<212> TYPE: DNA
<213> ORGANISM: Artificial Sequence
<220> FEATURE:

<223> OTHER INFORMATION: Synthetic Construct

<400> SEQUENCE: 220
actcagagga ggagc                                                          15

<210> SEQ ID NO 221
<211> LENGTH: 15
<212> TYPE: DNA
<213> ORGANISM: Artificial Sequence
<220> FEATURE:
<223> OTHER INFORMATION: Synthetic Construct

<400> SEQUENCE: 221
ttaccactca gagga                                                          15

<210> SEQ ID NO 222
<211> LENGTH: 17
<212> TYPE: DNA
<213> ORGANISM: Artificial Sequence
<220> FEATURE:
<223> OTHER INFORMATION: Synthetic Construct

<400> SEQUENCE: 222
ttaccactca gaggagg                                                        17

<210> SEQ ID NO 223
<211> LENGTH: 16
<212> TYPE: DNA
<213> ORGANISM: Artificial Sequence
<220> FEATURE:
<223> OTHER INFORMATION: Synthetic Construct

<400> SEQUENCE: 223
ttaacactca gaggag                                                         16

<210> SEQ ID NO 224
<211> LENGTH: 17
<212> TYPE: DNA
<213> ORGANISM: Artificial Sequence
<220> FEATURE:
<223> OTHER INFORMATION: Synthetic Construct

<400> SEQUENCE: 224
ttaccaatca gaggagg                                                        17

<210> SEQ ID NO 225
<211> LENGTH: 18
<212> TYPE: DNA
<213> ORGANISM: Artificial Sequence
<220> FEATURE:
<223> OTHER INFORMATION: Synthetic Construct

<400> SEQUENCE: 225
aaatagcaga aataaaag                                                       18

<210> SEQ ID NO 226
<211> LENGTH: 17
<212> TYPE: DNA
<213> ORGANISM: Artificial Sequence
<220> FEATURE:
<223> OTHER INFORMATION: Synthetic Construct

<400> SEQUENCE: 226
gaaataaaag attggaa                                                        17

```
<210> SEQ ID NO 227
<211> LENGTH: 15
<212> TYPE: DNA
<213> ORGANISM: Artificial Sequence
<220> FEATURE:
<223> OTHER INFORMATION: Synthetic Construct

<400> SEQUENCE: 227
agaaataaaa gattg                                                          15

<210> SEQ ID NO 228
<211> LENGTH: 15
<212> TYPE: DNA
<213> ORGANISM: Artificial Sequence
<220> FEATURE:
<223> OTHER INFORMATION: Synthetic Construct

<400> SEQUENCE: 228
gaaataaatg aatgg                                                          15

<210> SEQ ID NO 229
<211> LENGTH: 15
<212> TYPE: DNA
<213> ORGANISM: Artificial Sequence
<220> FEATURE:
<223> OTHER INFORMATION: Synthetic Construct

<400> SEQUENCE: 229
cagaaataaa agatt                                                          15

<210> SEQ ID NO 230
<211> LENGTH: 14
<212> TYPE: DNA
<213> ORGANISM: Artificial Sequence
<220> FEATURE:
<223> OTHER INFORMATION: Synthetic Construct

<400> SEQUENCE: 230
tttgggtgtc taag                                                           14

<210> SEQ ID NO 231
<211> LENGTH: 18
<212> TYPE: DNA
<213> ORGANISM: Artificial Sequence
<220> FEATURE:
<223> OTHER INFORMATION: Synthetic Construct

<400> SEQUENCE: 231
gggtgtctaa gcaccact                                                       18

<210> SEQ ID NO 232
<211> LENGTH: 15
<212> TYPE: DNA
<213> ORGANISM: Artificial Sequence
<220> FEATURE:
<223> OTHER INFORMATION: Synthetic Construct

<400> SEQUENCE: 232
ctaagcacca cttttt                                                         15

<210> SEQ ID NO 233
<211> LENGTH: 14
<212> TYPE: DNA
<213> ORGANISM: Artificial Sequence
<220> FEATURE:
<223> OTHER INFORMATION: Synthetic Construct
```

```
<400> SEQUENCE: 233
ttttgggtgt ctaa                                                    14

<210> SEQ ID NO 234
<211> LENGTH: 15
<212> TYPE: DNA
<213> ORGANISM: Artificial Sequence
<220> FEATURE:
<223> OTHER INFORMATION: Synthetic Construct

<400> SEQUENCE: 234
ggtgtctaag cacca                                                   15

<210> SEQ ID NO 235
<211> LENGTH: 17
<212> TYPE: DNA
<213> ORGANISM: Artificial Sequence
<220> FEATURE:
<223> OTHER INFORMATION: Synthetic Construct

<400> SEQUENCE: 235
aagtgagaag tacctaa                                                 17

<210> SEQ ID NO 236
<211> LENGTH: 14
<212> TYPE: DNA
<213> ORGANISM: Artificial Sequence
<220> FEATURE:
<223> OTHER INFORMATION: Synthetic Construct

<400> SEQUENCE: 236
tcaaaccaag tgag                                                    14

<210> SEQ ID NO 237
<211> LENGTH: 15
<212> TYPE: DNA
<213> ORGANISM: Artificial Sequence
<220> FEATURE:
<223> OTHER INFORMATION: Synthetic Construct

<400> SEQUENCE: 237
accaagtgag aagta                                                   15

<210> SEQ ID NO 238
<211> LENGTH: 17
<212> TYPE: DNA
<213> ORGANISM: Artificial Sequence
<220> FEATURE:
<223> OTHER INFORMATION: Synthetic Construct

<400> SEQUENCE: 238
agctcaaacc aagtgag                                                 17

<210> SEQ ID NO 239
<211> LENGTH: 15
<212> TYPE: DNA
<213> ORGANISM: Artificial Sequence
<220> FEATURE:
<223> OTHER INFORMATION: Synthetic Construct

<400> SEQUENCE: 239
gcacctactg ctgaa                                                   15

<210> SEQ ID NO 240
<211> LENGTH: 16
```

```
<212> TYPE: DNA
<213> ORGANISM: Artificial Sequence
<220> FEATURE:
<223> OTHER INFORMATION: Synthetic Construct

<400> SEQUENCE: 240
acctactgct gaaaag                                                        16

<210> SEQ ID NO 241
<211> LENGTH: 17
<212> TYPE: DNA
<213> ORGANISM: Artificial Sequence
<220> FEATURE:
<223> OTHER INFORMATION: Synthetic Construct

<400> SEQUENCE: 241
tgctgaaaag agagagt                                                       17

<210> SEQ ID NO 242
<211> LENGTH: 18
<212> TYPE: DNA
<213> ORGANISM: Artificial Sequence
<220> FEATURE:
<223> OTHER INFORMATION: Synthetic Construct

<400> SEQUENCE: 242
cctactgctg aaaagaga                                                      18

<210> SEQ ID NO 243
<211> LENGTH: 17
<212> TYPE: DNA
<213> ORGANISM: Artificial Sequence
<220> FEATURE:
<223> OTHER INFORMATION: Synthetic Construct

<400> SEQUENCE: 243
gcagaaaaaa actattg                                                       17

<210> SEQ ID NO 244
<211> LENGTH: 19
<212> TYPE: DNA
<213> ORGANISM: Artificial Sequence
<220> FEATURE:
<223> OTHER INFORMATION: Synthetic Construct

<400> SEQUENCE: 244
cagaaaaaaa ctattgatt                                                     19

<210> SEQ ID NO 245
<211> LENGTH: 21
<212> TYPE: DNA
<213> ORGANISM: Artificial Sequence
<220> FEATURE:
<223> OTHER INFORMATION: Synthetic Construct

<400> SEQUENCE: 245
agaaagaggc agaaaaaaac t                                                  21

<210> SEQ ID NO 246
<211> LENGTH: 17
<212> TYPE: DNA
<213> ORGANISM: Artificial Sequence
<220> FEATURE:
<223> OTHER INFORMATION: Synthetic Construct
```

```
<400> SEQUENCE: 246
gaggcagaaa aaaacta                                              17
```

IMAGE DIFFERENTIATED MULTIPLEX ASSAYS FOR MULTIPLEX DETECTION OF DNA MUTATIONS

CROSS REFERENCE TO RELATED APPLICATIONS

This application claims the priority benefit of U.S. Provisional Application Ser. No. 62/432,534, filed Dec. 9, 2016, and U.S. application Ser. No. 15/836,809, filed Dec. 8, 2017, each of which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 695502001220SUBSEQLIST2.TXT, date recorded: Jan. 8, 2018, Apr. 2, 2018, size: 121 KB).

FIELD

Provided herein are methods for multiplex detection of DNA mutations in a sample using microcarriers, as well as kits related thereto. The microcarriers are encoded with an identifier and include a probe for detection of a DNA mutation of interest.

BACKGROUND

Early detection is a critically important factor in reducing the number of deaths attributable to cancer, since growth and metastasis of more advanced tumors are associated with increased mortality. Most cases of colorectal cancer are sporadic, rather than hereditary, but several genes and even types of specific mutations are commonly seen in these sporadic cases. For example, the KRAS gene is thought to be mutated in 30-50% of colorectal cancers (Mundade, R. et al. (2014) *Oncoscience* 1:400-6). While existing techniques such as colonoscopy and sigmoidoscopy are effective in detecting many types of early colorectal cancers, they suffer from low patient acceptance due to their invasive nature. Alternatives such as fecal DNA tests have been tested (Carethers, J. M. (2014) *Clin. Gastroenterol. Hepatol.* 12:377-81), but there is a need for comprehensive tests that examine multiple genes simultaneously with a high level of accuracy, rather than individual gene testing.

Immunological and molecular diagnostic assays play a critical role both in the research and clinical fields. Often it is necessary to perform assays for a panel of multiple targets to gain a meaningful or bird's-eye view of results to facilitate research or clinical decision-making. This is particularly true in the era of genomics and proteomics, where an abundance of genetic markers and/or biomarkers are thought to influence or be predictive of particular disease states. In theory, assays of multiple targets can be accomplished by testing each target separately in parallel or sequentially in different reaction vessels (i.e., multiple singleplexing). However, not only are assays adopting a singleplexing strategy often cumbersome, but they also typically required large sample volumes, especially when the targets to be analyzed are large in number.

A multiplex assay simultaneously measures multiple analytes (two or more) in a single assay. Multiplex assays are commonly used in high-throughput screening settings, where many specimens can be analyzed at once. It is the ability to assay many analytes simultaneously and many specimens in parallel that is the hallmark of multiplex assays and is the reason that such assays have become a powerful tool in fields ranging from drug discovery to functional genomics to clinical diagnostics. In contrast to singleplexing, by combining all targets in the same reaction vessel, the assay is much less cumbersome and much easier to perform, since only one reaction vessel is handled per sample. The required test samples can thus be dramatically reduced in volume, which is especially important when samples (e.g., tumor tissues, cerebral spinal fluid, or bone marrow) are difficult and/or invasive to retrieve in large quantities. Equally important is the fact that the reagent cost can be decreased and assay throughput increased drastically.

Many assays of complex macromolecule samples are composed of two steps. In the first step, agents capable of specifically capturing the target macromolecules are attached to a solid phase surface. These immobilized molecules may be used to capture the target macromolecules from a complex sample by various means, such as hybridization (e.g., in DNA, RNA based assays). In the second step, detection molecules are incubated with and bind to the complex of capture molecule and the target, emitting signals such as fluorescence or other electromagnetic signals. The amount of the target is then quantified by the intensity of those signals.

Multiplex assays may be carried out by utilizing multiple capture agents, each specific for a different target macromolecule. In chip-based array multiplex assays, each type of capture agent (e.g., a single-stranded oligonucleotide probe) is attached to a pre-defined position on the chip. The amount of multiplex targets in a complex sample is determined by measuring the signal of the detection molecule at each position corresponding to a type of capture agent. In suspension array multiplex assays, microparticles or microcarriers are suspended in the assay solution. These microparticles or microcarriers contain an identification element, which may be embedded, printed, or otherwise generated by one or more elements of the microparticle/microcarrier. Each type of capture agent is immobilized to particles with the same ID, and the signals emitted from the detection molecules on the surface of the particles with a particular ID reflect the amount of the corresponding target.

One application for which multiplex assays are particularly well-suited is detection of DNA mutations. In particular, detecting mutations associated with cancer can aid in early diagnosis of cancer and in detection of tumors that are small and/or in locations not easily found through conventional diagnostic tools, such as colonoscopies. See, e.g., U.S. Pat. No. 7,833,757. However, existing diagnostic techniques are often expensive or time-consuming Methods for detecting multiple gene mutations using serial, individual assays are time consuming and suffer from lack of uniformity if carried out using different assay types (see Schneider, M. et al. (2011) *Cancers* 3:91-105). Applying multiplex assay technologies such as analog-encoded microcarriers to this problem can provide cheaper, quicker assays with more accurate results while enabling multiplex screening for many mutations known to be correlated with tumorigenesis in a single assay.

Therefore, a need exists for applying a robust and sensitive multiplex assay system to the problem of screening for DNA mutations. This provides a mechanism for multiplex detection of many DNA mutations in a single assay.

All publications, patents, and patent applications cited herein are hereby incorporated by reference in their entirety for all purposes.

BRIEF SUMMARY

To meet this need, provided herein, inter alia, are methods and kits using microcarriers, encoded with a unique identifier, that include a probe for detecting a DNA mutation, e.g., a mutation associated with colorectal cancer. These microcarriers may be used in multiplexed assays in which each microcarrier includes a probe for detecting a particular DNA mutation (e.g., a mutation in the KRAS, BRAF, CTNNB1, or APC gene) and an identifier for correlation of the microcarrier and its associated probe. The methods and kits disclosed herein may find use, e.g., in monitoring colorectal cancer, monitoring response to treatment of colorectal cancer, and/or early screening/detection of colorectal cancer.

Accordingly, in one aspect, provided herein is a method for detecting the presence of DNA mutations in the KRAS, BRAF, CTNNB1, and APC genes, the method comprising: (a) isolating DNA from a sample; (b) amplifying the isolated DNA by polymerase chain reaction (PCR) using primer pairs specific for the loci of one or more DNA mutations in each of the KRAS, BRAF, CTNNB1, and APC genes; (c) hybridizing the amplified DNA with at least four probes, said at least four probes comprising one or more probes specific for a DNA mutation in each of the KRAS, BRAF, CTNNB1, and APC genes, wherein each of said at least four probes is coupled to a microcarrier, and wherein each of the microcarriers comprises an identifier corresponding to the probe coupled thereto; (d) detecting presence or absence of hybridization of the amplified DNA with said at least four probes, wherein hybridization between the amplified DNA and one of the probes indicates the presence of the DNA mutation corresponding to the probe; (e) detecting the identifiers of the microcarriers; and (f) correlating the detected identifiers of the microcarriers with the detected presence or absence of hybridization of the amplified DNA to the corresponding probes of the microcarriers. Further provided herein is a method for detecting the presence of DNA mutations in the KRAS, BRAF, CTNNB1, and APC genes, the method comprising: (a) amplifying isolated DNA from a sample by polymerase chain reaction (PCR) using primer pairs specific for the loci of one or more DNA mutations in each of the KRAS, BRAF, CTNNB1, and APC genes; (b) hybridizing the amplified DNA with at least four probes, said at least four probes comprising one or more probes specific for a DNA mutation in each of the KRAS, BRAF, CTNNB1, and APC genes, wherein each of said at least four probes is coupled to a microcarrier, and wherein each of the microcarriers comprises an identifier corresponding to the probe coupled thereto; (c) detecting presence or absence of hybridization of the amplified DNA with said at least four probes, wherein hybridization between the amplified DNA and one of the probes indicates the presence of the DNA mutation corresponding to the probe; (d) detecting the identifiers of the microcarriers; and (e) correlating the detected identifiers of the microcarriers with the detected presence or absence of hybridization of the amplified DNA to the corresponding probes of the microcarriers. In some embodiments, the KRAS, BRAF, CTNNB1, and APC genes are human genes. In some embodiments, step (b) comprises amplifying the isolated DNA by PCR in the presence of at least four blocking nucleic acids, wherein each of said at least four blocking nucleic acids hybridizes with a wild-type DNA locus corresponding with one of the DNA mutations in the KRAS, BRAF, CTNNB1, or APC genes and prevents amplification of the wild-type DNA locus. In some embodiments, each of said at least four blocking nucleic acids comprises: a single-stranded oligonucleotide that hybridizes with the corresponding wild-type DNA locus; and a 3' terminal moiety that blocks extension from the single-stranded oligonucleotide. In some embodiments, the 3' terminal moiety comprises one or more inverted deoxythymidines. In some embodiments, each of said at least four blocking nucleic acids comprises one or more modified nucleotides selected from the group consisting of locked nucleic acids (LNAs), peptide nucleic acids (PNAs), hexose nucleic acids (HNAs), threose nucleic acids (TNAs), glycol nucleic acids (GNAs), and cyclohexenyl nucleic acids (CeNAs). In some embodiments, the one or more DNA mutations in the KRAS gene comprise one or more DNA mutations encoding a G12D, G12V, G12S, or G13D mutated KRAS protein. In some embodiments, at least one of the at least four blocking nucleic acids comprises the sequence TACGCCACCAGCT(invdT)$_n$, wherein n is 1, 2, or 3 (SEQ ID NO:3), TTGGAGCTGGTGGCGTA(invdT)$_n$, wherein n is 1, 2, or 3 (SEQ ID NO:142), GCTGGTGGCGTAGGCA (invdT)$_n$, wherein n is 1, 2, or 3 (SEQ ID NO:143), GCTGGTGGCGTAGGC(invdT)$_n$, wherein n is 1, 2, or 3 (SEQ ID NO:144), or TTGGAGCTGGTGGCGT(invdT)$_n$, wherein n is 1, 2, or 3 (SEQ ID NO:145), with italicized nucleic acids representing locked nucleic acids. In some embodiments, the one or more DNA mutations in the BRAF gene comprise one or more DNA mutations encoding a V600E mutated BRAF protein. In some embodiments, at least one of the at least four blocking nucleic acids comprises the sequence GAGATTTCACTGTAGC(invdT)$_n$, wherein n is 1, 2, or 3 (SEQ ID NO:10), GAGATTT-CACTGTAGC(invdT)$_n$, wherein n is 1, 2, or 3 (SEQ ID NO:146), GAGATTTCACTGTAGC(invdT)$_n$, wherein n is 1, 2, or 3 (SEQ ID NO: 147), GAGATTTCACTGTAGC (invdT)$_n$, wherein n is 1, 2, or 3 (SEQ ID NO:148), or GAGATTTCACTGTAGC(invdT)$_n$, wherein n is 1, 2, or 3 (SEQ ID NO:149), with italicized nucleic acids representing locked nucleic acids. In some embodiments, the one or more DNA mutations in the CTNNB1 gene comprise at least a first CTNNB1 mutation encoding a T41A or T41I mutated CTNNB1 protein. In some embodiments, at least one of the at least four blocking nucleic acids comprises the sequence GCCACTACCACAGCT(invdT)$_n$, wherein n is 1, 2, or 3 (SEQ ID NO:15), TGCCACTACCACAG(invdT)$_n$, wherein n is 1, 2, or 3 (SEQ ID NO:150), CACTACCACAGCTCC (invdT)$_n$, wherein n is 1, 2, or 3 (SEQ ID NO:151), GCCAC-TACCACAGCT(invdT)$_n$, wherein n is 1, 2, or 3 (SEQ ID NO:152), or GCCACTACCACAGCT(invdT)$_n$, wherein n is 1, 2, or 3 (SEQ ID NO: 153), with italicized nucleic acids representing locked nucleic acids. In some embodiments, the one or more DNA mutations in the CTNNB1 gene comprise at least a first CTNNB1 mutation encoding an S45F or S45P mutated CTNNB1 protein. In some embodiments, at least one of the at least four blocking nucleic acids comprises the sequence GCTCCTTCTCTGAGT(invdT)$_n$, wherein n is 1, 2, or 3 (SEQ ID NO:20), TCCTTCTCTGAGTGG(invdT)$_n$, wherein n is 1, 2, or 3 (SEQ ID NO:174), GCTCCTTCTCT-GAGT(invdT)n, wherein n is 1, 2, or 3 (SEQ ID NO:175), TCCTTCTCTGAGTGG(invdT)n, wherein n is 1, 2, or 3 (SEQ ID NO:176), or GCTCCTTCTCTGAGT(invdT)n, wherein n is 1, 2, or 3 (SEQ ID NO:177), with italicized nucleic acids representing locked nucleic acids. In some embodiments, the one or more DNA mutations in the APC gene comprise at least a first APC mutation encoding a Q1367* mutated APC protein. In some embodiments, at least one of the at least 5 blocking nucleic acids comprises the sequence GTGCTCAGACACC(invdT)$_n$, wherein n is 1, 2, or 3 (SEQ ID NO:33), GTGCTCAGACACC (invdT)n, wherein n is 1, 2, or 3 (SEQ ID NO:158), AGTGGTGCTCAGACACCCA(invdT)n, wherein n is 1, 2, or 3 (SEQ ID NO:159), AGTGGTGCTCAGACACCCA (invdT)n, wherein n is 1, 2, or 3 (SEQ ID NO:160), or AGTGGTGCTCAGACACCCA(invdT)n, wherein n is 1, 2, or 3 (SEQ ID NO:161), with italicized nucleic acids representing locked nucleic acids. In some embodiments, the one or more DNA mutations in the APC gene comprise at least a first APC mutation encoding an R1450* mutated APC protein. In some embodiments, at least one of the at least four blocking nucleic acids comprises the sequence CTTCTCGCTTGGTT(invdT)$_n$, wherein n is 1, 2, or 3 (SEQ ID NO:37), GTACTTCTCGCTTGGT(invdT)n, wherein n is 1, 2, or 3 (SEQ ID NO:162), CTTCTCGCTTGGTT (invdT)n, wherein n is 1, 2, or 3 (SEQ ID NO:163), GTACTTCTCGCTTGGT(invdT)n, wherein n is 1, 2, or 3 (SEQ ID NO: 164), or GTACTTCTCGCTTGGT(invdT)n, wherein n is 1, 2, or 3 (SEQ ID NO: 165), with italicized nucleic acids representing locked nucleic acids. In some embodiments, the one or more DNA mutations in the APC gene comprise at least a first APC mutation encoding an E1309 frameshift mutated APC protein. In some embodiments, at least one of the at least four blocking nucleic acids comprises the sequence CTTTTCTTTTATTTCTGC (invdT)$_n$, wherein n is 1, 2, or 3 (SEQ ID NO:29), CTTTCTTTTATTTCTGC(invdT)n, wherein n is 1, 2, or 3 (SEQ ID NO:154), CTTTTCTTTTATTTCTGC(invdT)n, wherein n is 1, 2, or 3 (SEQ ID NO:155), CTTTTCTTTT-ATTTCTGC(invdT)n, wherein n is 1, 2, or 3 (SEQ ID NO:156), or CTTTTCTTTTATTTCTGC(invdT)n, wherein n is 1, 2, or 3 (SEQ ID NO:157), with italicized nucleic acids representing locked nucleic acids. In some embodiments, the one or more DNA mutations in the APC gene comprise at least a first APC mutation encoding an S1465 frameshift mutated APC protein. In some embodiments, at least one of the at least four blocking nucleic acids comprises the sequence CCACTCTCTCTCTTTCAGC(invdT)$_n$, wherein n is 1, 2, or 3 (SEQ ID NO:25), TAGGTCCACTCTCTCTCTTTTCAGCA(invdT)n, wherein n is 1, 2, or 3 (SEQ ID NO:166), TAGGTCCACTCTCTCTCTTTTCAGCA(invdT)n, wherein n is 1, 2, or 3 (SEQ ID NO:167), CCACTCTCTCTCTTTTCAGC (invdT)n, wherein n is 1, 2, or 3 (SEQ ID NO:168), or TAGGTCCACTCTCTCTCTTTTCAGCA (invdT)n, wherein n is 1, 2, or 3 (SEQ ID NO:169), with italicized nucleic acids representing locked nucleic acids. In some embodiments, the one or more DNA mutations in the APC gene comprise at least a first APC mutation encoding a T1556 frameshift mutated APC protein. In some embodiments, at least one of the at least four blocking nucleic acids comprises the sequence CAATAGTTTTTTCTGCC (invdT)$_n$, wherein n is 1, 2, or 3 (SEQ ID NO:41), GAAT-CAATAGTTTTTTCTGCCTC (invdT)n, wherein n is 1, 2, or 3 (SEQ ID NO:170), TCAGAATCAATAGTTTTTTCTG (invdT)n, wherein n is 1, 2, or 3 (SEQ ID NO:171), GAATCAATAGATTTTACTGCCTC (invdT)n, wherein n is 1, 2, or 3 (SEQ ID NO:172), or AAT-CAATAGTTTTTTCTGCCTC (invdT)n, wherein n is 1, 2, or 3 (SEQ ID NO:173), with italicized nucleic acids representing locked nucleic acids. In some embodiments, each of the primer pairs comprises a primer coupled to a detection reagent. In some embodiments, the detection reagent comprises a fluorescent detection reagent, and wherein detecting the presence or absence of hybridization of the amplified DNA with said at least four probes in step (d) comprises fluorescence imaging of the fluorescent detection reagent. In some embodiments, the detection reagent comprises biotin, and wherein detecting the presence or absence of hybridization of the amplified DNA with said at least four probes in step (d) comprises: (1) after hybridization in step (c), contacting the microcarriers with streptavidin conjugated to a signal-emitting entity; and (2) detecting a signal from the signal-emitting entity in association with the microcarriers. In some embodiments, the signal-emitting entity comprises phycoerythrin (PE). In some embodiments, detecting the identifiers of the microcarriers in step (e) comprises bright field imaging of the identifiers.

In some embodiments, the one or more DNA mutations in the KRAS gene comprise KRAS mutations encoding G12D, G12V, G12S, and G13D mutated KRAS proteins. In some embodiments, the probes specific for one or more DNA mutations in the KRAS gene comprise four probes comprising the sequences GGAGCTGATGG (SEQ ID NO:4), GGAGCTGTTGG (SEQ ID NO:5), TGGAGCTAGTGG (SEQ ID NO:6), and TGGAGCTGGTGACGT (SEQ ID NO:7), and wherein each of the four probes is coupled to a microcarrier with a different identifier. In some embodiments, each of the four probes further comprises eight nucleotides at the 5' end, wherein the eight nucleotides at the 5' end are adenine or thymine nucleotides, and wherein each of the four probes comprises at least 24 total nucleotides. In some embodiments, the four probes comprise: (1) a first probe comprising a sequence selected from the group consisting of GGAGCTGATGG (SEQ ID NO:4), AGCT-GATGGCGTA (SEQ ID NO:178), TGGAGCTGATGGCG (SEQ ID NO:179), TGGAGCTGATGG (SEQ ID NO:180), and GCTGATGGCGTA (SEQ ID NO:181); (2) a second probe comprising a sequence selected from the group consisting of GGAGCTGTTGG (SEQ ID NO:5), TGGAGCTGTTGGTGGC (SEQ ID NO:182), GGAGCTGTTGGTG (SEQ ID NO:183), TGGAGCTGTTGGT (SEQ ID NO:184), and TGGAGCTGTaGGTGG (SEQ ID NO:185); (3) a third probe comprising a sequence selected from the group consisting of TTGGAGCTAGTGGCGTA (SEQ ID NO:186), GCTAGTGGCGTAGGC (SEQ ID NO:187), AGCTAGTGGCGT (SEQ ID NO:188), GTTGGAGCTAGTGG (SEQ ID NO:189), and GGAGCTAGTGG (SEQ ID NO:190); and (4) a fourth probe comprising a sequence selected from the group consisting of GGTGACGTAGGCAA (SEQ ID NO: 191), TGACGTAGGCAAGAG (SEQ ID NO:192), GCTGGTGACGTAGG (SEQ ID NO:193), AGCTGGTGACGTAG (SEQ ID NO:194), and GGAGCTGGTGACGT (SEQ ID NO:195); and wherein each of the four probes is coupled to a microcarrier with a different identifier. In some embodiments, the four probes comprise: (1) a first probe comprising a sequence selected from the group consisting of TTTTTTTTTTT-TAAGGAGCTGATGG (SEQ ID NO:47), TTTTTTTTTTT-TAGCTGATGGCGTA (SEQ ID NO:74), TTTTTTTTT-TATGGAGCTGATGGCG (SEQ ID NO:75), TTTTTTTTTTTTATGGAGCTGATGG (SEQ ID NO:76), and TTTTTTTTTTTTGCTGATGGCGTA (SEQ ID NO:77); (2) a second probe comprising a sequence selected from the group consisting of TTTTTTTTTTT-TAAGGAGCTGTTGG (SEQ ID NO:48), TTTTTTTTATG-GAGCTGTTGGTGGC (SEQ ID NO:78), TTTTTTTTT-TAAGGAGCTGTTGGT (SEQ ID NO:79), TTTTTTTTTTTTATGGAGCTGTTGGT (SEQ ID NO:80), and TTTTTTTTTATGGAGCTGTAGGTGG (SEQ ID NO:81); (3) a third probe comprising a sequence selected from the group consisting of TTTTTTTTTTATG-GAGCTAGTGG (SEQ ID NO:49), TTTTTTTTTG-GAGCTAGTGGCGTA (SEQ ID NO:82), TTTTTAAT-TTGCTAGTGGCGTAGGC (SEQ ID NO:83), TTTTTTTTTATTTAGCTAGTGGCGT (SEQ ID NO:84), TTTTTTTTTTTGTTGGAGCTAGTGG (SEQ ID NO:85), and TTTTTTTTTTTAAGGAGCTAGTGG (SEQ ID NO:86); and (4) a fourth probe comprising a sequence selected from the group consisting of TTTTTTTTTATG-GAGCTGGTGACGT (SEQ ID NO:50), TTTTTTT-TAAAGGTGACGTAGGCAA (SEQ ID NO:87), TTTTTTTTTATGACGTAGGCAAGAG (SEQ ID NO:88), TTTTTTTTTTTGCTGGTGACGTAGG (SEQ ID NO:89), TTTTTTTTTTAAGCTGGTGACGTAG (SEQ ID NO:90), and TTTTTTTTTAAGGAGCTGGTGACGT (SEQ ID NO:91); and wherein each of the four probes is coupled to a microcarrier with a different identifier. In some embodiments, step (b) comprises amplifying the isolated DNA by PCR using a primer pair comprising the sequences GTACTGGTGGAGTATTTGATAGTG (SEQ ID NO:1) and ATCGTCAAGGCACTCTTGCCTAC (SEQ ID NO:2). In some embodiments, step (b) comprises amplifying the isolated DNA by PCR in the presence of a blocking nucleic acid comprising the sequence of TACGCCACCAGCT(invdT)$_n$, wherein n is 1, 2, or 3 (SEQ ID NO:3), TTG-GAGCTGGTGGCGTA(invdT)$_n$, wherein n is 1, 2, or 3 (SEQ ID NO:142), GCTGGTGGCGTAGGCA(invdT)$_n$, wherein n is 1, 2, or 3 (SEQ ID NO:143), GCTGGTGGCGTAGGC(invdT)$_n$, wherein n is 1, 2, or 3 (SEQ ID NO:144), or TTGGAGCTGGTGGCGT(invdT)$_n$, wherein n is 1, 2, or 3 (SEQ ID NO:145), with italicized nucleic acids representing locked nucleic acids.

In some embodiments, the one or more DNA mutations in the BRAF gene comprise two or more BRAF mutations encoding a V600E mutated BRAF protein. In some embodiments, the probes specific for one or more DNA mutations in the BRAF gene comprise two probes comprising the sequences TCTAGCTACAGAGAAAT (SEQ ID NO: 11) and GTCTAGCTACAGAAAAAT (SEQ ID NO: 12), and wherein each of the two probes is coupled to a microcarrier with a different identifier. In some embodiments, each of the two probes further comprises eight nucleotides at the 5' end, wherein the eight nucleotides at the 5' end are adenine or thymine nucleotides, and wherein each of the two probes comprises at least 24 total nucleotides. In some embodiments, the probes comprise: (1) a first probe comprising a sequence selected from the group consisting of TACAGAGAAATCTCGAT (SEQ ID NO:196), TACAGAGAAATCTC (SEQ ID NO:197), CTAGCTA-CAGAGAAAT (SEQ ID NO:198), CTAGCTA-CAGAGAAA (SEQ ID NO:199), and TCTAGCTACAGAG (SEQ ID NO:200); and (2) a second probe comprising a sequence selected from the group consisting of GTCTAGC-TACAGAAAAATC (SEQ ID NO:201), GTCTAGCTA-CAGAAAAAT (SEQ ID NO:12), TAGCTACAGAAAAA (SEQ ID NO:202), TCTAGCTACAGAAAAAT (SEQ ID NO:203), and TCTAGCTACAGAAAAATC (SEQ ID NO:204); and wherein each of the two probes is coupled to a microcarrier with a different identifier. In some embodiments, the probes comprise: (1) a first probe comprising a sequence selected from the group consisting of TTTTT-TAATTCTAGCTACAGAGAAAT (SEQ ID NO:51), TTTTTTTTTATACAGAGAAATCTCGAT (SEQ ID NO:92), TTTTTTTTTAATTTACAGAGAAATCTC (SEQ ID NO:93), TTTTTTAATTACTAGCTACAGAGAAAT (SEQ ID NO:94), TTTTTTTAATTACTAGCTA-CAGAGAAA (SEQ ID NO:95), and TTTTTTTTTTAAT-TTCTAGCTACAGAG (SEQ ID NO:96); and (2) a second probe comprising a sequence selected from the group consisting of TTTTTTTATGTCTAGCTACAGAAAAAT (SEQ ID NO:52), TTTTATGTCTAGCTACAGAAAAATC (SEQ ID NO:97), TTTTTTTTATTTTAGCTACAGAAAAA (SEQ ID NO:98), TTTTTTTATTTCTAGCTA-CAGAAAAAT (SEQ ID NO:99), and TTTTTTTTAT-TCTAGCTACAGAAAAATC (SEQ ID NO: 100); and wherein each of the two probes is coupled to a microcarrier with a different identifier. In some embodiments, step (b) comprises amplifying the isolated DNA by PCR using a primer pair comprising the sequences GGACCCACTC-CATCGAGATTT (SEQ ID NO:8) and CAGATATAT-TTCTTCATGAAGACCTCACAGTAA (SEQ ID NO:9). In some embodiments, step (b) comprises amplifying the isolated DNA by PCR in the presence of a blocking nucleic acid comprising the sequence of GAGATTTCACTGTAGC(invdT), wherein n is 1, 2, or 3 (SEQ ID NO:10), GAGATTT-CACTGTAGC(invdT)$_n$, wherein n is 1, 2, or 3 (SEQ ID NO:146), GAGATTTCACTGTAGC(invdT)$_n$, wherein n is 1, 2, or 3 (SEQ ID NO: 147), GAGATTCACTGTAGC (invdT), wherein n is 1, 2, or 3 (SEQ ID NO:148), or GAGATTTCACTGTAGC(invdT)$_n$, wherein n is 1, 2, or 3 (SEQ ID NO: 149), with italicized nucleic acids representing locked nucleic acids.

In some embodiments, the one or more DNA mutations in the CTNNB1 gene comprise CTNNB1 mutations encoding T41A, T41I, S45F, and S45P mutated CTNNB1 proteins. In some embodiments, the probes specific for one or more DNA mutations in the CTNNB1 gene comprise four probes comprising the sequences AGGAGCTGTGGCAG (SEQ ID NO:16), GGAGCTGTGATA (SEQ ID NO:17), TTTAC-CACTCAGAAAAG (SEQ ID NO:21), and TAC-CACTCAGAGGAG (SEQ ID NO:22), and wherein each of the four probes is coupled to a microcarrier with a different identifier. In some embodiments, each of the four probes further comprises eight nucleotides at the 5' end, wherein the eight nucleotides at the 5' end are adenine or thymine nucleotides, and wherein each of the four probes comprises at least 24 total nucleotides. In some embodiments, the probes comprise: (1) a first probe comprising a sequence selected from the group consisting of AGGAGCTGTGGCAGT (SEQ ID NO:205), AGGAGCTGTGGCAGTG (SEQ ID NO:206), GCTGTGGCAGTGGC (SEQ ID NO:207), GCTGTGGCAGTGGCA (SEQ ID NO:208), and AAGGAGCTGTGGCAG (SEQ ID NO:209); (2) a second probe comprising a sequence selected from the group consisting of GGAGCTGTGATAGTGG (SEQ ID NO:210), GAGCTGTGATAGTGGC (SEQ ID NO:211), AGCTGT-GATAGTGGCA (SEQ ID NO:212), AGAAGGAGCTGT-GATA (SEQ ID NO:213), and GGAGCTGTGAT (SEQ ID NO:214); (3) a third probe comprising a sequence selected from the group consisting of ACTCAGAAAAGGAGCT (SEQ ID NO:215), TACCACTCAGAAAAGGA (SEQ ID NO:216), TTTACCACTCAGAAAAGGAG (SEQ ID NO:217), TTACCACTCAGAAAAG (SEQ ID NO:218), and CAGAAAAGGAGCTGTG (SEQ ID NO:219); and (4) a fourth probe comprising a sequence selected from the group consisting of ACTCAGAGGAGGAGC (SEQ ID NO:220), TTACCACTCAGAGGA (SEQ ID NO:221), TTACCACTCAGAGGAGG (SEQ ID NO:222), TTAACACTCAGAGGAGG (SEQ ID NO:223), and TTAC-CAATCAGAGGAGG (SEQ ID NO:224); and wherein each of the four probes is coupled to a microcarrier with a different identifier. In some embodiments, the probes comprise: (1) a first probe comprising a sequence selected from the group consisting of TTTTTTTTTTTAG-GAGCTGTGGCAG (SEQ ID NO:53), TTTTTTTTT-TAGGAGCTGTGGCAGTG (SEQ ID NO:101), TTTTTTTTTTTAGCTGTGGCAGTGGC (SEQ ID NO: 102), TTTTTTTTTTTGCTGTGGCAGTGGCA (SEQ ID NO: 103), and TTTTTTTTTTAAGGAGCTGTGGCAG (SEQ ID NO: 104); (2) a second probe comprising a sequence selected from the group consisting of TTTTTTTTTTTTTGGAGCTGTGATA (SEQ ID NO:54), TTTTTTTTTGGAGCTGTGATAGTGG (SEQ ID NO: 105), TTTTTTTTTGAGCTGTGATAGTGGC (SEQ ID NO: 106), TTTTTTTTTAGCTGTGATAGTGGCA (SEQ ID NO: 107), TTTTTTTTTAGAAGGAGCTGTGATA (SEQ ID NO: 108), and TTTTTTTTTTTTTGGAGCTGT-GAT (SEQ ID NO:109); (3) a third probe comprising a sequence selected from the group consisting of TTTTTTTTTTTACCACTCAGAAAAG (SEQ ID NO:55), TTTAATTTTACTCAGAAAAGGAGCT (SEQ ID NO:110), TTTTTTAATACCACTCAGAAAAGGA (SEQ ID NO:111), TTTTTTTTACCACTCAGAAAAGGAG (SEQ ID NO:112), TTTTTTTTATTACCACTCAGAAAAG (SEQ ID NO:113), and TTTTTTTTTCAGAAAAGGAGCTGTG (SEQ ID NO: 114); and (4) a fourth probe comprising a sequence selected from the group consisting of TTTTTTTTTAATAC-CACTCAGAGGAG (SEQ ID NO:56), TTTTTTTT-TAAAACTCAGAGGAGGAGC (SEQ ID NO:115), TTTTTTTTTTTATTACCACTCAGAGGA (SEQ ID NO: 116), TTTTTTTTTATTACCACTCAGAGGAGG (SEQ ID NO:117), TTTTTTTTTTATTAACACTCAGAGGAG (SEQ ID NO:118), and TTTTTTTTTATTACCAATCAGAG-GAGG (SEQ ID NO: 119), and wherein each of the four probes is coupled to a microcarrier with a different identifier. In some embodiments, step (b) comprises amplifying the isolated DNA by PCR using a first primer pair comprising the sequences GGAATCCATTCTGGTGCCACT (SEQ ID NO:13) and AGAAAATCCCTGTTCCCACTCATA (SEQ ID NO: 14), and a second primer pair comprising the sequences GGTGCCACTACCACAGCTCCT (SEQ ID NO:18) and TCTCAAAACTGCATTCTGACTTTCA (SEQ ID NO: 19). In some embodiments, step (b) comprises amplifying the isolated DNA by PCR in the presence of a first blocking nucleic acid comprising the sequence of GCCACTACCACAGCT(invdT)$_n$, wherein n is 1, 2, or 3 (SEQ ID NO:15), TGCCACTACCACAG(invdT)$_n$, wherein n is 1, 2, or 3 (SEQ ID NO:150), CACTACCACAGCTCC (invdT)$_n$, wherein n is 1, 2, or 3 (SEQ ID NO:151), GCCAC-TACCACAGCT(invdT)$_n$, wherein n is 1, 2, or 3 (SEQ ID NO:152), or GCCACTACCACAGCT(invdT)$_n$, wherein n is 1, 2, or 3 (SEQ ID NO: 153), and a second blocking nucleic acid comprising the sequence of GCTCCTTCTCTGAGT (invdT), wherein n is 1, 2, or 3 (SEQ ID NO:20), TCCTTCTCTGAGTGG(invdT)$_n$, wherein n is 1, 2, or 3 (SEQ ID NO:174), GCTCCTTCTCTGAGT(invdT)n, wherein n is 1, 2, or 3 (SEQ ID NO:175), TCCTTCTCT-GAGTGG(invdT)n, wherein n is 1, 2, or 3 (SEQ ID NO:176), or GCTCCTTCTCTGAGT(invdT)n, wherein n is 1, 2, or 3 (SEQ ID NO:177), with italicized nucleic acids representing locked nucleic acids.

In some embodiments, the one or more DNA mutations in the APC gene comprise APC mutations encoding Q1367*, R1450*, E1309 frameshift, S1465 frameshift, and T1556 frameshift mutated APC proteins. In some embodiments, the probes specific for one or more DNA mutations in the APC gene comprise five probes comprising the sequences ACTGCTGAAAAGAGAGAGT (SEQ ID NO:26), GAAATAAAAGATTGG (SEQ ID NO:30), TTTTGGGTGTCTAAG (SEQ ID NO:34), CAAAC-CAAGTGAGAA (SEQ ID NO:38), and AGAGGCAGAAAAAAACT (SEQ ID NO:42), and wherein each of the five probes is coupled to a microcarrier with a different identifier. In some embodiments, each of the five probes further comprises eight nucleotides at the 5' end, wherein the eight nucleotides at the 5' end are adenine or thymine nucleotides, and wherein each of the five probes comprises at least 24 total nucleotides. In some embodiments, the probes comprise: (1) a first probe comprising a sequence selected from the group consisting of AAATAGCAGAAATAAAAG (SEQ ID NO:225), GAAATAAAAGATTGGAA (SEQ ID NO:226), AGAAATAAAAGATTG (SEQ ID NO:227), GAAATAAATGAATGG (SEQ ID NO:228), and CAGAAATAAAAGATT (SEQ ID NO:229); (2) a second probe comprising a sequence selected from the group consisting of TTTGGGTGTCTAAG (SEQ ID NO:230), GGGTGTCTAAGCACCACT (SEQ ID NO:231), CTAAGCACCACTTTT (SEQ ID NO:232), TTTTGGGTGTCTAA (SEQ ID NO:233), and GGTGTCTAAGCACCA (SEQ ID NO:234); (3) a third probe comprising a sequence selected from the group consisting of AAGTGAGAAGTACCTAA (SEQ ID NO:235), CAAACCAAGTGAGAA (SEQ ID NO:38), TCAAAC-CAAGTGAG (SEQ ID NO:236), ACCAAGTGAGAAGTA (SEQ ID NO:237), and AGCTCAAACCAAGTGAG (SEQ ID NO:238); (4) a fourth probe comprising a sequence selected from the group consisting of GCACCTACTGCT-GAA (SEQ ID NO:239), ACCTACTGCTGAAAAG (SEQ ID NO:240), TGCTGAAAAGAGAGAGT (SEQ ID NO:241), ACTGCTGAAAAGAGAGAGT (SEQ ID NO:26), and CCTACTGCTGAAAAGAGA (SEQ ID NO:242); and (5) a fifth probe comprising a sequence selected from the group consisting of GCAGAAAAAAAC-TATTG (SEQ ID NO:243), AGAGGCAGAAAAAAACT (SEQ ID NO:42), CAGAAAAAAACTATTGATT (SEQ ID NO:244), AGAAAGAGGCAGAAAAAAACT (SEQ ID NO:245), and GAGGCAGAAAAAAACTA (SEQ ID NO:246); and wherein each of the five probes is coupled to a microcarrier with a different identifier. In some embodiments, the probes comprise: (1) a first probe comprising a sequence selected from the group consisting of TTTTTTTTTTTTTGAAATAAAAGATTGG (SEQ ID NO:58), TTTTTTTTTTAAATAGCAGAAATAAAAG (SEQ ID NO:120), TTTTTTTTTTTGAAATAAAAGAT-TGGAA (SEQ ID NO:121), TTTTTTTTTTT-TAGAAATAAAAGATTG (SEQ ID NO:122), TTTTTTTTTTTTTGAAATAAATGAATGG (SEQ ID NO: 123), and TTTTTTTTTTTTTCAGAAATAAAAGATT (SEQ ID NO: 124); (2) a second probe comprising a sequence selected from the group consisting of TTTTTTTTTTTTTGGGTGTCTAAG (SEQ ID NO:59), TTTTTTTTTATTGGGTGTCTAAG (SEQ ID NO: 125), TTTTTTGGGTGTCTAAGCACCACT (SEQ ID NO:126), TTTTTTTTTCTAAGCACCACTTTT (SEQ ID NO: 127), TTTTTTTTTTTTTGGGTGTCTAA (SEQ ID NO: 128), and TTTTTTTTGGTGTCTAAGCACCA (SEQ ID NO:129); (3) a third probe comprising a sequence selected from the group consisting of TTTTTTTTTACAAAC-CAAGTGAGAA (SEQ ID NO:60), TTTTTTTTAAGT-GAGAAGTACCTAA (SEQ ID NO: 130), TTTTTTTTTTTTCAAACCAAGTGAG (SEQ ID NO:131), TTTTTTTTTTACCAAGTGAGAAGTA (SEQ ID NO:132), and TTTTTTTTAGCTCAAACCAAGTGAG (SEQ ID NO:133); (4) a fourth probe comprising a sequence selected from the group consisting of TTTTTTTTACTGCT-GAAAAGAGAGAGT (SEQ ID NO:57), TTTTTTTTTTGCACCTACTGCTGAA (SEQ ID NO: 134), TTTTTTTTTACCTACTGCTGAAAAG (SEQ ID NO:135), TTTTTTTTTGCTGAAAAGAGAGAGT (SEQ ID NO:136), and TTTTTTTTTCCTACTGCT-GAAAAGAGA (SEQ ID NO:137); and (5) a fifth probe comprising a sequence selected from the group consisting of TTTTTTTTTAGAGGCAGAAAAAAACT (SEQ ID NO:61), TTTTTTTTTGCAGAAAAAAACTATTG (SEQ ID NO:138), TTTTTTTTTTCAGAAAAAAACTATT-GATT (SEQ ID NO:139), TTTTTT-TAGAAAGAGGCAGAAAAAAACT (SEQ ID NO:140), and TTTTTTTTTTGAGGCAGAAAAAAACTA (SEQ ID NO:141); and wherein each of the five probes is coupled to a microcarrier with a different identifier. In some embodiments, step (b) comprises amplifying the isolated DNA by PCR using a first primer pair comprising the sequences TAAAAATAAAGCACCTACTGCTGAAA (SEQ ID NO:23) and AGCTTGCTTAGGTCCACTCTCTCT (SEQ ID NO:24); a second primer pair comprising the sequences TAGGATGTAATCAGACGACACAGGA (SEQ ID NO:27) and CAGCTGACCTAGTTCCAATCTTTTA (SEQ ID NO:28); a third primer pair comprising the sequences TCTCCCTCCAAAAGTGGTGCT (SEQ ID NO:31) and TGGCAATCGAACGACTCTCAA (SEQ ID NO:32); a fourth primer pair comprising the sequences GCAGAAGTAAAACACCTCCACCA (SEQ ID NO:35) and GGTGCTTTATTTTTAGGTACTTC (SEQ ID NO:36), with italicized nucleic acids representing locked nucleic acids; and a fifth primer pair comprising the sequences CAGGAAAATGACAATGGGAATG (SEQ ID NO:39) and ATCTAATAGGTCCTTTTCAGAATCAATAG (SEQ ID NO:40). In some embodiments, step (b) comprises amplifying the isolated DNA by PCR in the presence of a first blocking nucleic acid comprising the sequence of CCACTCTCTCTCTTTTCAGC(invdT), wherein n is 1, 2, or 3 (SEQ ID NO:25), TAGGTC-CACTCTCTCTCTTTTCAGCA(invdT)n, wherein n is 1, 2, or 3 (SEQ ID NO: 166), TAGGTC-CACTCTCTCTCTTTTCAGCA (invdT)n, wherein n is 1, 2, or 3 (SEQ ID NO:167), CCACTCTCTCTCTTTTCAGC (invdT)n, wherein n is 1, 2, or 3 (SEQ ID NO:168), or TAGGTCCACTCTCTCTCTTTTCAGCA (invdT)n, wherein n is 1, 2, or 3 (SEQ ID NO: 169), a second blocking nucleic acid comprising the sequence of CTTTTCTTTTAT-TTCTGC(invdT), wherein n is 1, 2, or 3 (SEQ ID NO:29), CTTTCTTTTATTTCTGC(invdT)n, wherein n is 1, 2, or 3 (SEQ ID NO:154), CTTTTCTTTTATTTCTGC(invdT)n, wherein n is 1, 2, or 3 (SEQ ID NO:155), CTTTTCTTTT-ATTTCTGC(invdT)n, wherein n is 1, 2, or 3 (SEQ ID NO:156), or CTTTTCTTTTATTTCTGC(invdT)n, wherein n is 1, 2, or 3 (SEQ ID NO:157), a third blocking nucleic acid comprising the sequence of GTGCTCAGACACC(invdT)$_n$, wherein n is 1, 2, or 3 (SEQ ID NO:33), GTGCTCA-GACACC(invdT)n, wherein n is 1, 2, or 3 (SEQ ID NO:158), AGTGGTGCTCAGACACCCA(invdT)n, wherein n is 1, 2, or 3 (SEQ ID NO:159), AGTGGTGCTCAGACACCCA(invdT)n, wherein n is 1, 2, or 3 (SEQ ID NO:160), or AGTGGTGCTCAGACACCCA (invdT)n, wherein n is 1, 2, or 3 (SEQ ID NO:161), a fourth blocking nucleic acid comprising the sequence of CTTCTCGCTTGGTT(invdT)$_n$, wherein n is 1, 2, or 3 (SEQ ID NO:37), GTACTTCTCGCTTGGT(invdT)n, wherein n is 1, 2, or 3 (SEQ ID NO:162), CTTCTCGCTTGGTT (invdT)n, wherein n is 1, 2, or 3 (SEQ ID NO:163), GTACTTCTCGCTTGGT(invdT)n, wherein n is 1, 2, or 3 (SEQ ID NO:164), or GTACTTCTCGCTTGGT(invdT)n, wherein n is 1, 2, or 3 (SEQ ID NO: 165), and a fifth blocking nucleic acid comprising the sequence of CAATAGTTTTTTCTGCC(invdT)$_n$, wherein n is 1, 2, or 3 (SEQ ID NO:41), GAATCAATAGTTTTTTCTGCCTC (invdT)n, wherein n is 1, 2, or 3 (SEQ ID NO: 170), TCAGAATCAATAGTTTTTTCTG (invdT)n, wherein n is 1, 2, or 3 (SEQ ID NO:171), GAATCAATAGATTT-TACTGCCTC (invdT)n, wherein n is 1, 2, or 3 (SEQ ID NO:172), or AATCAATAGTTTTTTCTGCCTC (invdT)n, wherein n is 1, 2, or 3 (SEQ ID NO: 173), with italicized nucleic acids representing locked nucleic acids.

In some embodiments of any of the above embodiments, n is 1, 2, 3, 4, 5, 6, 7, 8, 9, or 10. In some embodiments, the method further comprises: amplifying a positive control DNA sequence using a primer pair specific for the positive control DNA sequence; hybridizing the amplified positive control gene sequence with a probe specific for the positive control gene sequence, wherein the probe specific for the positive control gene sequence is coupled to a microcarrier with an identifier corresponding to a positive control; detecting presence or absence of hybridization of the amplified positive control DNA sequence with the probe specific for the positive control gene sequence; and detecting the identifier corresponding to the positive control. In some embodiments, the positive control DNA sequence comprises a sequence of a human leukocyte antigen gene. In some embodiments, the primer pair specific for the positive control DNA sequence comprises the sequences TGAGTGT-TACTTCTTCCCACACTC (SEQ ID NO:43) and ATTGCTTTTGCGCAATCCCT (SEQ ID NO:44). In some embodiments, the probe specific for the positive control gene sequence comprises the sequence TTTTTTTTTTTTG-GAGACGGTCTG (SEQ ID NO:45). In some embodiments, the primer pair specific for the positive control DNA sequence comprises the sequences AATCCCATCAC-CATCTTCCA (SEQ ID NO:71) and TGGACTC-CACGACGTACTCA (SEQ ID NO:72). In some embodiments, the probe specific for the positive control gene sequence comprises the sequence CTGTCTTCCACT-CACTCC (SEQ ID NO:73).

In some embodiments, the method further comprises: detecting absence of hybridization of the amplified DNA with a microcarrier having an identifier corresponding to a negative control, wherein the microcarrier with the identifier corresponding to the negative control comprises a probe that does not hybridize with the amplified DNA; and detecting the identifier corresponding to the negative control. In some embodiments, the microcarrier with the identifier corresponding to the negative control comprises a probe comprising the sequence AATATAATATATTAT (SEQ ID NO:46). In some embodiments, the identifiers of the microcarriers comprise digital barcodes. In some embodiments, each of the microcarriers comprises: (i) a first photopolymer layer; (ii) a second photopolymer layer; and (iii) an intermediate layer between the first layer and the second layer, the intermediate layer having an encoded pattern representing the identifier defined thereon, wherein the intermediate layer is partially substantially transmissive and partially substantially opaque to light, representing a code corresponding to the microcarrier, wherein the outermost surface of the microcarrier comprises a photoresist photopolymer, and said photoresist photopolymer is functionalized with the probe specific for the DNA mutation, and wherein said microcarrier has about the same density as water. In some embodiments, the identifiers of the microcarriers comprise analog codes. In some embodiments, each of the microcarriers comprises: (i) a substantially transparent polymer layer having a first surface and a second surface, the first and the second surfaces being parallel to each other; (ii) a substantially non-transparent polymer layer, wherein the substantially non-transparent polymer layer is affixed to the first surface of the substantially transparent polymer layer and encloses a center portion of the substantially transparent polymer layer, and wherein the substantially non-transparent polymer layer comprises a two-dimensional shape representing an analog code, wherein the analog code represents the identifier; and (iii) the probe specific for the DNA mutation, wherein the probe is coupled to at least one of the first surface and the second surface of the substantially transparent polymer layer in at least the center portion of the substantially transparent polymer layer. In some embodiments, each of the microcarriers further comprises: (iv) a second substantially transparent polymer layer aligned with the first substantially transparent polymer layer, the second substantially transparent polymer layer having a center portion that is aligned with the center portion of the first substantially transparent polymer layer, wherein the second substantially transparent polymer layer is affixed to the second surface of the first substantially transparent polymer layer and does not extend beyond the two-dimensional shape of the first substantially transparent polymer layer; and (v) a magnetic, substantially non-transparent layer that encloses the center portion of the first substantially transparent polymer layer between the substantially non-transparent polymer layer and the center portion of the substantially transparent polymer layer, wherein the magnetic, substantially non-transparent layer is affixed between the first and the second substantially transparent polymer layers. In some embodiments, each of the microcarriers further comprises an orientation indicator for orienting the analog code of the substantially non-transparent polymer layer. In some embodiments, the two-dimensional shape of the substantially non-transparent polymer layer comprises a gear shape comprising a plurality of gear teeth, and wherein the analog code is represented by one or more aspects selected from the group consisting of the height of one or more gear teeth of the plurality, the width of one or more gear teeth of the plurality, the number of gear teeth in the plurality, and the arrangement of one or more gear teeth within the plurality. In some embodiments, each of the microcarriers further comprises: (vi) one or more columns projecting from the first surface of the first substantially transparent polymer layer, wherein the one or more columns are not within the center portion of the first substantially transparent polymer layer; and/or (vii) one or more columns projecting from the second surface of the first substantially transparent polymer layer or a surface of the second substantially transparent polymer layer that is not affixed to the first substantially transparent polymer layer, wherein the one or more columns are not within the center portions of the first or the second substantially transparent polymer layer. In some embodiments, the substantially transparent polymer of the first or the second substantially transparent polymer layer comprises an epoxy-based polymer. In some embodiments, the epoxy-based polymer is SU-8. In some embodiments, the sample is a stool sample. In some embodiments, multiple stool samples from a patient are obtained. In some embodiments, multiple stool samples from a single stool specimen are obtained. In some embodiments, the methods of the present disclosure comprise detecting the presence or absence of hybridization of amplified DNA with a total of between about 1 and about 1000 microcarriers per probe per well of an assay plate. In some embodiments, the methods of the present disclosure are used to detect colon cancer, rectal cancer, colorectal cancer, colon adenoma, rectal adenoma, or colorectal adenoma, e.g., in a patient from whom the sample is collected.

Accordingly, in another aspect, provided herein is a kit comprising at least four microcarriers, wherein each of said at least four microcarriers comprises: (i) a probe coupled to the microcarrier, wherein the probe is specific for a DNA mutation in the KRAS, BRAF, CTNNB1, or APC gene; and (ii) an identifier corresponding to the probe coupled thereto; wherein the kit comprises at least one microcarrier comprising a probe specific for a DNA mutation in the KRAS gene, at least one microcarrier comprising a probe specific for a DNA mutation in the BRAF gene, at least one microcarrier comprising a probe specific for a DNA mutation in the CTNNB1 gene, and at least one microcarrier comprising a probe specific for a DNA mutation in the APC gene. In some embodiments, the KRAS, BRAF, CTNNB1, and APC genes are human genes. In some embodiments, the kit further comprises: at least four blocking nucleic acids, wherein each of said at least four blocking nucleic acids hybridizes with a wild-type DNA locus corresponding with one of the DNA mutations in the KRAS, BRAF, CTNNB1, or APC genes. In some embodiments, each of said at least four blocking nucleic acids comprises: a single-stranded oligonucleotide that hybridizes with the corresponding wild-type DNA locus; and a 3' terminal moiety that blocks extension from the single-stranded oligonucleotide. In some embodiments, the 3' terminal moiety comprises one or more inverted deoxythymidines. In some embodiments, each of said at least four blocking nucleic acids comprises one or more modified nucleotides selected from the group consisting of locked nucleic acids (LNAs), peptide nucleic acids (PNAs), hexose nucleic acids (HNAs), threose nucleic acids (TNAs), glycol nucleic acids (GNAs), and cyclohexenyl nucleic acids (CeNAs). In some embodiments, the DNA mutation in the KRAS gene comprises one or more DNA mutations encoding a G12D, G12V, G12S, or G13D mutated KRAS protein. In some embodiments, at least one of the at least four blocking nucleic acids comprises the sequence TACGCCACCAGCT(invdT)$_n$, wherein n is 1, 2, or 3 (SEQ ID NO:3), TTGGAGCTGGTGGCGTA(invdT)$_n$, wherein n is 1, 2, or 3 (SEQ ID NO:142), GCTGGTGGCGTAGGCA (invdT)$_n$, wherein n is 1, 2, or 3 (SEQ ID NO:143), GCTGGTGGCGTAGGC(invdT)$_n$, wherein n is 1, 2, or 3 (SEQ ID NO:144), or TTGGAGCTGGTGGCGT(invdT)$_n$, wherein n is 1, 2, or 3 (SEQ ID NO:145), with italicized nucleic acids representing locked nucleic acids. In some embodiments, the DNA mutation in the BRAF gene comprises one or more DNA mutations encoding a V600E mutated BRAF protein. In some embodiments, at least one of the at least four blocking nucleic acids comprises the sequence GAGATTCACTGTAGC(invdT), wherein n is 1, 2, or 3 (SEQ ID NO:10), GAGATTTCACTGTAGC(invdT), wherein n is 1, 2, or 3 (SEQ ID NO:146), GAGATTT-CACTGTAGC(invdT)$_n$, wherein n is 1, 2, or 3 (SEQ ID NO: 147), GAGATTCACTGTAGC(invdT), wherein n is 1, 2, or 3 (SEQ ID NO:148), or GAGATTTCACTGTAGC(invdT)$_n$, wherein n is 1, 2, or 3 (SEQ ID NO: 149), with italicized nucleic acids representing locked nucleic acids. In some embodiments, the DNA mutation in the CTNNB1 gene comprises at least a first CTNNB1 mutation encoding a T41A or T41I mutated CTNNB1 protein. In some embodiments, at least one of the at least four blocking nucleic acids comprises the sequence GCCACTACCACAGCT(invdT)$_n$, wherein n is 1, 2, or 3 (SEQ ID NO:15), TGCCACTAC-CACAG(invdT)$_n$, wherein n is 1, 2, or 3 (SEQ ID NO: 150), CACTACCACAGCTCC(invdT)$_n$, wherein n is 1, 2, or 3 (SEQ ID NO:151), GCCACTACCACAGCT(invdT)$_n$, wherein n is 1, 2, or 3 (SEQ ID NO:152), or GCCACTAC-CACAGCT(invdT)$_n$, wherein n is 1, 2, or 3 (SEQ ID NO: 153), with italicized nucleic acids representing locked nucleic acids. In some embodiments, the DNA mutation in the CTNNB1 gene comprises at least a first CTNNB1 mutation encoding an S45F or S45P mutated CTNNB1 protein. In some embodiments, at least one of the at least four blocking nucleic acids comprises the sequence GCTCCTTCTCTGAGT(invdT)$_n$, wherein n is 1, 2, or 3 (SEQ ID NO:20), TCCTTCTCTGAGTGG(invdT)$_n$, wherein n is 1, 2, or 3 (SEQ ID NO:174), GCTCCTTCTCT-GAGT(invdT)n, wherein n is 1, 2, or 3 (SEQ ID NO:175), TCCTTCTCTGAGTGG(invdT)n, wherein n is 1, 2, or 3 (SEQ ID NO:176), or GCTCCTTCTCTGAGT(invdT)n, wherein n is 1, 2, or 3 (SEQ ID NO:177), with italicized nucleic acids representing locked nucleic acids. In some embodiments, the DNA mutation in the APC gene comprise at least a first APC mutation encoding a Q1367* mutated APC protein. In some embodiments, at least one of the at least four blocking nucleic acids comprises the sequence GTGCTCAGACACC(invdT)$_n$, wherein n is 1, 2, or 3 (SEQ ID NO:33), GTGCTCAGACACC(invdT)n, wherein n is 1, 2, or 3 (SEQ ID NO:158), AGTGGTGCTCAGACACCCA (invdT)n, wherein n is 1, 2, or 3 (SEQ ID NO:159), AGTGGTGCTCAGACACCCA(invdT)n, wherein n is 1, 2, or 3 (SEQ ID NO:160), or AGTGGTGCTCAGACACCCA (invdT)n, wherein n is 1, 2, or 3 (SEQ ID NO:161), with italicized nucleic acids representing locked nucleic acids. In some embodiments, the DNA mutation in the APC gene comprises at least a first APC mutation encoding an R1450* mutated APC protein. In some embodiments, at least one of the at least four blocking nucleic acids comprises the sequence CTTCTCGCTTGGTT(invdT)$_n$, wherein n is 1, 2, or 3 (SEQ ID NO:37), GTACTTCTCGCTTGGT(invdT)n, wherein n is 1, 2, or 3 (SEQ ID NO:162), CTTCTCGCTTGGTT(invdT)n, wherein n is 1, 2, or 3 (SEQ ID NO:163), GTACTTCTCGCTTGGT(invdT)n, wherein n is 1, 2, or 3 (SEQ ID NO: 164), or GTACTTCTCGCTTGGT (invdT)n, wherein n is 1, 2, or 3 (SEQ ID NO: 165), with italicized nucleic acids representing locked nucleic acids. In some embodiments, the DNA mutation in the APC gene comprises at least a first APC mutation encoding an E1309 frameshift mutated APC protein. In some embodiments, at least one of the at least four blocking nucleic acids comprises the sequence CTTTTCTTTTATTTCTGC(invdT), wherein n is 1, 2, or 3 (SEQ ID NO:29), CTTTTCTTTT-ATTTCTGC(invdT)n, wherein n is 1, 2, or 3 (SEQ ID NO: 154), CTTTTCTTTTATTTCTGC(invdT)n, wherein n is 1, 2, or 3 (SEQ ID NO:155), CTTTTCTTTTATTTCTGC (invdT)n, wherein n is 1, 2, or 3 (SEQ ID NO:156), or CTTTTCTTTTATTTCTGC(invdT)n, wherein n is 1, 2, or 3 (SEQ ID NO:157), with italicized nucleic acids representing locked nucleic acids. In some embodiments, the DNA mutation in the APC gene comprises at least a first APC mutation encoding an S1465 frameshift mutated APC protein. In some embodiments, at least one of the at least four blocking nucleic acids comprises the sequence CCACTCTCTCTCTTTCAGC(invdT)$_n$, wherein n is 1, 2, or 3 (SEQ ID NO:25), TAGGTC-CACTCTCTCTCTTTCAGCA(invdT)n, wherein n is 1, 2, or 3 (SEQ ID NO:166), TAGGTC-CACTCTCTCTTTTCAGCA (invdT)n, wherein n is 1, 2, or 3 (SEQ ID NO:167), CCACTCTCTCTCTTTTCAGC (invdT)n, wherein n is 1, 2, or 3 (SEQ ID NO:168), or TAGGTCCACTCTCTCTCTTTTCAGCA (invdT)n, wherein n is 1, 2, or 3 (SEQ ID NO: 169), with italicized nucleic acids representing locked nucleic acids. In some embodiments, the DNA mutation in the APC gene comprises at least a first APC mutation encoding a T1556 frameshift mutated APC protein. In some embodiments, at least one of the at least four blocking nucleic acids comprises the sequence CAATAGTTTTTTCTGCC(invdT)$_n$, wherein n is 1, 2, or 3 (SEQ ID NO:41), GAAT-CAATAGTTTTTTCTGCCTC (invdT)n, wherein n is 1, 2, or 3 (SEQ ID NO:170), TCAGAATCAATAGTTTTTTCTG (invdT)n, wherein n is 1, 2, or 3 (SEQ ID NO:171), GAATCAATAGATTTTACTGCCTC (invdT)n, wherein n is 1, 2, or 3 (SEQ ID NO:172), or AAT-CAATAGTTTTTTCTGCCTC (invdT)n, wherein n is 1, 2, or 3 (SEQ ID NO:173), with italicized nucleic acids representing locked nucleic acids. In some embodiments, the kit further comprises at least four primer pairs, wherein the kit comprises a primer pair specific for the locus of one or more DNA mutations in each of the KRAS, BRAF, CTNNB1, and APC genes. In some embodiments, each of said at least four primer pairs comprises a primer coupled to a detection reagent. In some embodiments, the detection reagent comprises a fluorescent detection reagent. In some embodiments, the detection reagent comprises biotin, and wherein the kit further comprises streptavidin conjugated to a signal-emitting entity. In some embodiments, the signal-emitting entity comprises phycoerythrin (PE).

In some embodiments, the DNA mutation in the KRAS gene comprises KRAS mutations encoding G12D, G12V, G12S, and G13D mutated KRAS proteins. In some embodiments, the kit comprises four probes comprising the sequences GGAGCTGATGG (SEQ ID NO:4), GGAGCTGTTGG (SEQ ID NO:5), TGGAGCTAGTGG (SEQ ID NO:6), and TGGAGCTGGTGACGT (SEQ ID NO:7), and wherein each of the four probes is coupled to a microcarrier with a different identifier. In some embodiments, the kit comprises: (1) a first probe comprising a sequence selected from the group consisting of GGAGCT-GATGG (SEQ ID NO:4), AGCTGATGGCGTA (SEQ ID NO: 178), TGGAGCTGATGGCG (SEQ ID NO:179), TGGAGCTGATGG (SEQ ID NO:180), and GCT-GATGGCGTA (SEQ ID NO:181); (2) a second probe comprising a sequence selected from the group consisting of GGAGCTGTTGG (SEQ ID NO:5), TGGAGCTGTTGGTGGC (SEQ ID NO:182), GGAGCTGTTGGTG (SEQ ID NO:183), TGGAGCTGTTGGT (SEQ ID NO:184), and TGGAGCTGTaGGTGG (SEQ ID NO: 185); (3) a third probe comprising a sequence selected from the group consisting of TTGGAGCTAGTGGCGTA (SEQ ID NO: 186), GCTAGTGGCGTAGGC (SEQ ID NO:187), AGCTAGTGGCGT (SEQ ID NO:188), GTTG-GAGCTAGTGG (SEQ ID NO:189), and GGAGCTAGTGG (SEQ ID NO: 190); and (4) a fourth probe comprising a sequence selected from the group consisting of GGTGACGTAGGCAA (SEQ ID NO:191), TGACGTAGGCAAGAG (SEQ ID NO: 192), GCTGGTGACGTAGG (SEQ ID NO:193), AGCTGGTGACGTAG (SEQ ID NO:194), and GGAGCTGGTGACGT (SEQ ID NO: 195), and wherein each of the four probes is coupled to a microcarrier with a different identifier. In some embodiments, each of the four probes further comprises eight nucleotides at the 5' end, wherein the eight nucleotides at the 5' end are adenine or thymine nucleotides, and wherein each of the four probes comprises at least 24 total nucleotides. In some embodiments, the kit comprises: (1) a first probe comprising a sequence selected from the group consisting of TTTTTTTTTTTTAAGGAGCTGATGG (SEQ ID NO:47), TTTTTTTTTTTTAGCTGATGGCGTA (SEQ ID NO:74), TTTTTTTTTTTTATGGAGCTGATGGCG (SEQ ID NO:75), TTTTTTTTTTTTTATGGAGCTGATGG (SEQ ID NO:76), and TTTTTTTTTTTTTGCTGATGGCGTA (SEQ ID NO:77); (2) a second probe comprising a sequence selected from the group consisting of TTTTTTTTTTT-TAAGGAGCTGTTGG (SEQ ID NO:48), TTTTTTTTATG-GAGCTGTTGGTGGC (SEQ ID NO:78), TTTTTTTTT-TAAGGAGCTGTTGGTG (SEQ ID NO:79), TTTTTTTTTTTATGGAGCTGTTGGT (SEQ ID NO:80), and TTTTTTTTTATGGAGCTGTAGGTGG (SEQ ID NO:81); (3) a third probe comprising a sequence selected from the group consisting of TTTTTTTTTTATG-GAGCTAGTGG (SEQ ID NO:49), TTTTTTTTTTG-GAGCTAGTGGCGTA (SEQ ID NO:82), TTTTTAAT-TTGCTAGTGGCGTAGGC (SEQ ID NO:83), TTTTTTTTTATTTAGCTAGTGGCGT (SEQ ID NO:84), TTTTTTTTTTTGTTGGAGCTAGTGG (SEQ ID NO:85), and TTTTTTTTTTTAAGGAGCTAGTGG (SEQ ID NO:86); and (4) a fourth probe comprising a sequence selected from the group consisting of TTTTTTTTTATG-GAGCTGGTGACGT (SEQ ID NO:50), TTTTTTT-TAAAGGTGACGTAGGCAA (SEQ ID NO:87), TTTTTTTTTATGACGTAGGCAAGAG (SEQ ID NO:88), TTTTTTTTTTTGCTGGTGACGTAGG (SEQ ID NO:89), TTTTTTTTTTAAGCTGGTGACGTAG (SEQ ID NO:90), and TTTTTTTTTAAGGAGCTGGTGACGT (SEQ ID NO:91), and wherein each of the four probes is coupled to a microcarrier with a different identifier. In some embodiments, the kit further comprises a primer pair comprising the sequences GTACTGGTGGAGTATTTGATAGTG (SEQ ID NO:1) and ATCGTCAAGGCACTCTTGCCTAC (SEQ ID NO:2). In some embodiments, the kit further comprises a blocking nucleic acid comprising the sequence of TACGC-CACCAGCT(invdT)$_n$, wherein n is 1, 2, or 3 (SEQ ID NO:3), TTGGAGCTGGTGGCGTA(invdT)$_n$, wherein n is 1, 2, or 3 (SEQ ID NO: 142), GCTGGTGGCGTAGGCA(invdT)$_n$, wherein n is 1, 2, or 3 (SEQ ID NO:143), GCTGGTGGCGTAGGC(invdT)$_n$, wherein n is 1, 2, or 3 (SEQ ID NO:144), or TTGGAGCTGGTGGCGT(invdT)$_n$, wherein n is 1, 2, or 3 (SEQ ID NO:145), with italicized nucleic acids representing locked nucleic acids.

In some embodiments, the DNA mutations in the BRAF gene comprises two or more BRAF mutations encoding a V600E mutated BRAF protein. In some embodiments, the kit comprises two probes comprising the sequences TCTAGCTACAGAGAAAT (SEQ ID NO: 11) and GTCTAGCTACAGAAAAAT (SEQ ID NO: 12), and wherein each of the two probes is coupled to a microcarrier with a different identifier. In some embodiments, the kit comprises: (1) a first probe comprising a sequence selected from the group consisting of TACAGAGAAATCTCGAT (SEQ ID NO:196), TACAGAGAAATCTC (SEQ ID NO:197), CTAGCTACAGAGAAAT (SEQ ID NO: 198), CTAGCTACAGAGAAA (SEQ ID NO:199), and TCTAGC-TACAGAG (SEQ ID NO:200); and (2) a second probe comprising a sequence selected from the group consisting of GTCTAGCTACAGAAAAATC (SEQ ID NO:201), GTCTAGCTACAGAAAAAT (SEQ ID NO:12), TAGCTA-CAGAAAAAA (SEQ ID NO:202), TCTAGCTA-CAGAAAAAT (SEQ ID NO:203), and TCTAGCTA-CAGAAAAATC (SEQ ID NO:204); and wherein each of the two probes is coupled to a microcarrier with a different identifier. In some embodiments, each of the two probes further comprises eight nucleotides at the 5' end, wherein the eight nucleotides at the 5' end are adenine or thymine nucleotides, and wherein each of the two probes comprises at least 24 total nucleotides. In some embodiments, the kit comprises: (1) a first probe comprising a sequence selected from the group consisting of TTTTTTAATTTCTAGCTA-CAGAGAAAT (SEQ ID NO:51), TTTTTTTTTATA-CAGAGAAATCTCGAT (SEQ ID NO:92), TTTTTTTT-TAATTTACAGAGAAATCTC (SEQ ID NO:93), TTTTTTAATTACTAGCTACAGAGAAAT (SEQ ID NO:94), TTTTTTTAATTACTAGCTACAGAGAAA (SEQ ID NO:95), and TTTTTTTTTTAATTTCTAGCTACAGAG (SEQ ID NO:96); and (2) a second probe comprising a sequence selected from the group consisting of TTTTTT-TATGTCTAGCTACAGAAAAAT (SEQ ID NO:52), TTT-TATGTCTAGCTACAGAAAAATC (SEQ ID NO:97), TTTTTTTTATTTTAGCTACAGAAAAA (SEQ ID NO:98), TTTTTTTATTTCTAGCTACAGAAAAAT (SEQ ID NO:99), and TTTTTTTTATTCTAGCTA-CAGAAAAATC (SEQ ID NO: 100); and wherein each of the two probes is coupled to a microcarrier with a different identifier. In some embodiments, the kit further comprises a primer pair comprising the sequences GGACCCACTC-CATCGAGATTT (SEQ ID NO:8) and CAGATATAT-TTCTTCATGAAGACCTCACAGTAA (SEQ ID NO:9).

In some embodiments, the kit further comprises a blocking nucleic acid comprising the sequence of GAGATT-CACTGTAGC(invdT), wherein n is 1, 2, or 3 (SEQ ID NO:10), GAGATTTCACTGTAGC(invdT), wherein n is 1, 2, or 3 (SEQ ID NO:146), GAGATTTCACTGTAGC(invdT)$_n$, wherein n is 1, 2, or 3 (SEQ ID NO: 147), GAGAT-TCACTGTAGC(invdT), wherein n is 1, 2, or 3 (SEQ ID NO:148), or GAGATTTCACTGTAGC(invdT)$_n$, wherein n is 1, 2, or 3 (SEQ ID NO: 149), with italicized nucleic acids representing locked nucleic acids.

In some embodiments, the DNA mutation in the CTNNB1 gene comprises CTNNB1 mutations encoding T41A, T41I, S45F, and S45P mutated CTNNB1 proteins. In some embodiments, the kit comprises four probes comprising the sequences AGGAGCTGTGGCAG (SEQ ID NO:16), GGAGCTGTGATA (SEQ ID NO:17), TTTAC-CACTCAGAAAAG (SEQ ID NO:21), and TAC-CACTCAGAGGAG (SEQ ID NO:22), and wherein each of the four probes is coupled to a microcarrier with a different identifier. In some embodiments, each of the four probes further comprises eight nucleotides at the 5' end, wherein the eight nucleotides at the 5' end are adenine or thymine nucleotides, and wherein each of the four probes comprises at least 24 total nucleotides. In some embodiments, the kit comprises: (1) a first probe comprising a sequence selected from the group consisting of AGGAGCTGTGGCAGT (SEQ ID NO:205), AGGAGCTGTGGCAGTG (SEQ ID NO:206), GCTGTGGCAGTGGC (SEQ ID NO:207), GCTGTGGCAGTGGCA (SEQ ID NO:208), and AAGGAGCTGTGGCAG (SEQ ID NO:209); (2) a second probe comprising a sequence selected from the group consisting of GGAGCTGTGATAGTGG (SEQ ID NO:210), GAGCTGTGATAGTGGC (SEQ ID NO:211), AGCTGT-GATAGTGGCA (SEQ ID NO:212), AGAAGGAGCTGT-GATA (SEQ ID NO:213), and GGAGCTGTGAT (SEQ ID NO:214); (3) a third probe comprising a sequence selected from the group consisting of ACTCAGAAAAGGAGCT (SEQ ID NO:215), TACCACTCAGAAAAGGA (SEQ ID NO:216), TTTACCACTCAGAAAAGGAG (SEQ ID NO:217), TTACCACTCAGAAAAG (SEQ ID NO:218), and CAGAAAAGGAGCTGTG (SEQ ID NO:219); and (4) a fourth probe comprising a sequence selected from the group consisting of ACTCAGAGGAGGAGC (SEQ ID NO:220), TTACCACTCAGAGGA (SEQ ID NO:221), TTACCACTCAGAGGAGG (SEQ ID NO:222), TTAACACTCAGAGGAG (SEQ ID NO:223), and TTAC-CAATCAGAGGAGG (SEQ ID NO:224); and wherein each of the four probes is coupled to a microcarrier with a different identifier. In some embodiments, each of the four probes further comprises eight nucleotides at the 5' end, wherein the eight nucleotides at the 5' end are adenine or thymine nucleotides, and wherein each of the four probes comprises at least 24 total nucleotides. In some embodiments, the kit comprises: (1) a first probe comprising a sequence selected from the group consisting of TTTTTTTTTTTAGGAGCTGTGGCAG (SEQ ID NO:53), TTTTTTTTTTTAGGAGCTGTGGCAGTG (SEQ ID NO:101), TTTTTTTTTTTAGCTGTGGCAGTGGC (SEQ ID NO: 102), TTTTTTTTTTTGCTGTGGCAGTGGCA (SEQ ID NO: 103), and TTTTTTTTT-TAAGGAGCTGTGGCAG (SEQ ID NO: 104); (2) a second probe comprising a sequence selected from the group consisting of TTTTTTTTTTTTTGGAGCTGTGATA (SEQ ID NO:54), TTTTTTTTTGGAGCTGTGATAGTGG (SEQ ID NO: 105), TTTTTTTTTGAGCTGTGATAGTGGC (SEQ ID NO: 106), TTTTTTTTTAGCTGTGATAGTGGCA (SEQ ID NO: 107), TTTTTTTTTAGAAGGAGCTGT-GATA (SEQ ID NO: 108), and TTTTTTTTTTTTTG-GAGCTGTGAT (SEQ ID NO:109); (3) a third probe comprising a sequence selected from the group consisting of TTTTTTTTTTTACCACTCAGAAAAG (SEQ ID NO:55), TTTAATTTTACTCAGAAAAGGAGCT (SEQ ID NO:110), TTTTTTAATACCACTCAGAAAAGGA (SEQ ID NO:111), TTTTTTTTTACCACTCAGAAAAGGAG (SEQ ID NO:112), TTTTTTTTTATTACCACTCAGAAAAG (SEQ ID NO:113), and TTTTTTTTTCAGAAAAGGAGCTGTG (SEQ ID NO: 114); and (4) a fourth probe comprising a sequence selected from the group consisting of TTTTTTTTTAATAC-CACTCAGAGGAG (SEQ ID NO:56), TTTTTTTT-TAAAACTCAGAGGAGGAGC (SEQ ID NO:115), TTTTTTTTTTTATTACCACTCAGAGGA (SEQ ID NO: 116), TTTTTTTTTATTACCACTCAGAGGAGG (SEQ ID NO:117), TTTTTTTTTTATTAACACTCAGAGGAG (SEQ ID NO:118), and TTTTTTTTTATTACCAATCAGAG-GAGG (SEQ ID NO: 119), and wherein each of the four probes is coupled to a microcarrier with a different identifier. In some embodiments, the kit further comprises a first primer pair comprising the sequences GGAATCCAT-TCTGGTGCCACT (SEQ ID NO:13) and AGAAAATCCCTGTTCCCACTCATA (SEQ ID NO: 14), and a second primer pair comprising the sequences GGTGCCACTACCACAGCTCCT (SEQ ID NO:18) and TCTCAAAACTGCATTCTGACTTTCA (SEQ ID NO: 19). In some embodiments, the kit further comprises a first blocking nucleic acid comprising the sequence of GCCAC-TACCACAGCT(invdT)$_n$, wherein n is 1, 2, or 3 (SEQ ID NO:15), TGCCACTACCACAG(invdT)$_n$, wherein n is 1, 2, or 3 (SEQ ID NO:150), CACTACCACAGCTCC(invdT)$_n$, wherein n is 1, 2, or 3 (SEQ ID NO:151), GCCACTAC-CACAGCT(invdT)$_n$, wherein n is 1, 2, or 3 (SEQ ID NO:152), or GCCACTACCACAGCT(invdT)$_n$, wherein n is 1, 2, or 3 (SEQ ID NO: 153), and a second blocking nucleic acid comprising the sequence of GCTCCTTCTCTGAGT (invdT), wherein n is 1, 2, or 3 (SEQ ID NO:20), TCCTTCTCTGAGTGG(invdT)$_n$, wherein n is 1, 2, or 3 (SEQ ID NO:174), GCTCCTTCTCTGAGT(invdT)n, wherein n is 1, 2, or 3 (SEQ ID NO:175), TCCTTCTCT-GAGTGG(invdT)n, wherein n is 1, 2, or 3 (SEQ ID NO:176), or GCTCCTTCTCTGAGT(invdT)n, wherein n is 1, 2, or 3 (SEQ ID NO:177), with italicized nucleic acids representing locked nucleic acids.

In some embodiments, the DNA mutation in the APC gene comprises APC mutations encoding Q1367*, R1450*, E1309 frameshift, S1465 frameshift, and T1556 frameshift mutated APC proteins. In some embodiments, the kit comprises five probes comprising the sequences ACTGCT-GAAAAGAGAGAGT (SEQ ID NO:26), GAAATAAAA-GATTGG (SEQ ID NO:30), TTTTGGGTGTCTAAG (SEQ ID NO:34), CAAACCAAGTGAGAA (SEQ ID NO:38), and AGAGGCAGAAAAAAACT (SEQ ID NO:42), and wherein each of the five probes is coupled to a microcarrier with a different identifier. In some embodiments, the kit comprises: (1) a first probe comprising a sequence selected from AAATAGCAGAAATAAAAG (SEQ ID NO:225), GAAATAAAAGATTGGAA (SEQ ID NO:226), AGAAATAAAAGATTG (SEQ ID NO:227), GAAATAAATGAATGG (SEQ ID NO:228), and CAGAAATAAAAGATT (SEQ ID NO:229); (2) a second probe comprising a sequence selected from TTTGGGTGTCTAAG (SEQ ID NO:230), GGGTGTCTAAGCACCACT (SEQ ID NO:231), CTAAGCACCACTTTT (SEQ ID NO:232), TTTTGGGTGTCTAA (SEQ ID NO:233), and GGTGTCTAAGCACCA (SEQ ID NO:234); (3) a third probe comprising a sequence selected from the group consisting of AAGTGAGAAGTACCTAA (SEQ ID NO:235), CAAACCAAGTGAGAA (SEQ ID NO:38), TCAAAC-CAAGTGAG (SEQ ID NO:236), ACCAAGTGAGAAGTA (SEQ ID NO:237), and AGCTCAAACCAAGTGAG (SEQ ID NO:238); (4) a fourth probe comprising a sequence selected from GCACCTACTGCTGAA (SEQ ID NO:239), ACCTACTGCTGAAAAG (SEQ ID NO:240), TGCT-GAAAAGAGAGAGT (SEQ ID NO:241), ACTGCT-GAAAAGAGAGAGT (SEQ ID NO:26), and CCTACTGCTGAAAAGAGA (SEQ ID NO:242); and (5) a fifth probe comprising a sequence selected from GCAGAAAAAAACTATTG (SEQ ID NO:243), AGAGGCAGAAAAAAACT (SEQ ID NO:42), CAGAAAAAAACTATTGATT (SEQ ID NO:244), AGAAAGAGGCAGAAAAAAACT (SEQ ID NO:245), and GAGGCAGAAAAAAACTA (SEQ ID NO:246); and wherein each of the five probes is coupled to a microcarrier with a different identifier. In some embodiments, each of the five probes further comprises eight nucleotides at the 5' end, wherein the eight nucleotides at the 5' end are adenine or thymine nucleotides, and wherein each of the five probes comprises at least 24 total nucleotides. In some embodiments, the kit comprises: (1) a first probe comprising a sequence selected from the group consisting of TTTTTTTTTTTTTGAAATAAAAGATTGG (SEQ ID NO:58), TTTTTTTTTTAAATAGCAGAAATAAAAG (SEQ ID NO:120), TTTTTTTTTTTGAAATAAAAGAT-TGGAA (SEQ ID NO:121), TTTTTTTTTTT-TAGAAATAAAAGATTG (SEQ ID NO:122), TTTTTTTTTTTTTGAAATAAATGAATGG (SEQ ID NO: 123), and TTTTTTTTTTTTTCAGAAATAAAAGATT (SEQ ID NO: 124); (2) a second probe comprising a sequence selected from the group consisting of TTTTTTTTTTTTTGGGTGTCTAAG (SEQ ID NO:59), TTTTTTTTTATTGGGTGTCTAAG (SEQ ID NO: 125), TTTTTTGGGTGTCTAAGCACCACT (SEQ ID NO:126), TTTTTTTTTCTAAGCACCACTTTT (SEQ ID NO: 127), TTTTTTTTTTTTTGGGTGTCTAA (SEQ ID NO: 128), and TTTTTTTTTGGTGTCTAAGCACCA (SEQ ID NO:129); (3) a third probe comprising a sequence selected from the group consisting of TTTTTTTTTACAAAC- CAAGTGAGAA (SEQ ID NO:60), TTTTTTTTAAGT-GAGAAGTACCTAA (SEQ ID NO: 130), TTTTTTTTTTTCAAACCAAGTGAG (SEQ ID NO:131), TTTTTTTTTACCAAGTGAGAAGTA (SEQ ID NO:132), and TTTTTTTTAGCTCAAACCAAGTGAG (SEQ ID NO:133); (4) a fourth probe comprising a sequence selected from the group consisting of TTTTTTTTACTGCT-GAAAAGAGAGT (SEQ ID NO:57), TTTTTTTTTTGCACCTACTGCTGAA (SEQ ID NO: 134), TTTTTTTTTACCTACTGCTGAAAAG (SEQ ID NO:135), TTTTTTTTTGCTGAAAAGAGAGT (SEQ ID NO:136), and TTTTTTTTTCCTACTGCT-GAAAAGAGA (SEQ ID NO:137); and (5) a fifth probe comprising a sequence selected from the group consisting of TTTTTTTTTAGAGGCAGAAAAAAACT (SEQ ID NO:61), TTTTTTTTTTGCAGAAAAAAACTATTG (SEQ ID NO:138), TTTTTTTTTTCAGAAAAAAACTATT-GATT (SEQ ID NO:139), TTTTTT-TAGAAAGAGGCAGAAAAAAACT (SEQ ID NO:140), and TTTTTTTTTTTGAGGCAGAAAAAAACTA (SEQ ID NO:141); and wherein each of the five probes is coupled to a microcarrier with a different identifier. In some embodiments, the kit further comprises a first primer pair comprising the sequences TAAAAATAAAGCACCTACTGCT-GAAA (SEQ ID NO:23) and AGCTTGCTTAGGTCCACTCTCTCT (SEQ ID NO:24); a second primer pair comprising the sequences TAG-GATGTAATCAGACGACACAGGA (SEQ ID NO:27) and CAGCTGACCTAGTTCCAATCTTTTA (SEQ ID NO:28); a third primer pair comprising the sequences TCTCCCTC-CAAAAGTGGTGCT (SEQ ID NO:31) and TGGCAATCGAACGACTCTCAA (SEQ ID NO:32); a fourth primer pair comprising the sequences GCAGAAGTAAAACACCTCCACCA (SEQ ID NO:35) and GGTGCTTTATTTTAGGTACTTC (SEQ ID NO:36), with italicized nucleic acids representing locked nucleic acids; and a fifth primer pair comprising the sequences CAGGAAAATGACAATGGGAATG (SEQ ID NO:39) and ATCTAATAGGTCCTTTTCAGAATCAATAG (SEQ ID NO:40). In some embodiments, the kit further comprises a first blocking nucleic acid comprising the sequence of CCACTCTCTCTCTTITCAGC(invdT), wherein n is 1, 2, or 3 (SEQ ID NO:25), TAGGTCCACTCTCTCT-TITCAGCA(invdT)n, wherein n is 1, 2, or 3 (SEQ ID NO:166), TAGGTCCACTCTCTCTCTTTTCAGCA (in-vdT)n, wherein n is 1, 2, or 3 (SEQ ID NO: 167), CCACTCICTCTCTTTTCAGC (invdT)n, wherein n is 1, 2, or 3 (SEQ ID NO:168), or TAGGTC-CACTCTCTCTCTTTTCAGCA (invdT)n, wherein n is 1, 2, or 3 (SEQ ID NO:169), a second blocking nucleic acid comprising the sequence of CTTTTCTTTTATTCTGC(in-vdT)$_n$, wherein n is 1, 2, or 3 (SEQ ID NO:29), CTTTTCTTTTATTTCTGC(invdT)n, wherein n is 1, 2, or 3 (SEQ ID NO:154), CTTTTCTTTTATTTCTGC(invdT)n, wherein n is 1, 2, or 3 (SEQ ID NO:155), CTTTTCTTTT-ATTTCTGC(invdT)n, wherein n is 1, 2, or 3 (SEQ ID NO:156), or CTTTTCTTTTATTTCTGC(invdT)n, wherein n is 1, 2, or 3 (SEQ ID NO:157), a third blocking nucleic acid comprising the sequence of GTGCTCAGACACC(in-vdT)$_n$, wherein n is 1, 2, or 3 (SEQ ID NO:33), GTGCTCA-GACACC(invdT)n, wherein n is 1, 2, or 3 (SEQ ID NO:158), AGTGGTGCTCAGACACCCA(invdT)n, wherein n is 1, 2, or 3 (SEQ ID NO:159), AGTGGTGCTCAGACACCCA(invdT)n, wherein n is 1, 2, or 3 (SEQ ID NO:160), or AGTGGTGCTCAGACACCCA (invdT)n, wherein n is 1, 2, or 3 (SEQ ID NO:161), a fourth blocking nucleic acid comprising the sequence of CTTCTCGCTTGGTT(invdT)$_n$, wherein n is 1, 2, or 3 (SEQ ID NO:37), GTACTTCTCGCTTGGT(invdT)n, wherein n is 1, 2, or 3 (SEQ ID NO:162), CTTCTCGCTTGGTT (invdT)n, wherein n is 1, 2, or 3 (SEQ ID NO:163), GTACTTCTCGCTTGGT(invdT)n, wherein n is 1, 2, or 3 (SEQ ID NO:164), or GTACTTCTCGCTTGGT(invdT)n, wherein n is 1, 2, or 3 (SEQ ID NO: 165), and a fifth blocking nucleic acid comprising the sequence of CAATAGTTTTTTCTGCC(invdT)$_n$, wherein n is 1, 2, or 3 (SEQ ID NO:41), GAATCAATAGTTTTTTCTGCCTC (in-vdT)n, wherein n is 1, 2, or 3 (SEQ ID NO: 170), TCAGAATCAATAGTTTTTTCTG (invdT)n, wherein n is 1, 2, or 3 (SEQ ID NO:171), GAATCAATAGATTT-TACTGCCTC (invdT)n, wherein n is 1, 2, or 3 (SEQ ID NO:172), or AATCAATAGTTTTTTCTGCCTC (invdT)n, wherein n is 1, 2, or 3 (SEQ ID NO: 173), with italicized nucleic acids representing locked nucleic acids.

In some embodiments of any of the above embodiments, n is 1, 2, 3, 4, 5, 6, 7, 8, 9, or 10. In some embodiments, the kit further comprises a microcarrier with an identifier corresponding to a positive control and to which a probe specific for a positive control gene sequence is coupled; and a primer pair specific for the positive control DNA sequence. In some embodiments, the positive control DNA sequence comprises a sequence of a human leukocyte antigen gene. In some embodiments, the primer pair specific for the positive control DNA sequence comprises the sequences TGAGTGTTACTTCTTCCCACACTC (SEQ ID NO:43) and ATTGCTTTTGCGCAATCCCT (SEQ ID NO:44). In some embodiments, the probe specific for the positive control gene sequence comprises the sequence TTTTTTTTTTTTGGAGACGGTCTG (SEQ ID NO:45). In some embodiments, the primer pair specific for the positive control DNA sequence comprises the sequences AATCC-CATCACCATCTTCCA (SEQ ID NO:71) and TGGACTC-CACGACGTACTCA (SEQ ID NO:72). In some embodiments, the probe specific for the positive control gene sequence comprises the sequence CTGTCTTCCACT-CACTCC (SEQ ID NO:73). In some embodiments, the kit further comprises a microcarrier with an identifier corresponding to a negative control and to which is coupled a probe that does not hybridize with the amplified DNA. In some embodiments, the microcarrier with the identifier corresponding to the negative control comprises a probe comprising the sequence AATATAATATATTAT (SEQ ID NO:46).

In some embodiments, the identifiers of the microcarriers comprise digital barcodes. In some embodiments, each of the microcarriers comprises: (i) a first photopolymer layer; (ii) a second photopolymer layer; and (iii) an intermediate layer between the first layer and the second layer, the intermediate layer having an encoded pattern representing the identifier defined thereon, wherein the intermediate layer is partially substantially transmissive and partially substantially opaque to light, representing a code corresponding to the microcarrier, wherein the outermost surface of the microcarrier comprises a photoresist photopolymer, and said photoresist photopolymer is functionalized with the probe specific for the DNA mutation, and wherein said microcarrier has about the same density as water. In some embodiments, the identifiers of the microcarriers comprise analog codes. In some embodiments, each of the microcarriers comprises: (i) a substantially transparent polymer layer having a first surface and a second surface, the first and the second surfaces being parallel to each other; (ii) a substantially non-transparent polymer layer, wherein the substantially non-transparent polymer layer is affixed to the first surface of the substantially transparent polymer layer and encloses a center portion of the substantially transparent polymer layer, and wherein the substantially non-transparent polymer layer comprises a two-dimensional shape representing an analog code, wherein the analog code represents the identifier; and (iii) the probe specific for the DNA mutation, wherein the probe is coupled to at least one of the first surface and the second surface of the substantially transparent polymer layer in at least the center portion of the substantially transparent polymer layer. In some embodiments, each of the microcarriers further comprises: (iv) a second substantially transparent polymer layer aligned with the first substantially transparent polymer layer, the second substantially transparent polymer layer having a center portion that is aligned with the center portion of the first substantially transparent polymer layer, wherein the second substantially transparent polymer layer is affixed to the second surface of the first substantially transparent polymer layer and does not extend beyond the two-dimensional shape of the first substantially transparent polymer layer; and (v) a magnetic, substantially non-transparent layer that encloses the center portion of the first substantially transparent polymer layer between the substantially non-transparent polymer layer and the center portion of the substantially transparent polymer layer, wherein the magnetic, substantially non-transparent layer is affixed between the first and the second substantially transparent polymer layers. In some embodiments, each of the microcarriers further comprises an orientation indicator for orienting the analog code of the substantially non-transparent polymer layer. In some embodiments, the two-dimensional shape of the substantially non-transparent polymer layer comprises a gear shape comprising a plurality of gear teeth, and wherein the analog code is represented by one or more aspects selected from the group consisting of the height of one or more gear teeth of the plurality, the width of one or more gear teeth of the plurality, the number of gear teeth in the plurality, and the arrangement of one or more gear teeth within the plurality. In some embodiments, each of the microcarriers further comprises: (vi) one or more columns projecting from the first surface of the first substantially transparent polymer layer, wherein the one or more columns are not within the center portion of the first substantially transparent polymer layer; and/or(vii) one or more columns projecting from the second surface of the first substantially transparent polymer layer or a surface of the second substantially transparent polymer layer that is not affixed to the first substantially transparent polymer layer, wherein the one or more columns are not within the center portions of the first or the second substantially transparent polymer layer. In some embodiments, the substantially transparent polymer of the first or the second substantially transparent polymer layer comprises an epoxy-based polymer. In some embodiments, the epoxy-based polymer is SU-8. In some embodiments, the kit further comprises instructions for using the kit to detect colon cancer, rectal cancer, colorectal cancer, colon adenoma, rectal adenoma, or colorectal adenoma.

In another aspect, provided herein are kits or articles of manufacture comprising (a) a plurality of probes, the plurality of probes comprising a first probe comprising the sequence TTTTTTTTTTATGGAGCTGATGGCG (SEQ ID NO:75), a second probe comprising the sequence TTTTTTTTTTAAGGAGCTGTTGGTG (SEQ ID NO:79), a third probe comprising the sequence TTTTTTTTTTG-GAGCTAGTGGCGTA (SEQ ID NO:82), a fourth probe comprising the sequence TTTTTTT-TAAAGGTGACGTAGGCAA (SEQ ID NO:87), a fifth probe comprising the sequence TTTTTTTTTATA-CAGAGAAATCTCGAT (SEQ ID NO:92), a sixth probe comprising the sequence TTTTTTTTATTCTAGCTA-CAGAAAAATC (SEQ ID NO:100), a seventh probe comprising the sequence TTTTTTTTTTTAG-GAGCTGTGGCAG (SEQ ID NO:53), an eighth probe comprising the sequence TTTTTTTTTGAGCTGTGA-TAGTGGC (SEQ ID NO: 106), a ninth probe comprising the sequence TTTTTTAATACCACTCAGAAAAGGA (SEQ ID NO:111), a tenth probe comprising the sequence TTTTTTTTTTTATTACCACTCAGAGGA (SEQ ID NO:116), an eleventh probe comprising the sequence TTTTTTTTTTTTAGAAATAAAAGATTG (SEQ ID NO: 122), a twelfth probe comprising the sequence TTTTTTTT-TATTTGGGTGTCTAAG (SEQ ID NO: 125), a thirteenth probe comprising the sequence TTTTTTTTTTACCAAGT-GAGAAGTA (SEQ ID NO:132), a fourteenth probe comprising the sequence TTTTTTTTACTGCT-GAAAAGAGAGAGT (SEQ ID NO:57), and a fifteenth probe comprising the sequence TTTTTTTTTTT-GAGGCAGAAAAAAACTA (SEQ ID NO:141); (b) a plurality of primer pairs, the plurality of primer pairs comprising a first primer pair comprising the sequences GTACTGGTGGAGTATTTGATAGTG (SEQ ID NO: 1) and ATCGTCAAGGCACTCTTGCCTAC (SEQ ID NO:2), a second primer pair comprising the sequences GGACC-CACTCCATCGAGATTT (SEQ ID NO:8) and CAGATAT-ATTTCTTCATGAAGACCTCACAGTAA (SEQ ID NO:9), a third primer pair comprising the sequences GGAATCCAT-TCTGGTGCCACT (SEQ ID NO: 13) and AGAAAATCCCTGTTCCCACTCATA (SEQ ID NO: 14), a fourth primer pair comprising the sequences GGTGCCAC-TACCACAGCTCCT (SEQ ID NO:18) and TCT-CAAAACTGCATTCTGACTTTCA (SEQ ID NO: 19), a fifth primer pair comprising the sequences TAAAAATAAAGCACCTACTGCTGAAA (SEQ ID NO:23) and AGCTTGCTTAGGTCCACTCTCTCT (SEQ ID NO:24), a sixth primer pair comprising the sequences TAGGATGTAATCAGACGACACAGGA (SEQ ID NO:27) and CAGCTGACCTAGTTCCAATCTTTTA (SEQ ID NO:28), a seventh primer pair comprising the sequences TCTCCCTCCAAAAGTGGTGCT (SEQ ID NO:31) and TGGCAATCGAACGACTCTCAA (SEQ ID NO:32), an eighth primer pair comprising the sequences GCAGAAGTAAAACACCTCCACCA (SEQ ID NO:35) and GGTGCTTTATTTTTAGGTACTTC (SEQ ID NO:36), and a ninth primer pair comprising the sequences CAG-GAAAATGACAATGGGAATG (SEQ ID NO:39) and ATCTAATAGGTCCTTTTCAGAATCAATAG (SEQ ID NO:40), respectively; and a plurality of blocking nucleic acids, the plurality of blocking nucleic acids comprising a first blocking nucleic acid comprising the sequence TACGCCACCAGCT(invdT)$_n$, wherein n is 1, 2, or 3 (SEQ ID NO:3), a second blocking nucleic acid comprising the sequence GAGATTCACTGTAGC(invdT), wherein n is 1, 2, or 3 (SEQ ID NO:10), a third blocking nucleic acid comprising the sequence TGCCACTACCACAG(invdT)$_n$, wherein n is 1, 2, or 3 (SEQ ID NO:150), a fourth blocking nucleic acid comprising the sequence TCCTTCTCT-GAGTGG(invdT)n, wherein n is 1, 2, or 3 (SEQ ID NO:176), a fifth blocking nucleic acid comprising the sequence AGTGGTGCTCAGACACCCA(invdT)n, wherein n is 1, 2, or 3 (SEQ ID NO: 161), a sixth blocking nucleic acid comprising the sequence CTTCTCGCTTGGT-T(invdT)n, wherein n is 1, 2, or 3 (SEQ ID NO:163), a seventh blocking nucleic acid comprising the sequence CTTTTCTTTTATTTCTGC(invdT)n, wherein n is 1, 2, or 3

(SEQ ID NO: 157), an eighth blocking nucleic acid comprising the sequence CCACTCTCTCTCTTTTCAGC(invdT), wherein n is 1, 2, or 3 (SEQ ID NO:25), and a ninth blocking nucleic acid comprising the sequence TCAGAATCAATAGTTTTTTCTG (invdT)n, wherein n is 1, 2, or 3 (SEQ ID NO:171), with italicized nucleic acids representing locked nucleic acids.

In another aspect, provided herein are kits or articles of manufacture comprising (a) a plurality of probes, the plurality of probes comprising a first probe comprising the sequence TTTTTTTTTTATGGAGCTGATGGCG (SEQ ID NO:75), a second probe comprising the sequence TTTTTTTTTATGGAGCTGTAGGTGG (SEQ ID NO:81), a third probe comprising the sequence TTTTTTTTTTATGGAGCTAGTGG (SEQ ID NO:49), a fourth probe comprising the sequence TTTTTTTTTATGGAGCTGGTGACGT (SEQ ID NO:50), a fifth probe comprising the sequence TTTTTTTTTATACAGAGAAATCTCGAT (SEQ ID NO:92), a sixth probe comprising the sequence TTTTTTTATGTCTAGCTACAGAAAAAT (SEQ ID NO:52), a seventh probe comprising the sequence TTTTTTTTTTTAGGAGCTGTGGCAGTG (SEQ ID NO: 101), an eighth probe comprising the sequence TTTTTTTTTTTTTGGAGCTGTGATA (SEQ ID NO:54), a ninth probe comprising the sequence TTTTTTAATACCACTCAGAAAAGGA (SEQ ID NO:111), a tenth probe comprising the sequence TTTTTTTTTATTACCAATCAGAGGAGG (SEQ ID NO: 119), an eleventh probe comprising the sequence TTTTTTTTTTTTAGAAATAAAAGATTG (SEQ ID NO: 122), a twelfth probe comprising the sequence TTTTTTTTTTTTTGGGTGTCTAAG (SEQ ID NO:59), a thirteenth probe comprising the sequence TTTTTTTTTACCAAGTGAGAAGTA (SEQ ID NO:132), a fourteenth probe comprising the sequence TTTTTTTTTACCTACTGCTGAAAAG (SEQ ID NO:135), and a fifteenth probe comprising the sequence TTTTTTTTTTGAGGCAGAAAAAAACTA (SEQ ID NO:141); (b) a plurality of primer pairs, the plurality of primer pairs comprising a first primer pair comprising the sequences GTACTGGTGGAGTATTTGATAGTG (SEQ ID NO: 1) and ATCGTCAAGGCACTCTTGCCTAC (SEQ ID NO:2), a second primer pair comprising the sequences GGACCCACTCCATCGAGATTT (SEQ ID NO:8) and CAGATATATTTCTTCATGAAGACCTCACAGTAA (SEQ ID NO:9), a third primer pair comprising the sequences GGAATCCATTCTGGTGCCACT (SEQ ID NO: 13) and AGAAAATCCCTGTTCCCACTCATA (SEQ ID NO: 14), a fourth primer pair comprising the sequences GGTGCCACTACCACAGCTCCT (SEQ ID NO:18) and TCTCAAAACTGCATTCTGACTTTCA (SEQ ID NO: 19), a fifth primer pair comprising the sequences TAAAAATAAAGCACCTACTGCTGAAA (SEQ ID NO:23) and AGCTTGCTTAGGTCCACTCTCTCT (SEQ ID NO:24), a sixth primer pair comprising the sequences TAGGATGTAATCAGACGACACAGGA (SEQ ID NO:27) and CAGCTGACCTAGTTCCAATCTTTTA (SEQ ID NO:28), a seventh primer pair comprising the sequences TCTCCCTCCAAAAGTGGTGCT (SEQ ID NO:31) and TGGCAATCGAACGACTCTCAA (SEQ ID NO:32), an eighth primer pair comprising the sequences GCAGAAGTAAAACACCTCCACCA (SEQ ID NO:35) and GGTGCTTTATTTTAGGTACTTC (SEQ ID NO:36), and a ninth primer pair comprising the sequences CAGGAAAATGACAATGGGAATG (SEQ ID NO:39) and ATCTAATAGGTCCTTTTCAGAATCAATAG (SEQ ID NO:40), respectively; and (c) a plurality of blocking nucleic acids, the plurality of blocking nucleic acids comprising a first blocking nucleic acid comprising the sequence TTGGAGCTGGTGGCGTA(invdT)$_n$, wherein n is 1, 2, or 3 (SEQ ID NO: 142), a second blocking nucleic acid comprising the sequence GAGATTCACTGTAGC(invdT), wherein n is 1, 2, or 3 (SEQ ID NO:148), a third blocking nucleic acid comprising the sequence GCCACTACCACAGCT(invdT)$_n$, wherein n is 1, 2, or 3 (SEQ ID NO:15), a fourth blocking nucleic acid comprising the sequence TCCTTCTCTGAGTGG(invdT)$_n$, wherein n is 1, 2, or 3 (SEQ ID NO:174), a fifth blocking nucleic acid comprising the sequence AGTGGTGCTCAGACACCCA (invdT)n, wherein n is 1, 2, or 3 (SEQ ID NO: 161), a sixth blocking nucleic acid comprising the sequence CTTCTCGCTTGGTT(invdT)n, wherein n is 1, 2, or 3 (SEQ ID NO:163), a seventh blocking nucleic acid comprising the sequence CTTTCTTTTATTTCTGC(invdT)$_n$, wherein n is 1, 2, or 3 (SEQ ID NO:29), an eighth blocking nucleic acid comprising the sequence CCACTCICTCTCTTTTCAGC (invdT)n, wherein n is 1, 2, or 3 (SEQ ID NO:168), and a ninth blocking nucleic acid comprising the sequence CAATAGTTTTTCTGCC(invdT)$_n$, wherein n is 1, 2, or 3 (SEQ ID NO:41), with italicized nucleic acids representing locked nucleic acids.

In another aspect, provided herein are kits or articles of manufacture comprising (a) a plurality of probes, the plurality of probes comprising a first probe comprising the sequence TTTTTTTTTTTTAAGGAGCTGATGG (SEQ ID NO:47), a second probe comprising the sequence TTTTTTTTTTTTAAGGAGCTGTTGG (SEQ ID NO:48), a third probe comprising the sequence TTTTTTTTTTTAAGGAGCTAGTGG (SEQ ID NO:86), a fourth probe comprising the sequence TTTTTTTTTAAGGAGCTGGTGACGT (SEQ ID NO:91), a fifth probe comprising the sequence TTTTTTTAATTACTAGCTACAGAGAAA (SEQ ID NO:95), a sixth probe comprising the sequence TTTTTTTATTTCTAGCTACAGAAAAAT (SEQ ID NO:99), a seventh probe comprising the sequence TTTTTTTTTAAGGAGCTGTGGCAG (SEQ ID NO: 104), an eighth probe comprising the sequence TTTTTTTTTTTTTGGAGCTGTGAT (SEQ ID NO: 109), a ninth probe comprising the sequence TTTTTTTTATTACCACTCAGAAAAG (SEQ ID NO: 113), a tenth probe comprising the sequence TTTTTTTTTATTACCAATCAGAGGAGG (SEQ ID NO: 119), an eleventh probe comprising the sequence TTTTTTTTTTTTAGAAATAAAAGATTG (SEQ ID NO: 122), a twelfth probe comprising the sequence TTTTTTTTTATTTGGGTGTCTAAG (SEQ ID NO: 125), a thirteenth probe comprising the sequence TTTTTTTTTACAAACCAAGTGAGAA (SEQ ID NO:60), a fourteenth probe comprising the sequence TTTTTTTTACTGCTGAAAAGAGAGAGT (SEQ ID NO:57), and a fifteenth probe comprising the sequence TTTTTTTTTAGAGGCAGAAAAAAACT (SEQ ID NO:61); (b) a plurality of primer pairs, the plurality of primer pairs comprising a first primer pair comprising the sequences GTACTGGTGGAGTATTTGATAGTG (SEQ ID NO: 1) and ATCGTCAAGGCACTCTTGCCTAC (SEQ ID NO:2), a second primer pair comprising the sequences GGACCCACTCCATCGAGATTT (SEQ ID NO:8) and CAGATATATTTCTTCATGAAGACCTCACAGTAA (SEQ ID NO:9), a third primer pair comprising the sequences GGAATCCATTCTGGTGCCACT (SEQ ID NO: 13) and AGAAAATCCCTGTTCCCACTCATA (SEQ ID NO: 14), a fourth primer pair comprising the sequences GGTGCCACTACCACAGCTCCT (SEQ ID NO:18) and TCTCAAAACTGCATTCTGACTTTCA (SEQ ID NO: 19), a fifth primer pair comprising the sequences TAAAAATAAAGCACCTACTGCTGAAA (SEQ ID NO:23) and AGCTTGCTTAGGTCCACTCTCTCT (SEQ ID NO:24), a sixth primer pair comprising the sequences TAGGATGTAATCAGACGACACAGGA (SEQ ID NO:27) and CAGCTGACCTAGTTCCAATCTTTTA (SEQ ID NO:28), a seventh primer pair comprising the sequences TCTCCCTCCAAAAGTGGTGCT (SEQ ID NO:31) and TGGCAATCGAACGACTCTCAA (SEQ ID NO:32), an eighth primer pair comprising the sequences GCAGAAGTAAAACACCTCCACCA (SEQ ID NO:35) and GGTGCTTTATTTTTAGGTACTTC (SEQ ID NO:36), and a ninth primer pair comprising the sequences CAGGAAAATGACAATGGGAATG (SEQ ID NO:39) and ATCTAATAGGTCCTTTTCAGAATCAATAG (SEQ ID NO:40), respectively; and (c) a plurality of blocking nucleic acids, the plurality of blocking nucleic acids comprising a first blocking nucleic acid comprising the sequence a plurality of blocking nucleic acids, the plurality of blocking nucleic acids comprising a first blocking nucleic acid comprising the sequence TACGCCACCAGCT(invdT)$_n$, wherein n is 1, 2, or 3 (SEQ ID NO:3), a second blocking nucleic acid comprising the sequence GAGATTCACTGTAGC(invdT), wherein n is 1, 2, or 3 (SEQ ID NO: 10), a third blocking nucleic acid comprising the sequence GCCACTACCACAGCT(invdT)$_n$, wherein n is 1, 2, or 3 (SEQ ID NO:15), a fourth blocking nucleic acid comprising the sequence GCTCCTTCTCTGAGT(invdT)$_n$, wherein n is 1, 2, or 3 (SEQ ID NO:20), a fifth blocking nucleic acid comprising the sequence GTGCTCAGACACC(invdT)$_n$, wherein n is 1, 2, or 3 (SEQ ID NO:33), a sixth blocking nucleic acid comprising the sequence CTTCTCGCTTGGTT(invdT), wherein n is 1, 2, or 3 (SEQ ID NO:37), a seventh blocking nucleic acid comprising the sequence CTTTTCTTTTATTTCTGC(invdT), wherein n is 1, 2, or 3 (SEQ ID NO:29), an eighth blocking nucleic acid comprising the sequence CCACTCTCTCTCTTTCAGC(invdT)$_n$, wherein n is 1, 2, or 3 (SEQ ID NO:25), and a ninth blocking nucleic acid comprising the sequence CAATAGTTTTTTCTGCC(invdT), wherein n is 1, 2, or 3 (SEQ ID NO:41), with italicized nucleic acids representing locked nucleic acids. In some embodiments of any of the above embodiments, each probe of the plurality is coupled to a microcarrier that has a unique identifier corresponding to the probe coupled thereto.

In another aspect, provided herein are kits or articles of manufacture comprising (1) a primer pair for amplifying the locus of a KRAS mutation (e.g., encoding or resulting in a G12D, G12V, G12S, or G13D mutated KRAS protein); (2) a blocking nucleic acid comprising the sequence TACGCCACCAGCT(invdT)$_n$, wherein n is 1, 2, or 3 (SEQ ID NO:3), TTGGAGCTGGTGGCGTA(invdT)$_n$, wherein n is 1, 2, or 3 (SEQ ID NO:142), GCTGGTGGCGTAGGCA(invdT)$_n$, wherein n is 1, 2, or 3 (SEQ ID NO:143), GCTGGTGGCGTAGGC(invdT)$_n$, wherein n is 1, 2, or 3 (SEQ ID NO:144), or TTGGAGCTGGTGGCGT(invdT)$_n$, wherein n is 1, 2, or 3 (SEQ ID NO:145), with italicized nucleic acids representing locked nucleic acids; (3a) a first probe comprising a sequence selected from the group consisting of GGAGCTGATGG (SEQ ID NO:4), AGCTGATGGCGTA (SEQ ID NO:178), TGGAGCTGATGGCG (SEQ ID NO:179), TGGAGCTGATGG (SEQ ID NO:180), and GCTGATGGCGTA (SEQ ID NO:181); (3b) a second probe comprising a sequence selected from the group consisting of GGAGCTGTTGG (SEQ ID NO:5), TGGAGCTGTTGGTGGC (SEQ ID NO:182), GGAGCTGTTGGTG (SEQ ID NO:183), TGGAGCTGTTGGT (SEQ ID NO:184), and TGGAGCTGTAGGTGG (SEQ ID NO:185) (3c) a third probe comprising a sequence selected from the group consisting of TTGGAGCTAGTGGCGTA (SEQ ID NO:186), GCTAGTGGCGTAGGC (SEQ ID NO:187), AGCTAGTGGCGT (SEQ ID NO:188), GTTGGAGCTAGTGG (SEQ ID NO:189), and GGAGCTAGTGG (SEQ ID NO:190); (3d) a fourth probe comprising a sequence selected from the group consisting of GGTGACGTAGGCAA (SEQ ID NO: 191), TGACGTAGGCAAGAG (SEQ ID NO:192), GCTGGTGACGTAGG (SEQ ID NO:193), AGCTGGTGACGTAG (SEQ ID NO:194), and GGAGCTGGTGACGT (SEQ ID NO:195); and wherein each of the four probes is coupled to a microcarrier with a different identifier; (4) a primer pair for amplifying the locus of a BRAF mutation (e.g., encoding or resulting in a V600E mutated BRAF protein); (5) a blocking nucleic acid comprising the sequence GAGATTCACTGTAGC(invdT), wherein n is 1, 2, or 3 (SEQ ID NO:10), GAGATTTCACTGTAGC(invdT), wherein n is 1, 2, or 3 (SEQ ID NO:146), GAGATTTCACTGTAGC(invdT)$_n$, wherein n is 1, 2, or 3 (SEQ ID NO: 147), GAGATTCACTGTAGC (invdT), wherein n is 1, 2, or 3 (SEQ ID NO:148), or GAGATTTCACTGTAGC(invdT)$_n$, wherein n is 1, 2, or 3 (SEQ ID NO: 149), with italicized nucleic acids representing locked nucleic acids; (6a) a first probe comprising a sequence selected from the group consisting of TACAGAGAAATCTCGAT (SEQ ID NO: 196), TACAGAGAAATCTC (SEQ ID NO:197), CTAGCTACAGAGAAAT (SEQ ID NO:198), CTAGCTACAGAGAAA (SEQ ID NO:199), and TCTAGCTACAGAG (SEQ ID NO:200); (6b) a second probe comprising a sequence selected from the group consisting of GTCTAGCTACAGAAAAATC (SEQ ID NO:201), GTCTAGCTACAGAAAAAT (SEQ ID NO:12), TAGCTACAGAAAAA (SEQ ID NO:202), TCTAGCTACAGAAAAAT (SEQ ID NO:203), and TCTAGCTACAGAAAAATC (SEQ ID NO:204); (7) a primer pair for amplifying the locus of a CTNNB1 mutation (e.g., encoding or resulting in a T41A, T41I, S45F, and S45P mutated CTNNB1 protein); (8a) a first blocking nucleic acid comprising the sequence of GCCACTACCACAGCT(invdT)$_n$, wherein n is 1, 2, or 3 (SEQ ID NO:15), TGCCACTACCACAG(invdT)$_n$, wherein n is 1, 2, or 3 (SEQ ID NO:150), CACTACCACAGCTCC(invdT)$_n$, wherein n is 1, 2, or 3 (SEQ ID NO:151), GCCACTACCACAGCT(invdT)$_n$, wherein n is 1, 2, or 3 (SEQ ID NO:152), or GCCACTACCACAGCT(invdT)$_n$, wherein n is 1, 2, or 3 (SEQ ID NO: 153), with italicized nucleic acids representing locked nucleic acids; (8b) a second blocking nucleic acid comprising the sequence of GCTCCTTCTCTGAGT(invdT)$_n$, wherein n is 1, 2, or 3 (SEQ ID NO:20), TCCTTCTCTGAGTGG(invdT)$_n$, wherein n is 1, 2, or 3 (SEQ ID NO:174), GCTCCTTCTCTGAGT(invdT)n, wherein n is 1, 2, or 3 (SEQ ID NO:175), TCCTTCTCTGAGTGG(invdT)n, wherein n is 1, 2, or 3 (SEQ ID NO:176), or GCTCCTTCTCTGAGT(invdT)n, wherein n is 1, 2, or 3 (SEQ ID NO:177), with italicized nucleic acids representing locked nucleic acids; (9a) a first probe comprising a sequence selected from the group consisting of AAATAGCAGAAATAAAAG (SEQ ID NO:225), GAAAATAAAAGATTGGAA (SEQ ID NO:226), AGAAATAAAAGATTG (SEQ ID NO:227), GAAATAAATGAATGG (SEQ ID NO:228), and CAGAAATAAAAGATT (SEQ ID NO:229); (9b) a second probe comprising a sequence selected from the group consisting of TTTGGGTGTCTAAG (SEQ ID NO:230), GGGTGTCTAAGCACCACT (SEQ ID NO:231), CTAAGCACCACTTTT (SEQ ID NO:232), TTTTGGGTGTCTAA (SEQ ID NO:233), and GGTGTCTAAGCACCA (SEQ ID NO:234); (9c) a third probe comprising a sequence selected from the group consisting of AAGTGAGAAGTACCTAA (SEQ ID NO:235), CAAACCAAGTGAGAA (SEQ ID NO:38), TCAAACCAAGTGAG (SEQ ID NO:236), ACCAAGTGAGAAGTA (SEQ ID NO:237), and AGCTCAAACCAAGTGAG (SEQ ID NO:238); (9d) a fourth probe comprising a sequence selected from the group consisting of GCACCTACTGCTGAA (SEQ ID NO:239), ACCTACTGCTGAAAAG (SEQ ID NO:240), TGCTGAAAAGAGAGAGT (SEQ ID NO:241), ACTGCTGAAAAGAGAGAGT (SEQ ID NO:26), and CCTACTGCTGAAAAGAGA (SEQ ID NO:242); (9e) a fifth probe comprising a sequence selected from the group consisting of GCAGAAAAAAACTATTG (SEQ ID NO:243), AGAGGCAGAAAAAAACT (SEQ ID NO:42), CAGAAAAAAACTATTGATT (SEQ ID NO:244), AGAAAGAGGCAGAAAAAAACT (SEQ ID NO:245), and GAGGCAGAAAAAAACTA (SEQ ID NO:246); and wherein each of the five probes is coupled to a microcarrier with a different identifier; (10) a primer pair for amplifying the locus of an APC mutation (e.g., encoding or resulting in the mutated APC proteins described infra); (11a) a first blocking nucleic acid comprising the sequence of CCACTCTCTCTCTTITCAGC(invdT)ₙ, wherein n is 1, 2, or 3 (SEQ ID NO:25), TAGGTCCACTCTCTCTCTTITCAGCA(invdT)n, wherein n is 1, 2, or 3 (SEQ ID NO:166), TAGGTCCACTCTCTCTCTTTTCAGCA (invdT)n, wherein n is 1, 2, or 3 (SEQ ID NO: 167), CCACTCICTCTCTTTTCAGC (invdT)n, wherein n is 1, 2, or 3 (SEQ ID NO:168), or TAGGTCCACTCTCTCTCTTTTCAGCA (invdT)n, wherein n is 1, 2, or 3 (SEQ ID NO:169), with italicized nucleic acids representing locked nucleic acids; (1 lb) a second blocking nucleic acid comprising the sequence of CTTTTCTTTTATTTCTGC(invdT), wherein n is 1, 2, or 3 (SEQ ID NO:29), CTTTTCTTTTATTTCTGC(invdT)n, wherein n is 1, 2, or 3 (SEQ ID NO:154), CTTTTCTTTTATTTCTGC(invdT)n, wherein n is 1, 2, or 3 (SEQ ID NO:155), CTTTTCTTTTATTTCTGC(invdT)n, wherein n is 1, 2, or 3 (SEQ ID NO:156), or CTTTTCTTTTATTTCTGC(invdT)n, wherein n is 1, 2, or 3 (SEQ ID NO:157), with italicized nucleic acids representing locked nucleic acids; (11c) a third blocking nucleic acid comprising the sequence of GTGCTCAGACACC(invdT)ₙ, wherein n is 1, 2, or 3 (SEQ ID NO:33), GTGCTCAGACACC(invdT)n, wherein n is 1, 2, or 3 (SEQ ID NO:158), AGTGGTGCTCAGACACCCA(invdT)n, wherein n is 1, 2, or 3 (SEQ ID NO:159), AGTGGTGCTCAGACACCCA(invdT)n, wherein n is 1, 2, or 3 (SEQ ID NO:160), or AGTGGTGCTCAGACACCCA(invdT)n, wherein n is 1, 2, or 3 (SEQ ID NO:161), with italicized nucleic acids representing locked nucleic acids; (11d) a fourth blocking nucleic acid comprising the sequence of CTTCTCGCTTGGTT(invdT)ₙ, wherein n is 1, 2, or 3 (SEQ ID NO:37), GTACTTCTCGCTTGGT(invdT)n, wherein n is 1, 2, or 3 (SEQ ID NO:162), CTTCTCGCTTGGTT(invdT)n, wherein n is 1, 2, or 3 (SEQ ID NO:163), GTACTTCTCGCTTGGT(invdT)n, wherein n is 1, 2, or 3 (SEQ ID NO:164), or GTACTTCTCGCTTGGT (invdT)n, wherein n is 1, 2, or 3 (SEQ ID NO: 165), with italicized nucleic acids representing locked nucleic acids; (Ile) a fifth blocking nucleic acid comprising the sequence of CAATAGTTTTTTCTGCC(invdT)ₙ, wherein n is 1, 2, or 3 (SEQ ID NO:41), GAATCAATAGTTTTTTCTGCCTC (invdT)n, wherein n is 1, 2, or 3 (SEQ ID NO:170), TCAGAATCAATAGTTTTTTCTG (invdT)n, wherein n is 1, 2, or 3 (SEQ ID NO:171), GAATCAATAGATTTTACTGCCTC (invdT)n, wherein n is 1, 2, or 3 (SEQ ID NO:172), or AATCAATAGTTTTTTCTGCCTC (invdT)n, wherein n is 1, 2, or 3 (SEQ ID NO:173), with italicized nucleic acids representing locked nucleic acids; (12a) a first probe comprising a sequence selected from AAATAGCAGAAATAAAAG (SEQ ID NO:225), GAAATAAAAGATTGGAA (SEQ ID NO:226), AGAAATAAAAGATTG (SEQ ID NO:227), GAAATAAATGAATGG (SEQ ID NO:228), and CAGAAATAAAAGATT (SEQ ID NO:229); (12b) a second probe comprising a sequence selected from TTTGGGTGTCTAAG (SEQ ID NO:230), GGGTGTCTAAGCACCACT (SEQ ID NO:231), CTAAGCACCACTTTT (SEQ ID NO:232), TTTTGGGTGTCTAA (SEQ ID NO:233), and GGTGTCTAAGCACCA (SEQ ID NO:234); (12c) a third probe comprising a sequence selected from AAGTGAGAAGTACCTAA (SEQ ID NO:235), CAAACCAAGTGAGAA (SEQ ID NO:38), TCAAACCAAGTGAG (SEQ ID NO:236), ACCAAGTGAGAAGTA (SEQ ID NO:237), and AGCTCAAACCAAGTGAG (SEQ ID NO:238); (12d) a fourth probe comprising a sequence selected from GCACCTACTGCTGAA (SEQ ID NO:239), ACCTACTGCTGAAAAG (SEQ ID NO:240), TGCTGAAAAGAGAGAGT (SEQ ID NO:241), ACTGCTGAAAAGAGAGAGT (SEQ ID NO:26), and CCTACTGCTGAAAAGAGA (SEQ ID NO:242); and (12e) a fifth probe comprising a sequence selected from GCAGAAAAAAACTATTG (SEQ ID NO:243), AGAGGCAGAAAAAAACT (SEQ ID NO:42), CAGAAAAAAACTATTGATT (SEQ ID NO:244), AGAAAGAGGCAGAAAAAAACT (SEQ ID NO:245), and GAGGCAGAAAAAAACTA (SEQ ID NO:246). In some embodiments, each of the probes is coupled to a microcarrier with a different identifier. In some embodiments, the primer pair for amplifying the locus of a KRAS mutation comprises the sequences GTACTGGTGGAGTATTTGATAGTG (SEQ ID NO:1) and ATCGTCAAGGCACTCTTGCCTAC (SEQ ID NO:2). In some embodiments, the primer pair for amplifying the locus of a BRAF mutation comprises the sequences GGACCCACTCCATCGAGATTT (SEQ ID NO:8) and CAGATATATTTCTTCATGAAGACCTCACAGTAA (SEQ ID NO:9). In some embodiments, the primer pair for amplifying the locus of a CTNNB1 mutation comprises: a first primer pair comprising the sequences GGAATCCATTCTGGTGCCACT (SEQ ID NO:13) and AGAAAATCCCTGTTCCCACTCATA (SEQ ID NO: 14), and a second primer pair comprising the sequences GGTGCCACTACCACAGCTCCT (SEQ ID NO:18) and TCTCAAAACTGCATTCTGACTTTCA (SEQ ID NO: 19). In some embodiments, the primer pair for amplifying the locus of an APC mutation comprises: a first primer pair comprising the sequences TAAAAATAAAGCACCTACTGCTGAAA (SEQ ID NO:23) and AGCTTGCTTAGGTCCACTCTCTCT (SEQ ID NO:24); a second primer pair comprising the sequences TAGGATGTAATCAGACGACACAGGA (SEQ ID NO:27) and CAGCTGACCTAGTTCCAATCTTTTA (SEQ ID NO:28); a third primer pair comprising the sequences TCTCCCTCCAAAAGTGGTGCT (SEQ ID NO:31) and TGGCAATCGAACGACTCTCAA (SEQ ID NO:32); a fourth primer pair comprising the sequences GCAGAAGTAAAACACCTCCACCA (SEQ ID NO:35) and GGTGCTTTATTTTTAGGTACTTC (SEQ ID NO:36), with italicized nucleic acids representing locked nucleic acids; and a fifth primer pair comprising the sequences CAGGAAAATGACAATGGGAATG (SEQ ID NO:39) and ATCTAATAGGTCCTTTTCAGAATCAATAG (SEQ ID NO:40).

It is to be understood that one, some, or all of the properties of the various embodiments described herein may be combined to form other embodiments of the present invention. These and other aspects of the invention will become apparent to one of skill in the art.

BRIEF DESCRIPTION OF THE DRAWINGS

FIGS. 1A & 1B show two views of an exemplary microcarrier.

FIG. 3 shows an exemplary analog encoding scheme that includes multiple shape variation points for generating unique analog codes.

FIG. 4A shows three examples of microcarriers, each having a unique analog code.

FIGS. 5A & 5B show two views of an exemplary microcarrier.

FIGS. 6A & 6B show two views of an exemplary microcarrier.

FIGS. 9A-9C show two views of an exemplary microcarrier (FIG. 9A and FIG. 9B), along with a depiction of an optional feature (FIG. 9C).

FIG. 10 shows a method for producing an exemplary microcarrier.

FIGS. 18A & 18B show the results of detecting the presence of DNA mutations in the KRAS, BRAF, CTNNB1, and APC genes, in accordance with some embodiments. Numbers report the fluorescence signal (in arbitrary units, AU) observed with each pairwise combination of isolated DNA (bearing a mutation or a wild-type sequence, as indicated in columns) and probe (as indicated in rows).

DETAILED DESCRIPTION

Figure 1D:
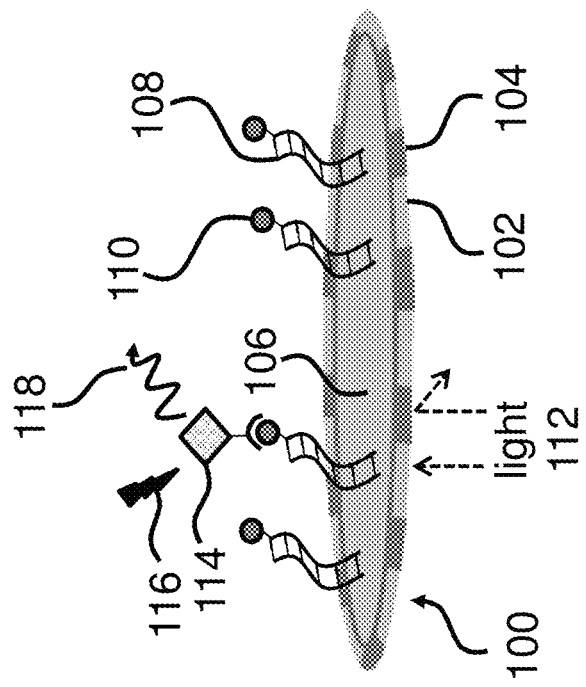
FIGS. 1C & 1D show an exemplary assay for DNA detection using an exemplary microcarrier.

In one aspect, provided herein are methods for detecting the presence of DNA mutations in the KRAS, BRAF, CTNNB1, and APC genes. In some embodiments, the methods include isolating DNA from a sample; amplifying the isolated DNA by polymerase chain reaction (PCR) using primer pairs specific for the loci of one or more DNA mutations in each of the KRAS, BRAF, CTNNB1, and APC genes; hybridizing the amplified DNA with at least four probes, said at least four probes comprising one or more probes specific for a DNA mutation in each of the KRAS, BRAF, CTNNB1, and APC genes, wherein each of said at least four probes is coupled to a microcarrier, and wherein each of the microcarriers comprises an identifier corresponding to the probe coupled thereto; detecting presence or absence of hybridization of the amplified DNA with said at least four probes, wherein hybridization between the amplified DNA and one of the probes indicates the presence of the DNA mutation corresponding to the probe; and detecting the identifiers of the microcarriers, e.g., in order to correlate each detected identifier with its corresponding probe (and the hybridization, or lack thereof, between the probe and the amplified DNA).

In another aspect, provided herein are kits or articles of manufacture comprising at least four microcarriers, wherein each of said at least four microcarriers comprises: a probe coupled to the microcarrier, wherein the probe is specific for a DNA mutation in the KRAS, BRAF, CTNNB1, or APC gene; and an identifier corresponding to the probe coupled thereto; wherein the kit comprises at least one microcarrier comprising a probe specific for a DNA mutation in the KRAS gene, at least one microcarrier comprising a probe specific for a DNA mutation in the BRAF gene, at least one microcarrier comprising a probe specific for a DNA mutation in the CTNNB1 gene, and at least one microcarrier comprising a probe specific for a DNA mutation in the APC gene.

In another aspect, provided herein are kits or articles of manufacture comprising (a) a plurality of probes, the plurality of probes comprising a first probe comprising sequence TTTTTTTTTTATGGAGCTGATGGCG (SEQ ID NO:75), a second probe comprising the sequence TTTTTTTTTTAAGGAGCTGTTGGTG (SEQ ID NO:79), a third probe comprising the sequence TTTTTTTTTTGGAGCTAGTGGCGTA (SEQ ID NO:82), a fourth probe comprising the sequence TTTTTTTTAAAGGTGACGTAGGCAA (SEQ ID NO:87), a fifth probe comprising the sequence TTTTTTTTTATACAGAGAAATCTCGAT (SEQ ID NO:92), a sixth probe comprising the sequence TTTTTTTTATTCTAGCTACAGAAAAATC (SEQ ID NO:100), a seventh probe comprising the sequence TTTTTTTTTTAGGAGCTGTGGCAG (SEQ ID NO:53), an eighth probe comprising the sequence TTTTTTTTTGAGCTGTGATAGTGGC (SEQ ID NO: 106), a ninth probe comprising the sequence TTTTTTAATACCACTCAGAAAAGGA (SEQ ID NO:111), a tenth probe comprising the sequence TTTTTTTTTTATTACCACTCAGAGGA (SEQ ID NO:116), an eleventh probe comprising the sequence TTTTTTTTTTTTAGAAATAAAAGATTG (SEQ ID NO: 122), a twelfth probe comprising the sequence TTTTTTTT-TATTTGGGTGTCTAAG (SEQ ID NO: 125), a thirteenth probe comprising the sequence TTTTTTTTTTACCAAGT-GAGAAGTA (SEQ ID NO:132), a fourteenth probe comprising the sequence TTTTTTTTACTGCT-GAAAAGAGAGAGT (SEQ ID NO:57), and a fifteenth probe comprising the sequence TTTTTTTTTTT-GAGGCAGAAAAAAACTA (SEQ ID NO:141); (b) a plurality of primer pairs, the plurality of primer pairs comprising a first primer pair comprising the sequences GTACTGGTGGAGTATTTGATAGTG (SEQ ID NO: 1) and ATCGTCAAGGCACTCTTGCCTAC (SEQ ID NO:2), a second primer pair comprising the sequences GGACC-CACTCCATCGAGATTT (SEQ ID NO:8) and CAGATAT-ATTTCTTCATGAAGACCTCACAGTAA (SEQ ID NO:9), a third primer pair comprising the sequences GGAATCCAT-TCTGGTGCCACT (SEQ ID NO: 13) and AGAAAATCCCTGTTCCCACTCATA (SEQ ID NO: 14), a fourth primer pair comprising the sequences GGTGCCAC-TACCACAGCTCCT (SEQ ID NO:18) and TCT-CAAAACTGCATTCTGACTTTCA (SEQ ID NO: 19), a fifth primer pair comprising the sequences TAAAAATAAAGCACCTACTGCTGAAA (SEQ ID NO:23) and AGCTTGCTTAGGTCCACTCTCTCT (SEQ ID NO:24), a sixth primer pair comprising the sequences TAGGATGTAATCAGACGACACAGGA (SEQ ID NO:27) and CAGCTGACCTAGTTCCAATCTTTTA (SEQ ID NO:28), a seventh primer pair comprising the sequences TCTCCCTCCAAAAGTGGTGCT (SEQ ID NO:31) and TGGCAATCGAACGACTCTCAA (SEQ ID NO:32), an eighth primer pair comprising the sequences GCAGAAGTAAAACACCTCCACCA (SEQ ID NO:35) and GGTGCTTTATTTTTAGGTACTTC (SEQ ID NO:36), and a ninth primer pair comprising the sequences CAG-GAAAATGACAATGGGAATG (SEQ ID NO:39) and ATCTAATAGGTCCTTTTCAGAATCAATAG (SEQ ID NO:40), respectively; and a plurality of blocking nucleic acids, the plurality of blocking nucleic acids comprising a first blocking nucleic acid comprising the sequence TACGCCACCAGCT(invdT)$_n$, wherein n is 1, 2, or 3 (SEQ ID NO:3), a second blocking nucleic acid comprising the sequence GAGATTCACTGTAGC(invdT), wherein n is 1, 2, or 3 (SEQ ID NO:10), a third blocking nucleic acid comprising the sequence TGCCACTACCACAGinvdT-invdTinvdT (SEQ ID NO:150), a fourth blocking nucleic acid comprising the sequence TCCTTCTCTGAGTGG-invdTinvdTinvdT (SEQ ID NO: 176), a fifth blocking nucleic acid comprising the sequence AGTGGTGCTCA-GACACCCAinvdTinvdTinvdT (SEQ ID NO:161), a sixth blocking nucleic acid comprising the sequence CTTCTCGCTTGGTTinvdTinvdTinvdT (SEQ ID NO:163), a seventh blocking nucleic acid comprising the sequence CTTTTCTTTTATTTCTGCinvdTinvdTinvdT (SEQ ID NO:157), an eighth blocking nucleic acid comprising the sequence CCACTCTCTCTCTTTCAGCinvdTinvdTinvdT (SEQ ID NO:25), and a ninth blocking nucleic acid comprising the sequence TCAGAATCAATAGTTTTTTCTG invdTinvdTinvdT (SEQ ID NO:171), with italicized nucleic acids representing locked nucleic acids. In another aspect, provided herein are kits or articles of manufacture comprising (a) a plurality of probes, the plurality of probes comprising a first probe comprising the sequence TTTTTTTT-TATGGAGCTGATGGCG (SEQ ID NO:75), a second probe comprising the sequence TTTTTTTTTATG-GAGCTGTAGGTGG (SEQ ID NO:81), a third probe comprising the sequence TTTTTTTTTTTATGGAGCTAGTGG (SEQ ID NO:49), a fourth probe comprising the sequence TTTTTTTTTATGGAGCTGGTGACGT (SEQ ID NO:50), a fifth probe comprising the sequence TTTTTTTTTATA-CAGAGAAATCTCGAT (SEQ ID NO:92), a sixth probe comprising the sequence TTTTTTTATGTCTAGCTA-CAGAAAAAT (SEQ ID NO:52), a seventh probe comprising the sequence TTTTTTTTTTTAG-GAGCTGTGGCAGTG (SEQ ID NO:101), an eighth probe comprising the sequence TTTTTTTTTTTTGGAGCTGT-GATA (SEQ ID NO:54), a ninth probe comprising the sequence TTTTTTAATACCACTCAGAAAAGGA (SEQ ID NO:111), a tenth probe comprising the sequence TTTTTTTTTATTACCAATCAGAGGAGG (SEQ ID NO:119), an eleventh probe comprising the sequence TTTTTTTTTTTTAGAAATAAAAGATTG (SEQ ID NO: 122), a twelfth probe comprising the sequence TTTTTTTTTTTTTGGGTGTCTAAG (SEQ ID NO:59), a thirteenth probe comprising the sequence TTTTTTTTT-TACCAAGTGAGAAGTA (SEQ ID NO:132), a fourteenth probe comprising the sequence TTTTTTTTTACC-TACTGCTGAAAAG (SEQ ID NO:135), and a fifteenth probe comprising the sequence TTTTTTTTTTT-GAGGCAGAAAAAAACTA (SEQ ID NO:141); (b) a plurality of primer pairs, the plurality of primer pairs comprising a first primer pair comprising the sequences GTACTGGTGGAGTATTTGATAGTG (SEQ ID NO: 1) and ATCGTCAAGGCACTCTTGCCTAC (SEQ ID NO:2), a second primer pair comprising the sequences GGACC-CACTCCATCGAGATTT (SEQ ID NO:8) and CAGATAT-ATTTCTTCATGAAGACCTCACAGTAA (SEQ ID NO:9), a third primer pair comprising the sequences GGAATCCAT-TCTGGTGCCACT (SEQ ID NO: 13) and AGAAAATCCCTGTTCCCACTCATA (SEQ ID NO: 14), a fourth primer pair comprising the sequences GGTGCCAC-TACCACAGCTCCT (SEQ ID NO:18) and TCT-CAAAACTGCATTCTGACTTTCA (SEQ ID NO: 19), a fifth primer pair comprising the sequences TAAAAATAAAGCACCTACTGCTGAAA (SEQ ID NO:23) and AGCTTGCTTAGGTCCACTCTCTCT (SEQ ID NO:24), a sixth primer pair comprising the sequences TAGGATGTAATCAGACGACACAGGA (SEQ ID NO:27) and CAGCTGACCTAGTTCCAATCTTTTA (SEQ ID NO:28), a seventh primer pair comprising the sequences TCTCCCTCCAAAAGTGGTGCT (SEQ ID NO:31) and TGGCAATCGAACGACTCTCAA (SEQ ID NO:32), an eighth primer pair comprising the sequences GCAGAAGTAAAACACCTCCACCA (SEQ ID NO:35) and GGTGCTTTATTTTTAGGTACTTC (SEQ ID NO:36), and a ninth primer pair comprising the sequences CAG-GAAAATGACAATGGGAATG (SEQ ID NO:39) and ATCTAATAGGTCCTTTTCAGAATCAATAG (SEQ ID NO:40), respectively; and (c) a plurality of blocking nucleic acids, the plurality of blocking nucleic acids comprising a first blocking nucleic acid comprising the sequence TTG-GAGCTGGTGGCGTAinvdTinvdTinvdT (SEQ ID NO: 142), a second blocking nucleic acid comprising the sequence GAGATTTCACTGTAGCinvdTinvdTinvdT (SEQ ID NO: 148), a third blocking nucleic acid comprising the sequence GCCACTACCACAGCT(invdT)$_n$, wherein n is 1, 2, or 3 (SEQ ID NO:15), a fourth blocking nucleic acid comprising the sequence TCCTTCTCTGAGTGGinvdT-invdTinvdT (SEQ ID NO: 174), a fifth blocking nucleic acid comprising the sequence AGTGGTGCTCAGACACCCA-invdTinvdTinvdT (SEQ ID NO:161), a sixth blocking nucleic acid comprising the sequence CTTCTCGCTTGGT-TinvdTinvdTinvdT (SEQ ID NO:163), a seventh blocking nucleic acid comprising the sequence CTTTTCTTTTAT-TTCTGC*invdTinvdTinvdT* (SEQ ID NO:29), an eighth blocking nucleic acid comprising the sequence CCACTCTCTCTCTTTTCAGC *invdTinvdTinvdT* (SEQ ID NO:168), and a ninth blocking nucleic acid comprising the sequence CAATAGTTTTTTCTGCC*invdTinvdTinvdT* (SEQ ID NO:41), with italicized nucleic acids representing locked nucleic acids. In another aspect, provided herein are kits or articles of manufacture comprising (a) a plurality of probes, the plurality of probes comprising a first probe comprising the sequence TTTTTTTTTTTTAAGGAGCT-GATGG (SEQ ID NO:47), a second probe comprising the sequence TTTTTTTTTTTTAAGGAGCTGTTGG (SEQ ID NO:48), a third probe comprising the sequence TTTTTTTTTTTAAGGAGCTAGTGG (SEQ ID NO:86), a fourth probe comprising the sequence TTTTTTTT-TAAGGAGCTGGTGACGT (SEQ ID NO:91), a fifth probe comprising the sequence TTTTTTTAATTACTAGCTA-CAGAGAAA (SEQ ID NO:95), a sixth probe comprising the sequence TTTTTTTATTTCTAGCTACAGAAAAAT (SEQ ID NO:99), a seventh probe comprising the sequence TTTTTTTTTTAAGGAGCTGTGGCAG (SEQ ID NO: 104), an eighth probe comprising the sequence TTTTTTTTTTTTTGGAGCTGTGAT (SEQ ID NO:109), a ninth probe comprising the sequence TTTTTTTTATTAC-CACTCAGAAAAG (SEQ ID NO: 113), a tenth probe comprising the sequence TTTTTTTTTATTAC-CAATCAGAGGAGG (SEQ ID NO: 119), an eleventh probe comprising the sequence TTTTTTTTTTTT-TAGAAATAAAAGATTG (SEQ ID NO: 122), a twelfth probe comprising the sequence TTTTTTTTTAT-TTGGGTGTCTAAG (SEQ ID NO: 125), a thirteenth probe comprising the sequence TTTTTTTTTACAAACCAAGT-GAGAA (SEQ ID NO:60), a fourteenth probe comprising the sequence TTTTTTTTACTGCTGAAAAGAGAGAGT (SEQ ID NO:57), and a fifteenth probe comprising the sequence TTTTTTTTTTAGAGGCAGAAAAAAACT (SEQ ID NO:61); (b) a plurality of primer pairs, the plurality of primer pairs comprising a first primer pair comprising the sequences GTACTGGTGGAGTATTTGATAGTG (SEQ ID NO: 1) and ATCGTCAAGGCACTCTTGCCTAC (SEQ ID NO:2), a second primer pair comprising the sequences GGACCCACTCCATCGAGATTT (SEQ ID NO:8) and CAGATATATTTCTTCATGAAGACCTCACAGTAA (SEQ ID NO:9), a third primer pair comprising the sequences GGAATCCATTCTGGTGCCACT (SEQ ID NO: 13) and AGAAAATCCCTGTTCCCACTCATA (SEQ ID NO: 14), a fourth primer pair comprising the sequences GGTGCCACTACCACAGCTCCT (SEQ ID NO:18) and TCTCAAAACTGCATTCTGACTTTCA (SEQ ID NO: 19), a fifth primer pair comprising the sequences TAAAAATAAAGCACCTACTGCTGAAA (SEQ ID NO:23) and AGCTTGCTTAGGTCCACTCTCTCT (SEQ ID NO:24), a sixth primer pair comprising the sequences TAGGATGTAATCAGACGACACAGGA (SEQ ID NO:27) and CAGCTGACCTAGTTCCAATCTTTTA (SEQ ID NO:28), a seventh primer pair comprising the sequences TCTCCCTCCAAAAGTGGTGCT (SEQ ID NO:31) and TGGCAATCGAACGACTCTCAA (SEQ ID NO:32), an eighth primer pair comprising the sequences GCAGAAGTAAAACACCTCCACCA (SEQ ID NO:35) and GGTGCTTTATTTTAGGTACTTC (SEQ ID NO:36), and a ninth primer pair comprising the sequences CAG-GAAAATGACAATGGGAATG (SEQ ID NO:39) and ATCTAATAGGTCCTTTTCAGAATCAATAG (SEQ ID NO:40), respectively; and (c) a plurality of blocking nucleic acids, the plurality of blocking nucleic acids comprising a first blocking nucleic acid comprising the sequence TACGCCACCAGCT(invdT)$_n$, wherein n is 1, 2, or 3 (SEQ ID NO:3), a second blocking nucleic acid comprising the sequence GAGATTCACTGTAGC(invdT), wherein n is 1, 2, or 3 (SEQ ID NO:10), a third blocking nucleic acid comprising the sequence GCCACTACCACAGCT(invdT)$_n$, wherein n is 1, 2, or 3 (SEQ ID NO:15), a fourth blocking nucleic acid comprising the sequence GCTCCTTCTCT-GAG*TinvdTinvdTinvdT* (SEQ ID NO:20), a fifth blocking nucleic acid comprising the sequence GTGCTCAGACAC-C*invdTinvdTinvdT* (SEQ ID NO:33), a sixth blocking nucleic acid comprising the sequence CTTCTCGCTTGGT-T*invdTinvdTinvdT* (SEQ ID NO:37), a seventh blocking nucleic acid comprising the sequence CTTTTCTTTTAT-TTCTGC*invdTinvdTinvdT* (SEQ ID NO:29), an eighth blocking nucleic acid comprising the sequence CCACTCTCTCTCTTTTCAGC*invdTinvdTinvdT* (SEQ ID NO:25), and a ninth blocking nucleic acid comprising the sequence CAATAGTTTTTTCTGCC*invdTinvdTinvdT* (SEQ ID NO:41), with italicized nucleic acids representing locked nucleic acids. In some embodiments, each probe of the plurality is coupled to a microcarrier that has a unique identifier corresponding to the probe coupled thereto.

I. General Techniques

The practice of the techniques described herein will employ, unless otherwise indicated, conventional techniques in polymer technology, microfabrication, micro-electro-mechanical systems (MEMS) fabrication, photolithography, microfluidics, organic chemistry, biochemistry, oligonucleotide synthesis and modification, bioconjugate chemistry, nucleic acid hybridization, molecular biology, microbiology, genetics, recombinant DNA, and related fields as are within the skill of the art. The techniques are described in the references cited herein and are fully explained in the literature.

For molecular biology and recombinant DNA techniques, see, for example, (Maniatis, T. et al. (1982), *Molecular Cloning: A Laboratory Manual*, Cold Spring Harbor; Ausubel, F. M. (1987), *Current Protocols in Molecular Biology*, Greene Pub. Associates and Wiley-Interscience; Ausubel, F. M. (1989), *Short Protocols in Molecular Biology: A Compendium of Methods from Current Protocols in Molecular Biology*, Greene Pub. Associates and Wiley-Interscience; Sambrook, J. et al. (1989), *Molecular Cloning: A Laboratory Manual*, Cold Spring Harbor; Innis, M. A. (1990), *PCR Protocols: A Guide to Methods and Applications*, Academic Press; Ausubel, F. M. (1992), *Short Protocols in Molecular Biology: A Compendium of Methods from Current Protocols in Molecular Biology*, Greene Pub. Associates; Ausubel, F. M. (1995), *Short Protocols in Molecular Biology: A Compendium of Methods from Current Protocols in Molecular Biology*, Greene Pub. Associates; Innis, M. A. et al. (1995), *PCR Strategies, Academic Press*; Ausubel, F. M. (1999), *Short Protocols in Molecular Biology: A Compendium of Methods from Current Protocols in Molecular Biology*, Wiley, and annual updates.

For DNA synthesis techniques and nucleic acids chemistry, see for example, Gait, M. J. (1990), *Oligonucleotide Synthesis: A Practical Approach*, IRL Press; Eckstein, F. (1991), *Oligonucleotides and Analogues: A Practical Approach*, IRL Press; Adams, R. L. et al. (1992), *The Biochemistry of the Nucleic Acids*, Chapman & Hall; Shabarova, Z. et al. (1994), *Advanced Organic Chemistry of Nucleic Acids*, Weinheim; Blackburn, G. M. et al. (1996),

*Nucleic Acids in Chemistry and Biology*, Oxford University Press; Hermanson, G. T. (1996), *Bioconjugate Techniques*, Academic Press).

For microfabrication, see for example, (Campbell, S. A. (1996), *The Science and Engineering of Microelectronic Fabrication*, Oxford University Press; Zaut, P. V. (1996), Microarray Fabrication: a Practical Guide to Semiconductor Processing, *Semiconductor Services*; Madou, M. J. (1997), *Fundamentals of Microfabrication*, CRC Press; Rai-Choudhury, P. (1997). Handbook of Microlithography, Micromachining, & Microfabrication: Microlithography).

II. Definitions

Before describing the invention in detail, it is to be understood that this invention is not limited to particular compositions or biological systems, which can, of course, vary. It is also to be understood that the terminology used herein is for the purpose of describing particular embodiments only, and is not intended to be limiting.

The term "microcarrier" as used herein may refer to a physical substrate onto which a capture agent or probe may be coupled. A microcarrier of the present disclosure may take any suitable geometric form or shape. In some embodiments, the microcarrier may be disc-shaped. Typically the form or shape of a microcarrier will include at least one dimension on the order of $10^{-4}$ to $10^{-7}$ m (hence the prefix "micro").

The term "polymer" as used herein may refer to any macromolecular structure comprising repeated monomers. A polymer may be natural (e.g., found in nature) or synthetic (e.g., man-made, such as a polymer composed of non-natural monomer(s) and/or polymerized in a configuration or combination not found in nature).

The terms "substantially transparent" and "substantially non-transparent" as used herein may refer to the ability of light (e.g., of a particular wavelength, such as infrared, visible, UV, and so forth) to pass through a substrate, such as a polymer layer. A substantially transparent polymer may refer to one that is transparent, translucent, and/or pervious to light, whereas a substantially non-transparent polymer may refer to one that reflects and/or absorbs light. It is to be appreciated that whether a material is substantially transparent or substantially non-transparent may depend upon the wavelength and/or intensity of light illuminating the material, as well as the means detecting the light traveling through the material (or a decrease or absence thereof). In some embodiments, a substantially non-transparent material causes a perceptible decrease in transmitted light as compared to the surrounding material or image field, e.g., as imaged by light microscopy (e.g., bright field, dark field, phase contrast, differential interference contrast (DIC), Nomarski interference contrast (NIC), Nomarski, Hoffman modulation contrast (HMC), or fluorescence microscopy). In some embodiments, a substantially transparent material allows a perceptible amount of transmitted light to pass through the material, e.g., as imaged by light microscopy (e.g., bright field, dark field, phase contrast, differential interference contrast (DIC), Nomarski interference contrast (NIC), Nomarski, Hoffman modulation contrast (HMC), or fluorescence microscopy).

The term "analog code" as used herein may refer to any code in which the encoded information is represented in a non-quantized and/or non-discrete manner, e.g., as opposed to a digital code. For example, a digital code is sampled at discrete positions for a limited set of values (e.g., 0/1 type values), whereas an analog code may be sampled at a greater range of positions (or as a continuous whole) and/or may contain a wider set of values (e.g., shapes). In some embodiments, an analog code may be read or decoded using one or more analog shape recognition techniques.

As used herein, "sample" refers to a composition containing a material, such as a molecule, to be detected. In one embodiment, the sample is a "biological sample" (i.e., any material obtained from a living source (e.g. human, animal, plant, bacteria, fungi, protist, virus)). The biological sample can be in any form, including solid materials (e.g. stool, tissue, cell pellets and biopsies) and biological fluids (e.g. urine, blood, stool, saliva, lymph, tears, sweat, prostatic fluid, seminal fluid, semen, bile, mucus, amniotic fluid and mouth wash (containing buccal cells)). Solid materials typically are mixed with a fluid. Sample can also refer to an environmental sample such as water, air, soil, or any other environmental source.

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

III. Methods of Detecting DNA Mutations

Certain aspects of the present disclosure relate to methods for detecting the presence of DNA mutations (e.g., one or more mutations in the KRAS, BRAF, CTNNB1, and/or APC genes) by using microcarriers, e.g., an encoded microcarrier described herein, or any of the microcarriers described in International Publication No. WO2016/198954. The methods of the present disclosure employ encoded microcarrier(s) with some or all of the microcarrier features and aspects described herein, e.g., in sections IV, V, and VI. Advantageously, these encoded microcarriers allow for detection of DNA mutations in improved multiplex assays with a large number of potential unique microcarriers and reduced recognition error, as compared to traditional multiplex assays. A flowchart described an exemplary method for detection of DNA mutations is provided in FIGS. 14-16. The detection methods used herein may be performed in any suitable assay vessel known in the art, for example a microplate, petri dish, or any number of other well-known assay vessels.

In some embodiments, the methods of the present disclosure include isolating DNA from a sample. Standard molecular techniques known in the art allow for the isolation of DNA from a variety of different types of samples. DNA isolation kits suitable for a variety of samples are commercially available. For example, the QIAamp® DNA Stool Mini Kit (QIAGEN; Hilden, Germany) can be used to isolate DNA from a stool sample (e.g., using an elution volume of 50 µL per 2 g of stool sample) according to manufacturer's instructions.

In some embodiments, the methods of the present disclosure use DNA from a sample at a concentration of between about 0.5 and 2.5 ng/µL. In some embodiments, the methods of the present disclosure use DNA from a sample at a concentration of at least about 0.5 ng/μL. For example, 20 μL of a 0.5 ng/μL DNA Stock (total of 10 ng DNA) or a 2.5 ng/μL DNA stock (total of 50 ng DNA) may be used (e.g., for PCR amplification).

In some embodiments, the methods of the present disclosure are used to detect, monitor, screen for, or monitor treatment response of colon cancer, rectal cancer, colorectal cancer, colon adenoma, rectal adenoma, or colorectal adenoma, e.g., in a patient from whom the sample is collected. As used herein, colon, rectal, and colorectal cancer can refer to various types of cancers, including without limitation adenocarcinomas, lymphomas, stromal tumors, leiomyosarcomas, carcinoid tumors, and melanomas. Colorectal cancers are thought to progress from benign neoplasias like adenomas (e.g., a polyp) to malignancies such as carcinomas and metastatic disease as DNA mutations accumulate, but even some early adenomas have DNA mutations such as the KRAS activating mutations described herein. See Fearon, E. F. and Vogelstein, B. (1990) *Cell* 61:759-67. Detecting DNA mutations from stool samples is particularly of interest in the early detection of colorectal cancer. See, e.g., U.S. Pat. No. 7,833,757; Imperiale, T. F. et al. (2014) *N. Engl. J. Med.* 370:1287-97; and the COLOGUARD® kit (Exact Sciences Corp.). Existing diagnostic techniques such as sigmoidoscopy and colonoscopy are highly invasive (and therefore can suffer from low patient acceptance) and can miss tumors that are very small and/or in inaccessible locations. In contrast, the methods described herein are thought to be highly accurate, robust, and non-invasive.

The methods of the present disclosure can be used to detect analytes (e.g., DNA mutations) in any suitable solution. In some embodiments, the solution comprises a biological sample. In some embodiments, the solution comprises DNA isolated from a biological sample and, optionally, a buffer. Suitable buffers for DNA isolation are well-known in the art. Examples of biological samples include without limitation stool, blood, urine, sputum, bile, cerebrospinal fluid, interstitial fluid of skin or adipose tissue, saliva, tears, bronchial-alveolar lavage, oropharyngeal secretions, intestinal fluids, cervico-vaginal or uterine secretions, and seminal fluid. In some embodiments, the sample is a stool sample. In some embodiments, multiple samples are obtained from a single specimen (e.g., representing different regions of the specimen, such as described in Example 2) and analyzed individually. In other embodiments, a single, large stool specimen is analyzed (e.g., an entire stool or stool sample is analyzed instead of sampling discrete, smaller samples). In some embodiments, the biological sample may be from a human. In other embodiments, the solution comprises a sample that is not a biological sample, such as an environmental sample, a sample prepared in a laboratory (e.g., a sample containing one or more analytes that have been prepared, isolated, purified, and/or synthesized), a fixed sample (e.g., a formalin-fixed, paraffin-embedded or FFPE sample), and so forth.

In some embodiments, the methods of the present disclosure include amplifying DNA (e.g., DNA isolated from a sample as described supra) by polymerase chain reaction (PCR). PCR techniques are well-known in the art. Briefly, a thermostable DNA polymerase is used to amplify copies of a DNA sequence of interest using template DNA strands (e.g., isolated from a sample and denatured) and a pair of oligonucleotide primers that are complementary to the 3' ends of the sense and anti-sense strands (respectively) of the DNA template. The DNA polymerase is mixed in a reaction with both primers, all four deoxynucleotides (dNTPs), a buffer, magnesium ions (e.g., $MgCl_2$), and potassium ions (e.g., KCl), and optionally other ingredients. The reaction mixture is then subjected to multiple cycles (e.g., 20-40) of temperature changes that allow for denaturation of the DNA template, annealing of the primers to the denatured, single-stranded template, and primer extension by the DNA polymerase. Various DNA polymerases with different properties of interest (e.g., ability to amplify long or repetitive templates, high fidelity, hot start, etc.) have been characterized for use in PCR and are commercially available.

In some embodiments, the methods of the present disclosure include amplifying (e.g., by PCR) from isolated DNA the loci of one or more DNA mutations in one or more specific genes of interest. As herein, a "locus" of a DNA mutation comprises the mutation itself and sufficient adjacent sequence on one or both sides of the mutation for PCR amplification of, and/or probe hybridization to, the mutated DNA sequence. As is known in the art, the minimum sequence length sufficient for PCR amplification can be influenced by several factors, including without limitation the polymerase, the melting temperature of the primers, the propensity of the primers to form primer dimers, the ratio of the template to primers, etc. In some embodiments, the locus of a DNA mutation comprises at least about 100 base pairs of adjacent sequence (i.e., including adjacent sequence both 5' and 3' to the DNA mutation). In some embodiments, the locus of a DNA mutation comprises less than or equal to about 200 base pairs of adjacent sequence (i.e., including adjacent sequence both 5' and 3' to the DNA mutation). As described above, the locus of a DNA mutation can be amplified using a pair of primers specific to the locus, using the locus as the DNA template. While mutations are described herein as DNA mutations, it will be appreciated that similar techniques could be applied to detecting RNA mutations, e.g., using mRNA or cDNA from a sample.

In some embodiments, multiple PCR reactions can be used, e.g., to detect various DNA mutations. In some embodiments, each PCR reaction can include multiple primer pairs, each specific for a DNA mutation of interest. For example, in some embodiments, as shown in Examples 1 and 2 below, the methods of the present disclosure can include two PCR reactions: a first PCR reaction with the reagents for detecting the following mutations: KRAS G12D, KRAS G12V, KRAS G12S, KRAS G13D, BRAF V600E1, BRAF V600E2, CTNNB1 T41A, CTNNB1 T41I, APC E1309, APC Q1367, APC R1450, and APC T1556; and a second PCR reaction with the reagents for detecting the following mutations: CTNNB1 S45F, CTNNB1 S45P, and APC S1465. In some embodiments, each PCR reaction includes: 10 μL of PCR reaction mix, 10 μL of primer mix, and 20 μL DNA (e.g., 20 μL of a 0.5 ng/μL DNA Stock, for a total of 10 ng DNA). In some embodiments, multiple PCR reactions are performed using the same temperature cycling conditions.

Mutations

In some embodiments, the methods of the present disclosure include amplifying the loci of one or more mutations in a KRAS gene. As used herein in reference to the KRAS, BRAF, CTNNB1, and APC genes, amplifying the locus of a DNA mutation encompasses amplifying either the mutant locus or the corresponding wild-type locus. It will be appreciated that in most instances, while four or more mutations are screened in a multiplex assay, any individual sample will typically include at most one of the mutations being screened. KRAS encodes the KRAS proto-oncogene, a small GTPase frequently mutated in human cancers, also known as the Kirsten rag sarcoma viral oncogene homolog, PR310 c-K-ras oncogene, c-Ki-ras, c-Kirsten-ras, K-Ras2, K-ras p21, GTPase KRas, cellular c-Ki-ras2 proto-oncogene, cellular transforming proto-oncogene, oncogene KRAS2, transforming protein p21, and v-Ki-ras2 Kirsten rat sarcoma 2 viral oncogene homolog. In some embodiments, the KRAS gene is a human KRAS gene. In some embodiments, a human KRAS gene refers to the gene described by NCBI Entrez Gene ID No. 3845, including mutants and variants thereof. In other embodiments, the KRAS gene is from one of the following organisms: mouse (see, e.g., NCBI Entrez Gene ID No. 16653), rat (see, e.g., NCBI Entrez Gene ID No. 24525), cynomolgus monkey (see, e.g., NCBI Entrez Gene ID No. 102131483), fish (see, e.g., NCBI Entrez Gene ID No. 445289), dog (see, e.g., NCBI Entrez Gene ID No. 403871), cattle (see, e.g., NCBI Entrez Gene ID No. 541140), horse (see, e.g., NCBI Entrez Gene ID No. 100064473), chicken (see, e.g., NCBI Entrez Gene ID No. 418207), chimpanzee (see, e.g., NCBI Entrez Gene ID No. 473387), rhesus monkey (see, e.g., NCBI Entrez Gene ID No. 707977), or cat (see, e.g., NCBI Entrez Gene ID No. 751104).

A variety of KRAS mutations associated with cancer are known and may be suitably detected by the methods described herein; see, e.g., Prior, I. A. et al. (2012) Cancer Res. 72:2457-67. For example, one study found that 30% of colorectal tumors in their cohort had KRAS mutations, predominantly at amino acid 12 (Smith, G. et al. (2002) Proc. Natl. Acad. Sci. 99:9433-8). In some embodiments described herein, a KRAS mutation is named based on the resulting amino acid substitution/deletion/frameshift according to a human KRAS protein, e.g., as set forth in MTEYKLVVVGAGGVGKSALTIQLIQNHFVDEYDP-TIEDSYRKQVVIDGETCLLDILDT AGQEEY-SAMRDQYMRTGEGFLCVFAINNTKSFEDIHHY-REQIKRVKDSEDVPMVLVG NKCDLPSRTVDTKQAQDLARSYGIPFIET-SAKTRQGVDDAFYTLVREIRKHKEKMSKD GKKKKKKSKTKCVIM (SEQ ID NO:62). An exemplary human KRAS cDNA sequence is set forth in TGTGCTCG-GAGCTCGAT-TTTCCTAGGCGGCGGCCGCGGCGGCG-GAGGCAGCAGCGGCGGCGGCAGTGGCGGCGGCG AAGGTGGCGGCGGCTCGGCCAGTACTCCCGGCCC CCGCCATTTCGGACTGG-GAGCGAGCGCGGCGCAGGCACTGAA GGCGGCGGCGGGGCCAGAGGCTCAGCGGCTCCC AGGCCTGCTGAAAATGACT-GAATATAAACTTGTGGTAGTTGGA GCTGGTGGCGTAGGCAAGAGTGCCTTGACGATA-CAGCTAATTCAGAATCATTTTGTGGACGAATAT-GATCCAACAA TAGAGGATTCCTACAG-GAAGCAAGTAGTAATTGATGGAGAAACCTGTCTC TTGGATATTCTCGACACAGCAGGTCA AGAG-GAGTACAGTGCAATGAGGGACCAGTACAT-GAGGACTGGGGAGGGCTTTCTTTGTGTATTTGC-CATAAATAAT ACTAAATCATTTGAAGATATTCACCAT-TATAGAGAACAAATTAAAAGAGTTAAGGACTCT-GAAGATGTACCTATGG TCCTAGTAG-GAAATAAATGTGATTTGCCTTCTAGAACAGTAGA CACAAAACAGGCTCAGGACTTAGCAAGAAGTTA TGGAATTCCTTTTATTGAAACATCAGCAAAGACAA-GACAGAGAGTGGAGGATGCTTTTTATACATTGGT-GAGAGAG ATCCGACAATACAGATT-GAAAAAAATCAGCAAAGAAGAAAAGACTCCTG GCTGTGTGAAAATTAAAAAATGCATTA TAATGTAATCTGGGTGTTGATGATGCCTTCTATA-CATTAGTTCGAGAAATTCGAAAACATAAAGAAAA-GATGAGCA AAGATGGTAAAAAGAAGAAAAAG (SEQ ID NO:66). In some embodiments, a DNA mutation results in the mutation of G12 or G13 according to SEQ ID NO:62 or SEQ ID NO:66. For example, in some embodiments, a DNA mutation in a KRAS gene encodes or results in a G12D, G12V, G12S, or G13D mutated KRAS protein (numbering according to SEQ ID NO:62). These DNA mutations are also described by their nucleotide positions (rather than mutated polypeptide codons) in Table A infra. For example, in some embodiments, a DNA mutation in a KRAS gene results in a c.35G>A, c.35G>T, c.34G>A, or c.38G>A mutation in the corresponding cDNA sequence of SEQ ID NO:66.

Since, as described supra, the sequences of a variety of KRAS genes and corresponding mutations are known, one of ordinary skill in the art may suitably select a primer pair to amplify the locus of one or more of these DNA mutation(s). Various factors influencing primer design are known, and tools for identifying primer pairs suitable for amplifying a given DNA template sequence are available (see, e.g., www.ncbi.nlm.nih.gov/tools/primer-blast/). In certain embodiments, a primer pair for amplifying the locus of a KRAS mutation (e.g., encoding or resulting in a G12D, G12V, G12S, or G13D mutated KRAS protein) comprises the sequences GTACTGGTGGAGTATTTGATAGTG (SEQ ID NO:1) and ATCGTCAAGGCACTCTTGCCTAC (SEQ ID NO:2), respectively.

In some embodiments, the methods of the present disclosure include amplifying the loci of one or more mutations in a BRAF gene. BRAF encodes the BRAF proto-oncogene, a serine/threonine kinase frequently mutated in human cancers, also known as B-Raf, BRAF1, B-RAF1, RAFB 1, NS7, 94 kDa B-raf protein, p94, murine sarcoma viral (v-raf) oncogene homolog B1, v-raf murine sarcoma viral oncogene homolog B, and v-raf murine sarcoma viral oncogene homolog B1. In some embodiments, the BRAF gene is a human BRAF gene. In some embodiments, a human BRAF gene refers to the gene described by NCBI Entrez Gene ID No. 673, including mutants and variants thereof. In other embodiments, the BRAF gene is from one of the following organisms: mouse (see, e.g., NCBI Entrez Gene ID No. 109880), rat (see, e.g., NCBI Entrez Gene ID No. 114486), cynomolgus monkey (see, e.g., NCBI Entrez Gene ID No. 101866436), fish (see, e.g., NCBI Entrez Gene ID No. 403065), dog (see, e.g., NCBI Entrez Gene ID No. 475526), cattle (see, e.g., NCBI Entrez Gene ID No. 536051), horse (see, e.g., NCBI Entrez Gene ID No. 100065760), chicken (see, e.g., NCBI Entrez Gene ID No. 396239), chimpanzee (see, e.g., NCBI Entrez Gene ID No. 463781), rhesus monkey (see, e.g., NCBI Entrez Gene ID No. 693554), or cat (see, e.g., NCBI Entrez Gene ID No. 101092346).

A variety of BRAF mutations associated with cancer are known and may be suitably detected by the methods described herein; see, e.g., Davies, H. et al. (2002) Nature 417:949-54; and Garnett, M. J. and Marais, R. (2004) Cancer Cell 6:313-9. For example, one review has described that BRAF mutations have been found in 9-14% of patients with colon and rectal cancers, are associated with poor overall survival, and are found in over 50% of microsatellite instability (MSI) high tumors (Clarke, C. N. and Kopetz, E. S. (2015) J. Gastrointest. Oncol. 6:660-7). In some embodiments described herein, a BRAF mutation is named based on the resulting amino acid substitution/deletion/frameshift according to a human BRAF protein, e.g., as set forth in MAALSGGGGGGAEPGQALFNGDMEPEA-GAGAGAAASSAADPAIPEEVWNIKQMIKL TQE- HIEALLDKFGGEHNPPSIYLEAYEEYTSKLDALQQREQQLLESLGNGTDFSVSSSA SMDTVTSSSSSSLSVLPSSLSVFQNPTDVARSNPKSPQKPIVRVFLPNKQRTVVPARCG VTVRDS LKKALMMRGLIPECCAVYRIQDGEKKPIGWDTDISWLTGEELHVEVLENVPL TTHNFVRKTFFTLAFCDFCRKLLFQGFRCQTCGYKFHQRCSTEVPLMCVNYDQLDLLF VSKFFEHHPIPQEEASLAETALTSGSSPSAPASDSIGPQILTSPSPSKSIPIPQPFRPADEDH RNQFGQRDRSSSAPNVHINTIEPVNIDDLIRDQGFRGDGGSTTGLSATPPASLPGSLTNV KALQKSPGPQRERKSSSSSEDRNRMKTLGRRDSSDDWEIPDGQITVGQRIGSGSFGTVY KGKWHGDVAVKMLNVTAPTPQQLQAFKNEVGVLRKTRHVNILLFMGYSTKPQLAIV TQWCEGSSLYHHLHIIETKFEMIKLIDIARQTAQGMDYLHAKSIIHRDLKSNNIFLHEDL TVKIGDFGLATVKSRWSGSHQFEQLSGSILWMAPEVIRMQDKNPYSFQSDVYAFGIVL YELMTGQLPYSNINNRDQIIFMVGRGYLSPDLSKVRSNCPKAMKRLMAECLKKKRDE RPLFPQILASIELLARSLPKIHRSASEPSLNRAGFQTEDFSLYACASPKTPIQAGGYGAFP VH (SEQ ID NO:63). An exemplary human BRAF cDNA sequence is set forth in GTTATAAGATGGCGGCGCTGAGCGGTGGCGGTGGTGGCGGCGCGAGCCGGGCCAGGCTCTGTTCAACGGGGACAT GGAGCCCGAGGCCGGCGCCGGCGCCGGCGCCG CGGCCTCTTCGGCTGCGGACCCTGCCATTCCGGAGGAGGTGTGG AATATCAAACAAATGATTAAGTTGACACAGGAACATATAGAGGCCCTATTGGACAAATTTGGTGGGGAGCATAATC CACCATCAATATATCTGGAGGCCTATGAAGAATACACCAGCAAGCTAGATGCACTCCAACAAAGAGAACAACAGTT ATTGGAATCTCTGGGGAACGGAACTGATTTTTCTGTT TCTAGCTCTGCATCAATGGATACCGTTACATCTTCTTCC TCTTCTAGCCTTTCAGTGCTACCTTCATCTCTTTCAGTTTTTCAAAATCCCACAGATGTGGCACGGAGCAACCCCA AGTCACCACAAAAACCTATCGTTAGAGTCTTCCTGCCCAACAAACAGAGGACAGTGGTACCTGCAAG GTGTGGAGT TACAGTCCGAGACAGTCTAAAGAAAGCACTGATGATGAGAGGTCTAATCCCAGAGTGCTGTGCTGTTTACAGAATT CAGGATGGAGAGAAGAAACCAATTGGTTGGGACACTGATATTTCCTGGCTTACTGAGAAGAATTGCATGTGGAAG TGTTGAGAATGTTCCACTTACAACACACAACTTTGT ACGAAAAACGTTTTTCACCTTAGCATTTTGTGACTTTTG TCGAAAGCTGCTTTTCCAGGGTTTCCGCTGTCAAACATGTGGTTATAAATTTCACCAGCGTTGTAGTACAGAAGTT CCACTGATGTGTGTTAATTATGACCAACTTGATTTGCTGTTTGTCTCCAAGTTCTTT GAACACCACCCAATACCAC AGGAAGAGGCGTCCTTAGCAGAGACTGCCCTAACATCTGGATCATCCCCTTCCGCACCCGCCTCGGACTCTATTGG GCCCAAATTCTCACCAGTCCGTCTCCTTCAAAATCCATTCCAATTCCACAGCCCTTCCGACCAGCAGATGAAGAT CATCGAAATCAATTTGGGCAACGAGACCGATCCTCATCAGCTCCCAATGTGCATATAAACACAATAGAACCTGTCA ATATT GATGACTTGATTAGAGACCAAGGATTTCGT GGTGATGGAGCCCCTTTGAACCAGCTGATGCGCTGTCTTCG GAAATACCAATCCCGGACTCCCAGTCCCCTCCTACATTCTGTCCCCAGTGAAATAGTGTTTGATTTTGA GCCTGGC CCAGTGTTCAGAGGATCAACCACAGGTTTGTCTGCTACCCCCCCTGCCTCATTACCTGGCTCACTAACTAACGTGA AAGCCTTACAGAAATCTCCAGGACCTCAGCGAGAAAGG AAGTCATCTTCATCCTCAGAAGACAGGAATCGAATGAA AACACTTGGTAGACGGGACTCGAGTGATGATTGGGAGATTCCTGATGGGCAGATTACAGTGGGACAAAGAATTGGA TCTGGATCATTTGGAACAGTCTACAAGGAAAGTGGCATGGTGATGTGGCAGTGAAAATGTTGAATGTGACAGCAC CTACACCTCAGCAGTTACAAGCCTTCAAAAATGAAGTAGGAGTACTC AGGAAAACACGACATGTGAATATCCTACT CTTCATGGGCTATTCCACAAAGCCACAACTGGCTATTGTTACCCAGTGGTGTGAGGGCTCCAGCTTGTATCACCAT CTCCATATCATTGAGACCAAATTTGAGATGATCAAACTTATAGATATTGCACGACAGACTGCACAGGGCATGGATT ACTTACACGCCAAGTCAATCATCCACAGAGACCTCAAGAGTAATAATATATTTCTTCATGAAGACCTCACAGTAAA AATAGGTGATTTTGGTCTAGCTACAGTGAAATCTCGATGGAGTGGGTCCCATCAGTTTGAACAGTTGTCTGGATCC ATTTTGTGGATGGCACCAGAAGTCATCAGAATGCAAGATAAAAATCCATACAGCTTTCAGTCAGATGTATATGCAT TTGGAATTGTTCTGTATGAATTGATGACTGGACAGTT ACCTTATTCAAACATCAACAACAGGGACCAGATAATTTT TATGGTGGGACGAGGATACCTGTCTCCAGATCTCAGTAAGGTACGGAGTAACTGTCCAAAAGCCATGAAGAGATTA ATGGCAGAGTGCCTCAAAAAGAAAAGAGATGAGACCACTCTTTCCCCAAATTCTCGCCTCTATTGAGCTGCTGG CCCGCTCATTGCCAAAAATTCACCGCAGTGCATCAGAACCCTCCTTGAAT CGGGCTGGTTTCCAACAGAGGATTT TAGTCTATATGCTTGTGCTTCTCCAAAAACACCCATCCAGGCAGGGGATATGGAGAATTTGCAGCCTTCAAGTAG CCACCATCATGGCAGCATCTGCTCTTATTTCTTAAGTCTTGTGTTCGTACAATTTGTTAACATCAAAACACAGTTC TGTTCCTCAAATCTTTTTTTAAAGATACAAAATTTCCAATGCATAAGCTGATGTGGAACAGAATGGAATTTCCCAT CCAACAAAAGAGGAAAGAATGTTTTAGGAATTCTCTGCTGCCAGAATTTGTTTCTTCAACAAAAATACCACGAG CATACAAGTCTGCCCAGTCCCAGGAAGAAAGAG GAGAGACCCTGAATTCTGACCTTTTGATGGTCAGGCATGATGG AAAGAAACTGCTGCTACAGCTTGGGAGATTTGCTATGGAAAGTCTGCCAGTCAACTTTGCCCTTCTAACCACCAGA TCAATTTGTGGCTGATCATCTGATGGGGCAGTTTCAATCAAGCATCGTTCTCTTTCCTGTTCTGGAATTTTGT TTTGGAGCTCTTTCCCCTAGTGACCACCAGTTAGTTTCTGAGGGATGGAACAA AATGCAGCTTGCCCTTTCTATG TGGTGCGTGTTCAGGCCTTGACAGATTTTATCAAAAGGAAACTATTTTATTTAAATGGAGGCTGAGTGGTGAGTAG ATGTGTCTTGGTATGGAGGAAAAGGGCATGCTGCATCTTCTTCCTGA CCTCCGGGGTCTCTGGCCTTTTGTTTCCT TGCT-
CACTGAGGGGTCTGTCTAACCAAGCAGGCTAGA-
TAGTGCTGGCACACATTGCCTTCTTTCTCAT-
TGGGTCCA
GCAATGAAGA-
TAAGTGTTTGGGTTTTTTTTTTTCCTC-
CACAATGTAGCAAATTCTCAGGAAATACAGTT-
TATATC
TTCCTCCTATGCTCTTCCAGTCACCAACTACT-
TATGCGGC-
TACTTTGTCCAGGGCACAAAATGCCGTGGCAGTATC
TAACTAAACCCCCACAAAACTGCT-
TAATAACAGTTTTGAATGTGAGAAATTTAGATAATT-
TAAATATAAGGTACAG GTTTTAATTTCT-
GAGTTTCTTCTTTTCTATTTTTATTAAAAAG
AAAATAATTTTCAGATTTAATTGAATTGGAAAA
AAACAATACTTCCCACCAGAATTATATATCCT-
GAAAATTGTATTTTGTTATATAAACAACTTT-
TAAGAAAGATCA TTATCCTTTTCTCTACCTAAATAT-
GAGGAGTCTTAGCATAATGACAAATATTT
ATAATTTTTCAATTAATGGTACT TGCTGGATC-
CACACTAACATCTTTGCTAATAATCTCAT-
TGTTTCTTCCAACTGATTCCTAACACTATATCCCA-
CAT
CTTCTTTCTAGTCTTT-
TATCTAGAATATGCAACCTAAAATAAAA
ATGGTGGCGTCTCCATTCATTCTCCTTCTTCC
TTTTTTCCCAAGCCTGGTCTT-
CAAAAGGTTGGGCAATTTGGCAGCTGAATTCCCA-
GACAGAGAATAGAGCAATTTT AGGGATATT-
AGGACTGAGGGAGGGTGTGGGAAAGCTG
TCATCAGTTGTTTTATAGAAAGAACTGGCATTCAT-
TAA GAACCTAAATCTTATCTTTGCACAAATG-
GAAAATATAACCTAGTTATAGCTTCCTTTGGCCTTT-
ATTAAAGGGTAA
TATCAATCACAGTCATAGCAAAGAAAGCGGATGT-
ATTAATGGCAAATTAATGGAAAACCTCCCT-
TATCAGGAATCT AGACTCAGAATTTAG-
GAACACAAATCAAATCAGACCAACCAAGCTATAGC-
CAAGGACTTGAAAGAAATTAAACAAG
ACCCAGAATAAATCAAGGAATTAGAAATTGTTATT-
TAAAAATTTCAGAT-
TGTAACTCCAGGCCCTGCTGTCTATAT TGCAGC-
CACTAAAAGCTCACTACCATTAGATTTTTGC
TAACATACATGTATTCAGAAGAAAGCCTATTGAAAT-
TTT CAT-
TGTCTTGTAAAAGGTTGTCCTAGTAAAATGGAAAA-
GATCCTTAAGTTATTAATCAGTTTGAAAAG
CAAATTTG TTTTTAAGTTTTA-
CATCAGCAGGGCAGTGTCTTACAAAATT CAGAAAT-
TGCAAAGGTGGAAATAATTCACGCTGAT
TTGAAGAACATCTTCTGTGCAATAATACTGCCTCTT-
GAAAAGCATTGGCTGTTTTTCTTTT-
TAAATATATCTC TAGATGCTTT-
TAAATGTGGCTGTGTTCCCTTTACCAAGA
TTGGCTTCAAGTTTCCGCAGGTAGAGA-
GACCTGGGCT TGAACAAGAGGATGTGTTT-
CATGTCCTGCTGAGGAGGTAGAA-
CATGTGCAGCCTGGGTCCGGGACTGCCTCCGTGG
GGCAGGGGCAGGGGCGGTACCATTAGGGAG-
GAAGCTTAGCATTTCAGTTTCTTAAACAATAT-
TCAGGGTGATACAC TTTTCTTCCCTTGCATTT-
TAGAATAGGCTGGTATCTCATTTGAACGGGG
GAGCAGACTTGATCTCAAATGAAGCT GTGCCCAG-
GAGCCAGGCTTAGCATATTGAGATTTTTATAGA-
TACCTTAAAAAATAAAATATTTAAACCTCTCTTTT
CTTCCTTTTTCTAT- GAAATAGGTTTTTTCTCTAGTTTACAAATGAC
ATGAAAATAGGTTTTATTTGTGTTTTATCT GCTTTAT-
TTTTTGATGCTTAGACAACAGTTAGACTTACT-
GAGCTCCTAAAAAAACGAGGAAGAAGTCCTTAT-
TTGT
GAAAAGCACTTTATGAGTAATTGTATA-
GACAGTATGTGGCTGCGTCACTGAT-
CATCTTGTAAGGGTGTAACAGTCT
TGTCTGTAAAGTGGCTGCAGTGCCTTCTGT
AGTGTGTTTTATTTTTGGTAGGGAGAGGT-
GAAGCCTTCTGAAAAAT TTGAGAGCAACTA-
CAGAGGATTGTTTGTAACTGTGTAGTATTCCT-
GATGGACTTTTTTCATCGTTAGAGTCAAGGA
CCTAGACTTTTGCCACTGAAATAATATTGAC-
CAAATAGTTATAAAAGGGATTTGTGAATAGAAAAT-
TCAGT GTGATCATTTGTTGTTAATGTGCACCT-
TAAAAGAAGATTCTGTCTAGCTGTCAAATT
CTGGTTCCCGAATATCTCA CCCCTGATTGTATTT-
GAGATCTAGTAGGGCATACTGGGGCATTTTAGAA-
GATAAAATCCCATACAAATGATATATG CTATATT-
TATGTTGGTGTTGGAGAAGAAAGAGCAGT
ATATAAAGAAATAATTCAAGACTGCAGCACTGT-
CAACCTG AAACTTTGTAAATAT-
TTCCTAGCTTCTGGTTTGGTGCGGTGACAGCACTTT-
CATCACAGGATGTTACCTTGTATTC
ACCAGGCGGAGTGCGAGCTGCTGCA-
CATCCTCCTCAGATCTCACCTGTCCCCACTGTA-
CATCCACCCGCCAGCTGC TTGCAAACCT-
CATCTCTAGCTTTAGTTCGAAACCAC
ATTGCAGGGTTCAGGTGACCTCTACAAAAAC-
TACCTCTT CAGAATGAGGTAATGAATAGTTATTTAT-
TTTAAAATATGAAAAGTCAGGAGCTCTAGAA-
CATGACGATGATTTAAG
ATTTTAACTTTTTTGTGTACTTGTATTTGAGCACTCT-
CATTTTGTCCTAAAGGGCATTATACATT-
TAAGCAGTAAT ACTGTAAAAAAATGTGTTGCTCG-
GAATATCTGAATGTTGTTGAAAGTGGT
GCCAGAACCGGTTTAGGGGTACGTTT CAGAATCT-
TAACCTTGAGTCAATTGCATGAAAT-
TAAATAGCTGTGGTATCACTTCACTAACAGT-
GATGTAATTTA
ATTTTCAGTAGGCTTGGCATGACAGTACATCCTCAT-
AATGAGTTTGCTGCAGCTTTGTCACATGCACAGG-
CATTCA TAGAAAGAC-
CACCCAGCTAAGAGGGTAGAATGAT
TACTCTTTTTGCAAGATTCTCTTCTTTGTC-
CAAGTTGGCATT GTTAGTGCTAG-
GAATACCAGCACCTTGAGACGAGCAGATTCCAAC-
CATTAGGCTATAAACACCATAGCCAGAGATG
GAAGGTTTACTGTGAGTATGAACAGCAAATAGCT-
TACAGGTCATGAGTTGAAATGGTGTAGGT-
GAGGCTCTAGAAA AATACCTTGACAATTTGC-
CAAATGATCTTACTGTGCCTTCATGATG
CAATAAAAAAGCTAACATTTTAGCAGAAAT CAGT-
GATTTGTGAAGAGCAGCCACTCTGGTT-
TAACTCAGCTGTGTTAATAATTTTTAGAGTGCAATT-
TAGACTG
CATAGGTAAATGCACTAAAGAGTTTATAGC-
CAAAATCACATTTAACAAT-
GAGAAAACACACAGGTAAATTTTCAGT
GAACAAAATTATTTTTTAAAGCACAT-
AATCCCTAGTATAGTCAGATATATTTATCACAT-
AGAGCAACTAGGTTGC AAATATAGTTCAGTGACAT-
TCTAGAGAAACTTTTTCTACTCCCATAG
GCTCTTCAAAGCATGGAACTTTTATACA
ACAGAAATGTTGACAGAAATTGCTGTAGTT-
TAGGGTTGAAGTACTGTATGATGGGCAGCAAT-
CATGTATTAACTTA GAAGGGGAAATT-
GAAATATAGGACCGAATTTGGTTTTAT
CAGTTTCCAGAGTACTGCTGC- CAACCTAGACACTGAT
TTTTCAGAGTTTGAAATGTAAATTTCTTCCCGGGACTTGATTGCACATGAAGCTGGACTGCGTTAGTCATCCTGTC
CCAAAGCGCTGTGGGGGCCAGGGTGGAGGTCTCAAGGCATCCTTTATGACCTGGCCATTGGATGTAAAAGAAAACA TATTCCATGCTGTGGTTCTTGTATCTTGT
TTCATTCCTCACCATTGAAAGAGAAAGTCCATGTATTGTCTCCAGCA CATCCTTGAAATGTTATACTGGGATGGATTACTGATGCCCATCGGTAGTTGAGCCCCAGAAGAGGGTAGTAGCATC
TCTGCCTCAGGTGATGATTTGTAGCTTGGCCAGAGGAGAGCGGAGTCACCAGTATATCTGTGGTCCATGTTGCTAG CTCTGGTAAAATTAAAAATACTGGTAAGATGTTTG
TTTTATTAGTACACTAGACAGTAAGCTCTGTTTTGTTGTTT TCAAATAACCTATTTTCACTTTTGTTTGGGCAAAGACATTTAAATTGAAATTCAATTCTAATTTTTGTTAATTGTG
GAAAGGGTAATTAACAGTTCCTATCAGGTATTTTTAATGTGGAAAAGGACAGAAACCCAACTCCTAAAATCTTAAA
TTAAGGTAACAGTGCTTTAAAAAAAAAAATGCATGGGCAATTAGTCGGCAACTCAATGAGTGACTAAAGTACTT TTATTTAACATCCACAACTTCAACTGTTAAGTTTTATTA
ATTACTAAATCAGCTTTATTAAAATGTTGACATTTAT
TTAGCTATTTTGAATAATTATAGTGACTTGACGAGTGTGTATGAGGACACAGCCAATGTAAGCCAGTGTATCCATT TTTTAGAGGTGCATTTTTTTTAAAGAATTCTGTAGATA
GAAGTGCTCTGAAAACAACTAAAATATGTTTATTCAT GGTAGTATCAAAAAATGTTTGTACAAACCATCTGCTTCTCCCGGCCAGCCGAGTTCATTCTCCAGCACCGTGACCG
CTGGTTCTCATGTACAGCACATATGCGGGAGAGTTGGCAGAAAATTTGTGAAGAGATGCCGCAAAGGAAGGGTCTG
TTGACGGGTGGGATTGGGGGTTTTGATGAAGTTGCTTAGTCCTGGTTTTGTTTGAAAATTACTGCGTTGCATTTT TGTGTTAAGTTTTTGAACCCACGTGTGTTTTGGTGGAGTATGA
GTTGGAAGTCACTGCAAACTAGCATAAACAACA
AAGCTCACAGAGTAGGCACAGATGTAGAGAACAGAGACCAAAATGGGGTGAGGTGGCAGTAAATCTAGGATAGGGA AAAATTAATGTGAGGGTGGGAAATAAACTGTA
ATTACCTGAAATCAAATGTAAGAGTGCAATAAGTATGCTTTTTA
TTCTAAGCTGTGAACGGTTTTTTTAAGAATCATTCCTTCCTAATACATTTGTGTATGTTCCATAGCTGATTAAAAC CAGCTATATCAACATATAATGCCTTTTTATTCATGTTAATGACCAACGTAAGTGGCTAGCC
TTTATGTCTTATTTA TCTTCATGTTATGTTAGTTTACATACAGGGGTGTATGTCTCTGTGCTGTCCCC
TTCTCCTGCCTTCATTTAAAAT GCATCCATGGGTCCTCCGTGTTTCCTTTGGCCATGCCACATATATAGACTCAGTTTGGCCTTCATGATATCGCCTG
ATTTTTGAGGACTGTATCACAGTGATATGTATTTGTGGTAATCTCATTTGTTGGTTGTACATCTGATCCTTTCCTC AACATGGCAATTGCTGCCTTTCCTAAGATAGGATCATAC
AACTGATCAGGGGATTGAATTTGATCATTCATCAACA TGTGTCTCTGAATTTTATTCAGTAGTTGTCATTGCTCTTTGGTTTAGACCAAGAAAAAGGAAATCCCCCCTTTTCA
TGTATTCCTTGGTTTGAGGACATGACTCCTGTAAGGGAGAGGAAAGGGAGATGCTTCCTGTTTGAACTGCAGTGAA
TTCACGGTTCCTGTTTCACCACTCCAAACCTTATGGCGACTCACACACACATTCCTCTTTTCTGTTACTGCCAAAG GTTCGGGTTTAGTACACTTCAGTTCCACTCAAGCATTGAAA
AGGTTCTCGTGGAGTCTGGGGCGTGCCCAGTGAAA
AGATGGGGACTTTTTAATTGTCCACAGACCTCTCTATACCTGCTTTGCAAAAATTACAATGGAGTAACTATTTTTA AAGCTTATTTTTCAATTCATAAAAAAGACATTTATTTTCAGTCAAATGGATGATGT
CTCCCTCTTTTCCCCTATTC TCAATGTTTGCTTGAATCTTTTATTATTTTTTTAATTCTCCCCCATACCCACTTCCTGATACTTTGGTTCTCTTT
CCTGCTCAGGTCCCTTCATTTGTACTTTGGAGTTTTTCTCATGTAAATTTGTATAACAGAAAATATTGTTCAGTTT GGATAGAAAGCATGGAGAATAAAAAAAGATAGCTGAAA
TTCAGATTGAAGAAATTTATTTCTGTGTAAAGTTATTT AAAAACTGTATTATATAAAAGGCAAAAAAAGTTCTATGTACTTGATGTGAATATGCGAATACTGCTATAATAAAGA
TTGACTGCATGGAGAAGTC (SEQ ID NO:67). In some embodiments, a DNA mutation results in the mutation of V600 according to SEQ ID NO:63 or SEQ ID NO:67. For example, in some embodiments, a DNA mutation in a BRAF gene encodes or results in a V600E mutated BRAF protein (numbering according to SEQ ID NO:63). These DNA mutations are also described by their nucleotide positions (rather than mutated polypeptide codons) in Table A infra. It is to be appreciated that some references to the V600E BRAF mutation refer to it as V599E due to an early, incorrect BRAF protein sequence that was missing a codon at approximately amino acid 31 (see Garnett, M. J. and Marais, R. (2004) *Cancer Cell* 6:313-9 for description). For example, in some embodiments, a DNA mutation in a BRAF gene results in a c.1799T>A or c.1799_1800TG>AA mutation in the corresponding cDNA sequence of SEQ ID NO:67.

Since, as described supra, the sequences of a variety of BRAF genes and corresponding mutations are known, one of ordinary skill in the art may suitably select a primer pair to amplify the locus of one or more of these DNA mutation(s). Various factors influencing primer design are known, and tools for identifying primer pairs suitable for amplifying a given DNA template sequence are available (see, e.g., www.ncbi.nlm.nih.gov/tools/primer-blast/). In some embodiments, a primer pair for amplifying the locus of a BRAF mutation (e.g., encoding or resulting in a V600E mutated BRAF protein) comprises the sequences GGACCCACTCCATCGAGATTT (SEQ ID NO:8) and CAGATATATTTCTTCATGAAGACCTCACAGTAA (SEQ ID NO:9), respectively.

In some embodiments, the methods of the present disclosure include amplifying the loci of one or more mutations in a CTNNB1 gene. CTNNB1 encodes the CTNNB1 beta catenin 1 protein, a subunit of the cadherin protein complex that transduces Wnt signaling and is frequently mutated in human cancers, also known as CTNNB, MRD19, Armadillo, catenin (cadherin-associated protein) beta 1, and catenin (cadherin-associated protein) beta 188 kDa. In some embodiments, the CTNNB1 gene is a human CTNNB1 gene. In some embodiments, a human CTNNB1 gene refers to the gene described by NCBI Entrez Gene ID No. 1499, including mutants and variants thereof. In other embodiments, the CTNNB1 gene is from one of the following organisms: mouse (see, e.g., NCBI Entrez Gene ID No. 12387), rat (see, e.g., NCBI Entrez Gene ID No. 84353), cynomolgus monkey (see, e.g., NCBI Entrez Gene ID No. 102146984), fish (see, e.g., NCBI Entrez Gene ID No. 30265), dog (see, e.g., NCBI Entrez Gene ID No. 477032), cattle (see, e.g., NCBI Entrez Gene ID No. 539003), horse (see, e.g., NCBI Entrez Gene ID No. 100055241), chicken (see, e.g., NCBI Entrez Gene ID No. 395964), chimpanzee (see, e.g., NCBI Entrez Gene ID No. 450183), rhesus monkey (see, e.g., NCBI Entrez Gene ID No. 574265), or cat (see, e.g., NCBI Entrez Gene ID No. 101097342).

A variety of CTNNB1 mutations associated with cancer are known and may be suitably detected by the methods described herein; see, e.g., Morin, P. J. et al. (1997) *Science* 275:1787-90 and Polakis, P. (2000) *Genes Dev.* 14:1837-51. For example, CTNNB1 mutations resulting in amino acid changes at positions T41 and S45 of the human CTNNB1 protein have been found in both colorectal adenomas and carcinomas, particularly in tumors that lack APC mutations (Sparks, A. B. et al. (1998) *Cancer Res.* 58:1130-4). In some embodiments described herein, a CTNNB1 mutation is named based on the resulting amino acid substitution/deletion/frameshift according to a human CTNNB1 protein, e.g., as set forth in MATQADLMELDMAMEPDRKAAVSH-WQQQSYLDSGIHSGATTTAPSLSGKGNPEEED VDTSQVLYEWEQGFSQSFTQEQVA-DIDGQYAMTRAQRVRAAMFPETLDEGMQIPSTQ FDAAHPTNVQRLAEPSQMLKHAVVNLINYQD-DAELATRAIPELTKLLNDEDQVVVNK AAVMVHQL-SKKEASRHAIMRSPQMVSAIVRTMQNTND-VETARCTAGTLHNLSHHRE GLLAIFKSGGIPALVKMLGSPVDSVLFYAIT-TLHNLLLHQEGAKMAVRLAGGLQKMV ALLNKTNVKFLAITTDCLQILAYGNQESKLIILAS-GGPQALVNIMRTYTYEKLLWTTSR VLKVLSVCSSNKPAIVEAGGMQALGLHLTDP-SQRLVQNCLWTLRNLSDAATKQEGM EGLLGTLVQLLGSDDINVVTCAAGILSNLTCN-NYKNKMMVCQVGGIEALVRTVLRAG DREDITEPA-ICALRHLTSRHQEAEMAQ-NAVRLHYGLPVVVKLLHPPSHWPLIKATVGL IRNLALCPANHAPLREQGAIPRLVQLL-VRAHQDTQRRTSMGGTQQQFVEGVRMEEIVE GCT-GALHILARDVHNRIVIRGLNTIPLFVQLLYSPIENIQR-VAAGVLCELAQDKEAAEAI EAEGATAPLTELLHSRNEGVATYAAAVLFRM-SEDKPQDYKKRLSVELTSSLFRTEPMA WNETADLGL-DIGAQGEPLGYRQDDPSYRSFHSGGYGQDAL-GMDPMMEHEMGGHHP GADYPVDGLPDLGHAQDLMDG-LPPGDSNQLAWFDTDL (SEQ ID NO:64). An exemplary human CTNNB1 cDNA sequence is set forth in AAGTCC-CATCAGTCCTGGG-GATCGGACCAGTGGACTTTCTCTTAAGAT-TTCCTCTTTCATTCTTAAGAATAGAAGT GTTATTATTTTTTTAATGCCCTGGCTATGTGAGTTT-GAATCGAAGCAACTTTAAACCT-TAGAGCAACTAAACTCT AAGTGCAGCGGGTGC-GATGCGTCAGTAGGGTGAGCACATAAAAA ATCCATGTCTTGCACCTGTATTTAGCGTACT ATGCAGGGTATTTGAAGTATACCATACAACTGTTTT-GAAAATCCAGCGTGGACAATGGCTACTCAAGCT-GATTTGA TGGAGTTGGACATGGCCATGGAACCA-GACAGAAAAGCGGCTGTTAGTCACTGG CAGCAACAGTCTTACCTGGACTC TGGAATCCAT-TCTGGTGCCACTAC-CACAGCTCCTTCTCTGAGTGGTAAAGGCAATCCT-GAGGAAGAGGATGTGGAT ACCTCC-CAAGTCCTGTATGAGTGGGAACAGGGAT TTTCTCAGTCCTTCACTCAAGAACAAGTAGCTGAT-ATTGATG GACAGTATGCAATGACTCGAGCTCA GAGGGTACGAGCTGCTATGTTCCCTGAGACATTA-GATGAGGGCATGCAGAT CCCATCTACACAGTTT-GATGCTGCTCATCCCACTAATGTCCAGCGTTTGGCT-GAACCATCACAGATGCTGAAACAT GCAGTTGTAAACTTGATTAACTATCAAGAT-GATGCAGAACTTGCCACACGTGCAATCCCT-GAACTGACAAAACTGC TAAATGACGAGGACCAGGTGGTGGT-TAATAAGGCTGCAGTTATGGTC-CATCAGCTTTCTAAAAAGGAAGCTTCCAG ACACGCTATCATGCGTTCTCCTCA-GATGGTGTCTGCTATTGTACGTACCATGCAGAATA-CAAATGATGTAGAAACA GCTCGTTGTACCGCTGGGACCTTGCAT-AACCTTTCCCATCATCGTGAGGGCTTACTGGC-CATCTTTAAGTCTGGAG GCATTCCTGCCCTGGT-GAAAATGCTTGGTTCACCAGTGGATT CTGTGTTGTTTTATGCCATTACAACTCTCCACAA CCTTTTATTACAT-CAAGAAGGAGCTAAAATGGCAGTGCGTT-TAGCTGGTGGGCTGCAGAAAATGGTTGCCTTGCTC AACAAAACAAATGTTAAATTCTTGGCTAT-TACGACAGACTGCCTTCAAATTTTAGCT-TATGGCAACCAAGAAAGCA AGCTCATCAT-ACTGGCTAGTGGTGGACCCCAAGC TTTAGTAAATATAATGAGGACCTATACT-TACGAAAAACTACT GTGGAC-CACAAGCAGAGTGCTGAAGGTGC-TATCTGTCTGCTCTAGTAATAAGCCG GCTATTGTAGAAGCTGGTGGA ATGCAAGCTT-TAGGACTTCACCTGACAGATCCAAGT-CAACGTCTTGTTCAGAACTGTCTTTGGACTCTCAG-GAATC TTTCAGATGCTGCAACTAAACAGGAAGGGATG-GAAGGTCTCCTTGGGACTCTTGTTC AGCTTCTGGGTTCAGATGA TATAAATGTGGT-CACCTGTGCAGCTGGAATTCTTTCTAACCT-CACTTGCAATAATTATAAGAACAAGATGATGGTC TGCCAAGTGGGTGGTATAGAGGCTCTT GTGCGTACTGTCCTTCGGGCTGGTGACAGGGAA-GACATCACTGAGCCTG CCATCTGTGCTCTTCGT-CATCTGACCAGCCGACAC-CAAGAAGCAGAGATGGCCCAGAAT GCAGTTCGCCTTCACTA TGGACTACCAGTTGTGGT-TAAGCTCTTACACCCACCATCCCACTGGCCTCTGA-TAAAGGCTACTGTTGGATTGATT CGAAATCTTGCCCTTTGTCCCGCAAAT-CATGCACCTTTGCGTGAGCAGGGTGCCATTC-CACGACTAGTTCAGTTGC TTGTTCGTGCACATCAG-GATACCCAGCGCCGTACGTCCATGG GTGGGACACAGCAGCAATTTGTGGAGGGGGTCCG CATGGAAGAAATAGTTGAAGGTTGTACCG-GAGCCCTTCACATCCTAGCTCGGGATGTT-CACAACCGAATTGTTATC AGAGGACTAAATACCAT-TCCATTGTTTGTGCAGCTGCTTTATT CTCCCATTGAAAACATCCAAAGAGTAGCTGCAG GGGTCCTCTGT-GAACTTGCTCAGGACAAGGAAGCTGCAGAAGCT-ATTGAAGCTGAGGGAGCCACAGCTCCTCTGAC AGAGTTACTTCACTCTAGGAAT-GAAGGTGTGGCGA-CATATGCAGCTGCTGTTTTGTTCCGAATGTCT-GAGGACAAG CCACAAGATTACAAGAAACGGCTTTCAGTT-GAGCTGACCAGCTCTCTCTTCAGAACAGAGC- CAATGGCTTGGAATG AGACTGCTGATCTTGGACTT-
GATATTGGTGCCCAGGGAGAACCCCTTGG
ATATCGCCAGGATGATCCTAGCTATCG TTCTTTT-
CACTCTGGTGGATATGGCCAG-
GATGCCTTGGGTATGGACCCCATGATGGAACAT-
GAGATGGGTGGCCAC
CACCCTGGTGCTGACTATCCAGTT-
GATGGGCTGCCAGATCTGGGGCATGCCCAGGACCT-
CATGGATGGGCTGCCTC
CAGGTGACAGCAATCAGCTGGCCTGGTTTGA-
TACTGACCTGTAAATCATCCTTTAGGAGTAACAATA-
CAAATGGAT TTTGGGAGTGACTCAAGAAGT-
GAAGAATGCACAAGAATGGATCACAAGATGGAATT-
TATCAAACCCTAGCCTTGCT
TGTTAAATTTTTTTTTTTTTTTTT-
TAAGAATATCTGTAATGGTACTGACTTTGCTTGCTTT-
GAAGTAGCTCTTTT
TTTTTTTTTTTTTTTTTTTTGCAGTAACTGTTTTT-
TAAGTCTCTCGTAGTGTTAAGTTATAGT-
GAATACTGCTAC AGCAATTTCTAATTTTTAAGAATT-
GAGTAATGGTGTAGAACACTAATTCATAAT
CACTCTAATTAATTGTAATCTG
AATAAAGTGTAACAAT-
TGTGTAGCCTTTTTGTATAAAATA-
GACAAATAGAAAATGGTCCAATTAGTTTCCTTTTTA
ATATGCTTAAAATAAGCAGGTGGATCTATTT-
CATGTTTTTGATCAAAAACTATTTGGGA-
TATGTATGGGTAGGGTAAATCAGTAAGAGGTGTTAT-
TTGGAACCTTGTTTTGGACAGTTTACC
AGTTGCCTTTTATCCCAAAGTTGTTGTAAC
CTGCTGTGATACGATGCTTCAAGAGAAAATGCGGT-
TATAAAAAATGGTTCAGAATTAAACTTTTAATTCAT-
TCGA (SEQ ID NO:68). In some embodiments, a DNA mutation results in the mutation of T41 or S45 according to SEQ ID NO:64 or SEQ ID NO:68. For example, in some embodiments, a DNA mutation in a CTNNB1 gene encodes or results in a T41A, T41I, S45F, or S45P mutated CTNNB1 protein (numbering according to SEQ ID NO:64). These DNA mutations are also described by their nucleotide positions (rather than mutated polypeptide codons) in Table A infra. For example, in some embodiments, a DNA mutation in a CTNNB1 gene results in a 121A>G, 122C>T, 133T>C, or 134C>T mutation in the corresponding cDNA sequence of SEQ ID NO:68.

Since, as described supra, the sequences of a variety of CTNNB1 genes and corresponding mutations are known, one of ordinary skill in the art may suitably select a primer pair to amplify the locus of one or more of these DNA mutation(s). Various factors influencing primer design are known, and tools for identifying primer pairs suitable for amplifying a given DNA template sequence are available (see, e.g., www.ncbi.nlm.nih.gov/tools/primer-blast/). In some embodiments, a primer pair for amplifying the locus of a CTNNB1 mutation (e.g., encoding or resulting in a T41A, T41I, S45F, and S45P mutated CTNNB1 protein) comprises the sequences GGAATCCATTCTGGTGCCACT (SEQ ID NO:13) and AGAAAATCCCTGTTCCCACTCATA (SEQ ID NO: 14), respectively (for the T41 locus); or GGTGC-CACTACCACAGCTCCT (SEQ ID NO:18) and TCT-CAAAACTGCATTCTGACTTTCA (SEQ ID NO: 19), respectively (for the S45 locus). In some embodiments, two primer pairs are used for PCR: a first primer pair comprising the sequences GGAATCCATTCTGGTGCCACT (SEQ ID NO:13) and AGAAAATCCCTGTTCCCACTCATA (SEQ ID NO: 14), and a second primer pair comprising the sequences GGTGCCACTACCACAGCTCCT (SEQ ID NO:18) and TCTCAAAACTGCATTCTGACTTTCA (SEQ ID NO:19).

In some embodiments, the methods of the present disclosure include amplifying the loci of one or more mutations in an APC gene. APC encodes the APC tumor suppressor, a negative regulator of beta catenin and Wnt signaling that is frequently mutated in human cancers, also known as GS, DP2, DP3, BTPS2, DP2.5, PPP1R46, adenomatous polyposis *coli* protein, WNT signaling pathway negative regulator, adenomatous polyposis *coli* tumor suppressor, deleted in polyposis 2.5, protein phosphatase 1 regulatory subunit 46, and truncated adenomatous polyposis *coli*. In some embodiments, the APC gene is a human APC gene. In some embodiments, a human APC gene refers to the gene described by NCBI Entrez Gene ID No. 324, including mutants and variants thereof. In other embodiments, the APC gene is from one of the following organisms: mouse (see, e.g., NCBI Entrez Gene ID No. 11789), rat (see, e.g., NCBI Entrez Gene ID No. 24205), cynomolgus monkey (see, e.g., NCBI Entrez Gene ID No. 102126553), fish (see, e.g., NCBI Entrez Gene ID No. 386762), dog (see, e.g., NCBI Entrez Gene ID No. 479139), cattle (see, e.g., NCBI Entrez Gene ID No. 533233), horse (see, e.g., NCBI Entrez Gene ID No. 100064431), chicken (see, e.g., NCBI Entrez Gene ID No. 415607), chimpanzee (see, e.g., NCBI Entrez Gene ID No. 461999), rhesus monkey (see, e.g., NCBI Entrez Gene ID No. 693443), or cat (see, e.g., NCBI Entrez Gene ID No. 101096138).

A variety of APC mutations associated with cancer are known and may be suitably detected by the methods described herein; see, e.g., Morin, P. J. et al. (1997) *Science* 275:1787-90 and Polakis, P. (2000) *Genes Dev.* 14:1837-51. APC mutations often result in frameshifted or truncated APC mutant proteins, and are particularly frequent in a region known as the mutation cluster region (MCR). See Miyoshi, Y. et al. (1992) *Hum. Mol. Genet.* 1:229-33; and Segditsas, S. and Tomlinson, I. (2006) *Oncogene* 25:7531-7. One study found mutations in the MCR of the APC gene in 72% of colorectal cancer patients, and frameshift or nonsense mutations at the codons encoding human APC residues Q1367, R1450, E1309, and S1465 were frequently observed (Luchtenborg, M. et al. (2004) *Carcinogenesis* 25:1219-26). In some embodiments described herein, an APC mutation is named based on the resulting amino acid substitution/deletion/frameshift according to a human APC protein, e.g., as set forth in MAAASYDQLLKQVEALK-MENSNLRQELEDNSNHLTKLETEASNMKEV-
LKQLQGSIE DEAMASSGQIDLLER-
LKELNLDSSNFPGVKLRSKMSLRSYGSREG
SVSSRSGECSPVPM GSFPRRGFVNGS-
RESTGYLEELEKERSLLLADLD-
KEEKEKDWYYAQLQNLTKRIDSLP
LTENFSLQTDMTRRQLEYEARQIRVAMEEQLGTCQD-
MEKRAQRRIARIQQIEKDILRIR QLLQSQATE-
AERSSQNKHETGSHDAERQNEGQGVGEIN-
MATSGNGQGSTTRMDHET
ASVLSSSSTHSAPRRLTSHLGTKVEMVYS-
LLSMLGTHDKDDMSRTLLAMSSSQDSCIS
MRQSGCLPLLIQLLHGNDKDSVLLGNSRGSKEARA-
RASAALHNIIHSQPDDKRGRREI RVLHLLEQI-
RAYCETCWEWQEAHEPGMDQDKNPM-
PAPVEHQICPAVCVLMKLSFDE
EHRHAMNELGGLQAIAELLQVDCE-
MYGLTNDHYSITLRRYAGMALTNLTFGDVANK
ATLCSMKGCMRALVAQLKSESEDLQQVIASVLRNLS-
WRADVNSKKTLREVGSVKAL MECA-
LEVKKESTLKSVLSALWNLSAHCTENKADICAVD-
GALAFLVGTLTYRSQTNTL
AIIESGGGILRNVSSLIATNEDHRQILRENN-
CLQTLLQHLKSHSLTIVSNACGTLWNLSA RNPKDQEALWDMGAVSMLKNLIHSKHKMIAM-GSAAALRNLMANRPAKYKDANIMS PGSSLPSLHVRKQKALEAELDAQHLSETFDNIDNL-SPKASHRSKQRHKQSLYGDYVFD TNRHDDNRSDNFNTGNMTVL-SPYLNTTVLPSSSSSRGSLDSSRSEKDRSLERER-GIGLG NYHPATENPGTSSKRGLQIST-TAAQIAKVMEEVSAIHTSQEDRSSGSTTEL HCVTDERN ALRRSSAAHTHSNTYNFTKSENSNRT-CSMPYAKLEYKRSSNDSLNSVSSSDGYGKRGQ MKP-SIESYSEDDESKFCSYGQYPADLAHKIH-SANHMDDNDGELDTPINYSLKYSDEQL NSGRQSPSQNERWARPKHIIEDEIKQSEQRQSRNQST-TYPVYTESTDDKHLKFQPHFGQ QECVSPYRSR-GANGSETNRVGSNHGINQNVSQSLCQED-DYEDDKPTNYSERYSEEEQ HEEEERPTNYSIKYNEEKRHVDQPIDYSLKYAT-DIPSSQKQSFSFSKSSSGQSSKTEHMS SSSENT-STPSSNAKRQNQLHPSSAQSRSGQPQKAATCKVSS-INQETIQTYCVEDTPICFS RCSSLSSLSSAEDEIGCNQTTQEADSANTLQI-AEIKEKIGTRSAEDPVSEVPAVSQHPRT KSSRLQGSSLSSESARHKAVEFSSGAK-SPSKSGAQTPKSPPEHYVQETPLMFSRCTSVSS LDS-FESRSIASSVQSEPCSGMVSGIISPSDLPD-SPGQTMPPSRSKTPPPPPQTAQTKREVP KNKAPTAEKRESGPKQAAVNAAVQRVQVLP-DADTLLHFATESTPDGFSCSS SLSALSL DEPFIQKD-VELRIMPPVQENDNGNETESEQPKESNENQEKE-AEKTIDSEKDLLDDSDDD DIEILEECIISAMPTKSSRKAKKPAQTASKLPPP-VARKPSQLPVYKLLPSQNRLQPQKHV SFTPGDDM-PRVYCVEGTPINFSTATSLSDLTIESPP-NELAAGEGVRGGAQSGEFEKRDTI PTEGRSTDEAQGGKTSSVTIPELDDNKAEEGDI-LAECINSAMPKGKSHKPFRVKKIMDQ VQQASASS-SAPNKNQLDGKKKKPTSPVKPIPQNTEYR-TRVRKNADSKNNLNAERVFS DNKDSKKQNLKNNSKVFNDKLPNNEDRVRGSFAFD-SPHHYTPIEGTPYCFSRNDSLSS LDFDDDDVDLSRE-KAELRKAKENKESEAKVTSHTELTSNQQSANKTQA-IAKQPINRGQ PKPILQKQSTFPQSSKDIPDRGAATDEKLQNFA-IENTPVCFSHNSSLSSLSDIDQENNNK ENEPIKETEPPDSQGEPSKPQASG-YAPKSFHVEDTPVCFSRNSSLSSLSIDSEDDLLQECI SSAMPKKKKPSRLKGDNEKHSPRNMG-GILGEDLTLDLKDIQRPDSEHGLSPDSENFDW KAI-QEGANSIVSSLHQAAAAACLSRQASSDSDSILSLKSG-ISLGSPFHLTPDQEEKPFTSN KGPRILKPGEKSTLETKKIES-ESKGIKGGKKVYKSLITGKVRSNSEIS-GQMKQPLQANM PSISRGRTMIHIPGVRNSSSSTSPV-SKKGPPLKTPASKSPSEGQTATTSPRGAKPSVKSEL SPVARQTSQIGGSSKAPSRSGSRDSTPSR-PAQQPLSRPIQSPGRNSISPGRNGISPPNKLSQ LPRTSSPSTASTKSSGSGKMSYT-SPGRQMSQQNLTKQTGLSKNASSIPRSESASKGLNQ MNNGNGANKKVELSRMSSTKSSGSESDRSER-PVLVRQSTFIKEAPSPTLRRKLEESASF ESLSPSSR-PASPTRSQAQTPVLSPSLPDMSL-STHSSVQAGGWRKLPPNLSPTIEYNDGRP AKRHDIARSHSESPSRLPINRSGTWKREHSKHSSSL-PRVSTWRRTGSSSSILSASSESSEK AKSEDEKHVNSIS-GTKQSKENQVSAKGTWRKIKENEFSPTNSSTQTVSS-GATNGAESK TLIYQMAPAVSKTEDVWVRIEDCPINNPRSGR-SPTGNTPPVIDSVSEKANPNIKDSKDN QAKQNVGNGSVPMRTVGLENRLNSFIQVDAP-DQKGTEIKPGQNNPVPVSETNESSIVE RTPFSSSSSSKHSSPSGTVAARVTPFNYNPSPRKS-SADSTSARPSQIPTPVNNNTKKRDS KTD-STESSGTQSPKRHSGSYLVTSV (SEQ ID NO:65). An exemplary human APC cDNA sequence is set forth in GTATTGGTGCAGCCCGCCAGGGTGTCACTGGA-GACAGAATGGAGGTGCTGCCGGACTCG-GAAATGGGGTCCAAGGG TAGC-CAAGGATGGCTGCAGCTTCATATGATC AGTTGTTAAAGCAAGTTGAGGCACTGAAGATG-GAGAACTCAAATC TTCGACAAGAGCTAGAAGA-TAATTCCAATCATCTTACAAAACTGGAAACTGAGG-CATCTAATATGAAGGAAGTACT TAAACAACTACAAGGAAGTATTGAAGATGAAGC-TATGGCTTCTTCTGGACAGATTGATTTATT-AGAGCGTCTTAAA GAGCTTAACTTAGA-TAGCAGTAATTTCCCTGGAGTAAAA CTGCGGTCAAAAATGTCCCTCCGTTCTTATG-GAAGCC GGGAAGGATCTGTATCAAGCCGTTCTG-GAGAGTGCAGTCCTGTTCCTATGGGTTCATTTC-CAAGAAGAGGGTTTGT AAATGGAAGCAGAGAAAGTACTGGATATT-TAGAAGAACTTGAGAAAGAGAGGTCAT-TGCTTCTTGCTGATCTTGAC AAAGAAGAAAAGGAAAAAGACTGGTATTACGCT-CAACTTCAGAATCTCACTAAAAGAATAGA-TAGTCTTCCTTTAA CTGAAAATTTTCCTTA-CAAACAGATATGACCAGAAGGCAAT TGGAATATGAAGCAAGGCAAATCAGAGTTGCGAT GGAAGAACAACTAGGTACCTGCCAGGATATG-GAAAAACGAGCACAGCGAAGAATAGCCAGAAT-TCAGCAAATCGAA AAGGACAT-ACTTCGTATACGACAGCTTTTACAG TCCCACAGCCGGCAGAGAGGT-CATCTCAGAACAAGCATG AAACCGGCTCACAT-GATGCTGAGCGGCAGAATGAAGGTCAAGGAGTGG-GAGAAATCAACATGGCAACTTCTGGTAA TGGTCAGGGTTCAACTACACGAATGGACCAT-GAAACAGCCAGTGTTTT-GAGTTCTAGTAGCACACACTCTGCACCT CGAAGGCTGACAAGTCATCTGGGAACCAAGGTG-GAAATGGTGTATTCATTGTTGTCAATGCTTGGTACT-CATGATA AGGATGATATGTCGCGAACTTTGCTAGC-TATGTCTAGCTCCCAAGACAGCTGT ATATCCATGCGACAGTCTGGATG TCTTCCTCTCCT-CATCCAGCTTTTACATGGCAATGACAAA-GACTCTGTATTGTGGGAAAT-TCCCGGGGCAGTAAA GAGGCTCGGGCCAGGGCCAGTGCAGCACTC-CACAACATCATTCACTCACAGCCT-GATGACAAGAGAGGCAGGCGTG AAATCCGAGTCCTTCATCTTTTGGAACAGA-TACGCGCTTACTGTGAAACCTGTTGG-GAGTGGCAGGAAGCTCATGA ACCAGG-CATGGACCAGGACAAAAATCCAATGC CAGCTCCTGTTGAACATCA-GATCTGTCCTGCTGTGTGTTCTA ATGAAACTTT-CATTTGATGAAGAGCATAGACATGCAATGAAT-GAACTAGGGGACTACAGGCCATTGCAGAATTAT TGCACATGGACTGTGAAATGTATGGGCT-TACTAATGACCACTACAGTATTACACTAAGACGA-TATGCTGGAATGGC TTTGACAAACTTGACTTTTG-GAGATGTAGCCAACAAGGCTACGCTATG CTCTATGAAAGGCTGCATGAGAGCACTT GTGGCC-CAACTAAAATCTGAAAGTGAAGACTTA- CAGCAGGTTATTGCGAGTGTTTTGAGGAATTGTCTTGGCGAG
CAGATGTAAATAGTAAAAAGACGTTGCGAGAAGTTGGAAGTGTGAAAGCATTGATGGAATGTGCTTTAGAAGTTAA AAAGGAATCAACCCTCAAAAGCGTATTGAGTGCCT
TATGGAATTTGTCAGCACATTGCACTGAGAATAAAGCTGAT ATATGTGCTGTAGATGGTGCACTTGCATTTTTGGTTGGCACTCTTACTTACCGGAGCCAGACAAACACTTTAGCCA
TTATTGAAAGTGGAGGTGGGATATTACGGAATGTGTCCAGCTTGATAGCTACAAATGAGGACCACAGGCAAATCCT AAGAGAGAACAACTGTCTACAAACTTTATTACAACACTTAAAATCTCATAGTTTGACAATAGTCAGTAATGCATGT
GGAACTTTGTGGAATCTCTCAGCAAGAAATCCTAAAGACCAGGAAGCATTATGGGACATGGGGGCAGTTAGCATGC
TCAAGAACCTCATTCATTCAAAGCACAAAATGATTGCTATGGGAAGTGCTGCAGCTTTAAGGAATCTCATGGCAAA TAGGCCTGCGAAGTACAAGGATGCCAATATTATGTCTCCTGGCTCAAGCTTGCCATCT
CTTCATGTTAGGAAACAA AAAGCCCTAGAAGCAGAATTAGATGCTCAGCACTTATCAGAAACTTTTGACAATATAGACAATTTAAGTCCCAAGG CATCTCATCGTAGTAAGCAGAGACACAAGCAAAGTCTCTATGGTGATT
ATGTTTTTGACACCAATCGACATGATGATAATAGGTCAGACAATTTTAATACTGGCAACATGACTGTCCTTTCACCATATTTGAATACTACAGTGTTACCCAGC TCCTCTTCATCAAGAGGAAGCTTAGATAGTTCTCGTTCTGAAAAAG
ATAGAAGTTTGGAGAGAGAACGCGGAATTGGTCTAGGCAACTACCATCCAGCAACAGAAAATCCAGGAACTTCTTCAAAGCGAGGTTTGCAGATCTCCACCACTGC AGCCCAGATTGCCAAAGTCATGGAAGAAGTGTCAGCCATTCATACCTCTCAGGAAGACAGAAGTTCTGGGTCTACC ACTGAATTACATTGTGTGACAGATGAGAGAAATGCACTT
AGAAGAAGCTCTGCTGCCCATACACATTCAAACACTT ACAATTTCACTAAGTCGGAAAATTCAAATAGGACATGTTCTATGCCTTATGCCAAATTAGAATACAAGAGATCTTC AAATGATAGTTTAAATAGTGTCAGTAGTAGTGATGGTTATGGTAAAAGAGGTCAAATGAAACCCTCGATTGAATCC TATTCTGAAGATGATGAAAGTAAGTTTTGCAGTTATGGTCAAT
ACCCAGCCGACCTAGCCCATAAAATACATAGTGCAAATCATATGGATGATAATGATGGAGAACTAGATACACCAATAAATTATAGTCTTAAATATTCAGATGAGCAGTT GAACTCTGGAAGGCAAAGTCCTTCACAGAATGAAAGATGGGCAAGACCCA
AACACATAATAGAAGATGAAATAAAA CAAAGTGAGCAAAGACAATCAAGGAATCAAAGTACAACTTATCCTGTTTATACTGAGAGCACTGATGATAAACACC
TCAAGTTCCAACCACATTTTGGACAGCAGGAATGTGTTTCTCCATACAGGTCACGGGGAGCCAATGGTTCAGAAAC AAATCGAGTGGGTTCTAATCATGGAATTAATCAAAATGTAAGCCAGTCTTTGTGTCAAGAAGATGACTATGAAGAT
GATAAGCCTACCAATTATAGTGAACGTTACTCTGAAGGAAGAACAGCATGAAGAAGAAGAGAGCCAACAAATTATA GCATAAAATATAATGAAGAGAAACGTCATGTGGATCAGCCTATTGATTATAGTTTAAAATATGCCACAGATATTCC
TTCATCACAGAAACAGTCATTTTCATTCT CAAAGAGTTCATCTGGACAAAGCAGTAAAACCGAACATATGTCTTCA
AGCAGTGAGAATACGTCCACACCTTCATCTAATGCCAAGAGGCAGAATCAGCTCCATCCAAGTTCTGCACAGAGTA GAAGTGGTCAGCCTCAAAAGGCTGCCACTTGCAAAGTTTCTTCTATTAACCAAGAAACAATACAGACTTATTGTGT
AGAAGATACTCCAATATGTTTTTCAAGATGTAGTTCATTATCATCTTTGTCATCAGCTGAAGATGAAATAGGATGT AATCAGACGCACAGGAAGCAGATTCTGCTAATACCCTGCAAATAGCAGA
AATAAAAGAAAAGATTGGAACTAGGT CAGCTGAAGATCCTGTGAGCGAAGTTCCAGCAGTGTCACAGCACCCTAGAACCAAATCCAGCAGACTGCAGGGTTC
TAGTTTATCTTCAGAATCAGCCAGGCACAAAGCTGTTGAATTTTCTTCAGGAGCGAAATCTCCCTCCAAAAGTGGT
GCTCAGACACCCAAAAGTCCACCTGAACACTATGTTCAGGAGACCCCACTCATGTTTAGCAGATGTACTTCTGTCA GTTCACTTGATAGTTTTGAGAGTCGTTCAGCTCCGTTCAGATGTGAACCATGCAGTGGAATGGTAAGTGGCATTATAAGCCCCAGTGATCTTCCAGATAGCCCTGGACAAACCATGCCAC
CAAGCAGAAGTAAAACACCTCCACCA CCTCCTCAAACAGCTCAAACCAAGCGAGAAGTACCTAAAAATAAAGCACCTACTGCTGAAAAGAGAGAGAGTGGAC
CTAAGCAAGCTGCAGTAAATGCTGCAGTTCAGAGGGTCCAGGTTCTTCCAGATGCTGATACTTTATTACATTTTGC CACGGAAAGTACTCCAGATGGATTTTCTTGTTCATCCAGCCTGAGTGCTCT
GAGCCTCGATGAGCCATTTATACAG AAAGATGTGGAATTAAGAATAATGCCTCCAGTTCAGGAAAATGACAATGGGAATGAAACAGAATCAGAGCAGCCTA
AAGAATCAAATGAAAACCAAGAGAAAGAGGCAGAAAAAACTATTGATTCTGAAAAGGACCTATTAGATGATTCAGA TGATGATGATATTGAAATACTAGAAGAATGTATTATTTCTGCATGCCAACAAAGTCATCACGTAAAGCAAAAAAG
CCAGCCCAGACTGCTTCAAAATTACCTCCACCTGTGGCAAGGAAACCAAGTCAGCTGCCTGTGTACAAACTTCTAC CATCACAAAACAGGTTGCAACCCCAAAAGCATGTTAGTTTTACACCGGGGATGATATGCCACGGGTGT
ATTGTGT TGAAGGGACACCTATAAACTTTTCCACAGCTACATCTCTAAGTGATCTAACAATCGAATCCCCTCCAAATGAGTTA GCTGCTGGAGAAGGAGTTAGAGGAGGGGCACAGTCAGGTGAATTTGAAAAACGAGATACCATTCCTACAGAAGGCA GAAGTACAGAT
GAGGCTCAAGGAGGAAAAACCTCATCTGTAACCATACCTGAATTGGATGACAATAAAGCAGAGGA AGGTGATATTCTTGCAGAATGCATTAATTCTGCTATGCCCAAAGGGAAAAGT
CACAAGCCTTTCCGTGTGAAAAAG ATAATGGACCAGGTCCAGCAAGCATCTGCGTCTTCTTGCACCCAACAAAAATCAGTTAGATGGTAAGAAAAAGA AACCAACTTCACCAGTAAAACCTATACCACAAAATACT
GAATATAGGACACGTGTAAGAAAAAATGCA GACTCAAA AAATAATTTAAATGCTGAGAGAGTTTTCTCA GACAACAAAGATTCAAAGAAACAGAATTTGAAAAATAATTCCAAG GTCTTCAATGATAAGCTCCCAAATAATGAAGATAGAGTCAGAGGAAGT TTTGCTTTTGATTCACCTCATCATTACA CGCCTATTGAAGGAACTCCTTACTGTTTTTCACGAAATGATTCTTTGAGTTCTCTAGATTTTGATGATGATGATGT TGACCTTTCCAGGGAAAAGGCTGAATTAAGAAAGGCAAAAGAAAATAAGGAATCAG AGGCTAAAGTTACCAGCCAC ACAGAACTAACCTCCAACCAACAATCAGCTAATAAGACACAAGCTATTGCAAAGCAGCCAATAAATCGAGGTCAGC CTAAACCCATACTTCAGAAACAATCCACTTTTCCCCAGTCATCCAAAGACATACCAGACAGAGGGGCAGCAACTGA TGAAAAGTTACAGAATTTTGCTATTGAAAATACTCCGGTTTGC TTTTCTCATAATTCCTCTCTGAGTTCTCTCAGT GACATTGACCAAGAAACAACAATAAAGAAAATGAACCTATCAAAGAGACTGAGCCCCCTGACTCACAGGGAGAAC CAAGTAAACCTCAAGCATCAGGCTATGCTCCTAAATCATTTCATG TTGAAGATACCCCAGTTTGTTTCTCAAGAAA CAGTTCTCTCAGTTCTCTTAGTATTGACTCTGAAGATGACCTGTTGCAGGAATGTATAAGCTCCGCAATGCCAAAA AAGAAAAAGCCTTCAAGACTCAAGGGTGATAATGAAAAACATAGTCCCAGAAATATGGGTGGCATATTAGGTGAAG ATCTGACACTTGATTTGAAAGATATACAGAGACCAGATTCAGAACATGGTCTATCCCCT GATTCAGAAAATTTTGA TTGGAAAGCTATTCAGGAAGGTGCAAATTCCATAGTAAGTAGTTTACATCAAGCTGCTGCTGCTGCATGTTTATCT AGACAAGCTTCGTCTGATTCAGATTCCATCCTTTCCCTGAAATCAGGAATCTCTCTGGGATCACCATTTCATCTTA CACCTGATCAAGAAGAAAAACCCTTTACAAGTAATAAAGG CCCACGAATTCTAAAACCAGGGGAGAAAAGTACATT GGAAACTAAAAAGATAGAATCTGAAAGTAAAGGAATCAAAGGAGGAAAAAAAGTTTATAAAAGTTTGATTACTGGA AAAGTTCGATCTAATTCAGAAATTTCAGGCCAAATGAAACAGCCCCTTCAAGCAAACATGCCTTCAATCTCTCGAG GCAGGACAATGATTCATATTCCAGGAGTTCGAAATAGCTCCTCAAGTACAA GTCCTGTTTCTAAAAAAGGCCCACC CCTTAAGACTCCAGCCTCCAAAAGCCCTAGTGAAGGTCAAACAGCCACCACTTCTCCTAGAGGAGCCAAGCCATCT GTGAAATCAGAATTAAGCCCTGTTGCCAGGCAGACATCCCAAATAGGTGGGTCAAGTAAAGCACCTTCTAGATCAG GATCTAGAGATTCGACCCCTTCAAGACCTGCCCAGCAACCAT TAAGTAGACCTATACAGTCTCCTGGCCGAAACTC AATTTCCCCTGGTAGAAATGGAATAAGTCCTCCTAACAAATTATCTCAACTTCCAAGGACATCATCCCTAGTACT GCTTCAACTAAGTCCTCAGGTTCTGGAAAAATGTCAT ATACATCTCCAGGTAGACAGATGAGCCAACAGAACCTTA CCAAACAAACAGGTTTATCCAAGAATGCCAGTAGTATTCCAAGAAGTGAGTCTGCCTCCAAAGGACTAAATCAGAT GAATAATGGTAATGGAGCCAATAAAAAGGTAGAACTTTCTAGAATGTCTTCAACTAAATCAAGTGGAAGTGAATCT GATAGATCAGAAAAGACCTGTATTAGTACGCCAGTCA ACTTTCATCAAAGAAGCTCCAAGCCCAACCTTAAGAAGAA AATTGGAGGAATCTGCTTCATTTTGAATCTCTTTCTCCATCATCTAGACCAGCTTCTCCCACTAGGTCCCAGGCACA AACTCCAGTTTTAAGTCCTTCCCTTCCTGATATGTCTCTATCCACACATTCGTCTGTTCAGGCTGGTGGATGGCGA AAACTCCCACCTAATCTCAGTCCCACTATAGAGTATAA TGATGGAAGACCAGCAAAGCGCCATGATATTGCACGGT CTCATTCTGAAAGTCCTTCTAGACTTCCAATCAATAGGTCAGGAACCTGGAAACGTGAGCACAGCAAACATTCATC ATCCCTTCCTCGAGTAAGCACTTGGAGAAGAACTGGAAGTTCATCTTCAATTCTTTCTGCTTCATCAGAATCCAGT GAAAAAGCAAAAAGTGAGGATGAAAAACATGTGAACTCTATTTCAGGAACCAAACAAAGTAAAGAAAACCAAGTAT CCGCAAAAGGAACATGGAGAAAAATAAAAGAAAATGAATTTTCTCCCACAAATAGTACTTCTCAGACCGTTCCTC AGGTGCTACAAATGGTGCTGAATCAAAGACTCTAATTTATCAAATGGCACCTGCTGTTTCTAAAACAGAGGATGTT TGGGTGAGAATTGAGGACTGTCCCATTAACAATCCTAGATCTGGAAGATCTCCCACAGGTAATACTCCCCGGTGA TTGACAGTGTTTCAGAAAAGGCAAATCCAAACATTAAAGATTCAAAAGATAATCAGGCAAAACAAAATGTGGGTAA TGGCAGTGTTCCCATGCGTACCGTGGGTTTGGAAAATCGCCTGAACTCCTTTATTCAGGTGGATGCCCCTGACCAA AAAGGAACTGAGATAAAACCAGGACAAAATAATCCTGTCCCT GTATCAGAGACTAATGAAAGTTCTATAGTGGAAC GTACCCCATTCAGTTCTAGCAGCTCAAGCAAACACAGTTCACCTAGTGGGACTGTTGCTGCCAGAG TGACTCCTTT TAATTACAACCCAAGCCCTAGGAAAAGCAGCGCAGATAGCACTTCAGCTCGGCCATCTCAGATCCCAACTCCAGTG AATAACAACACAAAGAAGCGAGATTCCAAAACTGACAGCACAGAATCCAGTGGAACCCAAAGTCCTAAGCGCCATT CTGGGTCTTACCTTGTGACATCTGTTTAAAAGAGAGGA AGAATGAAACTAAGAAAATTCTATGTTAATTACAACTG CTATATAGACATTTTGTTTCAAATGAAACTTTAAAAGACTGAAAAATTTTGTAAATAGGTTTGATTCTTGTTAGAG GGTTTTTGTTCTGGAAGCCATATTTGATAGTATACTTTGTCTTCACTGGTCTTATTTTGGGAGGCACTCTTGATGG TTAGGAAAAAAATAGTAAAGCCAAGTATGTTTGTACAGTATGTTTTACATGTATTTAAAGTAGCATCCCATCCCAA CTTCCTTTAATTATTGCTTGTCTTAAAATAATGAACACTACAGATAGAAATATGATATATTGCTGTTATCAATCA TTTCTAGATTATAAACTGACTAAACTTACATCAGGGAAAAATTGGTATTTATGCAAAAAAAATGTTTTTGTCCTT GTGAGTCCATCTAACATCATAATTAATCATGTGGCTGTGAAATTCACAGTAATATGGTTCCCGATGAACAAGTTTA CCCAGCCTGCTTTGCTTTACTGCATGAATGAAACTGATGGTTCAATTTCAGAAGTAATGATTAACAGTTATGTGGT CACATGATGTGCATAGAGATAGCTACAGTGTAATAATTTACACTATTTTGTGCTCCA AACAAAACAAAAATCTGTG TAACTGTAAAACATTGAATGAAACTATTTTACCTGAACTAGATTTTATCTGAAAGTAGGTAGAATTTTTGCTATGC TGTAATTTGTTGTATATTCTGGTATTTGAGGTGAGATGGCTGCTCTTTTATTAATGAGACATGAATTGTGTCTCAA CAGAAACTAAATGAACATTTCAGAATAAATTAT-
TGCTGTATGTAAACTGTTACTGAAATTGGTAT-
TTGTTTGAAGG GTCTTGTTTCACATTTGTAT-
TAATAATTGTTTAAAATGCCTCTTTTAAAAGCTT
ATATAAATTTTTTTCTTCAGCT TCTATGCAT-
TAAGAGTAAAATTCCTCT-
TACTGTAATAAAAACAATTGAAGAAGACTGTTGC-
CACTTAACCATTCCA
TGCGTTGGCACTTATCTATTCCTGAAATTTCTTT-
TATGTGATTAGCTCATCTTGATTTTTAATATTTTC-
CACTTA AACTTTTTTTTCTTACTCCACTG-
GAGCTCAGTAAAAGTAAATTCATGTAATAGCAA
TGCAAGCAGCCTAGCACAGA CTAAGCATTGAG-
CATAATAGGCCCACATAATTTCCTCTTTCTTAATAT-
TATAGAATTCTGTACTTGAAATTGATTC TTAGACAT-
TGCAGTCTCTTCGAGGCTTTACAGTGTAAACTG
TCTTGCCCCTTCATCTTCTTGTTGCAACTGGGTCT
GACATGAACACTTTTTATCACCCTGTATGT-
TAGGGCAAGATCTCAGCAGT-
GAAGTATAATCAGCACTTTGCCATGC TCAGAAAAT-
TCAAATCACATGGAACTTTAGAGGTAGATTTAATAC-
GATTAAGATATTCAGAAGTATATTTTAGAAT
CCCTGCCTGTTAAGGAAACTTTAT-
TTGTGGTAGGTACAGTTCTGGGGTACATGT-
TAAGTGTCCCCTTATACAGTGG AGG-
GAAGTCTTCCTTCCTGAAGGAAAATAAACTGACACT-
TATTAACTAAGATAATTTACTTAATATATCTTCCCTG
ATTTGTTTTAAAAGATCAGAGGGTGACTGATGATA-
CATGCATACATATTTGTTGAATAAATGAAAATTTAT-
TTTTA GTGATAAGATTCATACACTCTGTATTTGGG-
GAGGGAAAACCTTTTTAAGCATGGTGGGGCACTCA-
GATAGGAGTGA
ATACACCTACCTGGTGCCTTGAAAATCACAT-
CAAGTAGTTAATTATCTACCCCTTACCTGTGTT-
TATAACTTCCAG GTAATGAGAATGATTTTTTT-
TAAAGCTAAAATGCCAGTAAATAAAAGTGCTATG
ACTTGAGCTAAGATATTTGACT
CCAATGCCTGTACTGTGTCTACTGCAC-
CACTTTGTAAACACTTCAATTTACTATCTTTGAAAT-
GATTGACCTTTAA ATTTTTGCCAAATGTTATCT-
GAAATTGTCTATGAATACCATCTACTTCTGTTGT
TTTCCCAGGCTTCCATAAACAA TGGAGATA-
CATGCAAAAAAAAAAA (SEQ ID NO:69). In some
embodiments, a DNA mutation results in a truncation of
APC protein at exon 15. In some embodiments, a DNA
mutation results in a truncation of APC protein between
codons 1250 and 1560, or between codons 1286 and 1513.
In some embodiments, a DNA mutation results in the
mutation of Q1367, R1450, E1309, S1465, or T1556 according to SEQ ID NO:65 or SEQ ID NO:69. For example, in
some embodiments, a DNA mutation in an APC gene
encodes or results in a Q1367*, R1450*, E1309 frameshift,
S1465 frameshift, or T1556 frameshift mutated APC protein
(numbering according to SEQ ID NO:65). These DNA
mutations are also described by their nucleotide positions
(rather than mutated polypeptide codons) in Table A infra.
For example, in some embodiments, a DNA mutation in an
APC gene results in a 3927-3931delAAAGA, 4099C>T,
4348C>T, 4385-4386delAG, or 4666-4667insA mutation in
the corresponding cDNA sequence of SEQ ID NO:69.

Since, as described supra, the sequences of a variety of
APC genes and corresponding mutations are known, one of
ordinary skill in the art may suitably select a primer pair to
amplify the locus of one or more of these DNA mutation(s).
Various factors influencing primer design are known, and
tools for identifying primer pairs suitable for amplifying a
given DNA template sequence are available (see, e.g.,
www.ncbi.nlm.nih.gov/tools/primer-blast/). In some
embodiments, a primer pair for amplifying the locus of an
APC mutation (e.g., encoding or resulting in the mutated
APC proteins described supra) comprises the sequences
TAAAAATAAAGCACCTACTGCTGAAA (SEQ ID
NO:23) and AGCTTGCTTAGGTCCACTCTCTCT (SEQ
ID NO:24), respectively (for the S1465 locus); TAG-
GATGTAATCAGACGACACAGGA (SEQ ID NO:27) and
CAGCTGACCTAGTTCCAATCTTTTA (SEQ ID NO:28),
respectively (for the E1309 locus); TCTCCCTC-
CAAAAGTGGTGCT (SEQ ID NO:31) and
TGGCAATCGAACGACTCTCAA (SEQ ID NO:32),
respectively (for the Q1367 locus);
GCAGAAGTAAAACACCTCCACCA (SEQ ID NO:35)
and GGTGCTTTATTTTTAGGTACTTC (SEQ ID NO:36),
respectively (for the R1450 locus); or CAG-
GAAAATGACAATGGGAATG (SEQ ID NO:39) and
ATCTAATAGGTCCTTTTCAGAATCAATAG (SEQ ID
NO:40), respectively (for the T1556 locus). In some
embodiments, five primer pairs are used for PCR: a first
primer pair comprising the sequences
TAAAAATAAAGCACCTACTGCTGAAA (SEQ ID
NO:23) and AGCTTGCTTAGGTCCACTCTCTCT (SEQ
ID NO:24); a second primer pair comprising the sequences
TAGGATGTAATCAGACGACACAGGA (SEQ ID NO:27)
and CAGCTGACCTAGTTCCAATCTTTTA (SEQ ID
NO:28); a third primer pair comprising the sequences
TCTCCCTCCAAAAGTGGTGCT (SEQ ID NO:31) and
TGGCAATCGAACGACTCTCAA (SEQ ID NO:32); a
fourth primer pair comprising the sequences
GCAGAAGTAAAACACCTCCACCA (SEQ ID NO:35)
and GGTGCTTTATTTTTAGGTACTTC (SEQ ID NO:36);
and a fifth primer pair comprising the sequences CAG-
GAAAATGACAATGGGAATG (SEQ ID NO:39) and
ATCTAATAGGTCCTTTTCAGAATCAATAG (SEQ ID
NO:40). In some embodiments, a primer pair for amplifying
the locus of one or more APC mutations (e.g., encoding or
resulting in the mutated APC protein(s) described supra)
comprises the sequences GCAGAAGTAAAACACCTC-
CACCA (SEQ ID NO:35) and AGCTTGCTTAGGTC-
CACTCTCTCT (SEQ ID NO:24).

In some embodiments, a primer pair of the present disclosure comprises one or more modified nucleotides, e.g.,
locked nucleic acids (as described in greater detail infra).
For example, in some embodiments, a primer pair for
amplifying the locus of an APC mutation (e.g., encoding or
resulting in the mutated APC proteins described supra)
comprises the sequences GCAGAAGTAAAACACCTC-
CACCA (SEQ ID NO:35) and GGTGCTTTATTTT-
TAGGTACTTC (SEQ ID NO:36), with italicized nucleic
acids representing locked nucleic acids. In some embodiments, a primer pair for amplifying the locus of an APC
mutation (e.g., encoding or resulting in the mutated APC
proteins described supra) comprises the sequences
GCAGAAGTAAAACACCTCCACCA (SEQ ID NO:35)
and GGTGCTTTATTTTTAGGTACTTC (SEQ ID NO:36),
with underlined nucleic acids representing locked nucleic
acids. In some embodiments, five primer pairs are used for
PCR to amplify loci of an APC gene: a first primer pair
comprising the sequences TAAAAATAAAGCACC-
TACTGCTGAAA (SEQ ID NO:23) and AGCTTGCT-
TAGGTCCACTCTCTCT (SEQ ID NO:24); a second
primer pair comprising the sequences TAGGATGTAATCA-
GACGACACAGGA (SEQ ID NO:27) and
CAGCTGACCTAGTTCCAATCTTTTA (SEQ ID NO:28);
a third primer pair comprising the sequences TCTCCCTC- CAAAAGTGGTGCT (SEQ ID NO:31) and TGGCAATCGAACGACTCTCAA (SEQ ID NO:32); a fourth primer pair comprising the sequences GCAGAAGTAAAACACCTCCACCA (SEQ ID NO:35) and GGTGCTTTATTTTTAGGTACTTC (SEQ ID NO:36), with italicized nucleic acids representing locked nucleic acids; and a fifth primer pair comprising the sequences CAGGAAAATGACAATGGGAATG (SEQ ID NO:39) and ATCTAATAGGTCCTTTTCAGAATCAATAG (SEQ ID NO:40). In some embodiments, five primer pairs are used for PCR to amplify loci of an APC gene: a first primer pair comprising the sequences TAAAAATAAAGCACC-TACTGCTGAAA (SEQ ID NO:23) and AGCTTGCT-TAGGTCCACTCTCTCT (SEQ ID NO:24); a second primer pair comprising the sequences TAGGATGTAATCA-GACGACACAGGA (SEQ ID NO:27) and CAGCTGACCTAGTTCCAATCTTTTA (SEQ ID NO:28); a third primer pair comprising the sequences TCTCCCTC-CAAAAGTGGTGCT (SEQ ID NO:31) and TGGCAATCGAACGACTCTCAA (SEQ ID NO:32); a fourth primer pair comprising the sequences GCAGAAGTAAAACACCTCCACCA (SEQ ID NO:35) and GGTGCTTTATTTTTAGGTACTTC (SEQ ID NO:36), with underlined nucleic acids representing locked nucleic acids; and a fifth primer pair comprising the sequences CAGGAAAATGACAATGGGAATG (SEQ ID NO:39) and ATCTAATAGGTCCTTTTCAGAATCAATAG (SEQ ID NO:40).

A multiplex assay of the present disclosure may include detecting two or more of the mutations described above in combination. For example, in some embodiments, the methods of the present disclosure include amplifying the loci of one or more mutations in a KRAS gene, one or more mutations in a BRAF gene, one or more mutations in a CTNNB1 gene, and one or more mutations in an APC gene. In certain embodiments, the methods of the present disclosure include amplifying the locus of a mutation encoding a G12D, G12V, G12S, or G13D mutated KRAS protein; the locus of a mutation encoding a V600E mutated BRAF protein; the locus of a mutation encoding a T41A or T41I mutated CTNNB1 protein and/or the locus of a mutation encoding an S45F or S45P mutated CTNNB1 protein; and one or more of: the locus of a mutation encoding a Q1367* mutated APC protein, the locus of a mutation encoding an R1450* mutated APC protein, the locus of a mutation encoding an E1309 frameshift mutated APC protein, the locus of a mutation encoding an S1465 frameshift mutated APC protein, and the locus of a mutation encoding a T1556 frameshift mutated APC protein. In certain embodiments, the methods of the present disclosure include amplifying the loci of mutations encoding G12D, G12V, G12S, and G13D mutated KRAS proteins; the loci of two or more different mutations encoding a V600E mutated BRAF protein; the loci of mutations encoding a T41A or T41I mutated CTNNB1 protein and/or the loci of mutations encoding an S45F or S45P mutated CTNNB1 protein; and the locus of a mutation encoding a Q1367* mutated APC protein, the locus of a mutation encoding an R1450* mutated APC protein, the locus of a mutation encoding an E1309 frameshift mutated APC protein, the locus of a mutation encoding an S1465 frameshift mutated APC protein, and the locus of a mutation encoding a T1556 frameshift mutated APC protein.

Blocking Nucleic Acids

In some embodiments, the methods of the present disclosure include amplifying isolated DNA by PCR in the presence of one or more blocking nucleic acid(s) (e.g., a blocking nucleic acid corresponding to each DNA mutation of interest). Advantageously, the blocking nucleic acid prevents amplification of the wild-type DNA locus, thus increasing the sensitivity of detecting the DNA mutation (cf. FIGS. 15 & 16). In some embodiments, the methods include amplifying isolated DNA by PCR in the presence of at least four blocking nucleic acids, each of which hybridizes with the wild-type DNA locus corresponding with a DNA mutation in the KRAS, BRAF, CTNNB1, or APC gene.

In some embodiments, a blocking nucleic acid of the present disclosure comprises: a single-stranded oligonucleotide that hybridizes with the corresponding wild-type DNA locus, and a 3' terminal moiety that blocks extension from the single-stranded oligonucleotide, thereby preventing amplification of the wild-type DNA locus. In some embodiments, the 3' terminal moiety comprises one or more inverted deoxythymidines (invdTs). In certain embodiments, the 3' terminal moiety comprises three consecutive inverted deoxythymidines.

In some embodiments, a blocking nucleic acid of the present disclosure comprises one or more modified nucleotides. Oligonucleotides comprising modified nucleotides in some or all sequence positions are contemplated and may have improved hybridization properties particularly advantageous for use as a blocking nucleic acid during PCR. For example, it is known that oligonucleotides partly or completely synthesized using locked nucleic acids (LNAs) possess greater thermal stability than corresponding oligonucleotides synthesized with only conventional nucleotides, thereby increasing the melting temperature of an oligo:LNA duplex and allowing for shorter sequences that retain stable hybridization during thermocycling. See Koshkin, A. A. et al. (1998) *Tetrahedron* 54:3607-30. A variety of modified nucleotides are known and include without limitation locked nucleic acids (LNAs), peptide nucleic acids (PNAs), hexose nucleic acids (HNAs), threose nucleic acids (TNAs), glycol nucleic acids (GNAs), and cyclohexenyl nucleic acids (CeNAs). For more detailed description of exemplary modified nucleotides, see, e.g., Schmidt, M. (2010) *BioEssays* 32:322-31.

In some embodiments, a blocking nucleic acid of the present disclosure hybridizes with a wild-type KRAS locus corresponding with the locus of one or more DNA mutations encoding a G12D, G12V, G12S, or G13D mutated KRAS protein. In some embodiments, the blocking nucleic acid comprises the sequence TACGCCACCAGCT(invdT)$_n$, wherein n is 1, 2, or 3 (SEQ ID NO:3), TTG-GAGCTGGTGGCGTA(invdT)$_n$, wherein n is 1, 2, or 3 (SEQ ID NO:142), GCTGGTGGCGTAGGCA(invdT)$_n$, wherein n is 1, 2, or 3 (SEQ ID NO: 143), GCTGGTGGCGTAGGC(invdT)$_n$, wherein n is 1, 2, or 3 (SEQ ID NO:144), or TTGGAGCTGGTGGCGT(invdT)$_n$, wherein n is 1, 2, or 3 (SEQ ID NO:145), with italicized nucleic acids representing locked nucleic acids. In some embodiments, n is 1, 2, 3, 4, 5, 6, 7, 8, 9, or 10. For example, in certain embodiments, the blocking nucleic acid comprises the sequence TACGCCACCAGCTinvdTinvdTinvdT (SEQ ID NO:3), TTGGAGCTGGTGGCGTAinvdTinvdTinvdT (SEQ ID NO:142), GCTGGTGGCGTAGGCAinvdTinvdTinvdT (SEQ ID NO:143), GCTGGTGGCGTAGGCinvdTinvdTinvdT (SEQ ID NO: 144), or TTGGAGCTGGTGGCGTinvdTinvdTinvdT (SEQ ID NO: 145), with italicized nucleic acids representing locked nucleic acids. In certain embodiments, the blocking nucleic acid comprises the sequence TACGCCACCAGCTinvdTinvdTinvdT (SEQ ID NO:3), TTGGAGCTGGTGGCGTAinvdTinvdTinvdT (SEQ ID NO:142), GCT GGTGGCGTAGGCAinvdTinvdTinvdT (SEQ ID NO: 143), GCTGGTGGCGTAGGCinvdTinvdTinvdT (SEQ ID NO: 144), or TTGGAGCTGGTGGCGTinvdTinvdTinvdT (SEQ ID NO: 145), with underlined nucleic acids representing locked nucleic acids. In some embodiments, the blocking nucleic acid comprises the sequence of SEQ ID NO:3 or 142-145 but optionally includes a different pattern or type of modified nucleotide(s). In some embodiments, the blocking nucleic acid comprises the sequence of SEQ ID NO:3 or 142-145 but includes a different 3' terminal moiety.

In some embodiments, a blocking nucleic acid of the present disclosure hybridizes with a wild-type BRAF locus corresponding with the locus of one or more DNA mutations encoding a V600E mutated BRAF protein. In some embodiments, the blocking nucleic acid comprises the sequence GAGATTCACTGTAGC(invdT), wherein n is 1, 2, or 3 (SEQ ID NO:10), GAGATTTCACTGTAGC(invdT), wherein n is 1, 2, or 3 (SEQ ID NO:146), GAGATTT-CACTGTAGC(invdT)$_n$, wherein n is 1, 2, or 3 (SEQ ID NO: 147), GAGATTCACTGTAGC(invdT), wherein n is 1, 2, or 3 (SEQ ID NO:148), or GAGATTTCACTGTAGC(invdT)$_n$, wherein n is 1, 2, or 3 (SEQ ID NO: 149), with italicized nucleic acids representing locked nucleic acids. In some embodiments, n is 1, 2, 3, 4, 5, 6, 7, 8, 9, or 10. For example, in certain embodiments, the blocking nucleic acid comprises the sequence GAGATTTCACTGTAGCinvdTinvdTinvdT (SEQ ID NO:10), GAGATTTCACTGTAGCinvdTinvdTinvdT (SEQ ID NO:146), GAGATTTCACTGTAGC invdTinvdTinvdT (SEQ ID NO: 147), GAGATTTCACTGTAGC-invdTinvdTinvdT (SEQ ID NO:148), or GAGATTTCACTGTAGCinvdTinvdTinvdT (SEQ ID NO: 149), with italicized nucleic acids representing locked nucleic acids. In certain embodiments, the blocking nucleic acid comprises the sequence G<u>AGATTTCACT</u> <u>GTAGC</u>invdTinvdTinvdT (SEQ ID NO: 10), G<u>AGAT</u> <u>TTCACTGTAGC</u>invdTinvdTinvdT (SEQ ID NO:146), G<u>AGATTTCACTGTAGC</u> invdTinvdTinvdT (SEQ ID NO: 147), G<u>AGATTTCACTGTAGC</u>invdTinvdTinvdT (SEQ ID NO:148), or G<u>AGATTTCACTGTAGC</u>invdTinvdTinvdT (SEQ ID NO:149), with underlined nucleic acids representing locked nucleic acids. In some embodiments, the blocking nucleic acid comprises the sequence of SEQ ID NO:10 or 146-149 but optionally includes a different pattern or type of modified nucleotide(s). In some embodiments, the blocking nucleic acid comprises the sequence of SEQ ID NO: 10 or 146-149 but includes a different 3' terminal moiety.

In some embodiments, a blocking nucleic acid of the present disclosure hybridizes with a wild-type CTNNB1 locus corresponding with the locus of one or more mutations encoding a T41A or T41I mutated CTNNB1 protein. In some embodiments, the blocking nucleic acid comprises the sequence GCCACTACCACAGCT(invdT)$_n$, wherein n is 1, 2, or 3 (SEQ ID NO:15), TGCCACTACCACAG(invdT)$_n$, wherein n is 1, 2, or 3 (SEQ ID NO: 150), CACTAC-CACAGCTCC(invdT)$_n$, wherein n is 1, 2, or 3 (SEQ ID NO:151), GCCACTACCACAGCT(invdT)$_n$, wherein n is 1, 2, or 3 (SEQ ID NO:152), or GCCACTACCACAGCT (invdT)$_n$, wherein n is 1, 2, or 3 (SEQ ID NO: 153), with italicized nucleic acids representing locked nucleic acids. In some embodiments, n is 1, 2, 3, 4, 5, 6, 7, 8, 9, or 10. For example, in certain embodiments, the blocking nucleic acid comprises the sequence GCCACTACCACAGCTinvdT-invdTinvdT (SEQ ID NO: 15), TGCCACTAC-CACAGinvdTinvdTinvdT (SEQ ID NO:150), CACTAC-CACAGCTCCinvdTinvdTinvdT (SEQ ID NO: 151), GCCACTACCACAGCTinvdTinvdTinvdT (SEQ ID NO:152), or GCCACTACCACAGCTinvdTinvdTinvdT (SEQ ID NO: 153), with italicized nucleic acids representing locked nucleic acids. In certain embodiments, the blocking nucleic acid comprises the sequence GC<u>CACTACCACAG</u>CTinvdTinvdTinvdT (SEQ ID NO: 15), T GCC<u>ACTACCACAG</u>invdTinvdTinvdT (SEQ ID NO:150), C<u>ACTACCACAGCT</u>CCinvdTinvdTinvdT (SEQ ID NO:151), GCC<u>ACTACCACAGC</u>TinvdTinvdTinvdT (SEQ ID NO:152), or GCC<u>ACTACCAC</u>AGCTinvdTinvdTinvdT (SEQ ID NO: 153), with underlined nucleic acids representing locked nucleic acids. In some embodiments, the blocking nucleic acid comprises the sequence of SEQ ID NO:15 or 150-153 but optionally includes a different pattern or type of modified nucleotide(s). In some embodiments, the blocking nucleic acid comprises the sequence of SEQ ID NO: 15 or 150-153 but includes a different 3' terminal moiety.

In some embodiments, a blocking nucleic acid of the present disclosure hybridizes with a wild-type CTNNB1 locus corresponding with the locus of one or more mutations encoding an S45F or S45P mutated CTNNB1 protein. In some embodiments, the blocking nucleic acid comprises the sequence GCTCCTTCTCTGAGT(invdT)$_n$, wherein n is 1, 2, or 3 (SEQ ID NO:20), TCCTTCTCTGAGTGG(invdT)$_n$, wherein n is 1, 2, or 3 (SEQ ID NO:174), GCTCCTTCTCT-GAGT(invdT)n, wherein n is 1, 2, or 3 (SEQ ID NO:175), TCCTTCTCTGAGTGG(invdT)n, wherein n is 1, 2, or 3 (SEQ ID NO:176), or GCTCCTTCTCTGAGT(invdT)n, wherein n is 1, 2, or 3 (SEQ ID NO:177), with italicized nucleic acids representing locked nucleic acids. In some embodiments, n is 1, 2, 3, 4, 5, 6, 7, 8, 9, or 10. For example, in certain embodiments, the blocking nucleic acid comprises the sequence GCTCCTTCTCTGAGTinvdTinvdTinvdT (SEQ ID NO:20), TCCTTCTCTGAGTGGinvdTinvdT-invdT (SEQ ID NO:174), GCTCCTTCTCTGAGTinvdT-invdTinvdT (SEQ ID NO: 175), TCCTTCTCTGAGTGG-invdTinvdTinvdT (SEQ ID NO: 176), or GCTCCTTCTCTGAGTinvdTinvdTinvdT (SEQ ID NO: 177), with italicized nucleic acids representing locked nucleic acids. In certain embodiments, the blocking nucleic acid comprises the sequence GC<u>TCCTTCTCTGAG</u>TinvdTinvdTinvdT (SEQ ID NO:20), T<u>CCTTCTCTGAG</u>TGGinvdTinvdTinvdT (SEQ ID NO:174), G<u>CTCCTTCTCTGAG</u>TinvdTinvdTinvdT (SEQ ID NO: 175), T<u>CCTTCTCTGAGTGG</u> invdTinvdTinvdT (SEQ ID NO: 176), or G<u>CTCCTTCTCTGAGT</u> invdTinvdT-invdT (SEQ ID NO:177), with underlined nucleic acids representing locked nucleic acids. In some embodiments, the blocking nucleic acid comprises the sequence of SEQ ID NO:20 or 174-177 but optionally includes a different pattern or type of modified nucleotide(s). In some embodiments, the blocking nucleic acid comprises the sequence of SEQ ID NO: 20 or 174-177 but includes a different 3' terminal moiety.

In some embodiments, a blocking nucleic acid of the present disclosure hybridizes with a wild-type APC locus corresponding with the locus of one or more mutations encoding a Q1367* mutated APC protein. In some embodiments, the blocking nucleic acid comprises the sequence GTGCTCAGACACC(invdT)$_n$, wherein n is 1, 2, or 3 (SEQ ID NO:33), GTGCTCAGACACC(invdT)n, wherein n is 1, 2, or 3 (SEQ ID NO:158), AGTGGTGCTCAGACACCCA (invdT)n, wherein n is 1, 2, or 3 (SEQ ID NO:159), AGTGGTGCTCAGACACCCA(invdT)n, wherein n is 1, 2, or 3 (SEQ ID NO:160), or AGTGGTGCTCAGACACCCA (invdT)n, wherein n is 1, 2, or 3 (SEQ ID NO:161), with italicized nucleic acids representing locked nucleic acids. In some embodiments, n is 1, 2, 3, 4, 5, 6, 7, 8, 9, or 10. For example, in certain embodiments, the blocking nucleic acid comprises the sequence GTGCTCAGACACCinvdTinvdTinvdT (SEQ ID NO:33), GTGCTCAGACACCinvdTinvdTinvdT (SEQ ID NO:158), AGTGGTGCTCAGACACCCAinvdTinvdTinvdT (SEQ ID NO:159), AGTGGTGCTCAGACACCCAinvdTinvdTinvdT (SEQ ID NO: 160), or AGTGGTGCTCAGACACCCAinvdTinvdTinvdT (SEQ ID NO:161), with italicized nucleic acids representing locked nucleic acids. In certain embodiments, the blocking nucleic acid comprises the sequence GTG CTCAGACACCinvdTinvdTinvdT (SEQ ID NO:33), G TGCTCAGACACCinvdTinvdTinvdT (SEQ ID NO: 158), AGTGGTGCTCAGACACCCAinvdTinvdTinvdT (SEQ ID NO: 159), AGTGGTGCTCAGAC ACCCAinvdTinvdTinvdT (SEQ ID NO: 160), or AGT GGTGCTCAGACACCCAinvdTinvdTinvdT (SEQ ID NO: 161), with underlined nucleic acids representing locked nucleic acids. In some embodiments, the blocking nucleic acid comprises the sequence of SEQ ID NO:33 or 158-161 but optionally includes a different pattern or type of modified nucleotide(s). In some embodiments, the blocking nucleic acid comprises the sequence of SEQ ID NO: 33 or 158-161 but includes a different 3' terminal moiety.

In some embodiments, a blocking nucleic acid of the present disclosure hybridizes with a wild-type APC locus corresponding with the locus of one or more mutations encoding an R1450* mutated APC protein. In some embodiments, the blocking nucleic acid comprises the sequence CTTCTCGCTTGGTT(invdT)$_n$, wherein n is 1, 2, or 3 (SEQ ID NO:37), GTACTTCTCGCTTGGT(invdT)n, wherein n is 1, 2, or 3 (SEQ ID NO:162), CTTCTCGCTTGGTT (invdT)n, wherein n is 1, 2, or 3 (SEQ ID NO:163), GTACTTCTCGCTTGGT(invdT)n, wherein n is 1, 2, or 3 (SEQ ID NO: 164), or GTACTTCTCGCTTGGT(invdT)n, wherein n is 1, 2, or 3 (SEQ ID NO: 165), with italicized nucleic acids representing locked nucleic acids. In some embodiments, n is 1, 2, 3, 4, 5, 6, 7, 8, 9, or 10. For example, in certain embodiments, the blocking nucleic acid comprises the sequence CTTCTCGCTTGGTTinvdTinvdTinvdT (SEQ ID NO:37), GTACTTCTCGCTTGGTinvdTinvdTinvdT (SEQ ID NO:162), CTTCTCGCTTGGTTinvdTinvdTinvdT (SEQ ID NO:163), GTACTTCTCGCTTGGTinvdTinvdTinvdT (SEQ ID NO:164), or GTACTTCTCGCTTGGTinvdTinvdTinvdT (SEQ ID NO:165), with italicized nucleic acids representing locked nucleic acids. In certain embodiments, the blocking nucleic acid comprises the sequence C TTCTCGCTTGGTTinvdTinvdTinvdT (SEQ ID NO:37), G TACTTCTCGCTTGGTinvdTinvdTinvdT (SEQ ID NO: 162), CTTCTCGCTTGGTTinvdTinvdTinvdT (SEQ ID NO:163), GTACTTCTCGCTTGGTinvdTinvdTinvdT (SEQ ID NO: 164), or GTACTTCTCGCTT GGTinvdTinvdTinvdT (SEQ ID NO:165), with underlined nucleic acids representing locked nucleic acids. In some embodiments, the blocking nucleic acid comprises the sequence of SEQ ID NO:37 OR 162-165 but optionally includes a different pattern or type of modified nucleotide(s). In some embodiments, the blocking nucleic acid comprises the sequence of SEQ ID NO: 37 OR 162-165 but includes a different 3' terminal moiety.

In some embodiments, a blocking nucleic acid of the present disclosure hybridizes with a wild-type APC locus corresponding with the locus of one or more mutations encoding an E1309 frameshift mutated APC protein. In some embodiments, the blocking nucleic acid comprises the sequence CTTTTCTTTTATTTCTGC(invdT)$_n$, wherein n is 1, 2, or 3 (SEQ ID NO:29), CTTTTCTTTTATTTCTGC (invdT)n, wherein n is 1, 2, or 3 (SEQ ID NO: 154), CTTTTCTTTTATTTCTGC(invdT)n, wherein n is 1, 2, or 3 (SEQ ID NO:155), CTTTTCTTTTATTTCTGC(invdT)n, wherein n is 1, 2, or 3 (SEQ ID NO:156), or CTTTTCTTTTATTTCTGC(invdT)n, wherein n is 1, 2, or 3 (SEQ ID NO:157), with italicized nucleic acids representing locked nucleic acids. In some embodiments, n is 1, 2, 3, 4, 5, 6, 7, 8, 9, or 10. For example, in certain embodiments, the blocking nucleic acid comprises the sequence CTTTTCTTTTATTTCTGCinvdTinvdTinvdT (SEQ ID NO:29), CTTTTCTTTTATTTCTGCinvdTinvdTinvdT (SEQ ID NO: 154), CTTTTCTTTTATTTCTGCinvdTinvdTinvdT (SEQ ID NO:155), CTTTTCTTTTATTTCTGCinvdTinvdTinvdT (SEQ ID NO:156), or CTTTTCTTTTATTTCTGCinvdTinvdTinvdT (SEQ ID NO:157), with italicized nucleic acids representing locked nucleic acids. In certain embodiments, the blocking nucleic acid comprises the sequence CTTTTCTTTTATTTCT GCinvdTinvdTinvdT (SEQ ID NO:29), CTTTTCTTTTAT TTCTGCinvdTinvdTinvdT (SEQ ID NO: 154), CTTTTCT TTATTTCTGCinvdTinvdTinvdT (SEQ ID NO: 155), C TTTTCTTTTATTTCTGCinvdTinvdTinvdT (SEQ ID NO:156), or CTTTTCTTTTATTTCTGCinvdTinvdTinvdT (SEQ ID NO:157), with underlined nucleic acids representing locked nucleic acids. In some embodiments, the blocking nucleic acid comprises the sequence of SEQ ID NO:29 or 154-157 but optionally includes a different pattern or type of modified nucleotide(s). In some embodiments, the blocking nucleic acid comprises the sequence of SEQ ID NO: 29 or 154-157 but includes a different 3' terminal moiety.

In some embodiments, a blocking nucleic acid of the present disclosure hybridizes with a wild-type APC locus corresponding with the locus of one or more mutations encoding an S1465 frameshift mutated APC protein. In some embodiments, the blocking nucleic acid comprises the sequence CCACTCTCTCTCTTTTCAGC(invdT)$_n$, wherein n is 1, 2, or 3 (SEQ ID NO:25), TAGGTCCACTCTCTCTCTTTCAGCA(invdT)n, wherein n is 1, 2, or 3 (SEQ ID NO:166), TAGGTCCACTCTCTCTCTTTTCAGCA (invdT)n, wherein n is 1, 2, or 3 (SEQ ID NO:167), CCACTCTCTCTCTTTTCAGC (invdT)n, wherein n is 1, 2, or 3 (SEQ ID NO: 168), or TAGGTCCACTCTCTCTCTTTTCAGCA (invdT)n, wherein n is 1, 2, or 3 (SEQ ID NO:169), with italicized nucleic acids representing locked nucleic acids. In some embodiments, n is 1, 2, 3, 4, 5, 6, 7, 8, 9, or 10. For example, in certain embodiments, the blocking nucleic acid comprises the sequence CCACTCTCTCTCTTTTCAGCinvdTinvdTinvdT (SEQ ID NO:25), TAGGTCCACTCTCTCTCTTTTCAGCAinvdTinvdTinvdT (SEQ ID NO: 166), TAGGTCCACTCTCTCTCTTTTCAGCAinvdTinvdTinvdT (SEQ ID NO: 167), CCACTCTCTCTCTTTTCAGC invdTinvdTinvdT (SEQ ID NO:168), or TAGGTCCACTCTCTCTCTTTTCAGCA invdTinvdTinvdT (SEQ ID NO: 169), with italicized nucleic acids representing locked nucleic acids. In certain embodiments, the blocking nucleic acid comprises the sequence CCACTCTCTCTCTTTTCAGCinvdTinvdTinvdT (SEQ ID NO:25), TAGGTCCACTCTCTCTCTTTTCA GCAinvdTinvdTinvdT (SEQ ID NO: 166), TAGGTCCACT CTCTCTCTTTTCAGCA invdTinvdTinvdT (SEQ ID NO: 167), CCACTCTCTCTCTTTTCAGC invdTinvdTinvdT (SEQ ID NO: 168), or TAGGTCCACTCTCTCTCTTTTCA GCA invdTinvdTinvdT (SEQ ID NO:169), with underlined nucleic acids representing locked nucleic acids. In some embodiments, the blocking nucleic acid comprises the sequence of SEQ ID NO:25 or 166-169 but optionally includes a different pattern or type of modified nucleotide(s).

In some embodiments, the blocking nucleic acid comprises the sequence of SEQ ID NO: 25 or 166-169 but includes a different 3' terminal moiety.

In some embodiments, a blocking nucleic acid of the present disclosure hybridizes with a wild-type APC locus corresponding with the locus of one or more mutations encoding a T1556 frameshift mutated APC protein. In some embodiments, the blocking nucleic acid comprises the sequence CAATAGTTTTTTCTGCC(invdT)$_n$, wherein n is 1, 2, or 3 (SEQ ID NO:41), GAAT-CAATAGTTTTTTCTGCCTC (invdT)n, wherein n is 1, 2, or 3 (SEQ ID NO:170), TCAGAATCAATAGTTTTTTCTG (invdT)n, wherein n is 1, 2, or 3 (SEQ ID NO:171), GAATCAATAGATTTTACTGCCTC (invdT)n, wherein n is 1, 2, or 3 (SEQ ID NO:172), or AAT-CAATAGTTTTTTCTGCCTC (invdT)n, wherein n is 1, 2, or 3 (SEQ ID NO:173), with italicized nucleic acids representing locked nucleic acids. In some embodiments, n is 1, 2, 3, 4, 5, 6, 7, 8, 9, or 10. For example, in certain embodiments, the blocking nucleic acid comprises the sequence CAATAGTTTTTTCTGCCinvdTinvdTinvdT (SEQ ID NO:41), GAATCAATAGTTTTTTCTGCCTC invdTinvdTinvdT (SEQ ID NO: 170), TCAGAAT-CAATAGTTTTTTCTG invdTinvdTinvdT (SEQ ID NO:171), GAATCAATAGATTTTACTGCCTC invdT-invdTinvdT (SEQ ID NO: 172), or AAT-CAATAGTTTTTTCTGCCTC invdTinvdTinvdT (SEQ ID NO: 173), with italicized nucleic acids representing locked nucleic acids. In certain embodiments, the blocking nucleic acid comprises the sequence CA<u>ATAGTTTTT</u>CTGCCinvdTinvdTinvdT (SEQ ID NO:41), GA<u>AT</u> <u>CAATAG</u>TTTTTTCTGCCTC invdTinvdTinvdT (SEQ ID NO: 170), TCAGA<u>ATCAATAG</u>TTTTTTCTG invdTinvdT-invdT (SEQ ID NO:171), GA<u>ATCAATAG</u>ATTTTA CTGCCTC invdTinvdTinvdT (SEQ ID NO: 172), or A<u>AT</u> <u>CAATAG</u>TTTTTTC<u>TGCCTC</u> invdTinvdTinvdT (SEQ ID NO: 173), with underlined nucleic acids representing locked nucleic acids. In some embodiments, the blocking nucleic acid comprises the sequence of SEQ ID NO:41 or 170-173 but optionally includes a different pattern or type of modified nucleotide(s). In some embodiments, the blocking nucleic acid comprises the sequence of SEQ ID NO: 41 or 170-173 but includes a different 3' terminal moiety.

Hybridization

In some embodiments, the methods of the present disclosure include hybridizing amplified DNA with one or more probes specific for a DNA mutation of the present disclosure (e.g., a DNA mutation in the KRAS, BRAF, CTNNB1, or APC gene as described supra). In some embodiments, the methods include hybridizing amplified DNA with at least four probes, comprising one or more probes specific for a DNA mutation in each of the KRAS, BRAF, CTNNB1, and APC genes (e.g., one or more probes representing a mutation in each gene). As used herein, a probe may refer to an oligonucleotide that is capable of hybridization with at least a portion of the locus of a DNA mutation of interest. For example, a probe may include a single-stranded oligonucleotide that is able to base pair with most or all of the base pairs of a single-stranded DNA template that includes a DNA mutation of interest. For specific detection of a DNA mutation, the probe is able to hybridize with a locus bearing the DNA mutation, but not with the corresponding wild-type locus (cf. FIGS. 15 & 16). Conditions suitable for hybridization of a probe with amplified DNA are known in the art (e.g., as referenced in the materials cited herein) and exemplified infra.

In some embodiments, a probe of the present disclosure is coupled to an encoded microcarrier of the present disclosure, e.g., as described in section IV. Exemplary methods for coupling a polynucleotide probe to a microcarrier surface are known in the art and provided in section IV. For multiplex assays, each type of probe can be coupled to a microcarrier with a particular identifier corresponding to the probe type. Advantageously, this allows the user to correlate a signal detected from the probe with the probe's identity, enabling multiplex assays in which multiple probes are utilized. In some embodiments, a probe of the present disclosure comprises a 5' modification, e.g., a 5'amino modifier C6.

In some embodiments, a probe of the present disclosure comprises (1) a sequence that hybridizes with at least a portion of the locus of a DNA mutation of interest; and (2) one or more additional nucleotides. The one or more additional nucleotides may be used, e.g., to couple the probe to the microcarrier surface and/or to provide spacing to reduce steric hindrance between the microcarrier surface and the amplified DNA during hybridization. In some embodiments, the one or more additional nucleotides are at the 5' end of the probe sequence. In other embodiments, the one or more additional nucleotides are at the 3' end of the probe sequence. In some embodiments, the one or more additional nucleotides are adenine or thymine nucleotides. Advantageously, this reduces the affinity of non-specific binding. In some embodiments, a probe of the present disclosure comprises 1 or more, 2 or more, 3 or more, 4 or more, 5 or more, 6 or more, 7 or more, or 8 or more adenine or thymine nucleotides at the 5' end. In some embodiments, a probe of the present disclosure comprises at least 20, at least 24, at least 25, or at least 30 total nucleotides.

Exemplary probe sequences are provided below. One of ordinary skill in the art can readily select any number of probe sequences suitable for hybridization with an amplified DNA sequence of interest (e.g., a locus comprising a DNA mutation of interest) using well-known techniques.

In some embodiments, a probe specific for a DNA mutation in a KRAS gene comprises the sequence GGAGCT-GATGG (SEQ ID NO:4), AGCTGATGGCGTA (SEQ ID NO:178), TGGAGCTGATGGCG (SEQ ID NO:179), TGGAGCTGATGG (SEQ ID NO:180), GCT-GATGGCGTA (SEQ ID NO:181), GGAGCTGTTGG (SEQ ID NO:5), TGGAGCTGTTGGTGGC (SEQ ID NO:182), GGAGCTGTTGGTG (SEQ ID NO:183), TGGAGCTGTTGGT (SEQ ID NO:184), TGGAGCTGTAGGTGG (SEQ ID NO:185), TGGAGCTAGTGG (SEQ ID NO:6), TTG-GAGCTAGTGGCGTA (SEQ ID NO:186), GCTAGTGGCGTAGGC (SEQ ID NO:187), AGCTAGTGGCGT (SEQ ID NO:188), GTTG-GAGCTAGTGG (SEQ ID NO:189), GGAGCTAGTGG (SEQ ID NO:190), or TGGAGCTGGTGACGT (SEQ ID NO:7). For example, a probe comprising the sequence GGAGCTGATGG (SEQ ID NO:4), AGCTGATGGCGTA (SEQ ID NO:178), TGGAGCTGATGGCG (SEQ ID NO:179), TGGAGCTGATGG (SEQ ID NO:180), or GCT-GATGGCGTA (SEQ ID NO: 181) can be used to detect a mutation encoding a G12D mutated KRAS protein; a probe comprising the sequence GGAGCTGTTGG (SEQ ID NO:5), TGGAGCTGTTGGTGGC (SEQ ID NO:182), GGAGCTGTTGGTG (SEQ ID NO:183), TGGAGCTGTTGGT (SEQ ID NO:184), or TGGAGCTGTaGGTGG (SEQ ID NO:185) can be used to detect a mutation encoding a G12V mutated KRAS protein; a probe comprising the sequence TGGAGCTAGTGG (SEQ ID NO:6), TTGGAGCTAGTGGCGTA (SEQ ID NO:186), GCTAGTGGCGTAGGC (SEQ ID NO:187), AGCTAGTGGCGT (SEQ ID NO:188), GTTGGAGCTAGTGG (SEQ ID NO:189), or GGAGCTAGTGG (SEQ ID NO:190) can be used to detect a mutation encoding a G12S mutated KRAS protein; and/or a probe comprising the sequence TGGAGCTGGTGACGT (SEQ ID NO:7), GGTGACGTAGGCAA (SEQ ID NO:191), TGACGTAGGCAAGAG (SEQ ID NO:192), GCTGGTGACGTAGG (SEQ ID NO:193), AGCTGGTGACGTAG (SEQ ID NO:194), or GGAGCTGGTGACGT (SEQ ID NO:195) can be used to detect a mutation encoding a G13D mutated KRAS protein. As described supra, in some embodiments, one or more probes of the present disclosure can comprise eight or more nucleotides (e.g., adenines or thymines) at its 5' end. In certain embodiments, a probe comprising the sequence TTTTTTTTTTTTAAGGAGCTGATGG (SEQ ID NO:47), TTTTTTTTTTTTAGCTGATGGCGTA (SEQ ID NO:74), TTTTTTTTTTTATGGAGCTGATGGCG (SEQ ID NO:75), TTTTTTTTTTTTTATGGAGCTGATGG (SEQ ID NO:76), or TTTTTTTTTTTTTGCTGATGGCGTA (SEQ ID NO:77) can be used to detect a mutation encoding a G12D mutated KRAS protein. In certain embodiments, a probe comprising the sequence TTTTTTTTTTTTAAGGAGCTGTTGG (SEQ ID NO:48), TTTTTTTTTATGGAGCTGTTGGTGGC (SEQ ID NO:78), TTTTTTTTTTAAGGAGCTGTTGGTG (SEQ ID NO:79), TTTTTTTTTTTATGGAGCTGTTGGT (SEQ ID NO:80), or TTTTTTTTTATGGAGCTGTAGGTGG (SEQ ID NO:81) can be used to detect a mutation encoding a G12V mutated KRAS protein. In certain embodiments, a probe comprising the sequence TTTTTTTTTTTATGGAGCTAGTGG (SEQ ID NO:49), TTTTTTTTTTGGAGCTAGTGGCGTA (SEQ ID NO:82), TTTTTAATTTGCTAGTGGCGTAGGC (SEQ ID NO:83), TTTTTTTTTATTTAGCTAGTGGCGT (SEQ ID NO:84), TTTTTTTTTTGTTGGAGCTAGTGG (SEQ ID NO:85), or TTTTTTTTTTTAAGGAGCTAGTGG (SEQ ID NO:86) can be used to detect a mutation encoding a G12S mutated KRAS protein. In certain embodiments, a probe comprising the sequence TTTTTTTTTATGGAGCTGGTGACGT (SEQ ID NO:50), TTTTTTTAAAGGTGACGTAGGCAA (SEQ ID NO:87), TTTTTTTTTATGACGTAGGCAAGAG (SEQ ID NO:88), TTTTTTTTTTTGCTGGTGACGTAGG (SEQ ID NO:89), TTTTTTTTTTAAGCTGGTGACGTAG (SEQ ID NO:90), or TTTTTTTTTAAGGAGCTGGTGACGT (SEQ ID NO:91) can be used to detect a mutation encoding a G13D mutated KRAS protein (probes comprising these sequences exclusive of the 5' adenine and/or thymines are also contemplated).

In some embodiments, a probe specific for a DNA mutation in a BRAF gene comprises the sequence TCTAGCTACAGAGAAAT (SEQ ID NO: 11) or GTCTAGCTACAGAAAAAT (SEQ ID NO: 12). For example, a probe comprising the sequence TCTAGCTACAGAGAAAT (SEQ ID NO:11), TACAGAGAAATCTCGAT (SEQ ID NO:196), TACAGAGAAATCTC (SEQ ID NO:197), CTAGCTACAGAGAAAT (SEQ ID NO:198), CTAGCTACAGAGAAA (SEQ ID NO:199), or TCTAGCTACAGAG (SEQ ID NO:200) can be used to detect a mutation encoding a V600E mutated BRAF protein (e.g., a c.1799T>A DNA mutation), and/or a probe comprising the sequence GTCTAGCTACAGAAAAAT (SEQ ID NO:12) can be used to detect a mutation encoding a V600E mutated BRAF protein (e.g., a c.1799_1800TG>AA DNA mutation). As described supra, in some embodiments, one or more probes of the present disclosure can comprise eight or more nucleotides (e.g., adenines or thymines) at its 5' end and/or comprise at least 24 total nucleotides. In certain embodiments, a probe comprising the sequence TTTTTTAATTTCTAGCTACAGAGAAAT (SEQ ID NO:51), TTTTTTTTTATACAGAGAAATCTCGAT (SEQ ID NO:92), TTTTTTTTTAATTTACAGAGAAATCTC (SEQ ID NO:93), TTTTTTAATTACTAGCTACAGAGAAAT (SEQ ID NO:94), TTTTTTTAATTACTAGCTACAGAGAAA (SEQ ID NO:95), or TTTTTTTTTTAATTTCTAGCTACAGAG (SEQ ID NO:96) can be used to detect a mutation encoding a V600E mutated BRAF protein (e.g., a c.1799T>A DNA mutation), and/or a probe comprising the sequence TTTTTTTATGTCTAGCTACAGAAAAAT (SEQ ID NO:52), TTTTATGTCTAGCTACAGAAAAATC (SEQ ID NO:97), TTTTTTTTATTTTAGCTACAGAAAAA (SEQ ID NO:98), TTTTTTTATTTCTAGCTACAGAAAAAT (SEQ ID NO:99), or TTTTTTTTATTCTAGCTACAGAAAAATC (SEQ ID NO: 100) can be used to detect a mutation encoding a V600E mutated BRAF protein (e.g., a c.1799_1800TG>AA DNA mutation) (probes comprising these sequences exclusive of the 5' adenine and/or thymines are also contemplated).

In some embodiments, a probe specific for a DNA mutation in a CTNNB1 gene comprises the sequence AGGAGCTGTGGCAG (SEQ ID NO:16), GGAGCTGTGATA (SEQ ID NO:17), TTTACCACTCAGAAAAG (SEQ ID NO:21), TACCACTCAGAGGAG (SEQ ID NO:22), AGGAGCTGTGGCAGT (SEQ ID NO:205), AGGAGCTGTGGCAGTG (SEQ ID NO:206), GCTGTGGCAGTGGC (SEQ ID NO:207), GCTGTGGCAGTGGCA (SEQ ID NO:208), AAGGAGCTGTGGCAG (SEQ ID NO:209), GGAGCTGTGATAGTGG (SEQ ID NO:210), GAGCTGTGATAGTGGC (SEQ ID NO:211), AGCTGTGATAGTGGCA (SEQ ID NO:212), AGAAGGAGCTGTGATA (SEQ ID NO:213), GGAGCTGTGAT (SEQ ID NO:214), ACTCAGAAAAGGAGCT (SEQ ID NO:215), TACCACTCAGAAAAGGA (SEQ ID NO:216), TTTACCACTCAGAAAAGGAG (SEQ ID NO:217), TTACCACTCAGAAAAG (SEQ ID NO:218), CAGAAAAGGAGCTGTG (SEQ ID NO:219), ACTCAGAGGAGGAGC (SEQ ID NO:220), TTACCACTCAGAGGA (SEQ ID NO:221), TTACCACTCAGAGGAGG (SEQ ID NO:222), TTAACACTCAGAGGAG (SEQ ID NO:223), or TTACCAATCAGAGGAGG (SEQ ID NO:224). For example, a probe comprising the sequence AGGAGCTGTGGCAG (SEQ ID NO:16), AGGAGCTGTGGCAGT (SEQ ID NO:205), AGGAGCTGTGGCAGTG (SEQ ID NO:206), GCTGTGGCAGTGGC (SEQ ID NO:207), GCTGTGGCAGTGGCA (SEQ ID NO:208), or AAGGAGCTGTGGCAG (SEQ ID NO:209) can be used to detect a mutation encoding a T41A mutated CTNNB1 protein; a probe comprising the sequence GGAGCTGTGATA (SEQ ID NO:17), GGAGCTGTGATAGTGG (SEQ ID NO:210), GAGCTGTGATAGTGGC (SEQ ID NO:211), AGCTGTGATAGTGGCA (SEQ ID NO:212), AGAAGGAGCTGTGATA (SEQ ID NO:213), or GGAGCTGTGAT (SEQ ID NO:214) can be used to detect a mutation encoding a T41I mutated CTNNB1 protein; a probe comprising the sequence TTTACCACTCAGAAAAG (SEQ ID NO:21), ACTCAGAAAAGGAGCT (SEQ ID NO:215), TACCACTCAGAAAAGGA (SEQ ID NO:216), TTTACCACTCAGAAAAGGAG (SEQ ID NO:217), TTACCACTCAGAAAAG (SEQ ID NO:218), or CAGAAAAGGAGCTGTG (SEQ ID NO:219 can be used to detect a mutation encoding an S45F mutated CTNNB1 protein; and/or a probe comprising the sequence TACCACTCAGAGGAG (SEQ ID NO:22), ACTCAGAGGAGGAGC (SEQ ID NO:220), TTACCACTCAGAGGA (SEQ ID NO:221), TTACCACTCAGAGGAGG (SEQ ID NO:222), TTAACACTCAGAGGAG (SEQ ID NO:223), or TTACCAATCAGAGGAGG (SEQ ID NO:224) can be used to detect a mutation encoding an S45P mutated CTNNB1 protein. As described supra, in some embodiments, one or more probes of the present disclosure can comprise eight or more nucleotides (e.g., adenines or thymines) at its 5' end and/or comprise at least 24 total nucleotides. In certain embodiments, a probe comprising the sequence TTTTTTTTTTTAGGAGCTGTGGCAG (SEQ ID NO:53), TTTTTTTTTTTAGGAGCTGTGGCAGTG (SEQ ID NO: 101), TTTTTTTTTTTAGCTGTGGCAGTGGC (SEQ ID NO: 102), TTTTTTTTTTTGCTGTGGCAGTGGCA (SEQ ID NO: 103), or TTTTTTTTTTAAGGAGCTGTGGCAG (SEQ ID NO: 104) can be used to detect a mutation encoding a T41A mutated CTNNB1 protein; a probe comprising the sequence TTTTTTTTTTTTGGAGCTGTGATA (SEQ ID NO:54), TTTTTTTTGGAGCTGTGATAGTGG (SEQ ID NO: 105), TTTTTTTTTGAGCTGTGATAGTGGC (SEQ ID NO: 106), TTTTTTTTTAGCTGTGATAGTGGCA (SEQ ID NO: 107), TTTTTTTTTAGAAGGAGCTGTGATA (SEQ ID NO: 108), or TTTTTTTTTTTTTGGAGCTGTGAT (SEQ ID NO: 109) can be used to detect a mutation encoding a T41I mutated CTNNB1 protein; a probe comprising the sequence TTTTTTTTTTTAC-CACTCAGAAAAG (SEQ ID NO:55), TTTAATTTTACTCAGAAAAGGAGCT (SEQ ID NO:110), TTTTTTAATACCACTCAGAAAAGGA (SEQ ID NO:111), TTTTTTTTACCACTCAGAAAAGGAG (SEQ ID NO:112), TTTTTTTTATTACCACTCAGAAAAG (SEQ ID NO:113), or TTTTTTTTTCAGAAAAGGAGCTGTG (SEQ ID NO: 114) can be used to detect a mutation encoding an S45F mutated CTNNB1 protein; and/or a probe comprising the sequence TTTTTTTTTAATACCACTCAGAGGAG (SEQ ID NO:56), TTTTTTTTTAAAACTCAGAGGAGGAGC (SEQ ID NO:115), TTTTTTTTTTTATTACCACTCAGAGGA (SEQ ID NO: 116), TTTTTTTTTATTACCACTCAGAGGAGG (SEQ ID NO:117), TTTTTTTTTATTAACACTCAGAGGAG (SEQ ID NO:118), or TTTTTTTTTATTACCAATCAGAGGAGG (SEQ ID NO: 119) can be used to detect a mutation encoding an S45P mutated CTNNB1 protein (probes comprising these sequences exclusive of the 5' adenine and/or thymines are also contemplated).

In some embodiments, a probe specific for a DNA mutation in an APC gene comprises the sequence ACTGCTGAAAAGAGAGAGT (SEQ ID NO:26), GAAATAAAAGATTGG (SEQ ID NO:30), TTTTGGGTGTCTAAG (SEQ ID NO:34), CAAACCAAGTGAGAA (SEQ ID NO:38), AGAGGCAGAAAAAAACT (SEQ ID NO:42), AAATAGCAGAAATAAAAG (SEQ ID NO:225), GAAATAAAAGATTGGAA (SEQ ID NO:226), AGAAATAAAAGATTG (SEQ ID NO:227), GAAATAAATGAATGG (SEQ ID NO:228), CAGAAATAAAAGATT (SEQ ID NO:229), TTTGGGTGTCTAAG (SEQ ID NO:230), GGGTGTCTAAGCACCACT (SEQ ID NO:231), CTAAGCACCACTTTT (SEQ ID NO:232), TTTTGGGTGTCTAA (SEQ ID NO:233), GGTGTCTAAGCACCA (SEQ ID NO:234), AAGTGAGAAGTACCTAA (SEQ ID NO:235), TCAAACCAAGTGAG (SEQ ID NO:236), ACCAAGTGAGAAGTA (SEQ ID NO:237), AGCTCAAACCAAGTGAG (SEQ ID NO:238), GCACCTACTGCTGAA (SEQ ID NO:239), ACCTACTGCTGAAAAG (SEQ ID NO:240), TGCTGAAAAGAGAGAGT (SEQ ID NO:241), CCTACTGCTGAAAAGAGA (SEQ ID NO:242), GCAGAAAAAAACTATTG (SEQ ID NO:243), CAGAAAAAAACTATTGATT (SEQ ID NO:244), AGAAAGAGGCAGAAAAAAACT (SEQ ID NO:245), or GAGGCAGAAAAAAACTA (SEQ ID NO:246). For example, a probe comprising the sequence ACTGCTGAAAAGAGAGAGT (SEQ ID NO:26), GCACCTACTGCTGAA (SEQ ID NO:239), ACCTACTGCTGAAAAG (SEQ ID NO:240), TGCTGAAAAGAGAGAGT (SEQ ID NO:241), or CCTACTGCTGAAAAGAGA (SEQ ID NO:242) can be used to detect a mutation encoding an S1465 frameshift mutated APC protein; a probe comprising the sequence GAAATAAAAGATTGG (SEQ ID NO:30), AAATAGCAGAAATAAAAG (SEQ ID NO:225), GAAATAAAAGATTGGAA (SEQ ID NO:226), AGAAATAAAAGATTG (SEQ ID NO:227), GAAATAAATGAATGG (SEQ ID NO:228), or CAGAAATAAAAGATT (SEQ ID NO:229) can be used to detect a mutation encoding an E1309 frameshift mutated APC protein; a probe comprising the sequence TTTTGGGTGTCTAAG (SEQ ID NO:34), TTTGGGTGTCTAAG (SEQ ID NO:230), GGGTGTCTAAGCACCACT (SEQ ID NO:231), CTAAGCACCACTTTT (SEQ ID NO:232), TTTTGGGTGTCTAA (SEQ ID NO:233), or GGTGTCTAAGCACCA (SEQ ID NO:234) can be used to detect a mutation encoding a Q1367* mutated APC protein; a probe comprising the sequence CAAACCAAGTGAGAA (SEQ ID NO:38), AAGTGAGAAGTACCTAA (SEQ ID NO:235), TCAAACCAAGTGAG (SEQ ID NO:236), ACCAAGTGAGAAGTA (SEQ ID NO:237), or AGCTCAAACCAAGTGAG (SEQ ID NO:238) can be used to detect a mutation encoding a R1450* mutated APC protein; and/or a probe comprising the sequence GCAGAAAAAAACTATTG (SEQ ID NO:243), AGAGGCAGAAAAAAACT (SEQ ID NO:42), CAGAAAAAAACTATTGATT (SEQ ID NO:244), AGAAAGAGGCAGAAAAAAACT (SEQ ID NO:245), and GAGGCAGAAAAAAACTA (SEQ ID NO:246) can be used to detect a mutation encoding a T1556 frameshift mutated APC protein. As described supra, in some embodiments, one or more probes of the present disclosure can comprise eight or more nucleotides (e.g., adenines or thymines) at its 5' end and/or comprise at least 24 total nucleotides. In certain embodiments, a probe comprising the sequence TTTTTTTTACTGCTGAAAAGAGAGAGT (SEQ ID NO:57), TTTTTTTTTTGCACCTACTGCTGAA (SEQ ID NO:134), TTTTTTTTTTACCTACTGCTGAAAAG (SEQ ID NO:135), TTTTTTTTTGCTGAAAAGAGAGAGT (SEQ ID NO:136), or TTTTTTTTTCCTACTGCTGAAAAGAGA (SEQ ID NO: 137) can be used to detect a mutation encoding an S1465 frameshift mutated APC protein; a probe comprising the sequence TTTTTTTTTTTTGAAATAAAAGATTGG (SEQ ID NO:58), TTTTTTTTTAAATAGCAGAAATAAAAG (SEQ ID NO:120), TTTTTTTTTTGAAATAAAAGATTGGAA (SEQ ID NO:121), TTTTTTTTTTTTAGAAATAAAAGATTG (SEQ ID NO:122), TTTTTTTTTTTTGAAATAAATGAATGG (SEQ ID NO: 123), or TTTTTTTTTTTTTCAGAAATAAAAGATT (SEQ ID NO: 124) can be used to detect a mutation encoding an E1309 frameshift mutated APC protein; a probe comprising the sequence TTTTTTTTTTTTGGGTGTCTAAG (SEQ ID NO:59), TTTTTTTTTATTTGGGTGTCTAAG (SEQ ID NO: 125), TTTTTTGGGTGTCTAAGCACCACT (SEQ ID NO: 126), TTTTTTTTTCTAAGCACCACTTTT (SEQ ID NO: 127), TTTTTTTTTTTTTTGGGTGTCTAA (SEQ ID NO: 128), or TTTTTTTTTGGTGTCTAAGCACCA (SEQ ID NO: 129) can be used to detect a mutation encoding a Q1367* mutated APC protein; a probe comprising the sequence TTTTTTTTTACAAACCAAGTGAGAA (SEQ ID NO:60), TTTTTTTTAAGTGAGAAGTACCTAA (SEQ ID NO: 130), TTTTTTTTTTTTCAAACCAAGTGAG (SEQ ID NO:131), TTTTTTTTTTACCAAGT-GAGAAGTA (SEQ ID NO:132), or TTTTTTTTAGCT-CAAACCAAGTGAG (SEQ ID NO:133) can be used to detect a mutation encoding a R1450* mutated APC protein; and/or a probe comprising the sequence TTTTTTTTT-TAGAGGCAGAAAAAAACT (SEQ ID NO:61), TTTTTTTTTGCAGAAAAAAACTATTG (SEQ ID NO:138), TTTTTTTTTTTCAGAAAAAAACTATTGATT (SEQ ID NO:139), TTTTTT-TAGAAAGAGGCAGAAAAAAACT (SEQ ID NO:140), or TTTTTTTTTTTGAGGCAGAAAAAAACTA (SEQ ID NO:141) can be used to detect a mutation encoding a T1556 frameshift mutated APC protein (probes comprising these sequences exclusive of the 5' adenine and/or thymines are also contemplated).

Detection

In some embodiments, the methods of the present disclosure include detecting presence or absence of hybridization of amplified DNA with a probe of the present disclosure. Hybridization between the amplified DNA and one of the probes indicates the presence of the DNA mutation corresponding to the probe in the amplified DNA. Exemplary hybridization conditions and detection techniques are described and exemplified herein. In some embodiments, hybridization is performed using 5×SSPE buffer.

In some embodiments, the amplified DNA is labeled with a detection reagent, and hybridization is measured by signal of the detection reagent associated with the microcarrier, e.g., after a washing step to reduce or eliminate non-specific binding. In some embodiments, a primer pair of the present disclosure comprises one or both primers coupled to the detection reagent. Thus, the amplified DNA is labeled with the detection reagent after PCR amplification using the labeled primer(s). In some embodiments, the detection reagent can be fluorescence-based including, but not limited to, phycoerythrin (PE), blue fluorescent protein, green fluorescent protein, yellow fluorescent protein, cyan fluorescent protein, and derivatives thereof. In other embodiments, the detection reagent can be radioisotope based, including, but not limited to, molecules labeled with $^{32}P$, $^{33}P$, $^{22}Na$, $^{36}Cl$, $^{2}H$, $^{3}H$, $^{35}S$, and $^{123}I$. In other embodiments, the detection reagent is light-based including, but not limited to, luciferase (e.g. chemiluminescence-based), horseradish peroxidase, alkaline phosphatase and derivatives thereof. In some embodiments, the amplified DNA can be labeled with the detection reagent prior to contact with the microcarrier composition. In some embodiments, the detection reagent emits a signal when in close proximity to the probe, e.g., as with Förster resonance energy transfer (FRET). A variety of nucleic acid labeling techniques are known in the art; see, e.g., Gibriel, A. A. Y. (2012) *Briefings in Functional Genomics* 11:311-8.

In some embodiments, the detection reagent can be a fluorescent detection reagent. In some embodiments, detecting the presence or absence of hybridization of amplified DNA with a probe is performed by fluorescence microscopy (e.g., a fluorescent microscope or plate reader). In some embodiments, the detection reagent can be colorimetric based. In some embodiments, the detection reagent can be luminescence based. In some embodiments, detecting the presence or absence of hybridization of amplified DNA with a probe is performed by luminescence microscopy (e.g., a luminescent microscope or plate reader).

In some embodiments, the detection reagent comprises a tag or other moiety that can be detected by the addition of a secondary reagent conjugated to a signal-emitting entity (e.g., as described above). For example, in some embodiments, the detection reagent comprises biotin (e.g., a primer such as the reverse or antisense primer may be labeled at the 5' end with biotin). Thus, in some embodiments, the detecting presence or absence of hybridization can include, after hybridization and optional washing, contacting microcarrier(s) with a secondary reagent conjugated to a signal-emitting entity and detecting a signal from the signal-emitting entity in association with the microcarrier(s) (e.g., after optional washing). For example, if the detection reagent comprises biotin, the microcarriers can be contacted with streptavidin conjugated to a signal-emitting entity such as phycoerythrin (PE), and signal from the signal-emitting entity can be detected.

Depending upon the particular detection reagent, a variety of techniques may be used to detect hybridization of the amplified DNA to a probe. For example, if the detection reagent comprises a fluorescent detection reagent, detecting the presence or absence of hybridization of the amplified DNA can comprise fluorescence imaging of the fluorescent detection reagent.

In some embodiments, detecting may include one or more washing steps, e.g., to reduce contaminants, remove any substances non-specifically bound to the probe, DNA, and/or microcarrier surface, and so forth. In some embodiments, a magnetic separation step may be used to wash a microcarrier containing a magnetic layer or material of the present disclosure. In other embodiments, other separation steps known in the art may be used.

In some embodiments, the methods of the present disclosure comprise detecting the presence or absence of hybridization of amplified DNA with a total of between about 1 and about 1000 microcarriers per probe per assay. In some embodiments, the methods of the present disclosure comprise detecting the presence or absence of hybridization of amplified DNA with a total of between about 1 and about 1000 microcarriers per probe per well of an assay plate. In some embodiments, the methods of the present disclosure comprise detecting the presence or absence of hybridization of amplified DNA with at least about 50 microcarriers per probe per assay. In some embodiments, the methods of the present disclosure comprise detecting the presence or absence of hybridization of amplified DNA with at least about 50 microcarriers per probe per well of an assay plate. In some embodiments, a microcarrier of the present disclosure comprises the probe coupled thereto at a concentration of 1 µM.

In some embodiments, the methods of the present disclosure comprise detecting the identifier of an encoded microcarrier. For example, in some embodiments, an image of the identifier of an encoded microcarrier can be obtained and decoded to identify the microcarrier and its corresponding probe. In some embodiments, the identifier detection step(s) may occur after the hybridization detection step(s). In other embodiments, the identifier detection step(s) may occur before the hybridization detection step(s). In still other embodiments, the identifier detection step(s) may occur simultaneously with the hybridization detection step(s). In some embodiments, after the hybridization detection step(s) and the identifier detection step(s), the methods of the present disclosure further comprise correlating the detected identifiers of the microcarriers with the detected presence or absence of hybridization of the amplified DNA to the corresponding probes of the microcarriers.

A variety of microcarrier coding schemes are described in section IV. In some embodiments, detecting the identifier of an encoded microcarrier comprises imaging a digital barcode of the microcarrier. In one embodiment, the coded microcarrier comprises a body having a series of alternating light transmissive and opaque sections, with relative widths bar code image (e.g., a series of narrow slits representing a "0" code and wide slits representing a "1" code, or vice versa). When the microcarrier is illuminated with a light beam, based on the either the "total intensity" of the transmission peak or the "bandwidth" of the transmission peak from the slit, the digital barcode either 0 or 1 can be determined by a line scan camera, a frame grabber, and a digital signal processor. In one embodiment, the bar code pattern with a series of narrow and wide bands provides an unambiguous signal and differentiation for 0's and 1's. The position of the slits on the pallet will determine which of the bits is the least significant (LSB) and most significant bit (MSB). The LSB will be placed closer to the edge of the pallet to distinguish it from the MSB at the other, longer end.

In some embodiments, detecting the identifier of an encoded microcarrier comprises imaging the identifier of the microcarrier, e.g., by bright field imaging of the identifier.

A variety of decoding techniques are contemplated. In some embodiments, an identifier is detected using analog shape recognition to identify the identifier (e.g., an analog-encoded identifier). Conceptually, this decoding may involve, for example, imaging the analog code of each microcarrier (e.g., in a solution or sample), comparing each image against a library of analog codes, and matching each image to an image from the library, thus positively identifying the code. Optionally, as described herein, when using microcarriers that include an orientation indicator (e.g., an asymmetry), the decoding may further include a step of rotating each image to align with a particular orientation (based in part, e.g., on the orientation indicator). For example, if the orientation indicator includes a gap, the image could be rotated until the gap reaches a predetermined position or orientation (e.g., a 0° position of the image).

Various shape recognition software, tools, and methods are known in the art. Examples of such APIs and tools include without limitation Microsoft® Research FaceSDK, OpenBR, Face and Scene Recognition from ReKognition, Betaface API, and various ImageJ plugins. In some embodiments, the analog shape recognition may include without limitation image processing steps such as foreground extraction, shape detection, thresholding (e.g., automated or manual image thresholding), and the like.

It will be appreciated by one of skill in the art that the methods and microcarriers described herein may be adapted for various imaging devices, including without limitation a microscope, plate reader, and the like. In some embodiments, decoding an identifier (e.g., an analog code) can include illuminating the microcarrier by passing light through a substantially transparent portion (e.g., substantially transparent polymer layer(s)) of the microcarrier and/or the surrounding solution). The light may then fail to pass through, or pass through with a lower intensity or other appreciable difference, the substantially non-transparent portions (e.g., substantially non-transparent polymer layer(s)) of the microcarrier to generate an analog-coded light pattern corresponding to the identifier. That is to say, the pattern of imaged light may correspond to the pattern of substantially transparent/substantially non-transparent areas of the microcarrier, thus producing an image of the analog code identifier. This imaging may include steps including without limitation capturing the image, thresholding the image, and any other image processing step desired to achieve more accurate, precise, or robust imaging of the identifier.

Any type of light microscopy may be used for the methods of the present disclosure, including without limitation one or more of: bright field, dark field, phase contrast, differential interference contrast (DIC), Nomarski interference contrast (NIC), Nomarski, Hoffman modulation contrast (HMC), or fluorescence microscopy. In certain embodiments, the identifiers may be decoded using bright field microscopy, and hybridization may be detected using fluorescence microscopy.

In some embodiments, decoding the identifiers may further include using analog shape recognition to match an analog-coded image with an analog code. In some embodiments, an image may be matched with an analog code (e.g., an image file from a library of image files, with each image file corresponding to a unique two-dimensional shape/analog code) within a predetermined threshold, e.g., that tolerates a predetermined amount of deviation or mismatch between the image and the exemplar analog code image. Such a threshold may be empirically determined and may naturally be based on the particular type of two-dimensional shapes used for the analog codes and the extent of variation among the set of potential two-dimensional shapes.

In some embodiments, the methods of the present disclosure further comprise the use of microcarriers with an identifier corresponding to a positive or negative control. In some embodiments, the methods of the present disclosure comprise amplifying a positive control DNA sequence using a primer pair specific for the positive control DNA sequence. The positive control DNA sequence can be any sequence that is likely to be present in all samples of a given type, e.g., a non-mutated or endogenous gene sequence from the organism from whence the sample is obtained. The positive control indicates that DNA (e.g., human DNA) is present in the sample at levels sufficient for detection. Like the mutated DNA sequences of interest, the positive control sequence is detected by amplifying a positive control DNA sequence using a primer pair specific for the positive control DNA sequence; hybridizing the amplified positive control gene sequence with a probe specific for the positive control gene sequence (the probe specific for the positive control gene sequence is coupled to a microcarrier with an identifier corresponding to a positive control); detecting presence or absence of hybridization of the amplified positive control DNA sequence with the probe specific for the positive control gene sequence; and detecting an analog code of the microcarrier with the identifier corresponding to the positive control.

In some embodiments, as exemplified infra, the positive control DNA sequence comprises a sequence of a human leukocyte antigen (HLA) gene. The sequences of a more than 150 HLA genes are known, including without limitation HLA-DRA (see NCBI Entrez Gene ID No. 3122), HLA-DRB1 (see NCBI Entrez Gene ID No. 3123), HLA-A (see NCBI Entrez Gene ID No. 3105), HLA-B (see NCBI Entrez Gene ID No. 3106), HLA-C(see NCBI Entrez Gene ID No. 3107), HLA-DQB1 (see NCBI Entrez Gene ID No. 3119), HLA-DPB1 (see NCBI Entrez Gene ID No. 3115), HLA-E (see NCBI Entrez Gene ID No. 3133), HLA-DQA2 (see NCBI Entrez Gene ID No. 3118), HLA-DPA1 (see NCBI Entrez Gene ID No. 3113), HLA-G (see NCBI Entrez Gene ID No. 3135), HLA-DRB5 (see NCBI Entrez Gene ID No. 3127), HLA-F (see NCBI Entrez Gene ID No. 3134), and HLA-DOA (see NCBI Entrez Gene ID No. 3111). For descriptions of other HLA genes, see Shiina, T. et al. (2009) *J. Hum. Genet.* 54:15-39.

In some embodiments, a primer pair specific for the positive control DNA sequence comprises the sequences TGAGTGTTACTTCTTCCCACACTC (SEQ ID NO:43) and ATTGCTTTTGCGCAATCCCT (SEQ ID NO:44). In some embodiments, the probe specific for the positive control gene sequence comprises the sequence TTTTTTTTTTTTGGAGACGGTCTG (SEQ ID NO:45). In some embodiments, a primer pair specific for the positive control DNA sequence comprises the sequences AATCC-CATCACCATCTTCCA (SEQ ID NO:71) and TGGACTC-CACGACGTACTCA (SEQ ID NO:72). In some embodiments, the probe specific for the positive control gene sequence comprises the sequence CTGTCTTCCACT-CACTCC (SEQ ID NO:73).

In some embodiments, the methods of the present disclosure comprise detecting absence of hybridization of amplified DNA with a microcarrier having an identifier corresponding to a negative control. For example, the microcarrier with the identifier corresponding to the negative control can comprise a probe that does not hybridize with amplified DNA. The use of a microcarrier with the identifier corresponding to the negative control improves the reliability of detecting presence or absence of hybridization. In some embodiments, the microcarrier comprises a probe comprising the sequence AATATAATATATTAT (SEQ ID NO:46).

Exemplary and non-limiting descriptions of microcarriers, and optional aspects thereof, suitable for use in the methods of the present disclosure are provided infra.

IV. Encoded Microcarriers

Provided herein are encoded microcarriers suitable for analyte detection, e.g., multiplex analyte detection. Multiple configurations for encoded microcarriers are contemplated, described, and exemplified herein. As used herein, an "encoded" microcarrier may refer to a microcarrier with an identifier that corresponds to the identity of a probe coupled thereto. This enables the data of an assay using the microcarrier to be associated with the identity of the probe, allowing for the use of multiple microcarriers in a single multiplex assay, since the results of any individual microcarrier can be correlated with the identity of its probe. Exemplary types of identifiers, including digital barcodes and analog codes, are described infra.

In some aspects, the methods and kits of the present disclosure use digital barcode identifiers. For example, in some embodiments, encoded microcarriers comprise: a first photopolymer layer; a second photopolymer layer; and an intermediate layer between the first layer and the second layer. In some embodiments, the intermediate layer has an encoded pattern representing the identifier defined thereon, wherein the intermediate layer is partially substantially transmissive and partially substantially opaque to light, representing a code corresponding to the microcarrier, wherein the outermost surface of the microcarrier comprises a photoresist photopolymer, and said photoresist photopolymer is functionalized with the probe specific for the DNA mutation, and wherein said microcarrier has about the same density as water. Exemplary microcarrier descriptions may be found, e.g., in U.S. Pat. Nos. 7,858,307; 7,871,770; 8,148,139; 8,232,092; and 9,255,922; as well as US PG Pub. Nos. US2009/201504, 2011/0007955, and 2012/0088691.

In one embodiment, a digitally encoded microcarrier of the present disclosure comprises a body having a series of alternating light transmissive and opaque sections, with relative positions, widths and/or spacing resembling a 1D or 2D bar code image (e.g., a series of narrow slits (e.g., about 1 to 5 microns in width) representing a "0" code and wide slits (e.g., about 1 to 10 microns in width) representing a "1" code, or vice versa, to form a binary code). In one embodiment, the size of the microcarrier is sized and configured to be 150×50×10 m, or proportionally smaller, and a slit width of about 2.5 m. Each digital barcode on such a microcarrier can consist of up to 14 slits (or bits), allowing 16,384 unique codes. In one embodiment, the body of the coded microcarrier may be configured to have at least two orthogonal cross sections that are different in relative geometry and/or size. Further, the geometry of the cross sections may be symmetrical or non-symmetrical, and/or regular or irregular shape. In one embodiment, the longest orthogonal axis of the coded microcarrier is less than 1 mm. In one embodiment, the coded microcarrier is provided with a reflective thin film, (e.g., plating or coating the coded microcarrier with a metal thin film, or providing an intermediate layer of metal thin film) to improve contrast and optical efficiency for image recognition for decoding. One alternate embodiment may include a metal layer as a layer sandwiched between two polymeric layers, by appropriately modifying the above described process. With this embodiment, surface condition could be made the same for both exposed planar surfaces of the microcarrier, to provide similar surface coating and immobilization conditions. Another embodiment is to coat the microcarrier with polymer or functional molecules, such as a probe of the present disclosure; therefore, the whole microcarrier has the same condition for molecular immobilization.

In some aspects, the methods and kits of the present disclosure use analog code identifiers. For example, in some embodiments, the methods and kits of the present disclosure use encoded microcarriers that comprise: a substantially transparent polymer layer having a first surface and a second surface, the first and the second surfaces being parallel to each other; a substantially non-transparent polymer layer, wherein the substantially non-transparent polymer layer is affixed to the first surface of the substantially transparent polymer layer and encloses a center portion of the substantially transparent polymer layer, and wherein the substantially non-transparent polymer layer comprises a two-dimensional shape representing an analog code; and a probe of the present disclosure specific for a DNA mutation, wherein the probe is coupled to at least one of the first surface and the second surface of the substantially transparent polymer layer in at least the center portion of the substantially transparent polymer layer. The analog code represents the identifier. Thus, the microcarrier contains at least two layers: one of which is substantially transparent, and the other of which is a substantially non-transparent, two-dimensional shape that represents an analog code identifier.

Advantageously, these microcarriers may employ a variety of two-dimensional shapes while still retaining a uniform overall form (e.g., the perimeter of the substantially transparent polymer layer) for uniformity of aspects including, for example, overall dimensions, physical properties, and/or behavior in solution. This is advantageous, for example, in allowing greater uniformity between different species of microcarriers (i.e., each has the same perimeter shape provided by the transparent polymer layer). Examples of this type of microcarrier and aspects thereof are illustrated in FIGS. 1A-5B (see, e.g., FIG. 4B).

FIGS. 1A & 1B show two views of exemplary microcarrier 100. Microcarrier 100 is a circular disc of approximately 50 µm in diameter and 10 µm in thickness. FIG. 1A provides a view of microcarrier 100 looking at a circular face of the disc, while FIG. 1B shows a side view of microcarrier 100 orthogonal to the surface shown in FIG. 1A. Two components of microcarrier 100 are shown. First, substantially transparent polymer layer 102 provides the body of the microcarrier. Layer 102 may be produced, e.g., using a polymer such as SU-8, as described herein.

Substantially non-transparent polymer layer 104 is affixed to a surface of layer 102. While the cross-section of microcarrier 100 shown in FIG. 1B shows a discontinuous view of layer 104, the view shown in FIG. 1A illustrates that layer 104 is shaped like a circular gear with a plurality of teeth. The shape, number, size, and spacing of these gear teeth constitutes a two-dimensional shape, and one or more of these aspects of the gear teeth may be modified in order to produce multiple two-dimensional shapes for analog encoding. Advantageously, the outside edge of layer 104's gear teeth fit within the perimeter of layer 102. This allows for a variety of analog codes, each representing a unique identifier for one species of microcarrier, while maintaining a uniform overall shape across multiple species of microcarrier. Stated another way, each microcarrier species within a population of multiple species may have a different two-dimensional gear shape (i.e., analog code), but each microcarrier will have the same perimeter, leading to greater uniformity of physical properties (e.g., size, shape, behavior in solution, and the like). Layer 104 may be produced, e.g., using a polymer such as SU-8 mixed with a dye, or using a black matrix resist, as described herein.

Layer 104 surrounds center portion 106 of layer 102. A probe is coupled to at least center portion 106 on one or both surfaces (i.e., upper/lower surfaces) of layer 102. Advantageously, this allows center portion 106 to be imaged without any potential for interference resulting from layer 104.

Figure 1C:
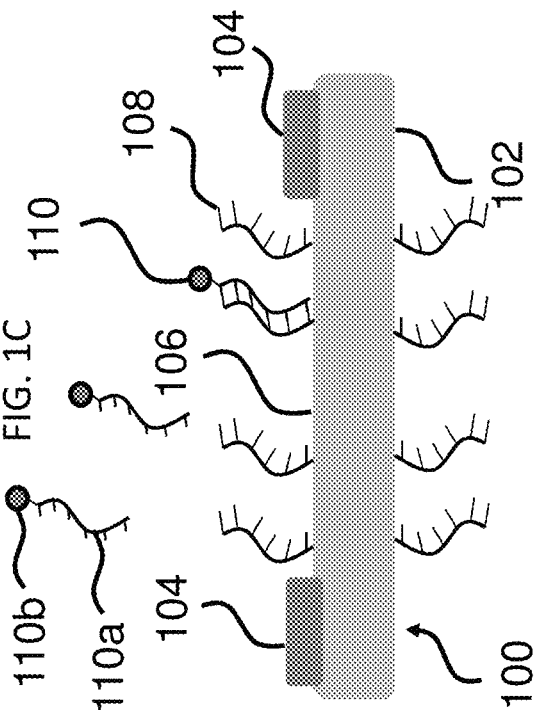

FIGS. 1C & 1D show an exemplary assay using microcarrier 100 for analyte detection. FIG. 1C shows that microcarrier 100 may include probe 108 coupled to one or more surfaces in at least center portion 106. Microcarrier 100 is contacted with a solution containing amplified DNA 110, which has been denatured prior to contacting microcarrier 100 and hybridizes to probe 108. As described above, amplified DNA 110 is coupled to a detection reagent. In this example, the detection reagent is biotin (e.g., resulting from amplification of DNA using a biotin-labeled primer). Thus, amplified DNA 110 includes DNA 110a (e.g., comprising the locus of a mutation described herein) and biotin 110b. FIG. 1C illustrates a single microcarrier species (i.e., microcarrier 100), which captures amplified DNA 110, but in a multiplex assay multiple microcarrier species are used, each species having a particular probe that recognizes a specific DNA mutation.

FIG. 1D illustrates an exemplary process for "reading" microcarrier 100. This process includes two steps that may be accomplished simultaneously or separately. First, the hybridization of amplified DNA 110 by probe 108 is detected. In the example shown in FIG. 1D, secondary detection reagent 114 (e.g., streptavidin conjugated to PE) binds to amplified DNA 110 via a biotin:streptavidin interaction. Amplified DNA not hybridized to a probe coupled to microcarrier 100 may have been washed off prior to detection, such that only DNA bound to microcarrier 100 is detected. The PE moiety of secondary detection reagent 114 emits light 118 (e.g., a photon) when excited by light 116 at a wavelength within the excitation spectrum of PE. Light 118 may be detected by any suitable detection means, such as a fluorescence microscope, plate reader, and the like.

In addition, microcarrier 100 is read for its unique identifier. In the example shown in FIG. 1D, light 112 is used to illuminate the field containing microcarrier 100 (in some embodiments, light 112 may have a different wavelength than lights 116 and 118). When light 112 illuminates the field containing microcarrier 100, it passes through substantially transparent polymer layer 102 but is blocked by substantially non-transparent polymer layer 104, as shown in FIG. 1D. This generates a light pattern that can be imaged, for example, by light microscopy (e.g., using differential interference contrast, or DIC, microscopy). This light pattern is based on the two-dimensional shape (i.e., analog code) of microcarrier 100. Standard image recognition techniques may be used to decode the analog code represented by the image of microcarrier 100.

As described in greater detail below, the analyte detection and identifier imaging steps may occur in any order, or simultaneously. Advantageously, both detection steps shown in FIG. 1D may be accomplished on one imaging device. As one example, a microscope capable of both fluorescence and light (e.g., bright field) microscopy may be used to quantify the amount of amplified DNA 110 bound to microcarrier 100 (e.g., as detected by detection reagent 114) and image the analog code created by layers 102 and 104. This allows for a more efficient assay process with fewer equipment requirements.

In some embodiments, the microcarrier further includes a magnetic, substantially non-transparent layer affixed to a surface of the substantially transparent polymer layer that encloses the center portion of the substantially transparent polymer layer. In some embodiments, the magnetic, substantially non-transparent layer is between the substantially non-transparent polymer layer and the center portion of the substantially transparent polymer layer.

In some embodiments, the microcarrier further includes a second substantially transparent polymer layer aligned with and affixed to the first substantially transparent polymer layer. In some embodiments, the first and second substantially transparent polymer layers each have a center portion, and the center portions of both the first and second substantially transparent polymer layers are aligned. In some embodiments, the microcarrier further includes a magnetic, substantially non-transparent layer that encloses the center portions of both the first and second substantially transparent polymer layers. In some embodiments, the magnetic, substantially non-transparent layer is affixed between the first and second substantially transparent polymer layers. In some embodiments, the magnetic, substantially non-transparent layer is between the substantially non-transparent polymer layer and the center portions of both the first and second substantially transparent polymer layers.

Figure 2B:
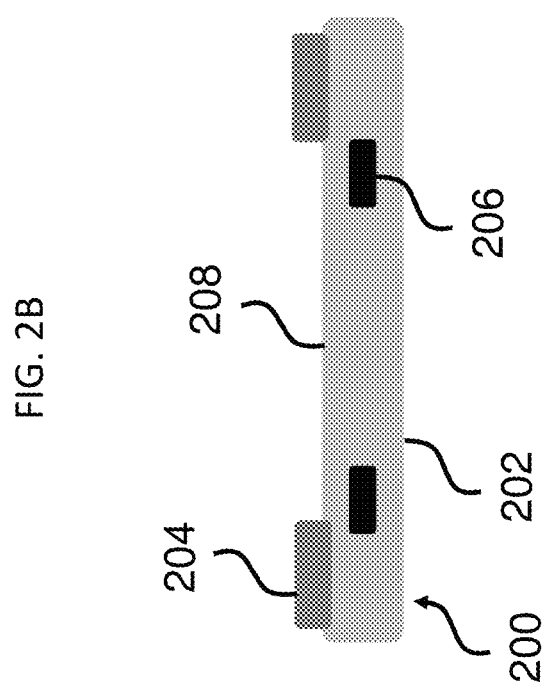
FIGS. 2A & 2B show two views of an exemplary microcarrier.
Figure 2A:
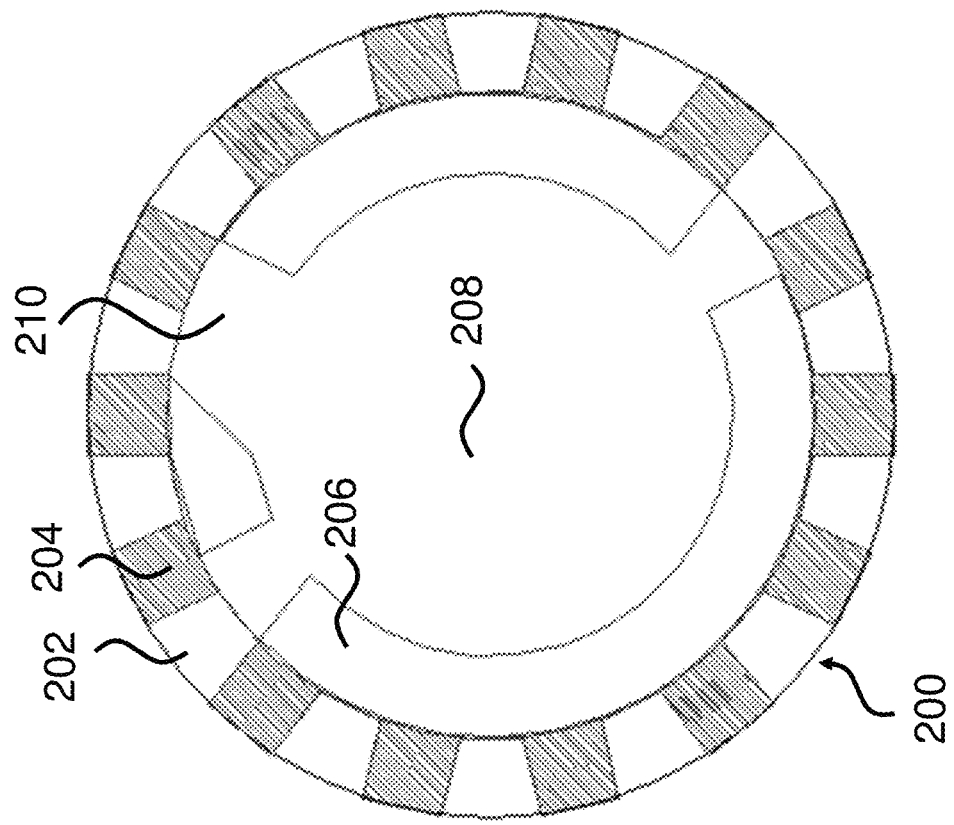

Turning now to FIGS. 2A & 2B, another exemplary microcarrier 200 is shown. Like microcarrier 100, microcarrier 200 includes substantially transparent polymer layer 202 and substantially non-transparent polymer layer 204. In addition, microcarrier 200 includes magnetic layer 206. As shown in FIG. 2A, magnetic layer 206 may be shaped as a ring between center portion 208 and substantially non-transparent layer 204.

FIG. 2B shows that magnetic layer 206 may be embedded within layer 202. Layer 202 may also include more than one layer, such that magnetic layer 206 is sandwiched between two substantially transparent polymer layers (e.g., as in FIG. 2B). Alternatively, magnetic layer 206 may be affixed to the same surface of layer 202 as layer 204, or magnetic layer 206 may be affixed to the surface of layer 202 opposite layer 204. In some embodiments, magnetic layer 206 may include nickel.

Magnetic layer 206 bestows magnetic properties onto microcarrier 200, which advantageously may be used for many applications. For example, microcarrier 200 may be affixed to a surface by magnetic attraction during a washing step, allowing for effective washing without losing or otherwise disrupting the microcarriers.

In addition to its magnetic properties, layer 206 is also substantially non-transparent. When imaged as shown in FIG. 1D (e.g., using light 112), layer 206 will block, either in part or in whole, transmitted light, thereby creating a pattern for imaging. As shown in FIG. 2A, layer 206 is also asymmetric—in this example, it includes gap 210. This asymmetry creates an orientation indicator that can be imaged, for example, as shown in FIG. 1D using light 112. Advantageously, an orientation indicator may be utilized during image recognition to orient the two-dimensional shape created by imaging layer 204 in a uniform orientation for easier analog code recognition. This allows microcarriers imaged in any orientation to be decoded.

In some embodiments, the magnetic, substantially non-transparent layer is between about 50 nm and about 10 μm in thickness. In some embodiments, the thickness of the magnetic, substantially non-transparent layer is less than about any of the following thicknesses (in nm): 10000, 9500, 9000, 8500, 8000, 7500, 7000, 6500, 6000, 5500, 5000, 4500, 4000, 3500, 3000, 2500, 2000, 1500, 1000, 950, 900, 850, 800, 750, 700, 650, 600, 550, 500, 450, 400, 350, 300, 250, 200, 150, or 100. In some embodiments, the thickness of the magnetic, substantially non-transparent layer is greater than about any of the following thicknesses (in nm): 50, 100, 150, 200, 250, 300, 350, 400, 450, 500, 550, 600, 650, 700, 750, 800, 850, 900, 950, 1000, 1500, 2000, 2500, 3000, 3500, 4000, 4500, 5000, 5500, 6000, 6500, 7000, 7500, 8000, 8500, 9000, or 9500. That is, the thickness of the magnetic, substantially non-transparent layer may be any of a range of thicknesses (in nm) having an upper limit of 10000, 9500, 9000, 8500, 8000, 7500, 7000, 6500, 6000, 5500, 5000, 4500, 4000, 3500, 3000, 2500, 2000, 1500, 1000, 950, 900, 850, 800, 750, 700, 650, 600, 550, 500, 450, 400, 350, 300, 250, 200, 150, or 100 and an independently selected lower limit of 50, 100, 150, 200, 250, 300, 350, 400, 450, 500, 550, 600, 650, 700, 750, 800, 850, 900, 950, 1000, 1500, 2000, 2500, 3000, 3500, 4000, 4500, 5000, 5500, 6000, 6500, 7000, 7500, 8000, 8500, 9000, or 9500, wherein the lower limit is less than the upper limit.

In some embodiments, the magnetic, substantially non-transparent layer is about 0.1 μm in thickness. In some embodiments, the magnetic, substantially non-transparent layer is about 50 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, about 1 μm, about 1.5 μm, about 2 μm, about 2.5 μm, about 3 μm, about 3.5 μm, about 4 μm, about 4.5 μm, about 5 μm, about 5.5 μm, about 6 μm, about 6.5 μm, about 7 μm, about 7.5 μm, about 8 μm, about 8.5 μm, about 9 μm, about 9.5 μm, or about 10 μm in thickness. In some embodiments, the thickness of the magnetic, substantially non-transparent layer is about 0.01 am, about 0.02 μm, about 0.03 μm, about 0.04 μm, about 0.05 μm, about 0.06 μm, about 0.07 am, about 0.08 μm, about 0.09 μm, about 0.1 μm, about 0.11 μm, about 0.12 μm, about 0.13 am, about 0.14 μm, about 0.15 μm, about 0.16 μm, about 0.17 μm, about 0.18 μm, about 0.19 am, about 0.20 μm, about 0.25 μm, about 0.30 μm, about 0.35 μm, about 0.40 μm, about 0.45 am, or about 0.50 μm.

In some embodiments, the microcarrier further includes an orientation indicator for orienting the analog code of the substantially non-transparent polymer layer. Any feature of the microcarrier that is visible and/or detectable by imaging (e.g., a form of microscopic or other imaging described herein) and/or by image recognition software may serve as an orientation indicator. An orientation indicator may serve as a point of reference, e.g., for an image recognition algorithm, to orient the image of an analog code in a uniform orientation (i.e., the shape of the substantially non-transparent polymer layer). Advantageously, this simplifies image recognition, as the algorithm would only need to compare the image of a particular analog code against a library of analog codes in the same orientation, and not against a library including all analog codes in all possible orientations. In some embodiments, the orientation indicator may be independent of the substantially non-transparent polymer layer. For example, it may be formed as a part of a magnetic layer and/or substantially transparent polymer layer. In other embodiments, the orientation indicator may be formed as part of the substantially non-transparent polymer layer. In some embodiments, the orientation indicator comprises an asymmetry of the magnetic, substantially non-transparent layer (e.g., as illustrated by gap 210 in FIG. 2A).

In some embodiments, the microcarrier further includes one or more columns projecting from a surface of the microcarrier (e.g., the top and/or bottom surface of the microcarrier). As used herein, a "column" may refer to any geometric shape that projects from the microcarrier surface and does not necessarily denote any regularity in dimensions, nor any cylindrical character. For example, the outer surface of a column may or may not be parallel with the microcarrier surface. Examples of columnar shapes that may project from a microcarrier include without limitation a rectangular prism, a triangle, a pyramid, a cube, a cylinder, a sphere or half-sphere, a cone, and so forth. In some embodiments, the one or more columns are not within a center portion of the first and/or the second substantially transparent polymer layer. In some embodiments, the one or more columns may project from an outside-facing surface (e.g., a surface not affixed to another layer) of one or more of the first and the second substantially transparent polymer layers. In some embodiments, the one or more columns are made from the magnetic, substantially non-transparent polymer layer. It is to be noted that any descriptions of microcarrier thickness herein do not include the one or more columns in the stated dimensions. That is to say, microcarrier thickness as described herein is independent of any optional columns projecting therefrom.

Turning now to FIGS. 5A & 5B, another exemplary microcarrier 500 is shown. Like microcarrier 200, microcarrier 500 includes substantially transparent polymer layer 502, substantially non-transparent polymer layer 504, magnetic layer 506, and center portion 508. In addition, microcarrier 500 has four columns including column 510, which may be of any shape that extends from the surface of layer 502. As shown in FIG. 5A, these columns may be arrayed in alignment with magnetic layer 506, preventing any potential for interfering with analyte detection in center portion 508 or with reading the two-dimensional shape (i.e., the analog code) of layer 504. FIG. 5B shows that these columns may extend from the upper and lower surfaces of microcarrier 500. Column 510 may be made, for example, using the same substantially transparent polymer as layer 502 (exemplary methods of production are described infra). Advantageously, one or more columns such as column 510 may be used to prevent microcarriers from sticking to each other and/or a container (e.g., the side of a well in a multiwell plate), e.g., through optical contact bonding.

In some embodiments, the one or more columns are between about 1 μm and about am tall. In some embodiments, the one or more columns are about 1 μm tall, about 1.5 μm tall, about 2 μm tall, about 2.5 μm tall, about 3 μm tall, about 3.5 μm tall, about 4 μm tall, about 4.5 μm tall, about 5 μm tall, about 5.5 μm tall, about 6 μm tall, about 6.5 μm tall, about 7 μm tall, about 7.5 μm tall, about 8 μm tall, about 8.5 μm tall, about 9 μm tall, about 9.5 μm tall, or about 10 μm tall. In some embodiments, the one or more columns are less than about any of the following heights (in m): 10, 9.5, 9, 8.5, 8, 7.5, 7, 6.5, 6, 5.5, 5, 4.5, 4, 3.5, 3, 2.5, 2, or 1.5. In some embodiments, the one or more columns are greater than about any of the following heights (in m): 1, 1.5, 2, 2.5, 3, 3.5, 4, 4.5, 5, 5.5, 6, 6.5, 7, 7.5, 8, 8.5, 9, or 9.5. That is, the one or more columns can be any of a range of heights having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit.

In some embodiments, the one or more columns may be cylindrical in shape. In some embodiments, the one or more columns have a diameter between about 1 μm and about 10 μm. In some embodiments, the one or more columns have a diameter of about 1 μm, about 1.5 μm, about 2 μm, about 2.5 μm, about 3 μm, about 3.5 μm, about 4 μm, about 4.5 μm, about 5 μm, about 5.5 μm, about 6 μm, about 6.5 μm, about 7 μm, about 7.5 μm, about 8 μm, about 8.5 μm, about 9 μm, about 9.5 μm, or about 10 μm. In some embodiments, the one or more columns have a diameter less than about any of the following lengths (in μm): 10, 9.5, 9, 8.5, 8, 7.5, 7, 6.5, 6, 5.5, 5, 4.5, 4, 3.5, 3, 2.5, 2, or 1.5. In some embodiments, the one or more columns have a diameter greater than about any of the following lengths (in μm): 1, 1.5, 2, 2.5, 3, 3.5, 4, 4.5, 5, 5.5, 6, 6.5, 7, 7.5, 8, 8.5, 9, or 9.5. That is, the one or more columns can have any of a range of diameters having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit. In other embodiments, the one or more columns may have roughly the same width as any diameter described supra, or a range of widths roughly the same as any range of diameters described supra, but the one or more columns may adopt the shape of an elliptical cylinder, parabolic cylinder, hyperbolic cylinder, or any other cylindrical or polyhedral shape described herein or known in the art.

In other aspects, provided herein are encoded microcarriers that comprise: a substantially non-transparent polymer layer having a first surface and a second surface, the first and the second surfaces being parallel to each other, wherein an outline of the substantially non-transparent polymer layer comprises a two-dimensional shape that represents an analog code; and a capture agent for capturing an analyte, wherein the capture agent is coupled to at least one of the first surface and the second surface of the substantially non-transparent polymer layer in at least a center portion of the substantially non-transparent polymer layer. Thus, the microcarrier is encoded by the shape (e.g., outline) of the microcarrier itself: a two-dimensional shape that represents an analog code. Advantageously, these microcarriers may be manufactured efficiently and with high precision, allowing for highly accurate decoding and cost-efficient production. Examples of this type of microcarrier and aspects thereof are illustrated in FIGS. 6A-9C.

FIGS. 6A & 6B show exemplary microcarrier 600 of this type. Microcarrier 600 is a gear-shaped disc approximately 80 μm in diameter and 15 μm in height, including optional column elements (similar to column 510 as described above). Microcarrier 600 is made of a single, non-transparent polymer layer 602, rather than separate transparent and non-transparent polymer layers. Microcarrier 600 may be imaged as shown in FIG. 1D, but its analog code is imaged based on the entire microcarrier shape (e.g., perimeter of the non-transparent polymer layer). One or both surfaces of microcarrier 600 may be used for coupling a capture agent as above, and a center portion or the entire surface may be used.

Figure 6C:
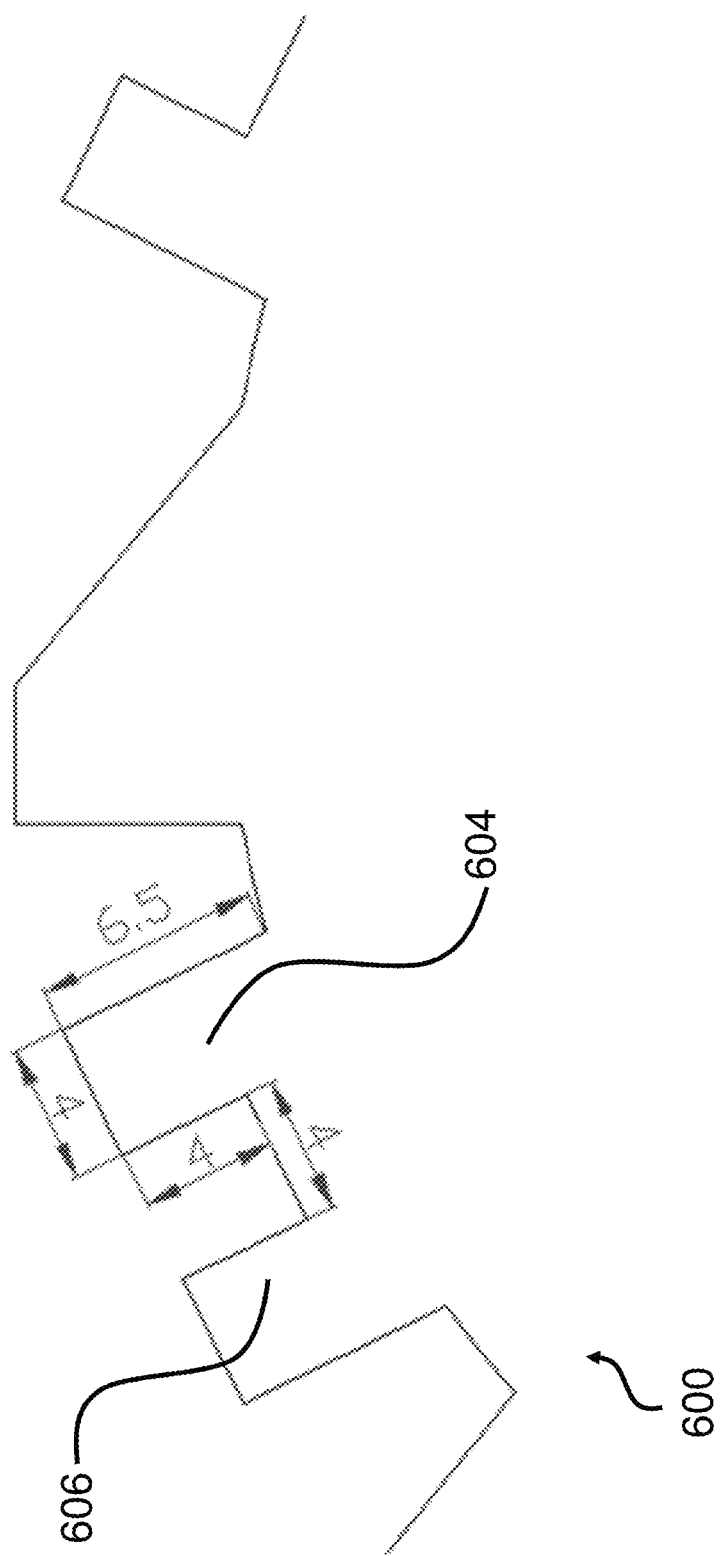
FIG. 6C shows the dimensions of an exemplary analog code. Dimensions are based on am units.

FIG. 6C illustrates the dimensions of gear tooth 604 of microcarrier 600. As shown, in this embodiment, gear tooth 604 is 4 μm wide and spaced 4 μm from adjacent gear tooth 606. Since the two-dimensional shape of microcarrier 600 is analog encoded, the perimeter between adjacent gear teeth may be variable, allowing for multiple gear tooth shapes. For example, gear tooth 604 extends 4 or 6.5 μm in height, relative to the adjacent perimeter segment immediately to the left or right, respectively.

Figure 7:
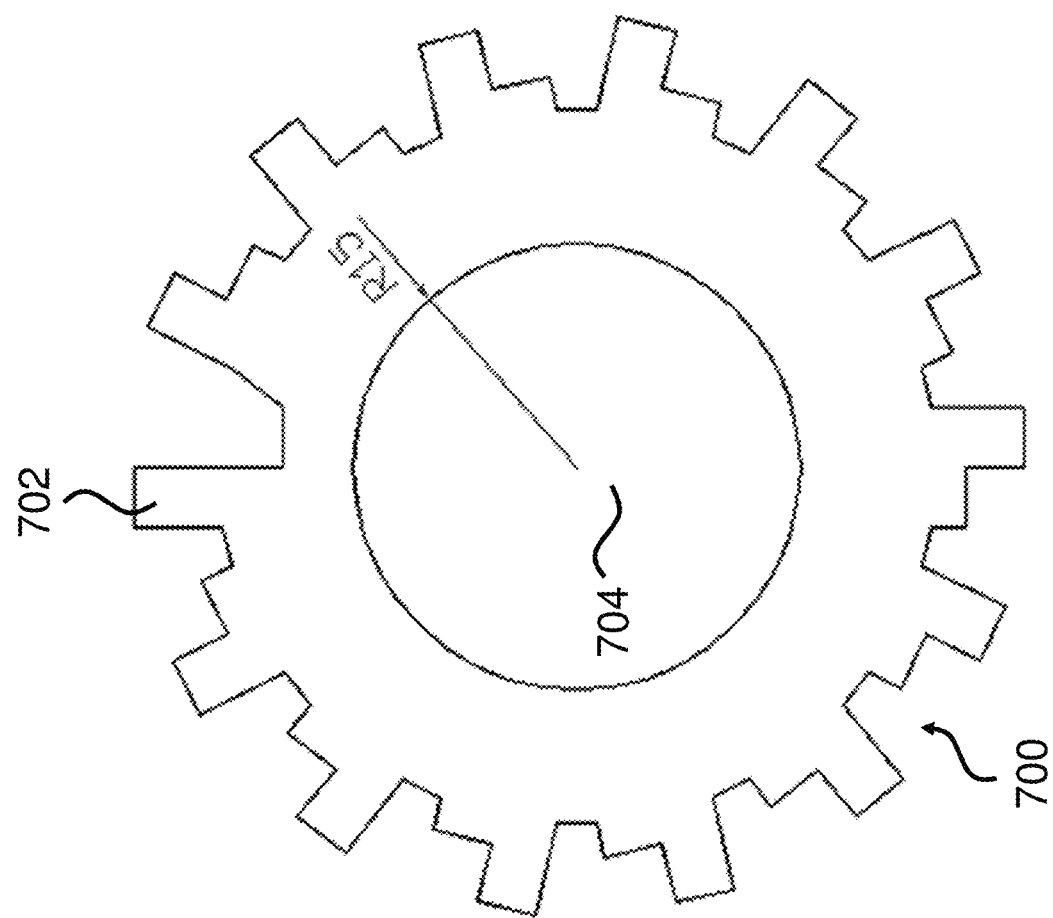
FIG. 7 shows an exemplary microcarrier.

FIG. 7 illustrates another embodiment of this type of microcarrier, microcarrier 700. Like microcarrier 600, microcarrier 700 is made from non-transparent polymer layer 702. In addition, microcarrier includes magnetic layer 704. Magnetic layer 704 may be affixed to one of the surfaces of microcarrier 700, or it may be embedded within microcarrier 700 (e.g., between two non-transparent polymer layers). Magnetic layer 704 may be generated, for example, by depositing nickel. As described above, a magnetic layer allows additional functionalities, such as the option for washing microcarrier 700 while magnetically attached to another surface.

In some embodiments, the microcarrier further includes one or more columns projecting from a surface of the substantially non-transparent polymer layer. As described in greater detail supra, a "column" may refer to any geometric shape that projects from the microcarrier surface and does not necessarily denote any regularity in columnar dimension(s). Any of the exemplary columnar shapes described above may be used.

In some embodiments, the one or more columns are between about 1 μm and about am tall. In some embodiments, the one or more columns are about 1 μm tall, about 1.5 μm tall, about 2 μm tall, about 2.5 μm tall, about 3 μm tall, about 3.5 μm tall, about 4 μm tall, about 4.5 μm tall, about 5 μm tall, about 5.5 μm tall, about 6 μm tall, about 6.5 μm tall, about 7 μm tall, about 7.5 μm tall, about 8 μm tall, about 8.5 μm tall, about 9 μm tall, about 9.5 μm tall, or about 10 μm tall. In some embodiments, the one or more columns are less than about any of the following heights (in m): 10, 9.5, 9, 8.5, 8, 7.5, 7, 6.5, 6, 5.5, 5, 4.5, 4, 3.5, 3, 2.5, 2, or 1.5. In some embodiments, the one or more columns are greater than about any of the following heights (in m): 1, 1.5, 2, 2.5, 3, 3.5, 4, 4.5, 5, 5.5, 6, 6.5, 7, 7.5, 8, 8.5, 9, or 9.5. That is, the one or more columns can be any of a range of heights having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit.

In some embodiments, the one or more columns may be cylindrical in shape. In some embodiments, the one or more columns have a diameter between about 1 µm and about 10 µm. In some embodiments, the one or more columns have a diameter of about 1 µm, about 1.5 µm, about 2 µm, about 2.5 µm, about 3 µm, about 3.5 µm, about 4 µm, about 4.5 µm, about 5 µm, about 5.5 µm, about 6 µm, about 6.5 µm, about 7 µm, about 7.5 µm, about 8 µm, about 8.5 µm, about 9 µm, about 9.5 µm, or about 10 µm. In some embodiments, the one or more columns have a diameter less than about any of the following lengths (in µm): 10, 9.5, 9, 8.5, 8, 7.5, 7, 6.5, 6, 5.5, 5, 4.5, 4, 3.5, 3, 2.5, 2, or 1.5. In some embodiments, the one or more columns have a diameter greater than about any of the following lengths (in µm): 1, 1.5, 2, 2.5, 3, 3.5, 4, 4.5, 5, 5.5, 6, 6.5, 7, 7.5, 8, 8.5, 9, or 9.5. That is, the one or more columns can have any of a range of diameters having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit. In other embodiments, the one or more columns may have roughly the same width as any diameter described supra, or a range of widths roughly the same as any range of diameters described supra, but the one or more columns may adopt the shape of an elliptical cylinder, parabolic cylinder, hyperbolic cylinder, or any other cylindrical or polyhedral shape described herein or known in the art.

In some embodiments, the microcarrier further includes a magnetic layer comprising a magnetic material affixed to a surface of the substantially non-transparent polymer layer. In some embodiments, the magnetic layer does not extend beyond the two-dimensional shape of the substantially non-transparent polymer layer. That is to say, if the outline of the substantially non-transparent polymer layer were to be imaged, the resulting image would not be altered by the presence or absence of the magnetic layer. In some embodiments, the magnetic layer may include the one or more columns described above. That is, the one or more columns described above may be made of a magnetic material described herein.

In some embodiments, the microcarrier further includes an orientation indicator for orienting the analog code of the substantially non-transparent polymer layer. Any feature of the microcarrier that is visible and/or detectable by imaging (e.g., a form of microscopic or other imaging described herein) and/or by image recognition software may serve as an orientation indicator. An orientation indicator may serve as a point of reference, e.g., for an image recognition algorithm, to orient the image of an analog code in a uniform orientation (i.e., the shape of the substantially non-transparent polymer layer). Advantageously, this simplifies image recognition, as the algorithm would only need to compare the image of a particular analog code against a library of analog codes in the same orientation, and not against a library including all analog codes in all possible orientations. In some embodiments, the orientation indicator comprises an asymmetry of the outline of the substantially non-transparent polymer layer. For example, the orientation indicator may comprise a visible feature, such as an asymmetry, of the outline of the microcarrier (e.g., as illustrated by start positions 804 and 904 in FIGS. 8A and 9A as described infra).

Figure 8A:
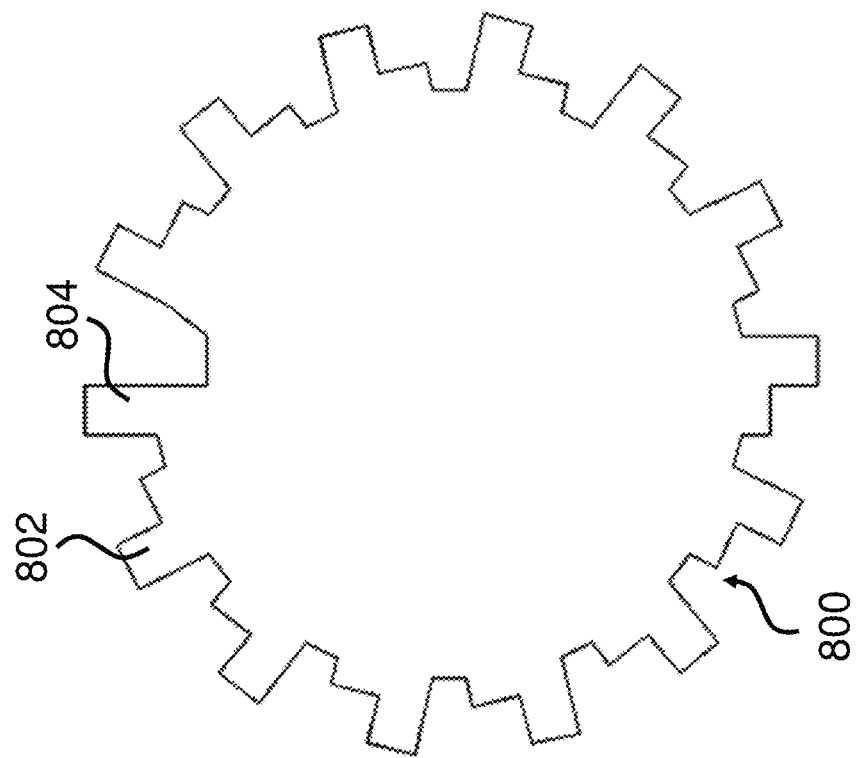
FIG. 8A shows an exemplary microcarrier that includes an asymmetric start position as an orientation indicator.

Turning now to FIG. 8A, another exemplary microcarrier 800 is shown. Like microcarrier 700, microcarrier 800 includes non-transparent polymer layer 802 (and optionally, a magnetic layer such as layer 704). In addition, microcarrier 800 includes start position 804, which has a different shape than the rest of the perimeter of microcarrier 800. Start position 804 may be used as an orientation indicator for image recognition, as described above in reference to gap 210 shown in FIG. 2A.

Figure 8B:
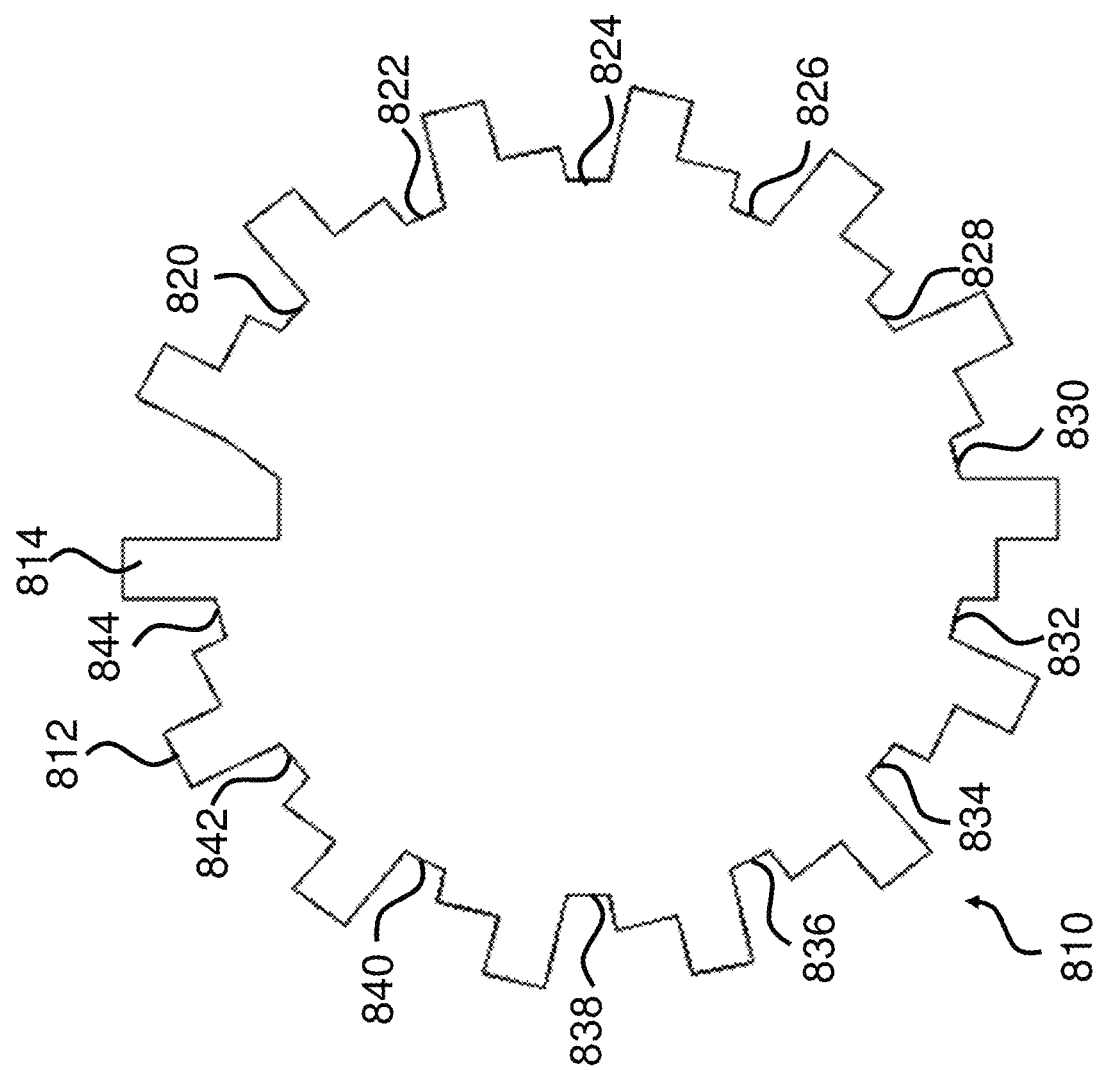
FIG. 8B shows an exemplary analog encoding scheme that includes multiple shape variation points for generating unique analog codes.

FIG. 8B illustrates a coding scheme that may be used. FIG. 8B shows microcarrier 810, which like microcarrier 800 includes non-transparent polymer layer 812 and start position 814 (and optionally, a magnetic layer such as layer 704). In this scheme, potential shape variation points around the gear are labeled, e.g., at positions 820, 822, 824, 826, 828, 830, 832, 834, 836, 838, 840, 842, and 844. As shown in FIG. 8B, even if only two potential shapes may be used for positions 820, 822, 824, 826, 828, 830, 832, 834, 836, 838, 840, 842, and 844, this embodiment allows up to $2^{13}$ unique codes. Further, as described above, the use of analog encoding greatly expands this number by allowing the use of more than two potential shapes at any or all of the indicated positions around the perimeter (e.g., at each shape variation point as labeled in FIG. 8B).

FIGS. 9A-9C illustrate yet another potential embodiment in microcarrier 900. Like microcarrier 800, microcarrier 900 is a gear-shaped microcarrier that includes non-transparent polymer layer 902 and start position 904 (and optionally, a magnetic layer such as layer 704). In addition, microcarrier 900 may have one or more columns (e.g., column 906) affixed to one or both surfaces of microcarrier 900. As shown in the cross-section in FIG. 9B, column 906 extends from a surface of layer 902. Advantageously, column 906 helps to reduce the potential for optical contact bonding (as described above in reference to column 510).

FIG. 9C illustrates the dimensions of column 906. In this example, column 906 is a cylinder 3 µm in height and 3 µm in diameter, although as described above such columns are in no way limited to a cylindrical shape. In some embodiments, column 906 is made of a magnetic material, such as nickel. This allows column 906 to function additionally as a magnetic element for magnetic manipulation of microcarrier 900, as described herein.

Any of the microcarriers described herein may include one or more of the features, elements, or aspects described below. In addition, one or more of the features, elements, or aspects described below may adopt different characteristics depending on the embodiment of the microcarrier, e.g., as described above.

In some embodiments, a substantially transparent polymer of the present disclosure comprises an epoxy-based polymer. Suitable epoxy-based polymers for fabrication of the compositions described herein include, but are not limited to, the EPON™ family of epoxy resins provided by Hexion Specialty Chemicals, Inc. (Columbus, Ohio) and any number of epoxy resins provided by The Dow Chemical Company (Midland, Mich.). Many examples of suitable polymers are commonly known in the art, including without limitation SU-8, EPON 1002F, EPON 165/154, and a poly (methyl methacrylate)/poly(acrylic acid) block copolymer (PMMA-co-PAA). For additional polymers, see, for example, Warad, *IC Packaging: Package Construction Analysis in Ultra Small IC Packaging*, LAP LAMBERT Academic Publishing (2010); *The Electronic Packaging Handbook*, CRC Press (Blackwell, ed.), (2000); and Pecht et al., *Electronic Packaging Materials and Their Properties*, CCR Press, $1^{st}$ ed., (1998). These types of materials have the advantage of not swelling in aqueous environments which ensures that uniform microcarrier size and shape are maintained within the population of microcarriers. In some embodiments, the substantially transparent polymer is a photoresist polymer. In some embodiments, the epoxy-based polymer is an epoxy-based, negative-tone, near-UV photoresist. In some embodiments, the epoxy-based polymer is SU-8.

In some embodiments, the substantially non-transparent polymer is a polymer described herein (e.g., SU-8) mixed with one or more non-transparent or colored dye(s). In other embodiments, the substantially non-transparent polymer is a black matrix resist. Any black matrix resist known in the art may be used; see, e.g., U.S. Pat. No. 8,610,848 for exemplary black matrix resists and methods related thereto. In some embodiments, the black matrix resist may be a photoresist colored with a black pigment, e.g., as patterned on the color filter of an LCD as part of a black matrix. Black matrix resists may include without limitation those sold by Toppan Printing Co. (Tokyo), Tokyo OHKA Kogyo (Kawasaki), and Daxin Materials Corp. (Taichung City, Taiwan).

In some embodiments, reference may be made to a center portion of one or more polymer layers. A center portion of the present disclosure may take any shape. In some embodiments, the shape of the center portion may reflect or correspond to the shape (e.g., outline) of the corresponding polymer layer. In other embodiments, the shape of the center portion may be independent of the shape (e.g., outline) of the corresponding polymer layer. For example, a center portion of a circular microcarrier surface may be circular in some embodiments and square in other embodiments. A center portion of a square microcarrier surface may be square in some embodiments and circular in other embodiments.

In some embodiments, a center portion of a polymer layer of the present disclosure is about 5%, about 7%, about 10%, about 15%, about 20%, about 25%, about 30%, about 35%, 0%, a 40%, about 45%, about 50%, about 55, about 60%, about 65%, about 70%, about 75%, about 80%, about 85%, or about 90% of the surface area of the polymer layer. In some embodiments, a center portion of a polymer layer of the present disclosure is less than about any of the following fractions of the substantially transparent polymer layer (in %): 90, 85, 80, 75, 70, 65, 60, 55, 50, 45, 40, 35, 30, 25, 20, 15, 10, or 7. In some embodiments, a center portion of a polymer layer of the present disclosure is greater than about any of the following fractions of the substantially transparent polymer layer (in %): 5, 7, 10, 15, 20, 25, 30, 35, 40, 45, 50, 55, 60, 65, 70, 75, 80, or 85. That is, the fraction of the polymer layer surface area included in the center portion may be any of a range of percentages having an upper limit of 90, 85, 80, 75, 70, 65, 60, 55, 50, 45, 40, 35, 30, 25, 20, 15, 10, or 7 and an independently selected lower limit of 5, 7, 10, 15, 20, 25, 30, 35, 40, 45, 50, 55, 60, 65, 70, 75, 80, or 85, wherein the lower limit is less than the upper limit. In some embodiments, the center portion of a polymer layer comprises about 25% of the surface area of the polymer layer. In some embodiments, a center portion of a microcarrier surface includes the entire surface minus an outline portion of the microcarrier.

As described above, a microcarrier of the present disclosure may further include a magnetic layer, which may adopt a variety of shapes as described herein. In some embodiments, the magnetic layer may be a substantially non-transparent layer. In some embodiments, the magnetic layer may comprise a magnetic material. A magnetic layer of the present disclosure may be made of any suitable magnetic material, such as a material with paramagnetic, ferromagnetic, or ferrimagnetic properties. Examples of magnetic materials include without limitation iron, nickel, cobalt, and some rare earth metals (e.g., gadolinium, dysprosium, neodymium, and so forth), as well as alloys thereof. In some embodiments, the magnetic material comprises nickel, including without limitation elemental nickel and magnetic nickel alloys such as alnico and permalloy. The inclusion of a magnetic layer in a microcarrier of the present disclosure may be advantageous, e.g., in facilitating magnetic separation, which may be useful for washing, collecting, and otherwise manipulating one or more microcarriers.

As described above, in some embodiments, the magnetic layer may be affixed to a surface of the substantially transparent polymer layer and enclose a center portion of the substantially transparent polymer layer. In other embodiments, as described above, the magnetic layer may include one or more columns; i.e., the one or more columns described above may be made of a magnetic material described herein.

In some aspects, provided herein are encoded microcarriers that comprise: a substantially transparent polymer layer having a first surface and a second surface, the first and the second surfaces being parallel to each other; a magnetic, substantially non-transparent polymer layer that is affixed to the first surface of the substantially transparent polymer layer, encloses a center portion of the substantially transparent polymer layer; and a probe specific for a DNA mutation in the KRAS, BRAF, CTNNB1, or APC gene, wherein the probe is coupled to at least one of the first surface and the second surface of the substantially transparent polymer layer in at least the center portion of the substantially transparent polymer layer. In some embodiments, the magnetic, substantially non-transparent polymer layer comprises a two-dimensional shape representing an analog code. In some embodiments, the magnetic, substantially non-transparent polymer layer comprises at least a portion of a two-dimensional shape representing an analog code. For example, part of the two-dimensional shape could be made from the magnetic, substantially non-transparent polymer layer, and part of the two-dimensional shape could be made from a non-magnetic, substantially non-transparent polymer layer (e.g., SU-8 as described herein). In other embodiments, the magnetic, substantially non-transparent polymer layer comprises all of the two-dimensional shape representing the analog code. Thus, the microcarrier contains at least two layers: one of which is substantially transparent, and the other of which is a magnetic, substantially non-transparent, two-dimensional shape that represents an analog code.

Advantageously, these microcarriers may employ a variety of two-dimensional shapes while still retaining a uniform overall form (e.g., the perimeter of the substantially transparent polymer layer) for uniformity of aspects including, for example, overall dimensions, physical properties, and/or behavior in solution. Various optional aspects and elements of this type of microcarrier are illustrated in FIGS. 1A-5B (see, e.g., FIG. 4B). The magnetic layer advantageously combines a two-dimensional shape for analog coding while also providing a magnetic functionality that allows for, e.g., facilitating magnetic separation, which may be useful for washing, collecting, and otherwise manipulating one or more microcarriers.

In some embodiments, an analog code of the present disclosure is made from a two-dimensional shape of a magnetic, substantially non-transparent polymer layer. Advantageously, this provides a microcarrier that can be produced efficiently on a large scale (e.g., using the techniques described herein). Moreover, generating the analog code using a magnetic, substantially non-transparent polymer layer facilitates multiplex assays by allowing for a variety of different microcarrier species (each with a unique analog code) while also providing facile manipulation via the resulting magnetic properties of the microcarrier.

In some embodiments, the magnetic, substantially non-transparent layer is between about 50 nm and about 10 µm in thickness. In some embodiments, the thickness of the magnetic, substantially non-transparent layer is less than about any of the following thicknesses (in nm): 10000, 9500, 9000, 8500, 8000, 7500, 7000, 6500, 6000, 5500, 5000, 4500, 4000, 3500, 3000, 2500, 2000, 1500, 1000, 950, 900, 850, 800, 750, 700, 650, 600, 550, 500, 450, 400, 350, 300, 250, 200, 150, or 100. In some embodiments, the thickness of the magnetic, substantially non-transparent layer is greater than about any of the following thicknesses (in nm): 50, 100, 150, 200, 250, 300, 350, 400, 450, 500, 550, 600, 650, 700, 750, 800, 850, 900, 950, 1000, 1500, 2000, 2500, 3000, 3500, 4000, 4500, 5000, 5500, 6000, 6500, 7000, 7500, 8000, 8500, 9000, or 9500. That is, the thickness of the magnetic, substantially non-transparent layer may be any of a range of thicknesses (in nm) having an upper limit of 10000, 9500, 9000, 8500, 8000, 7500, 7000, 6500, 6000, 5500, 5000, 4500, 4000, 3500, 3000, 2500, 2000, 1500, 1000, 950, 900, 850, 800, 750, 700, 650, 600, 550, 500, 450, 400, 350, 300, 250, 200, 150, or 100 and an independently selected lower limit of 50, 100, 150, 200, 250, 300, 350, 400, 450, 500, 550, 600, 650, 700, 750, 800, 850, 900, 950, 1000, 1500, 2000, 2500, 3000, 3500, 4000, 4500, 5000, 5500, 6000, 6500, 7000, 7500, 8000, 8500, 9000, or 9500, wherein the lower limit is less than the upper limit.

In some embodiments, the magnetic, substantially non-transparent layer is about 0.1 µm in thickness. In some embodiments, the magnetic, substantially non-transparent layer is about 50 nm, about 100 nm, about 150 nm, about 200 nm, about 250 nm, about 300 nm, about 350 nm, about 400 nm, about 450 nm, about 500 nm, about 550 nm, about 600 nm, about 650 nm, about 700 nm, about 750 nm, about 800 nm, about 850 nm, about 900 nm, about 950 nm, about 1 µm, about 1.5 µm, about 2 µm, about 2.5 µm, about 3 µm, about 3.5 µm, about 4 µm, about 4.5 µm, about 5 µm, about 5.5 µm, about 6 µm, about 6.5 µm, about 7 µm, about 7.5 µm, about 8 µm, about 8.5 µm, about 9 µm, about 9.5 µm, or about 10 µm in thickness. In some embodiments, the thickness of the magnetic, substantially non-transparent layer is about 0.01 am, about 0.02 µm, about 0.03 µm, about 0.04 µm, about 0.05 µm, about 0.06 µm, about 0.07 am, about 0.08 µm, about 0.09 µm, about 0.1 µm, about 0.11 µm, about 0.12 µm, about 0.13 am, about 0.14 µm, about 0.15 µm, about 0.16 µm, about 0.17 µm, about 0.18 µm, about 0.19 am, about 0.20 µm, about 0.25 µm, about 0.30 µm, about 0.35 µm, about 0.40 µm, about 0.45 am, or about 0.50 µm.

In some embodiments, a microcarrier of the present disclosure may be encoded with a substantially non-transparent layer that constitutes a two-dimensional shape. For example, as described above, the two-dimensional shape may constitute the shape of a substantially non-transparent layer that contrasts with a substantially transparent layer of the microcarrier, or it may constitute the shape of the microcarrier itself (e.g., the perimeter). Any two-dimensional shape that can encompass a plurality of resolvable and distinctive varieties may be used. In some embodiments, the two-dimensional shape comprises one or more of linear, circular, elliptical, rectangular, quadrilateral, or higher polygonal aspects, elements, and/or shapes. In some embodiments, the two-dimensional shape may be produced using a magnetic, substantially non-transparent layer of the present disclosure.

Figure 4B:
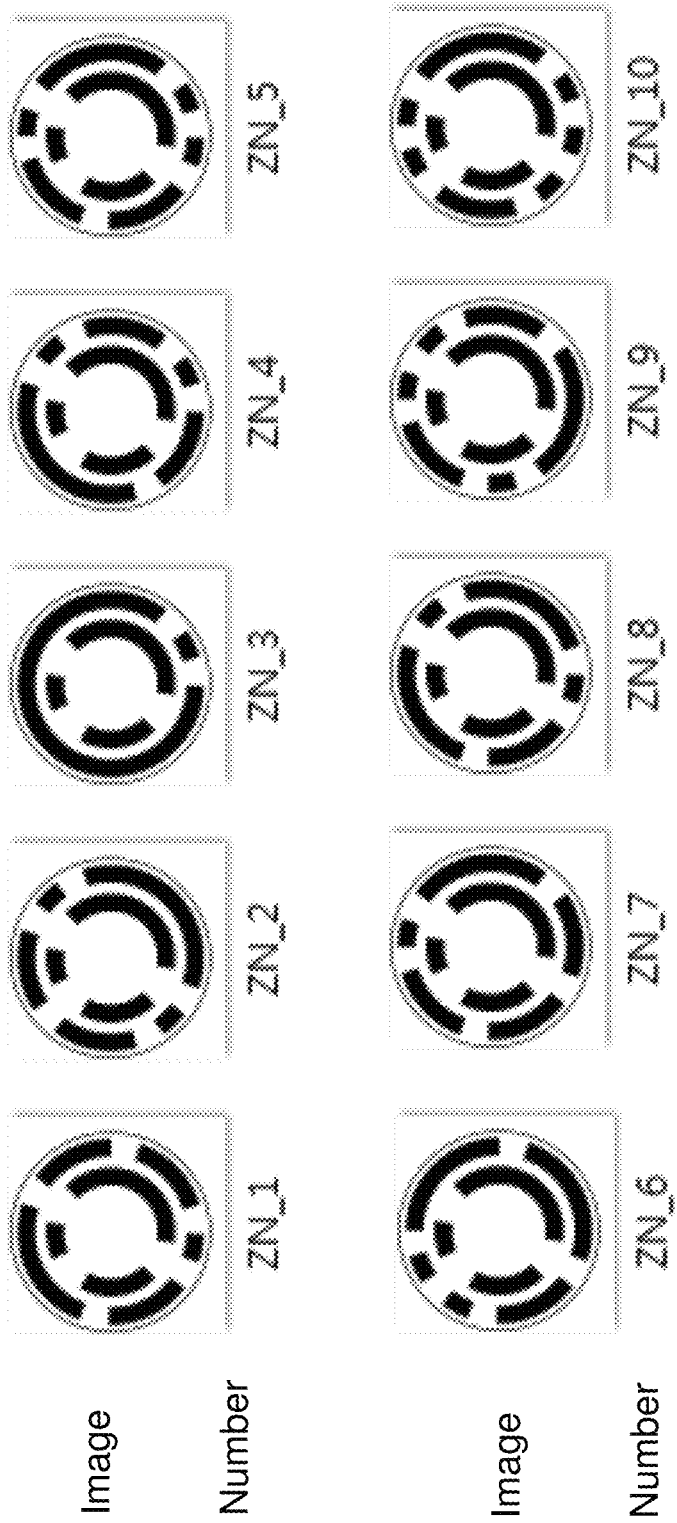
FIG. 4B shows examples of microcarriers with a unique analog code, in accordance with some embodiments.

FIG. 4A illustrates three exemplary embodiments of the coding scheme shown in FIG. 3: microcarriers 400, 402, and 404. The unique codes of microcarriers 400, 402, and 404 are generated using the simple "filled or not filled" scheme of FIG. 3. Importantly, as described above, more complex encoding schemes are available using analog image recognition, thereby greatly expanding the number of potential unique codes. In some embodiments, the two-dimensional shape of the substantially non-transparent polymer layer comprises one or more rings enclosing the center portion of the substantially transparent polymer layer. In some embodiments, at least one of the one or more rings comprises a discontinuity. Exemplary and non-limiting two-dimensional shapes formed using one or more rings (e.g., two rings) having varying numbers and configurations of discontinuities are illustrated in FIG. 4B. FIG. 4B illustrates 10 exemplary embodiments of the cod, inter alia, in terms of number of shapes (e.g., two distinct shapes in code ZN_3, as compared to seven distinct shapes in code ZN_10) and/or size of shapes (e.g., large, small, and intermediate-sized shapes in code ZN_2).

In some embodiments, the two-dimensional shape of the substantially non-transparent polymer layer comprises a gear shape. A gear shape as used herein may refer to a plurality of shapes (e.g., gear teeth) arrayed on the perimeter of a substantially round, elliptical, or circular body, where at least two of the shapes of the plurality are spatially separated. In some embodiments, the gear shape comprises a plurality of gear teeth. In some embodiments, the analog code is represented by one or more aspects selected from the height of one or more gear teeth of the plurality, the width of one or more gear teeth of the plurality, the number of gear teeth in the plurality, and the arrangement of one or more gear teeth within the plurality. Advantageously, a gear shape encompasses multiple aspects, including the height of gear teeth, the width of gear teeth, the number of gear teeth, and the arrangement of gear teeth, that may be varied in order to generate a large diversity of potential unique two-dimensional shapes. It is to be appreciated, however, that since the gear shapes of the present disclosure are used for encoding and are not required to physically intermesh with another gear (e.g., as with mechanical gears that transmit torque), gear teeth of the present disclosure are not constrained by the need for identical or intermeshing shapes, either within one gear shape or between multiple gear shapes. As such, the variety of shapes that may be considered a gear tooth of the present disclosure is significantly greater than with a mechanical gear.

FIG. 3 shows the vast number of potential analog codes possible using the gear shape shown in FIGS. 1A-2B. FIG. 3 illustrates an exemplary coding scheme in which multiple shape variation points are labeled, e.g., at positions 302, 304, 306, 308, 310, 312, 314, 316, 318, 320, 322, 324, 326, and 328 on exemplary microcarrier 300. Even if a simple "filled or not filled" scheme is used, up to $2^{14}$ unique codes are possible based on the use of 14 shape variation points. This scheme is convenient for both manufacturing and for generating two-dimensional shapes that are easily distinguishable for image recognition analysis. However, since analog encoding is used, more complex schemes using more than 2 possibilities (e.g., at each shape variation point as labeled in FIG. 3) are possible, thereby exponentially expanding the number of unique identifiers. For example, multiple gear tooth shapes and/or multiple sizes of gear teeth are possible. A two-dimensional gear shape as shown in FIGS. 1A-3 facilitates a wide range of unique analog codes while providing a large center portion (e.g., center portions 106 and 208) for analyte detection.

In some embodiments, the plurality of gear teeth comprises one or more gear teeth that are between about 1 µm and about 10 µm wide. In some embodiments, the plurality of gear teeth comprises one or more gear teeth that are about 1 µm wide, about 1.5 µm wide, about 2 µm wide, about 2.5 m wide, about 3 µm wide, about 3.5 µm wide, about 4 m wide, about 4.5 m wide, about 5 µm wide, about 5.5 µm wide, about 6 m wide, about 6.5 µm wide, about 7 µm wide, about 7.5 µm wide, about 8 µm wide, about 8.5 µm wide, about 9 µm wide, about 9.5 µm wide, or about 10 µm wide. In some embodiments, the plurality of gear teeth comprises one or more gear teeth that are less than about any of the following widths (in µm): 10, 9.5, 9, 8.5, 8, 7.5, 7, 6.5, 6, 5.5, 5, 4.5, 4, 3.5, 3, 2.5, 2, or 1.5. In some embodiments, the plurality of gear teeth comprises one or more gear teeth that are greater than about any of the following widths (in m): 1, 1.5, 2, 2.5, 3, 3.5, 4, 4.5, 5, 5.5, 6, 6.5, 7, 7.5, 8, 8.5, 9, or 9.5. That is, the plurality of gear teeth may comprise one or more gear teeth that can be any of a range of widths having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit.

In some embodiments, the plurality of gear teeth comprises one or more gear teeth that are between about 1 µm and about 10 µm tall. In some embodiments, the plurality of gear teeth comprises one or more gear teeth that are about 1 µm tall, about 1.5 µm tall, about 2 µm tall, about 2.5 µm tall, about 3 µm tall, about 3.5 µm tall, about 4 µm tall, about 4.5 µm tall, about 5 µm tall, about 5.5 µm tall, about 6 µm tall, about 6.5 µm tall, about 7 µm tall, about 7.5 µm tall, about 8 µm tall, about 8.5 µm tall, about 9 µm tall, about 9.5 µm tall, or about 10 µm tall. In some embodiments, the plurality of gear teeth comprises one or more gear teeth that are less than about any of the following heights (in µm): 10, 9.5, 9, 8.5, 8, 7.5, 7, 6.5, 6, 5.5, 5, 4.5, 4, 3.5, 3, 2.5, 2, or 1.5. In some embodiments, the plurality of gear teeth comprises one or more gear teeth that are greater than about any of the following heights (in µm): 1, 1.5, 2, 2.5, 3, 3.5, 4, 4.5, 5, 5.5, 6, 6.5, 7, 7.5, 8, 8.5, 9, or 9.5. That is, the plurality of gear teeth may comprise one or more gear teeth that can be any of a range of heights having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit. It is to be appreciated that a gear tooth may have different measurable heights, depending on the point of reference, if the adjacent perimeter segments from which the gear tooth extends are uneven (see, e.g., gear tooth 602 in FIG. 6C, which may be 4 or 6.5 µm tall, depending on the point of reference).

In some embodiments, the plurality of gear teeth comprises one or more gear teeth that are spaced between about 1 µm and about 10 µm apart. In some embodiments, the plurality of gear teeth comprises one or more gear teeth that are spaced about 1 µm apart, about 1.5 µm apart, about 2 m apart, about 2.5 m apart, about 3 µm apart, about 3.5 µm apart, about 4 m apart, about 4.5 m apart, about 5 µm apart, about 5.5 µm apart, about 6 µm apart, about 6.5 µm apart, about 7 µm apart, about 7.5 µm apart, about 8 µm apart, about 8.5 µm apart, about 9 µm apart, about 9.5 µm apart, or about 10 µm apart. In some embodiments, the plurality of gear teeth comprises one or more gear teeth that are spaced less than about any of the following widths apart (in m): 10, 9.5, 9, 8.5, 8, 7.5, 7, 6.5, 6, 5.5, 5, 4.5, 4, 3.5, 3, 2.5, 2, or 1.5. In some embodiments, the plurality of gear teeth comprises one or more gear teeth that are spaced greater than about any of the following widths apart (in µm): 1, 1.5, 2, 2.5, 3, 3.5, 4, 4.5, 5, 5.5, 6, 6.5, 7, 7.5, 8, 8.5, 9, or 9.5. That is, the plurality of gear teeth may comprise one or more gear teeth that can be spaced any of a range of widths apart having an upper limit of 10, 9.5, 9, 8.5, 8, 7.5, 7, 6.5, 6, 5.5, 5, 4.5, 4, 3.5, 3, 2.5, 2, or 1.5 and an independently selected lower limit of 1, 1.5, 2, 2.5, 3, 3.5, 4, 4.5, 5, 5.5, 6, 6.5, 7, 7.5, 8, 8.5, 9, or 9.5, wherein the lower limit is less than the upper limit.

In some embodiments, a microcarrier of the present disclosure is a substantially circular disc. As used herein, a substantially circular shape may refer to any shape having a roughly identical distance between all of the points of the shape's perimeter and the shape's geometric center. In some embodiments, a shape is considered to be substantially circular if the variation among any of the potential radii connecting the geometric center and a given point on the perimeter exhibit 10% or lesser variation in length. As used herein, a substantially circular disc may refer to any substantially circular shape wherein the thickness of the shape is significantly less than its diameter. For example, in some embodiments, the thickness of a substantially circular disc may be less than about 50%, less than about 40%, less than about 30%, less than about 20%, less than about 15%, less than about 10%, or less than about 5% of its diameter. In certain embodiments, the thickness of the substantially circular disc may about 20% of its diameter. It is to be appreciated that the microcarriers of the present disclosure whose outline is a gear shape may also be considered substantially circular discs; for example, the shape of the microcarrier excluding the one or more gear teeth may comprise a substantially circular disc.

In some embodiments, the microcarrier is less than about 200 µm in diameter. For example, in some embodiments, the diameter of the microcarrier is less than about 200 µm, less than about 180 µm, less than about 160 µm, less than about 140 µm, less than about 120 µm, less than about 100 µm, less than about 80 µm, less than about 60 µm, less than about 40 µm, or less than about 20 µm.

In some embodiments, the diameter of the microcarrier is about 180 lam, about 160 am, about 140 µm, about 120 µm, about 100 µm, about 90 µm, about 80 µm, about 70 µm, about 60 µm, about 50 µm, about 40 µm, about 30 µm, about 20 lam, or about 10 µm. In certain embodiments, the microcarrier is about 60 µm in diameter.

In some embodiments, the microcarrier is less than about 50 µm in thickness. For example, in some embodiments, the thickness of the microcarrier is less than about 70 µm, about 60 µm, about 50 µm, about 40 µm, about 30 µm, less than about 25 µm, less than about 20 µm, less than about 15 µm, less than about 10 µm, or less than about 5 µm. In some embodiments, the thickness of the microcarrier is less than about any of the following thicknesses (in µm): 70, 65, 60, 55, 50, 45, 40, 35, 30, 25, 20, 15, 10, 9, 8, 7, 6, 5, 4, 3, or 2. In some embodiments, the thickness of the microcarrier is greater than about any of the following thicknesses (in µm): 1, 2, 3, 4, 5, 6, 7, 8, 9, 10, 15, 20, 25, 30, 35, 40, 45, 50, 55, 60, or 65. That is, the thickness of the microcarrier may be any of a range of thicknesses (in lam) having an upper limit of 70, 65, 60, 55, 50, 45, 40, 35, 30, 25, 20, 15, 10, 9, 8, 7, 6, 5, 4, 3, or 2 and an independently selected lower limit of 1, 2, 3, 4, 5, 6, 7, 8, 9, 10, 15, 20, 25, 30, 35, 40, 45, 50, 55, 60, or 65, wherein the lower limit is less than the upper limit.

In some embodiments, the thickness of the microcarrier is about 50 µm, about 45 am, about 40 µm, about 35 µm, about 30 µm, about 25 µm, about 20 µm, about 19 µm, about 18 am, about 17 µm, about 16 µm, about 15 µm, about 14 µm, about 13 µm, about 12 µm, about 11 am, about 10 µm, about 9 µm, about 8 µm, about 7 µm, about 6 µm, about 5 µm, about 4 µm, about 3 µm, about 2 µm, or about 1 µm. In certain embodiments, the microcarrier is about 10 am in thickness.

A variety of techniques may be used to couple a probe of the present disclosure to an encoded microcarrier. In some embodiments, the probe is coupled to a surface of the microcarrier (in some embodiments, in at least a center portion of the microcarrier surface). In some embodiments, the probe may be coupled to one or both of a first or a second surface of the polymer layer. In some embodiments, the polymer comprises an epoxy-based polymer or otherwise contains an epoxide group.

In some embodiments, the probe can be chemically attached to the microcarrier. In other embodiments, the probe can be physically absorbed to the surface of the microcarrier. In some embodiments, the attachment linkage between the probe and the microcarrier surface can be a covalent bond. In other embodiments, the attachment linkage between the probe and the microcarrier surface can be a non-covalent bond including, but not limited to, a salt bridge or other ionic bond, one or more hydrogen bonds, hydrophobic interactions, Van der Waals force, London dispersion force, a mechanical bond, one or more halogen bonds, aurophilicity, intercalation, or stacking.

In some embodiments, coupling the probe involves reacting the polymer with a photoacid generator and light to generate a cross-linked polymer. In some embodiments, the light is of a wavelength that activates the photoacid generator, e.g., UV or near-UV light. Photoacid generators are commercially available from Sigma-Aldrich (St. Louis) and BASF (Ludwigshafen). Any suitable photoacid generator known in the art may be used, including without limitation triphenyl or triaryl sulfonium hexafluoroantimonate; triarylsulfonium hexafluorophosphate; triphenylsulfonium perfluoro-1-butanesulfonate; triphenylsulfonium triflate; Tris (4-tert-butylphenyl)sulfonium perfluoro-1-butanesulfonate or triflate; Bis(4-tert-butylphenyl)iodonium-containing photoacid generators such as Bis(4-tert-butylphenyl)iodonium perfluoro-1-butanesulfonate, p-toluenesulfonate, and triflate; Boc-methoxyphenyldiphenylsulfonium triflate; (tert-Butoxycarbonylmethoxynaphthyl)-diphenylsulfonium triflate; (4-tert-Butylphenyl)diphenylsulfonium triflate; diphenyliodonium hexafluorophosphate, nitrate, perfluoro-1-butanesulfonate, triflate, or p-toluenesulfonate; (4-fluorophenyl)diphenylsulfonium triflate; N-hydroxynaphthalimide triflate; N-hydroxy-5-norbornene-2,3-dicarboximide perfluoro-1-butanesulfonate; (4-iodophenyl)diphenylsulfonium triflate; (4-methoxyphenyl)diphenylsulfonium triflate; 2-(4-methoxystyryl)-4,6-bis(trichloromethyl)-1,3,5-triazine; (4-methylphenyl)diphenylsulfonium triflate; (4-methylthiophenyl)methyl phenyl sulfonium triflate; (4-phenoxyphenyl)diphenylsulfonium triflate; (4-phenylthiophenyl) diphenylsulfonium triflate; or any of the photoacid generators described in product-finder.basf.com/group/corporate/product-finder/de/literature-document:/Brand+Irgacure-Brochure--Photoacid+Generator+Selection+Guide-English.pdf. In some embodiments, the photoacid generator is a sulfonium-containing photoacid generator.

In some embodiments, coupling the probe involves reacting an epoxide of the cross-linked polymer with a functional group such as an amine, carboxyl, thiol, or the like. Alternatively, the epoxy group on the surface can be oxidized to hydroxyl group, which is subsequently used as initiation sites for graft polymerization of water soluble polymers such as poly(acrylic acid). The carboxyl groups in poly(acrylic acid) are then used to form covalent bonds with amino or hydroxyl groups in capture agents. For example, in certain embodiments, the carboxyl groups in poly(acrylic acid) are used to form covalent bonds with amino groups in the probe.

In some embodiments, coupling the probe involves reacting an epoxide of the cross-linked polymer with a compound that contains an amine and a carboxyl. In some embodiments, the amine of the compound reacts with the epoxide to form a compound-coupled, cross-linked polymer. Without wishing to be bound to theory, it is thought that the probe may be coupled to the polymer before the polymer is cross-linked; however, this may reduce the uniformity of the resulting surface. Any compound with a primary amine and a carboxyl group may be used. Compounds may include without limitation glycine, amino undecanoic acid, amino caproic acid, acrylic acid, 2-carboxyethyl acrylic acid, 4-vinylbenzoic acid, 3-acrylamido-3-methyl-1-butanoic acid, glycidyl methacrylate, and the like. In some embodiments, the carboxyl of the compound-coupled, cross-linked polymer reacts with an amine (e.g., a primary amine) of the probe to couple the capture agent to the substantially transparent polymer.

V. Kits

Further provided herein are kits or articles of manufacture containing a plurality of microcarriers of the present disclosure. These kits or articles of manufacture may find use, inter alia, in conducting a multiplex assay, such as the exemplary multiplex assays described herein (see, e.g., section III above). Any of the microcarriers described herein (see, e.g., section IV above) may find use in a kit or article of manufacture of the present disclosure In some embodiments, a kit or article of manufacture of the present disclosure comprises at least four encoded microcarriers. In some embodiments, each of the four encoded microcarriers comprises (i) a probe, specific for a DNA mutation in the KRAS, BRAF, CTNNB1, or APC gene, coupled to the microcarrier; and (ii) an identifier corresponding to the probe. In some embodiments, the kit comprises at least one microcarrier comprising a probe specific for a DNA mutation in the KRAS gene, at least one microcarrier comprising a probe specific for a DNA mutation in the BRAF gene, at least one microcarrier comprising a probe specific for a DNA mutation in the CTNNB1 gene, and at least one microcarrier comprising a probe specific for a DNA mutation in the APC gene. That is to say, each of the KRAS, BRAF, CTNNB1, and APC genes is represented in the kit by a microcarrier with a probe specific for a mutation in the gene. Exemplary KRAS, BRAF, CTNNB1, and APC genes and mutations are described supra. In some embodiments, the KRAS, BRAF, CTNNB1, and APC genes are human genes. In some embodiments, the kit comprises microcarriers with probes suitable for detecting each of the following mutations (e.g., with at least one microcarrier+probe species for each mutation in the kit): DNA mutations encoding G12D, G12V, G12S, and G13D mutated KRAS proteins; DNA mutation(s) encoding a V600E mutated BRAF protein; DNA mutations encoding T41A and T41I mutated CTNNB1 proteins; DNA mutations encoding S45F and S45P mutated CTNNB1 proteins; and DNA mutations encoding Q1367*, R1450*, E1309 frameshift, S1465 frameshift, and T1556 frameshift mutated APC proteins.

In some embodiments, the kit further comprises at least four blocking nucleic acids. In some embodiments, said at least four blocking nucleic acids hybridize with wild-type DNA loci corresponding with DNA mutations in the each of the KRAS, BRAF, CTNNB1, and APC genes. Exemplary descriptions of blocking nucleic acids are provided in section III. In some embodiments, the kit comprises a blocking nucleic acid comprising the sequence TACGCCACCAGCT(invdT)$_n$, wherein n is 1, 2, or 3 (SEQ ID NO:3), TTG-GAGCTGGTGGCGTAinvdTinvdTinvdT (SEQ ID NO:142), GCTGGTGGCGTAGGCAinvdTinvdTinvdT (SEQ ID NO:143), GCTGGTGGCGTAGGCinvdTinvdT-invdT (SEQ ID NO: 144), or TTGGAGCTGGTGGCGT-invdTinvdTinvdT (SEQ ID NO: 145); a blocking nucleic acid comprising the sequence GAGATTTCACTGTAGC(invdT)$_n$, wherein n is 1, 2, or 3 (SEQ ID NO:10), GAGAT-TTCACTGTAGCinvdTinvdTinvdT (SEQ ID NO: 146), GAGATTTCACTGTAGC invdTinvdTinvdT (SEQ ID NO: 147), GAGATTTCACTGTAGCinvdTinvdTinvdT (SEQ ID NO: 148), or GAGATTTCACTGTAGCinvdTinvdTinvdT (SEQ ID NO:149); a blocking nucleic acid comprising the sequence GCCACTACCACAGCT(invdT)$_n$, wherein n is 1, 2, or 3 (SEQ ID NO:15), TGCCACTACCACAGinvdT-invdTinvdT (SEQ ID NO:150), CACTACCACAGCT-CinvdTinvdTinvdT (SEQ ID NO: 151), GCCACTAC-CACAGCTinvdTinvdTinvdT (SEQ ID NO:152), or GCCACTACCACAGCTinvdTinvdTinvdT (SEQ ID NO: 153), and/or a blocking nucleic acid comprising the sequence GCTCCTTCTCTGAGTinvdTinvdTinvdT (SEQ ID NO:20), TCCTTCTCTGAGTGGinvdTinvdTinvdT (SEQ ID NO:174), GCTCCTTCTCTGAGTinvdTinvdT-invdT (SEQ ID NO: 175), TCCTTCTCTGAGTGGinvdT-invdTinvdT (SEQ ID NO: 176), or GCTCCTTCTCTGAGT-invdTinvdTinvdT (SEQ ID NO: 177); and one or more of: a blocking nucleic acid comprising the sequence GTGCTCAGACACCinvdTinvdTinvdT (SEQ ID NO:33), GTGCTCAGACACCinvdTinvdTinvdT (SEQ ID NO:158), AGTGGTGCTCAGACACCCAinvdTinvdTinvdT (SEQ ID NO:159), AGTGGTGCTCAGACACCCAinvdTinvdT-invdT (SEQ ID NO: 160), or AGTGGTGCTCAGACACC-CAinvdTinvdTinvdT (SEQ ID NO:161), a blocking nucleic acid comprising the sequence CTTCTCGCTTGGTTinvdT-invdTinvdT (SEQ ID NO:37), GTACTTCTCGCTTGGT-invdTinvdTinvdT (SEQ ID NO:162), CTTCTCGCTTGGT-TinvdTinvdTinvdT (SEQ ID NO:163), GTACTTCTCGCTTGGTinvdTinvdTinvdT (SEQ ID NO:164), or GTACTTCTCGCTTGGTinvdTinvdTinvdT (SEQ ID NO:165), a blocking nucleic acid comprising the sequence CTTTCTTTTATTTCTGCinvdTinvdTinvdT (SEQ ID NO:29), CTTTTCTTTTATTTCTGCinvdTinvdT-invdT (SEQ ID NO: 154), CTTTTCTTTTATTTCTGC-invdTinvdTinvdT (SEQ ID NO:155), CTTTTCTTTTAT-TTCTGCinvdTinvdTinvdT (SEQ ID NO:156), or CTTTTCTTTTATTTCTGCinvdTinvdTinvdT (SEQ ID NO:157), a blocking nucleic acid comprising the sequence CCACTCTCTCTTTTCAGCinvdTinvdTinvdT (SEQ ID NO:25), TAGGTCCACTCTCTCTTTTCAGCAinvdT-invdTinvdT (SEQ ID NO: 166), TAGGTC-CACTCTCTCTTTTCAGCA invdTinvdTinvdT (SEQ ID NO:167), CCACTCTCTCTTTTCAGC invdTinvdT-invdT (SEQ ID NO:168), or TAGGTC-CACTCTCTCTTTTCAGCA invdTinvdTinvdT (SEQ ID NO: 169), and a blocking nucleic acid comprising the sequence CAATAGTTTTTTCTGCCinvdTinvdTinvdT (SEQ ID NO:41), GAATCAATAGTTTTTTCTGCCTC invdTinvdTinvdT (SEQ ID NO: 170), TCAGAAT-CAATAGTTTTTTCTG invdTinvdTinvdT (SEQ ID NO:171), GAATCAATAGATTTTACTGCCTC invdT-invdTinvdT (SEQ ID NO: 172), or AAT-CAATAGTTTTTTCTGCCTC invdTinvdTinvdT (SEQ ID NO: 173), (italicized nucleic acids representing locked nucleic acids).

In some embodiments, the kit further comprises one or more primer pairs, e.g., for amplifying the locus of a DNA mutation of interest. In some embodiments, the kit comprises a primer pair specific for the locus of one or more DNA mutations in each of the KRAS, BRAF, CTNNB1, and APC genes, e.g., at least four primer pairs. In some embodiments, the kit comprises a primer pair comprising the sequences GTACTGGTGGAGTATTTGATAGTG (SEQ ID NO: 1) and ATCGTCAAGGCACTCTTGCCTAC (SEQ ID NO:2) for amplification of a locus comprising a KRAS mutation (e.g., one or more KRAS mutations encoding G12D, G12V, G12S, and G13D mutated KRAS proteins); a primer pair comprising the sequences GGACCCACTC-CATCGAGATTT (SEQ ID NO:8) and CAGATATAT-TCTTCATGAAGACCTCACAGTAA (SEQ ID NO:9) for amplification of a locus comprising a BRAF mutation (e.g., one, two, or more BRAF mutations encoding a V600E mutated BRAF protein); a primer pair comprising the sequences GGAATCCATTCTGGTGCCACT (SEQ ID NO:13) and AGAAAATCCCTGTTCCCACTCATA (SEQ ID NO: 14) and/or a primer pair comprising the sequences GGTGCCACTACCACAGCTCCT (SEQ ID NO:18) and TCTCAAAACTGCATTCTGACTTTCA (SEQ ID NO: 19) for amplification of a locus comprising a CTNNB1 mutation (e.g., one or more CTNNB1 mutations encoding T41A, T41I, S45F, or S45P mutated CTNNB1 proteins); and one or more of: a first primer pair comprising the sequences TAAAAATAAAGCACCTACTGCTGAAA (SEQ ID NO:23) and AGCTTGCTTAGGTCCACTCTCTCT (SEQ ID NO:24); a second primer pair comprising the sequences TAGGATGTAATCAGACGACACAGGA (SEQ ID NO:27) and CAGCTGACCTAGTTCCAATCTTTTA (SEQ ID NO:28); a third primer pair comprising the sequences TCTCCCTCCAAAAGTGGTGCT (SEQ ID NO:31) and TGGCAATCGAACGACTCTCAA (SEQ ID NO:32); a fourth primer pair comprising the sequences GCAGAAGTAAAACACCTCCACCA (SEQ ID NO:35) and GGTGCTTTATTTTTAGGTACTTC (SEQ ID NO:36), with italicized nucleic acids representing locked nucleic acids; and a fifth primer pair comprising the sequences CAGGAAAATGACAATGGGAATG (SEQ ID NO:39) and ATCTAATAGGTCCTTTTCAGAATCAATAG (SEQ ID NO:40) for amplification of a locus comprising an APC mutation (e.g., one or more APC mutations encoding Q1367*, R1450*, E1309 frameshift, S1465 frameshift, or T1556 frameshift mutated APC proteins).

Any of the probes described herein (e.g., in section III) may be included in the kit, e.g., coupled to an encoded microcarrier. For example, suitable probes for detecting a DNA mutation in the KRAS gene can include the sequences GGAGCTGATGG (SEQ ID NO:4), AGCTGATGGCGTA (SEQ ID NO:178), TGGAGCTGATGGCG (SEQ ID NO:179), TGGAGCTGATGG (SEQ ID NO:180), GCT-GATGGCGTA (SEQ ID NO:181), GGAGCTGTTGG (SEQ ID NO:5), TGGAGCTGTTGGTGGC (SEQ ID NO:182), GGAGCTGTTGGTG (SEQ ID NO:183), TGGAGCTGTTGGT (SEQ ID NO:184), TGGAGCTGTaGGTGG (SEQ ID NO:185), TGGAGCTAGTGG (SEQ ID NO:6), TTG-GAGCTAGTGGCGTA (SEQ ID NO:186), GCTAGTGGCGTAGGC (SEQ ID NO:187), AGCTAGTGGCGT (SEQ ID NO:188), GTTG- GAGCTAGTGG (SEQ ID NO:189), GGAGCTAGTGG (SEQ ID NO:190), TGGAGCTGGTGACGT (SEQ ID NO:7), GGTGACGTAGGCAA (SEQ ID NO:191), TGACGTAGGCAAGAG (SEQ ID NO: 192), GCTGGTGACGTAGG (SEQ ID NO:193), AGCTGGTGACGTAG (SEQ ID NO:194), GGAGCTGGTGACGT (SEQ ID NO:195), TTTTTTTTTTTTAAGGAGCTGATGG (SEQ ID NO:47), TTTTTTTTTTTTAGCTGATGGCGTA (SEQ ID NO:74), TTTTTTTTTTATGGAGCTGATGGCG (SEQ ID NO:75), TTTTTTTTTTTTATGGAGCTGATGG (SEQ ID NO:76), TTTTTTTTTTTTTGCTGATGGCGTA (SEQ ID NO:77), TTTTTTTTTTTTAAGGAGCTGTTGG (SEQ ID NO:48), TTTTTTTTATGGAGCTGTTGGTGGC (SEQ ID NO:78), TTTTTTTTTTAAGGAGCTGTTGGTG (SEQ ID NO:79), TTTTTTTTTTTATGGAGCTGTTGGT (SEQ ID NO:80), TTTTTTTTTATGGAGCTGTAGGTGG (SEQ ID NO:81), TTTTTTTTTTTATGGAGCTAGTGG (SEQ ID NO:49), TTTTTTTTTTGGAGCTAGTGGCGTA (SEQ ID NO:82), TTTTTAATTTGCTAGTGGCGTAGGC (SEQ ID NO:83), TTTTTTTTTTATTTAGCTAGTGGCGT (SEQ ID NO:84), TTTTTTTTTTTGTTGGAGCTAGTGG (SEQ ID NO:85), TTTTTTTTTTTTAAGGAGCTAGTGG (SEQ ID NO:86), TTTTTTTTTATGGAGCTGGTGACGT (SEQ ID NO:50), TTTTTTTTAAAGGTGACGTAGGCAA (SEQ ID NO:87), TTTTTTTTTATGACGTAGGCAAGAG (SEQ ID NO:88), TTTTTTTTTTTGCTGGTGACGTAGG (SEQ ID NO:89), TTTTTTTTTTAAGCTGGTGACGTAG (SEQ ID NO:90), and TTTTTTTTTAAGGAGCTGGTGACGT (SEQ ID NO:91). In some embodiments, a probe of the present disclosure can comprise eight or more nucleotides (e.g., adenines or thymines) at its 5' end. Suitable probes for detecting a DNA mutation in the BRAF gene can include the sequences TCTAGCTACAGAGAAAT (SEQ ID NO:11), GTCTAGCTACAGAAAAAT (SEQ ID NO:12), TACAGAGAAATCTCGAT (SEQ ID NO:196), TACAGAGAAATCTC (SEQ ID NO:197), CTAGCTACAGAGAAAT (SEQ ID NO:198), CTAGCTACAGAGAAA (SEQ ID NO:199), TCTAGCTACAGAG (SEQ ID NO:200), TTTTTTAATTTCTAGCTACAGAGAAAT (SEQ ID NO:51), TTTTTTTTTATACAGAGAAATCTCGAT (SEQ ID NO:92), TTTTTTTTTAATTTACAGAGAAATCTC (SEQ ID NO:93), TTTTTTAATTACTAGCTACAGAGAAAT (SEQ ID NO:94), TTTTTTTAATTACTAGCTACAGAGAAA (SEQ ID NO:95), TTTTTTTTTTAATTTCTAGCTACAGAG (SEQ ID NO:96), TTTTTTTATGTCTAGCTACAGAAAAAT (SEQ ID NO:52), TTTTATGTCTAGCTACAGAAAAATC (SEQ ID NO:97), TTTTTTTTATTTTAGCTACAGAAAAA (SEQ ID NO:98), TTTTTTTATTTCTAGCTACAGAAAAAT (SEQ ID NO:99), and/or TTTTTTTTATTCTAGCTACAGAAAAATC (SEQ ID NO:100). Suitable probes for detecting a DNA mutation in the CTNNB1 gene can include the sequences AGGAGCTGTGGCAG (SEQ ID NO:16), GGAGCTGTGATA (SEQ ID NO:17), TTTACCACTCAGAAAAG (SEQ ID NO:21), TACCACTCAGAGGAG (SEQ ID NO:22), TTTTTTTTTTAGGAGCTGTGGCAG (SEQ ID NO:53), TTTTTTTTTTTAGGAGCTGTGGCAGTG (SEQ ID NO: 101), TTTTTTTTTTTAGCTGTGGCAGTGGC (SEQ ID NO: 102), TTTTTTTTTTTGCTGTGGCAGTGGCA (SEQ ID NO: 103), TTTTTTTTTTAAGGAGCTGTGGCAG (SEQ ID NO:104), TTTTTTTTTTTTTGGAGCTGTGATA (SEQ ID NO:54), TTTTTTTTTGGAGCTGTGATAGTGG (SEQ ID NO: 105), TTTTTTTTTGAGCTGTGATAGTGGC (SEQ ID NO: 106), TTTTTTTTTAGCTGTGATAGTGGCA (SEQ ID NO: 107), TTTTTTTTTAGAAGGAGCTGTGATA (SEQ ID NO:108), TTTTTTTTTTTTTGGAGCTGTGAT (SEQ ID NO:109), TTTTTTTTTTTACCACTCAGAAAAG (SEQ ID NO:55), TTTAATTTTACTCAGAAAAGGAGCT (SEQ ID NO:110), TTTTTTAATACCACTCAGAAAAGGA (SEQ ID NO:111), TTTTTTTTACCACTCAGAAAAGGAG (SEQ ID NO:112), TTTTTTTTATTACCACTCAGAAAAG (SEQ ID NO:113), TTTTTTTTTCAGAAAAGGAGCTGTG (SEQ ID NO:114), TTTTTTTTTAATACCACTCAGAGGAG (SEQ ID NO:56), TTTTTTTTTAAAACTCAGAGGAGGAGC (SEQ ID NO:115), TTTTTTTTTTTATTACCACTCAGAGGA (SEQ ID NO: 116), TTTTTTTTTATTACCACTCAGAGGAGG (SEQ ID NO:117), TTTTTTTTTTATTAACACTCAGAGGAG (SEQ ID NO:118), and/or TTTTTTTTTATTACCAATCAGAGGAGG (SEQ ID NO: 119). Suitable probes for detecting a DNA mutation in the APC gene can include the sequences ACTGCTGAAAAGAGAGAGT (SEQ ID NO:26), GAAATAAAAGATTGG (SEQ ID NO:30), TTTTGGGTGTCTAAG (SEQ ID NO:34), CAAACCAAGTGAGAA (SEQ ID NO:38), AGAGGCAGAAAAAAACT (SEQ ID NO:42), TTTTTTTACTGCTGAAAAGAGAGAGT (SEQ ID NO:57), TTTTTTTTTTGCACCTACTGCTGAA (SEQ ID NO:134), TTTTTTTTTACCTACTGCTGAAAAG (SEQ ID NO:135), TTTTTTTTTGCTGAAAAGAGAGAGT (SEQ ID NO:136), and TTTTTTTTTCCTACTGCTGAAAAGAGA (SEQ ID NO:137), TTTTTTTTTTTTGAAATAAAAGATTGG (SEQ ID NO:58), TTTTTTTTTTAAATAGCAGAAATAAAAG (SEQ ID NO:120), TTTTTTTTTTTGAAATAAAAGATTGGAA (SEQ ID NO:121), TTTTTTTTTTTTAGAAATAAAAGATTG (SEQ ID NO:122), TTTTTTTTTTTTGAAATAAATGAATGG (SEQ ID NO: 123), TTTTTTTTTTTTCAGAAATAAAAGATT (SEQ ID NO: 124), TTTTTTTTTTTTGGGTGTCTAAG (SEQ ID NO:59), TTTTTTTTTATTTGGGTGTCTAAG (SEQ ID NO: 125), TTTTTTGGGTGTCTAAGCACCACT (SEQ ID NO: 126), TTTTTTTTTCTAAGCACCACTTTT (SEQ ID NO: 127), TTTTTTTTTTTTTGGGTGTCTAA (SEQ ID NO: 128), TTTTTTTTTGGTGTCTAAGCACCA (SEQ ID NO: 129), TTTTTTTTTACAAACCAAGTGAGAA (SEQ ID NO:60), TTTTTTTTAAGTGAGAAGTACCTAA (SEQ ID NO: 130), TTTTTTTTTTTCAAACCAAGTGAG (SEQ ID NO:131), TTTTTTTTTTACCAAGTGAGAAGTA (SEQ ID NO:132), TTTTTTTTAGCTCAAACCAAGTGAG (SEQ ID NO:133), TTTTTTTTTTAGAGGCAGAAAAAAACT (SEQ ID NO:61), TTTTTTTTTTGCAGAAAAAACTATTG (SEQ ID NO:138), TTTTTTTTTTTCAGAAAAAACTATTGATT (SEQ ID NO:139), TTTTTTTAGAAAGAGGCAGAAAAAAACT (SEQ ID NO:140), and/or TTTTTTTTTTTGAGGCAGAAAAAAACTA (SEQ ID NO: 141) (probes comprising these sequences exclusive of the 5' adenine and/or thymines are also contemplated). In some embodiments, each probe is coupled to a microcarrier of the present disclosure with a unique identifier.

A kit or article of manufacture of the present disclosure suitable for detecting mutations in a KRAS gene (e.g., KRAS mutations encoding G12D, G12V, G12S, and G13D mutated KRAS proteins) can optionally include: four probes of the present disclosure specific for mutation(s) in a KRAS gene, wherein each of the four probes is coupled to a microcarrier with a different identifier; a primer pair comprising the sequences GTACTGGTGGAGTATTTGA- TAGTG (SEQ ID NO:1) and ATCGT-CAAGGCACTCTTGCCTAC (SEQ ID NO:2); and/or a blocking nucleic acid comprising the sequence of TACGC-CACCAGCT(invdT)$_n$, wherein n is 1, 2, or 3 (SEQ ID NO:3), TTGGAGCTGGTGGCGTAinvdTinvdTinvdT (SEQ ID NO: 142), GCTGGTGGCGTAGGCAinvdTinvdT-invdT (SEQ ID NO:143), GCTGGTGGCGTAGGCinvdT-invdTinvdT (SEQ ID NO: 144), or TTG-GAGCTGGTGGCGTinvdTinvdTinvdT (SEQ ID NO: 145), with italicized nucleic acids representing locked nucleic acids. In some embodiments, the kit comprises: four probes comprising the sequences GGAGCTGATGG (SEQ ID NO:4), GGAGCTGTTGG (SEQ ID NO:5), TGGAGCTAGTGG (SEQ ID NO:6), and TGGAGCTGGTGACGT (SEQ ID NO:7), respectively; four probes comprising: a first probe comprising a sequence selected from GGAGCTGATGG (SEQ ID NO:4), AGCT-GATGGCGTA (SEQ ID NO:178), TGGAGCTGATGGCG (SEQ ID NO:179), TGGAGCTGATGG (SEQ ID NO:180), or GCTGATGGCGTA (SEQ ID NO: 181); a second probe comprising a sequence selected from GGAGCTGTTGG (SEQ ID NO:5), TGGAGCTGTTGGTGGC (SEQ ID NO:182), GGAGCTGTTGGTG (SEQ ID NO:183), TGGAGCTGTTGGT (SEQ ID NO:184), or TGGAGCTGTaGGTGG (SEQ ID NO: 185); a third probe comprising a sequence selected from TTG-GAGCTAGTGGCGTA (SEQ ID NO:186), GCTAGTGGCGTAGGC (SEQ ID NO:187), AGCTAGTGGCGT (SEQ ID NO:188), GTTG-GAGCTAGTGG (SEQ ID NO:189), or GGAGCTAGTGG (SEQ ID NO:190); and a fourth probe comprising a sequence selected from GGTGACGTAGGCAA (SEQ ID NO:191), TGACGTAGGCAAGAG (SEQ ID NO: 192), GCTGGTGACGTAGG (SEQ ID NO:193), AGCTGGTGACGTAG (SEQ ID NO:194), or GGAGCTGGTGACGT (SEQ ID NO: 195); respectively; or four probes comprising: a first probe comprising a sequence selected from TTTTTTTTTTTTAAGGAGCTGATGG (SEQ ID NO:47), TTTTTTTTTTTTAGCTGATGGCGTA (SEQ ID NO:74), TTTTTTTTTTATGGAGCTGATGGCG (SEQ ID NO:75), TTTTTTTTTTTATGGAGCTGATGG (SEQ ID NO:76), and TTTTTTTTTTTTTGCT-GATGGCGTA (SEQ ID NO:77); a second probe comprising a sequence selected from TTTTTTTTTT-TAAGGAGCTGTTGG (SEQ ID NO:48), TTTTTTTTATG-GAGCTGTTGGTGGC (SEQ ID NO:78), TTTTTTTTT-TAAGGAGCTGTTGGTG (SEQ ID NO:79), TTTTTTTTTTTATGGAGCTGTTGGT (SEQ ID NO:80), and TTTTTTTTTATGGAGCTGTAGGTGG (SEQ ID NO:81); a third probe comprising a sequence selected from TTTTTTTTTTTATGGAGCTAGTGG (SEQ ID NO:49), TTTTTTTTTTGGAGCTAGTGGCGTA (SEQ ID NO:82), TTTTTAATTTGCTAGTGGCGTAGGC (SEQ ID NO:83), TTTTTTTTTATTTAGCTAGTGGCGT (SEQ ID NO:84), TTTTTTTTTTTGTTGGAGCTAGTGG (SEQ ID NO:85), and TTTTTTTTTTTTAAGGAGCTAGTGG (SEQ ID NO:86); and TTTTTTTTTATGGAGCTGGTGACGT (SEQ ID NO:50), respectively (probes comprising these sequences exclusive of the 5' adenine and/or thymines are also contemplated). The kit may optionally include any of the elements described infra for detecting mutations in a BRAF, CTNNB1, and/or APC gene. In some embodiments, each probe is coupled to a microcarrier of the present disclosure with a unique identifier.

A kit or article of manufacture of the present disclosure suitable for detecting mutations in a BRAF gene (e.g., two or more BRAF mutations encoding a V600E mutated BRAF protein) can optionally include: two probes of the present disclosure specific for mutation(s) in a BRAF gene, wherein each of the two probes is coupled to a microcarrier with a different identifier; a primer pair comprising the sequences GGACCCACTCCATCGAGATTT (SEQ ID NO:8) and CAGATATATTTCTTCATGAAGACCTCACAGTAA (SEQ ID NO:9); and/or a blocking nucleic acid comprising the sequence of GAGATTTCACTGTAGC(invdT)$_n$, wherein n is 1, 2, or 3 (SEQ ID NO:10), GAGATTT-CACTGTAGCinvdTinvdTinvdT (SEQ ID NO:146), GAGATTTCACTGTAGC invdTinvdTinvdT (SEQ ID NO: 147), GAGATTTCACTGTAGCinvdTinvdTinvdT (SEQ ID NO: 148), or GAGATTTCACTGTAGCinvdTinvdTinvdT (SEQ ID NO: 149), with italicized nucleic acids representing locked nucleic acids. In some embodiments, the kit comprises: two probes comprising the sequences TCTAGC-TACAGAGAAAT (SEQ ID NO: 11) and GTCTAGCTA-CAGAAAAAT (SEQ ID NO: 12), respectively; two probes comprising the sequences TTTTTTAATTTCTAGCTA-CAGAGAAAT (SEQ ID NO:51) and TTTTTT-TATGTCTAGCTACAGAAAAAT (SEQ ID NO:52), respectively; (1) a first probe comprising a sequence selected from TACAGAGAAATCTCGAT (SEQ ID NO: 196), TACAGAGAAATCTC (SEQ ID NO:197), CTAGCTA-CAGAGAAAT (SEQ ID NO:198), CTAGCTA-CAGAGAAA (SEQ ID NO:199), and TCTAGCTACAGAG (SEQ ID NO:200); and (2) a second probe comprising a sequence selected from GTCTAGCTACAGAAAAATC (SEQ ID NO:201), GTCTAGCTACAGAAAAAT (SEQ ID NO:12), TAGCTACAGAAAAA (SEQ ID NO:202), TCTAGCTACAGAAAAAT (SEQ ID NO:203), and TCTAGCTACAGAAAAATC (SEQ ID NO:204), respectively; or (1) a first probe comprising a sequence selected from TTTTTTAATTTCTAGCTACAGAGAAAT (SEQ ID NO:51), TTTTTTTTTATACAGAGAAATCTCGAT (SEQ ID NO:92), TTTTTTTTTAATTTACAGAGAAATCTC (SEQ ID NO:93), TTTTTTAATTACTAGCTA-CAGAGAAAT (SEQ ID NO:94), TTTTTTTAAT-TACTAGCTACAGAGAAA (SEQ ID NO:95), and TTTTTTTTTTAATTTCTAGCTACAGAG (SEQ ID NO:96); and (2) a second probe comprising a sequence selected from TTTTTTTATGTCTAGCTACAGAAAAAT (SEQ ID NO:52), TTTTATGTCTAGCTACAGAAAAATC (SEQ ID NO:97), TTTTTTTTATTTTAGCTA-CAGAAAAA (SEQ ID NO:98), TTTTTTTATTTCTAGC-TACAGAAAAAT (SEQ ID NO:99), and TTTTTTTTAT-TCTAGCTACAGAAAAATC (SEQ ID NO: 100), respectively (probes comprising these sequences exclusive of the 5' adenine and/or thymines are also contemplated). The kit may optionally include any of the elements described supra for detecting mutations in a KRAS gene, and/or any of the elements described infra for detecting mutations in a CTNNB1 and/or APC gene. In some embodiments, each probe is coupled to a microcarrier of the present disclosure with a unique identifier.

A kit or article of manufacture of the present disclosure suitable for detecting mutations in a CTNNB1 gene (e.g., CTNNB1 mutations encoding T41A, T41I, S45F, and S45P mutated CTNNB1 proteins) can optionally include: four probes of the present disclosure specific for mutation(s) in a CTNNB1 gene, wherein each of the four probes is coupled to a microcarrier with a different identifier; a first primer pair comprising the sequences GGAATCCATTCTGGTGC-CACT (SEQ ID NO:13) and AGAAAATCCCTGTTCC-CACTCATA (SEQ ID NO: 14), and a second primer pair comprising the sequences GGTGCCACTAC-CACAGCTCCT (SEQ ID NO:18) and TCTCAAAACTG- CATTCTGACTTTCA (SEQ ID NO: 19); and/or a first blocking nucleic acid comprising the sequence of GCCAC-TACCACAGCT(invdT)$_n$, wherein n is 1, 2, or 3 (SEQ ID NO:15), TGCCACTACCACAGinvdTinvdTinvdT (SEQ ID NO:150), CACTACCACAGCTCCinvdTinvdTinvdT (SEQ ID NO: 151), GCCACTACCACAGCTinvdTinvdTinvdT (SEQ ID NO:152), or GCCACTACCACAGCTinvdTinvdT-invdT (SEQ ID NO: 153), and a second blocking nucleic acid comprising the sequence of GCTCCTTCTCTGAGT-invdTinvdTinvdT (SEQ ID NO:20), TCCTTCTCTGAGTG-GinvdTinvdTinvdT (SEQ ID NO:174), GCTCCTTCTCT-GAGTinvdTinvdTinvdT (SEQ ID NO: 175), TCCTTCTCTGAGTGGinvdTinvdTinvdT (SEQ ID NO: 176), or GCTCCTTCTCTGAGTinvdTinvdTinvdT (SEQ ID NO: 177), with italicized nucleic acids representing locked nucleic acids. In some embodiments, the kit comprises: four probes comprising the sequences AGGAGCTGTGGCAG (SEQ ID NO: 16), GGAGCTGTGATA (SEQ ID NO:17), TTTACCACTCAGAAAAG (SEQ ID NO:21), and TAC-CACTCAGAGGAG (SEQ ID NO:22), respectively; four probes comprising: a first probe comprising a sequence selected from AGGAGCTGTGGCAGT (SEQ ID NO:205), AGGAGCTGTGGCAGTG (SEQ ID NO:206), GCTGTGGCAGTGGC (SEQ ID NO:207), GCTGTGGCAGTGGCA (SEQ ID NO:208), and AAGGAGCTGTGGCAG (SEQ ID NO:209); a second probe comprising a sequence selected from GGAGCTGT-GATAGTGG (SEQ ID NO:210), GAGCTGTGA-TAGTGGC (SEQ ID NO:211), AGCTGTGATAGTGGCA (SEQ ID NO:212), AGAAGGAGCTGTGATA (SEQ ID NO:213), and GGAGCTGTGAT (SEQ ID NO:214); a third probe comprising a sequence selected from ACTCAGAAAAGGAGCT (SEQ ID NO:215), TAC-CACTCAGAAAAGGA (SEQ ID NO:216), TTTAC-CACTCAGAAAAGGAG (SEQ ID NO:217), TTAC-CACTCAGAAAAG (SEQ ID NO:218), and CAGAAAAGGAGCTGTG (SEQ ID NO:219); and (4) a fourth probe comprising a sequence selected from ACTCAGAGGAGGAGC (SEQ ID NO:220), TTAC-CACTCAGAGGA (SEQ ID NO:221), TTAC-CACTCAGAGGAGG (SEQ ID NO:222), TTAACACTCAGAGGAG (SEQ ID NO:223), and TTAC-CAATCAGAGGAGG (SEQ ID NO:224); or four probes comprising: a first probe comprising a sequence selected from TTTTTTTTTTTAGGAGCTGTGGCAG (SEQ ID NO:53), TTTTTTTTTTTAGGAGCTGTGGCAGTG (SEQ ID NO:101), TTTTTTTTTTTAGCTGTGGCAGTGGC (SEQ ID NO: 102), TTTTTTTTTTTGCTGTGGCAGTGGCA (SEQ ID NO: 103), and TTTTTTTTTTAAGGAGCTGTGGCAG (SEQ ID NO: 104); a second probe comprising a sequence selected from TTTTTTTTTTTTTGGAGCTGTGATA (SEQ ID NO:54), TTTTTTTTTGGAGCTGTGATAGTGG (SEQ ID NO: 105), TTTTTTTTTGAGCTGTGATAGTGGC (SEQ ID NO: 106), TTTTTTTTAGCTGTGA-TAGTGGCA (SEQ ID NO: 107), TTTTTTTT-TAGAAGGAGCTGTGATA (SEQ ID NO: 108), and TTTTTTTTTTTTTGGAGCTGTGAT (SEQ ID NO:109); a third probe comprising a sequence selected from the group consisting of TTTTTTTTTTTACCACTCAGAAAAG (SEQ ID NO:55), TTTAATTTTACTCAGAAAAGGAGCT (SEQ ID NO:110), TTTTTTAATAC-CACTCAGAAAAGGA (SEQ ID NO:111), TTTTTTT-TACCACTCAGAAAAGGAG (SEQ ID NO:112), TTTTTTTTATTACCACTCAGAAAAG (SEQ ID NO:113), and TTTTTTTTTCAGAAAAGGAGCTGTG (SEQ ID NO: 114); and (4) a fourth probe comprising a sequence selected from the group consisting of TTTTTTTTTAATAC-CACTCAGAGGAG (SEQ ID NO:56), TTTTTTTT-TAAAACTCAGAGGAGGAGC (SEQ ID NO:115), TTTTTTTTTTTATTACCACTCAGAGGA (SEQ ID NO: 116), TTTTTTTTTATTACCACTCAGAGGAGG (SEQ ID NO:117), TTTTTTTTTTATTAACACTCAGAGGAG (SEQ ID NO:118), and TTTTTTTTTATTACCAATCAGAG-GAGG (SEQ ID NO: 119), wherein each of the four probes is coupled to a microcarrier with a different identifier (probes comprising these sequences exclusive of the 5' adenine and/or thymines are also contemplated). The kit may optionally include any of the elements described supra for detecting mutations in a KRAS and/or BRAF gene, and/or any of the elements described infra for detecting mutations in an APC gene. In some embodiments, each probe is coupled to a microcarrier of the present disclosure with a unique identifier.

A kit or article of manufacture of the present disclosure suitable for detecting mutations in an APC gene (e.g., APC mutations encoding Q1367*, R1450*, E1309 frameshift, S1465 frameshift, and T1556 frameshift mutated APC proteins) can optionally include: five probes of the present disclosure specific for mutation(s) in a APC gene, wherein each of the five probes is coupled to a microcarrier with a different identifier; a first primer pair comprising the sequences TAAAAATAAAGCACCTACTGCTGAAA (SEQ ID NO:23) and AGCTTGCTTAGGTC-CACTCTCTCT (SEQ ID NO:24); a second primer pair comprising the sequences TAGGATGTAATCA-GACGACACAGGA (SEQ ID NO:27) and CAGCTGACCTAGTTCCAATCTTTTA (SEQ ID NO:28); a third primer pair comprising the sequences TCTCCCTC-CAAAAGTGGTGCT (SEQ ID NO:31) and TGGCAATCGAACGACTCTCAA (SEQ ID NO:32); a fourth primer pair comprising the sequences GCAGAAGTAAAACACCTCCACCA (SEQ ID NO:35) and GGTGCTTTATTTTTAGGTACTTC (SEQ ID NO:36), with italicized nucleic acids representing locked nucleic acids; and a fifth primer pair comprising the sequences CAGGAAAATGACAATGGGAATG (SEQ ID NO:39) and ATCTAATAGGTCCTTTTCAGAATCAAATAG (SEQ ID NO:40); and/or a first blocking nucleic acid comprising the sequence of CCACTCTCTCTCTTTTCAGCinvdTinvdT-invdT (SEQ ID NO:25), TAGGTC-CACTCTCTCTCTTTCAGCAinvdTinvdTinvdT (SEQ ID NO: 166), TAGGTCCACTCTCTCTCTTTTCAGCAinvdT-invdTinvdT (SEQ ID NO: 167), CCACTCTCTCTCTTTTCAGC invdTinvdTinvdT (SEQ ID NO:168), or TAGGTCCACTCTCTCTCTTTCAGCA invdTinvdTinvdT (SEQ ID NO: 169), a second blocking nucleic acid comprising the sequence of CTTTTCTTT-TAITTCTGCinvdTinvdTinvdT (SEQ ID NO:29), CTTTCTTTTATTCTGCinvdTinvdTinvdT (SEQ ID NO: 154), CTTTTCTTTTATTTCTGCinvdTinvdTinvdT (SEQ ID NO:155), CTTTCTTTTATTCTGCinvdTinvdTinvdT (SEQ ID NO:156), or CTTTCTTTTATTTCTGCinvdT-invdTinvdT (SEQ ID NO:157), a third blocking nucleic acid comprising the sequence of GTGCTCAGACACCinvdT-invdTinvdT (SEQ ID NO:33), GTGCTCAGACACCinvdT-invdTinvdT (SEQ ID NO:158), AGTGGTGCTCA-GACACCCAinvdTinvdTinvdT (SEQ ID NO:159), AGTGGTGCTCAGACACCCAinvdTinvdTinvdT (SEQ ID NO: 160), or AGTGGTGCTCAGACACCCAinvdTinvdT-invdT (SEQ ID NO:161), a fourth blocking nucleic acid comprising the sequence of CTTCTCGCTTGGTTinvdT-invdTinvdT (SEQ ID NO:37), GTACTTCTCGCTTGGT-invdTinvdTinvdT (SEQ ID NO:162), CTTCTCGCTTGGT- TinvdTinvdTinvdT (SEQ ID NO:163), GTACTTCTCGCTTGGTinvdTinvdTinvdT (SEQ ID NO:164), or GTACTTCTCGCTTGGTinvdTinvdTinvdT (SEQ ID NO:165), and a fifth blocking nucleic acid comprising the sequence of CAATAGTTTTTTCTGCCinvdT-invdTinvdT (SEQ ID NO:41), GAAT-CAATAGTTTTTTCTGCCTC invdTinvdTinvdT (SEQ ID NO: 170), TCAGAATCAATAGTTTTTTCTG invdTinvdT-invdT (SEQ ID NO:171), GAATCAATAGATTT-TACTGCCTC invdTinvdTinvdT (SEQ ID NO: 172), or AATCAATAGTTTTTTCTGCCTC invdTinvdTinvdT (SEQ ID NO: 173), with italicized nucleic acids representing locked nucleic acids. In some embodiments, the kit comprises: five probes comprising the sequences ACTGCT-GAAAAGAGAGAGT (SEQ ID NO:26), GAAATAAAA-GATTGG (SEQ ID NO:30), TTTTGGGTGTCTAAG (SEQ ID NO:34), CAAACCAAGTGAGAA (SEQ ID NO:38), and AGAGGCAGAAAAAAACT (SEQ ID NO:42), respectively; five probes comprising: (1) a first probe comprising a sequence selected from AAATAGCAGAAATAAAAG (SEQ ID NO:225), GAAATAAAAGATTGGAA (SEQ ID NO:226), AGAAATAAAAGATTG (SEQ ID NO:227), GAAATAAATGAATGG (SEQ ID NO:228), and CAGAAATAAAAGATT (SEQ ID NO:229); (2) a second probe comprising a sequence selected from TTTGGGTGTCTAAG (SEQ ID NO:230), GGGTGTCTAAGCACCACT (SEQ ID NO:231), CTAAGCACCACTTTT (SEQ ID NO:232), TTTTGGGTGTCTAA (SEQ ID NO:233), and GGTGTCTAAGCACCA (SEQ ID NO:234); (3) a third probe comprising a sequence selected from AAGT-GAGAAGTACCTAA (SEQ ID NO:235), CAAACCAAGT-GAGAA (SEQ ID NO:38), TCAAACCAAGTGAG (SEQ ID NO:236), ACCAAGTGAGAAGTA (SEQ ID NO:237), and AGCTCAAACCAAGTGAG (SEQ ID NO:238); (4) a fourth probe comprising a sequence selected from GCACC-TACTGCTGAA (SEQ ID NO:239), ACCTACTGCT-GAAAAG (SEQ ID NO:240), TGCT-GAAAAGAGAGAGT (SEQ ID NO:241), ACTGCTGAAAAGAGAGAGT (SEQ ID NO:26), and CCTACTGCTGAAAAGAGA (SEQ ID NO:242); and (5) a fifth probe comprising a sequence selected from GCAGAAAAAAACTATTG (SEQ ID NO:243), AGAGGCAGAAAAAAACT (SEQ ID NO:42), CAGAAAAAAACTATTGATT (SEQ ID NO:244), AGAAAGAGGCAGAAAAAAACT (SEQ ID NO:245), and GAGGCAGAAAAAAACTA (SEQ ID NO:246), respectively; or five probes comprising: (1) a first probe comprising a sequence selected from the group consisting of TTTTTTTTTTTTTGAAATAAAAGATTGG (SEQ ID NO:58), TTTTTTTTTTAAATAGCAGAAATAAAAG (SEQ ID NO:120), TTTTTTTTTTTGAAATAAAAGAT-TGGAA (SEQ ID NO:121), TTTTTTTTTTT-TAGAAATAAAAGATTG (SEQ ID NO:122), TTTTTTTTTTTTTGAAATAAATGAATGG (SEQ ID NO: 123), and TTTTTTTTTTTTTCAGAAATAAAAGATT (SEQ ID NO: 124); (2) a second probe comprising a sequence selected from the group consisting of TTTTTTTTTTTTTGGGTGTCTAAG (SEQ ID NO:59), TTTTTTTTTATTTGGGTGTCTAAG (SEQ ID NO: 125), TTTTTTGGGTGTCTAAGCACCACT (SEQ ID NO:126), TTTTTTTTTCTAAGCACCACTTTT (SEQ ID NO: 127), TTTTTTTTTTTTTGGGTGTCTAA (SEQ ID NO:128), and TTTTTTTTTGGTGTCTAAGCACCA (SEQ ID NO:129); (3) a third probe comprising a sequence selected from the group consisting of TTTTTTTTTACAAAC-CAAGTGAGAA (SEQ ID NO:60), TTTTTTTTAAGT-GAGAAGTACCTAA (SEQ ID NO: 130), TTTTTTTTTTTTCAAACCAAGTGAG (SEQ ID NO:131), TTTTTTTTTTACCAAGTGAGAAGTA (SEQ ID NO:132), and TTTTTTTTAGCTCAAACCAAGTGAG (SEQ ID NO:133); (4) a fourth probe comprising a sequence selected from the group consisting of TTTTTTTTACTGCT-GAAAAGAGAGAGT (SEQ ID NO:57), TTTTTTTTTTGCACCTACTGCTGAA (SEQ ID NO: 134), TTTTTTTTTACCTACTGCTGAAAAG (SEQ ID NO:135), TTTTTTTTTGCTGAAAAGAGAGAGT (SEQ ID NO:136), and TTTTTTTTTCCTACTGCT-GAAAAGAGA (SEQ ID NO:137); and (5) a fifth probe comprising a sequence selected from the group consisting of TTTTTTTTTTAGAGGCAGAAAAAAACT (SEQ ID NO:61), TTTTTTTTTTGCAGAAAAAAACTATTG (SEQ ID NO:138), TTTTTTTTTTCAGAAAAAAACTATT-GATT (SEQ ID NO:139), TTTTTT-TAGAAAGAGGCAGAAAAAAACT (SEQ ID NO:140), and TTTTTTTTTTTGAGGCAGAAAAAAACTA (SEQ ID NO:141), respectively; wherein each of the five probes is coupled to a microcarrier with a different identifier (probes comprising these sequences exclusive of the 5' adenine and/or thymines are also contemplated). The kit may optionally include any of the elements described supra for detecting mutations in a KRAS, BRAF, and/or CTNNB1 gene. In some embodiments, each probe is coupled to a microcarrier of the present disclosure with a unique identifier. In some embodiments of any of the above embodiments, combinations of primers, probes, and/or blocking nucleic acids for 1, 2, 3, 4, 5, 6, 7, 8, 9, 10, 11, 12, 13, 14, or 15 mutations described herein can be combined in any order or combination.

In some embodiments, the kit comprises a microcarrier with an identifier corresponding to a positive control and to which a probe specific for a positive control gene sequence is coupled, and a primer pair specific for the positive control DNA sequence. For example, in some embodiments, the positive control DNA sequence comprises a sequence of a human leukocyte antigen (HLA) gene, the primer pair specific for the positive control DNA sequence comprises the sequences TGAGTGTTACTTCTTCCCACACTC (SEQ ID NO:43) and ATTGCTTTTGCGCAATCCCT (SEQ ID NO:44), and/or the probe specific for the positive control gene sequence comprises the sequence TTTTTTTTTTTTG-GAGACGGTCTG (SEQ ID NO:45). In some embodiments, the positive control DNA sequence comprises a sequence of a human glyceraldehyde 3-phosphate dehydrogenase (GAPDH) gene, the primer pair specific for the positive control DNA sequence comprises the sequences AATCC-CATCACCATCTTCCA (SEQ ID NO:71) and TGGACTC-CACGACGTACTCA (SEQ ID NO:72), and/or the probe specific for the positive control gene sequence comprises the sequence CTGTCTTCCACTCACTCC (SEQ ID NO:73). In some embodiments, each probe is coupled to a microcarrier of the present disclosure with a unique identifier.

In some embodiments, the kit comprises a microcarrier of the present disclosure with an identifier corresponding to a negative control, e.g., with a probe that does not hybridize with the amplified DNA. In some embodiments, the microcarrier with the identifier corresponding to the negative control comprises a probe comprising the sequence AATATAATATATTAT (SEQ ID NO:46).

In some embodiments, the kit comprises a primer pair, with one or both primers of the pair labeled with a detection reagent, e.g., as described supra. In some embodiments, the detection reagent comprises a fluorescent detection reagent. In some embodiments, the detection reagent comprises biotin, and the kit comprises streptavidin conjugated to a signal-emitting entity (e.g., streptavidin conjugated to phycoerythrin).

In some embodiments, the kits or articles of manufacture may further include one or more detection reagents of the present disclosure for detecting an amount of the first analyte bound to the first microcarrier and an amount of the second analyte bound to the second microcarrier. In some embodiments, the detection reagent for the first analyte may be the same as the detection reagent for the second analyte. In other embodiments, the detection reagent for the first analyte may be different from the detection reagent for the second analyte.

In some embodiments, the kits or articles of manufacture may further include instructions for using the kit or articles of manufacture to detect one or more DNA mutations of the present disclosure. These instructions may be for using the kit or article of manufacture, e.g., in any of the methods described herein.

In some embodiments, the kits or articles of manufacture may further include one or more detection reagents (e.g., as described above, such as streptavidin conjugated to PE), along with any instructions or reagents suitable for coupling a detection reagent to one or more analytes, or for coupling a detection reagent to one or more macromolecules that recognize an analyte. The kits or articles of manufacture may further include any additional components for using the microcarriers in an assay (e.g., a multiplex assay), including without limitation a plate (e.g., a 96-well or other similar microplate), dish, microscope slide, or other suitable assay container; a non-transitory computer-readable storage medium (e.g., containing software and/or other instructions for analog shape or code recognition); washing agents; buffers; plate sealers; mixing containers; diluents or storage solutions; and the like.

VI. Methods of Making Encoded Microcarriers

Certain aspects of the present disclosure relate to methods for making an encoded microcarrier, e.g., a microcarrier described herein. The methods for making an encoded microcarrier may include one or more of the microcarrier features or aspects described herein, e.g., in section IV above.

In some embodiments, the methods include depositing a substantially transparent polymer layer, where the substantially transparent polymer layer has a first surface and a second surface, the first and the second surfaces being parallel to each other. In some embodiments, the first and the second surfaces that are parallel to each other may be the top and bottom surface of a single layer. Any suitable substantially transparent polymer known in the art or described herein may be used. In some embodiments, the substantially transparent polymer layer is deposited using spin coating.

In some embodiments, the substantially transparent polymer layer may be deposited on a substrate. Suitable substrates may include substrates used in standard semiconductor and/or micro-electro-mechanical systems (MEMS) fabrication techniques. In some embodiments, the substrate may comprise glass, silicon, quartz, plastic, polyethylene terephthalate (PET), an indium tin oxide (ITO) coating, or the like.

In some embodiments, a sacrificial layer may be deposited on the substrate, e.g., a substrate as described above. In some embodiments, the sacrificial layer may be made of a polymer, including without limitation polyvinyl alcohol (PVA) or OmniCoat™ (MicroChem; Newton, Mass.). Sacrificial layers may be applied, used, and dissolved or stripped, e.g., according to manufacturer's instructions.

In some embodiments, a substantially transparent polymer layer of the present disclosure is deposited on a sacrificial layer. To generate a planar microcarrier surface using a substantially transparent polymer layer, the substantially transparent polymer layer may be deposited onto a planar sacrificial layer. To generate a microcarrier surface with one or more columns projecting therefrom, a sacrificial layer (e.g., one deposited onto a substrate) may be patterned with one or more column-shaped holes or void areas, for example by using a standard lithographic process. In some embodiments, a substantially transparent polymer layer may be deposited over the sacrificial layer and optional substrate such that the layer is deposited in the one or more column-shaped holes or void areas. In some embodiments, another substantially transparent polymer layer may then be deposited over the sacrificial layer and the one or more column-shaped holes or void areas filled with the first substantially transparent polymer layer. In other embodiments (e.g., as illustrated at block 1540 of FIG. 15B), a second substantially transparent polymer layer is deposited or baked onto the first substantially transparent polymer layer, then patterned to generate one or more columns projecting from the first substantially transparent polymer layer.

In some embodiments, a magnetic, substantially non-transparent layer of the present disclosure is deposited on the first surface of the substantially transparent polymer layer. In some embodiments, the magnetic, substantially non-transparent layer is deposited by sputtering. The magnetic, substantially non-transparent layer may be made of, e.g., any of the magnetic materials described herein. For example, in some embodiments, the magnetic, substantially non-transparent layer comprises nickel (e.g., elemental nickel, or an alloy thereof).

In some embodiments, the magnetic, substantially non-transparent layer may be etched to remove a portion of the magnetic, substantially non-transparent layer that is deposited over a center portion of the substantially transparent polymer layer. The magnetic, substantially non-transparent layer may be etched by any means known in the art. For example, in some embodiments, the magnetic, substantially non-transparent layer is etched by conventional wet etching. Exemplary dimensions, shapes, and optional asymmetries for a magnetic, substantially non-transparent layer are provided supra. In some embodiments, the magnetic, substantially non-transparent layer is patterned into a ring shape of the present disclosure (e.g., one or more rings, with at least one having one or more discontinuities, enclosing the center portion of the substantially transparent polymer layer, as shown in FIG. 4B). In some embodiments, the magnetic, substantially non-transparent layer is patterned into a gear shape of the present disclosure. In some embodiments, the substantially non-transparent polymer layer is deposited over the second substantially transparent polymer layer and etched (e.g., using a standard lithographic or photolithographic process) into the desired two-dimensional shape.

In some embodiments, a second substantially transparent polymer layer of the present disclosure is deposited over the magnetic, substantially non-transparent layer. In some embodiments, the second substantially transparent polymer layer has a first surface and a second surface that are parallel to each other (e.g., the top and bottom surface of a single layer). In some embodiments, the second surface is affixed to the magnetic, substantially non-transparent layer. In some embodiments, the second substantially transparent polymer layer is aligned with the first substantially transparent polymer layer and has a center portion that is aligned with the center portion of the substantially transparent polymer layer. Exemplary dimensions for the center portion of a substantially transparent polymer layer are provided supra.

In some embodiments, a substantially non-transparent polymer layer of the present disclosure is deposited on the first surface of the second substantially transparent polymer layer. In some embodiments, the substantially non-transparent polymer layer encloses the center portions of the first and the second substantially transparent polymer layers. In some embodiments, the substantially non-transparent polymer layer comprises a two-dimensional shape representing an analog code. Any of the two-dimensional shapes described or exemplified herein may be used, e.g., a gear shape of the present disclosure. In some embodiments, the substantially non-transparent polymer layer is deposited over the second substantially transparent polymer layer and etched (e.g., using a standard lithographic process) into the desired two-dimensional shape.

In some embodiments, one or more columns may be deposited on the substantially transparent polymer, e.g., on the first surface of the second substantially transparent polymer layer at a portion not covered by the substantially non-transparent polymer layer. The one or more columns may be deposited as described herein, e.g., using a standard lithographic process.

In some embodiments that employ an optional sacrificial layer and/or substrate of the present disclosure, the sacrificial layer may be dissolved or stripped, and/or the substrate may be removed, using a solvent. A variety of solvents useful for fabrication (e.g., in standard semiconductor or MEMS fabrication processes, such as photoresist removal) are known in the art. In some embodiments, the solvent is a photoresist stripper solvent, such as a DMSO- or 1-methyl-2-pyrrolidon (NMP)-based solvent. In some embodiments, the solvent is an AZ® photoresist stripper, such as AZ® 300T (AZ Electronic Materials; Somerville, N.J.).

In some embodiments, the methods include depositing a sacrificial layer of the present disclosure on a substrate of the present disclosure. Sacrificial layers, substrates, and suitable deposition methods are described, e.g., as above.

In some embodiments, a substantially non-transparent polymer layer of the present disclosure is deposited on the sacrificial layer. In some embodiments, the substantially non-transparent polymer layer has a first and a second surface that are parallel to each other (e.g., the top and bottom surface of a single layer). In some embodiments, the second surface is affixed to the sacrificial layer.

In some embodiments, the outline of the substantially non-transparent polymer layer is shaped into a two-dimensional shape representing an analog code, e.g., as described herein. The substantially non-transparent polymer layer may be shaped by any method known in the art or described herein, e.g., using a standard lithographic process including but not limited to spin coating, soft baking, UV exposure, etching, and hard baking.

In some embodiments, the sacrificial layer may be dissolved or stripped, and/or the substrate may be removed, using a solvent, e.g., as described above.

In other embodiments, a magnetic layer comprising a magnetic material of the present disclosure is deposited on the sacrificial layer. Exemplary magnetic materials, magnetic layer shapes/dimensions, and deposition methods related thereto are provided supra. For example, in some embodiments, the magnetic layer may be shaped into one or more columns, e.g., as illustrated by column 906. In other embodiments, the magnetic layer may be between two non-transparent polymer layers, e.g., embedded as illustrated by magnetic layer 704. The magnetic material may contain, e.g., any of the magnetic materials described herein. For example, in some embodiments, the magnetic material comprises nickel (e.g., elemental nickel, or an alloy thereof).

In some embodiments, a substantially non-transparent polymer layer of the present disclosure is deposited on the magnetic layer. In some embodiments, the substantially non-transparent polymer layer has a first and a second surface that are parallel to each other (e.g., the top and bottom surface of a single layer). In some embodiments, a surface (e.g., the second surface) of the substantially non-transparent polymer layer is affixed to the magnetic layer.

In some embodiments, the outline of the substantially non-transparent polymer layer is shaped into a two-dimensional shape representing an analog code, e.g., as described above.

In some embodiments, the sacrificial layer may be dissolved or stripped, and/or the substrate may be removed, using a solvent, e.g., as described above.

Exemplary microcarrier shapes, dimensions, and optional features suitable for the methods described above are provided throughout the present disclosure. Exemplary processes 1000, 1100, 1200, and 1300 for making a variety of the microcarriers of the present disclosure are described below in reference to FIGS. 10-13C.

Process 1000 shown in FIG. 10 illustrates an exemplary workflow for manufacturing a single layer microcarrier, such as those described above. At block 1002, sacrificial layer 1006 is constructed on substrate 1004. In some embodiments, substrate 1004 may be a glass substrate. At block 1010, layer 1012 is deposited on sacrificial layer 1006. In some embodiments, layer 1012 is a non-transparent polymer layer. At block 1020, the perimeter of layer 1012 is shaped into a gear shape (as described above) using lithography to generate gear-shaped layer 1022. At block 1030, the entire structure (i.e., layer 1022, sacrificial layer 1006, and substrate 1004) is immersed in a solvent. This solvent treatment dissolves sacrificial layer 1006 and releases gear-shaped layer 1022 from substrate 1004, thereby generating microcarrier 1032. In some embodiments, microcarrier 1032 may be further modified, for example, by coupling a capture agent to one or both surfaces.

As described above, gear-shaped microcarriers may include optional elements such as magnetic components (e.g., columns and/or magnetic layers). Process 1100 shown in FIGS. 11A & 11B illustrates an exemplary workflow for manufacturing gear-shaped microcarriers with one or more magnetic components.

Figure 11A:
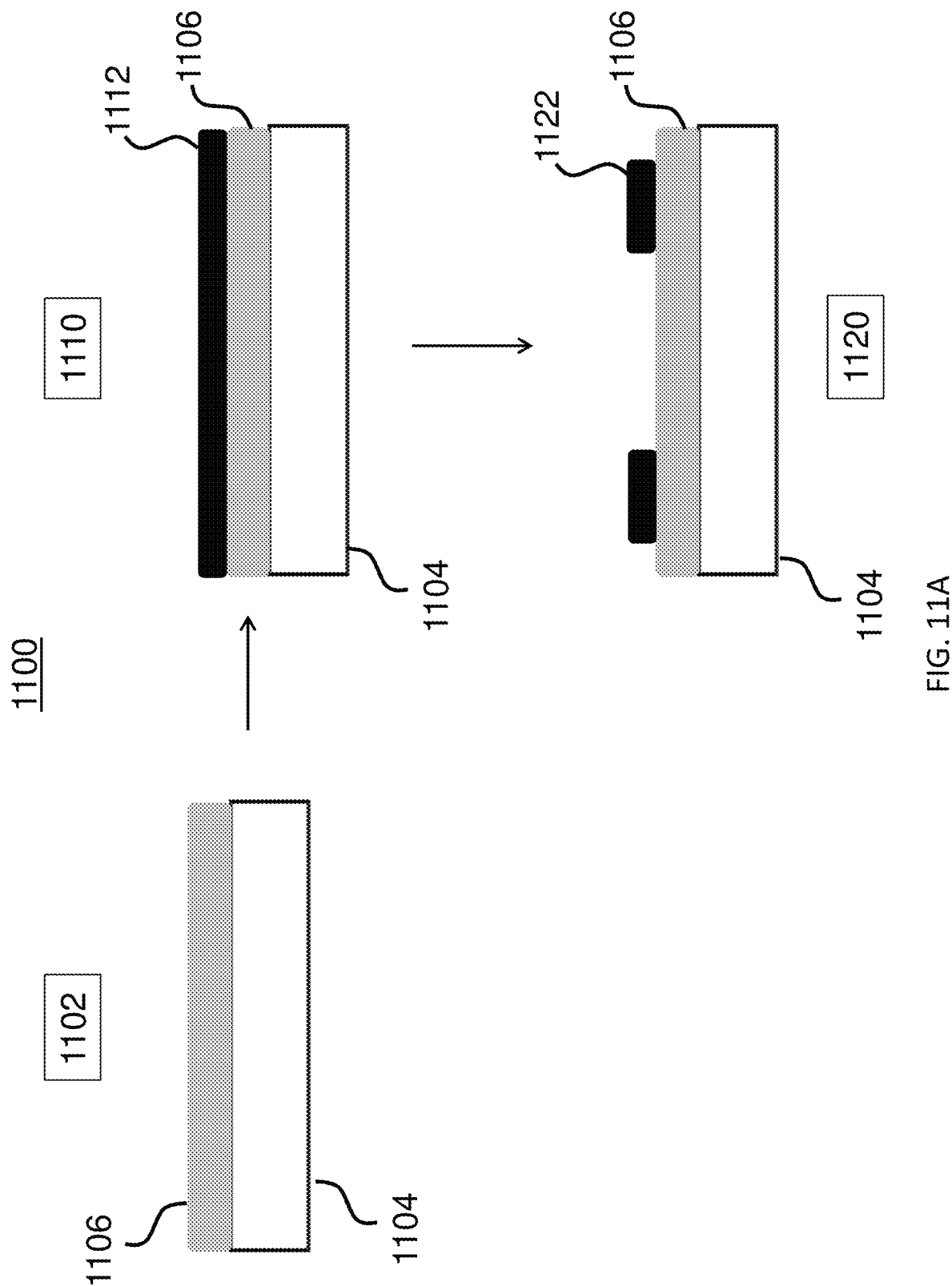
FIGS. 11A & 11B show a method for producing an exemplary microcarrier.

As shown in FIG. 11A, at block 1102, sacrificial layer 1106 is constructed on substrate 1104. In some embodiments, substrate 1104 may be a glass substrate. At block 1110, magnetic layer 1112 is deposited on sacrificial layer 1106. In some embodiments, magnetic layer 1112 includes nickel. At block 1120, magnetic layer 1112 is shaped by lithography into shaped magnetic layer 1122. Shaped magnetic layer 1122 may take any desired shape, e.g., it may be shaped into one or more columns, as illustrated in FIG. 9A with column 906.

Figure 11B:
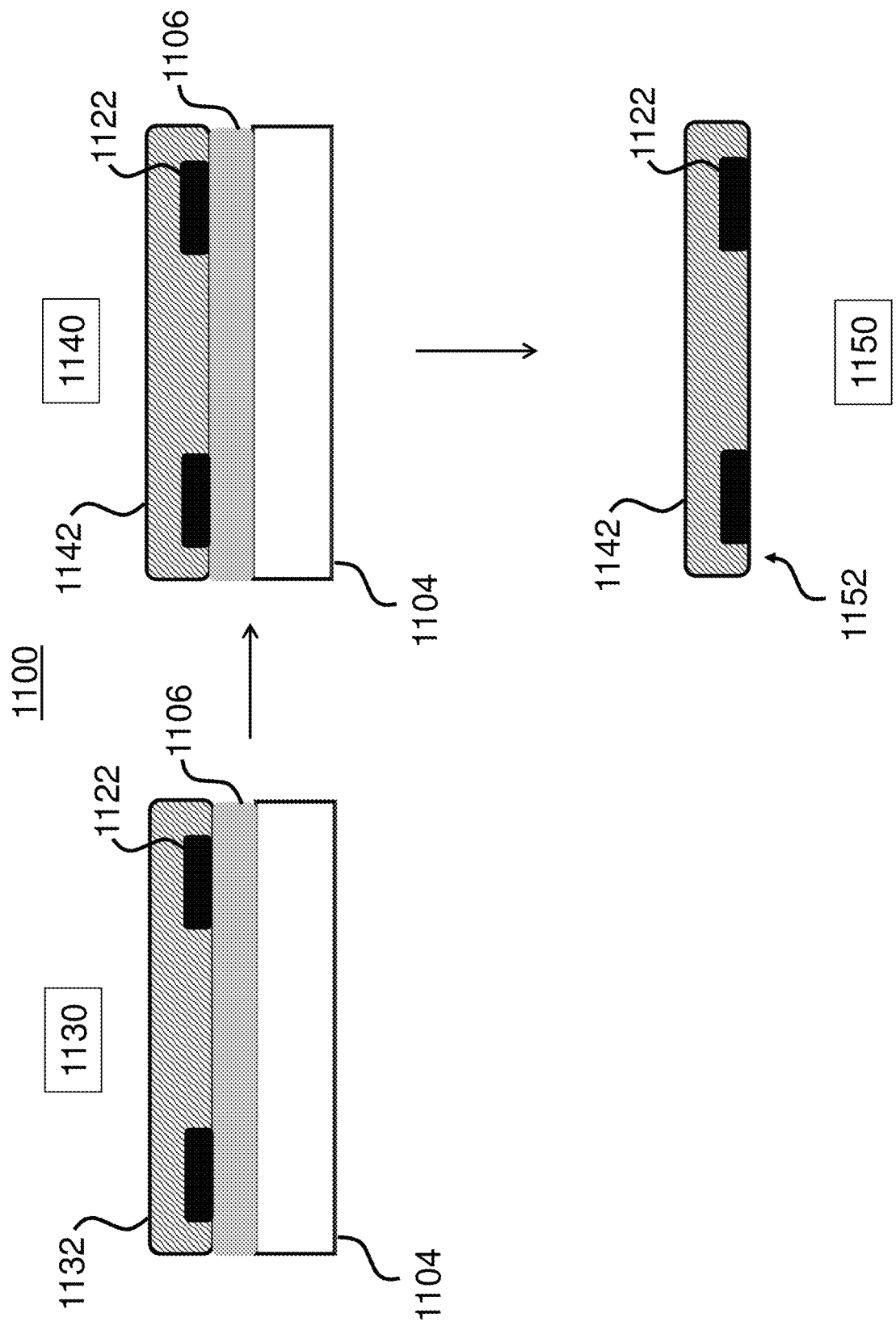

As shown in FIG. 11B, at block 1130, substantially non-transparent polymer layer 1132 is deposited over shaped magnetic layer 1122 and sacrificial layer 1106. At block 1140, the perimeter of layer 1132 is shaped by lithography into gear-shaped substantially non-transparent layer 1142 (such as one of the gear shapes illustrated in FIGS. 6A-9A). At block 1150, the entire structure (i.e., layer 1142, shaped magnetic layer 1122, sacrificial layer 1106, and substrate 1104) is immersed in a solvent. This solvent treatment dissolves sacrificial layer 1106 and releases gear-shaped layer 1142 and shaped magnetic layer 1122 from substrate 1104, thereby generating microcarrier 1152. In some embodiments, microcarrier 1152 may be further modified, for example, by coupling a capture agent to one or both surfaces.

FIGS. 12A-12E illustrate process 1200, an exemplary workflow for manufacturing microcarriers with a substantially transparent polymer layer, a substantially non-transparent polymer layer (whose two-dimensional shape constitutes an analog code), and one or more columns.

Figure 12A:
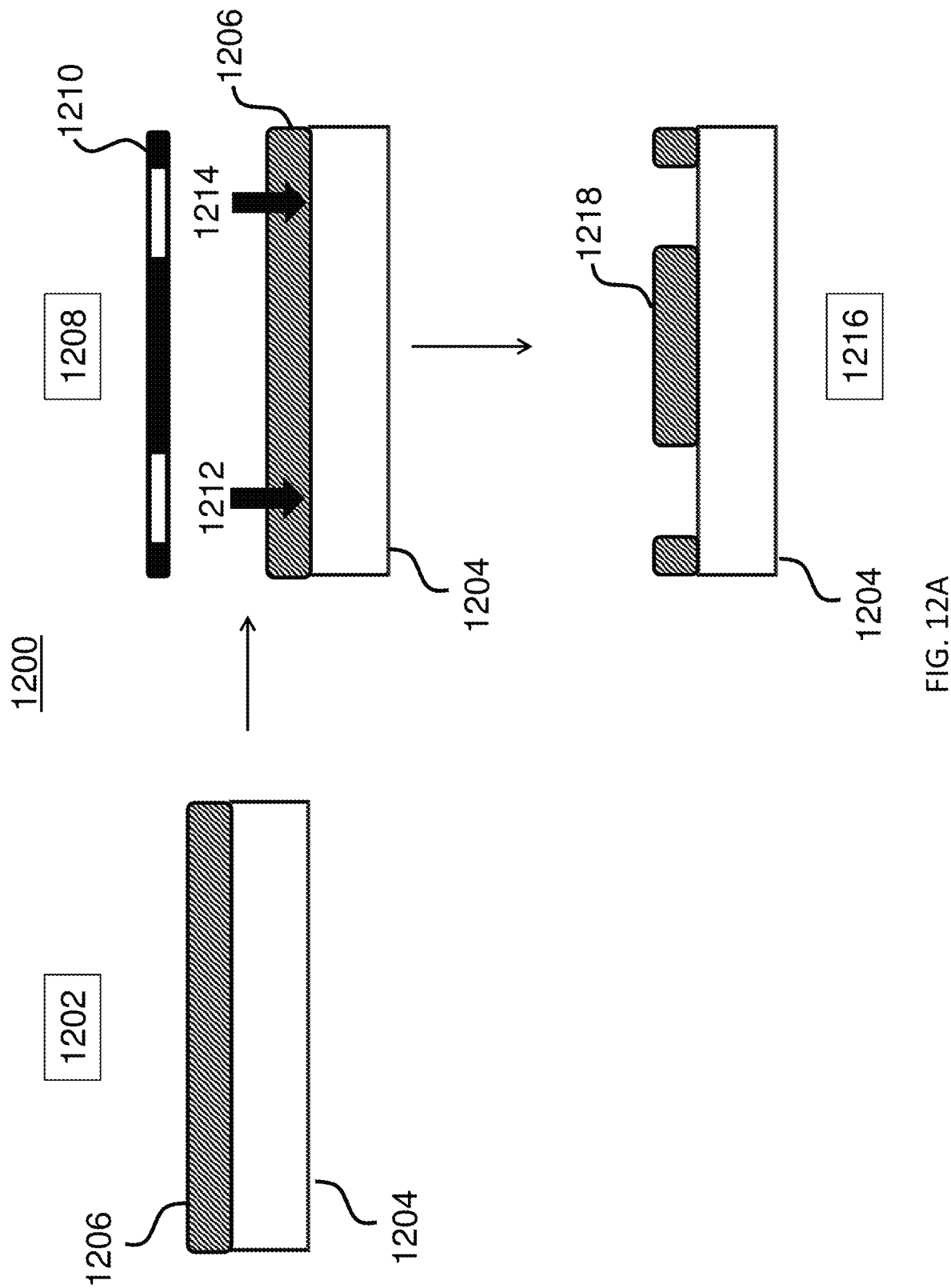
FIGS. 12A-12E show a method for producing an exemplary microcarrier.
Figure 12B:
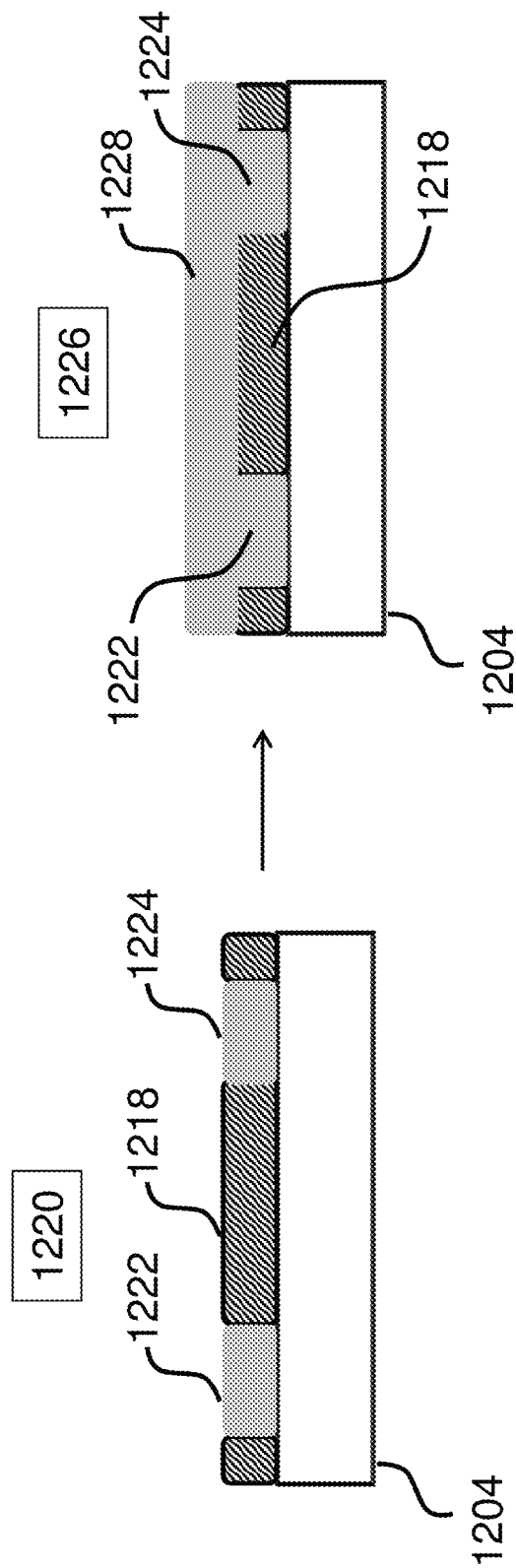
Figure 12C:
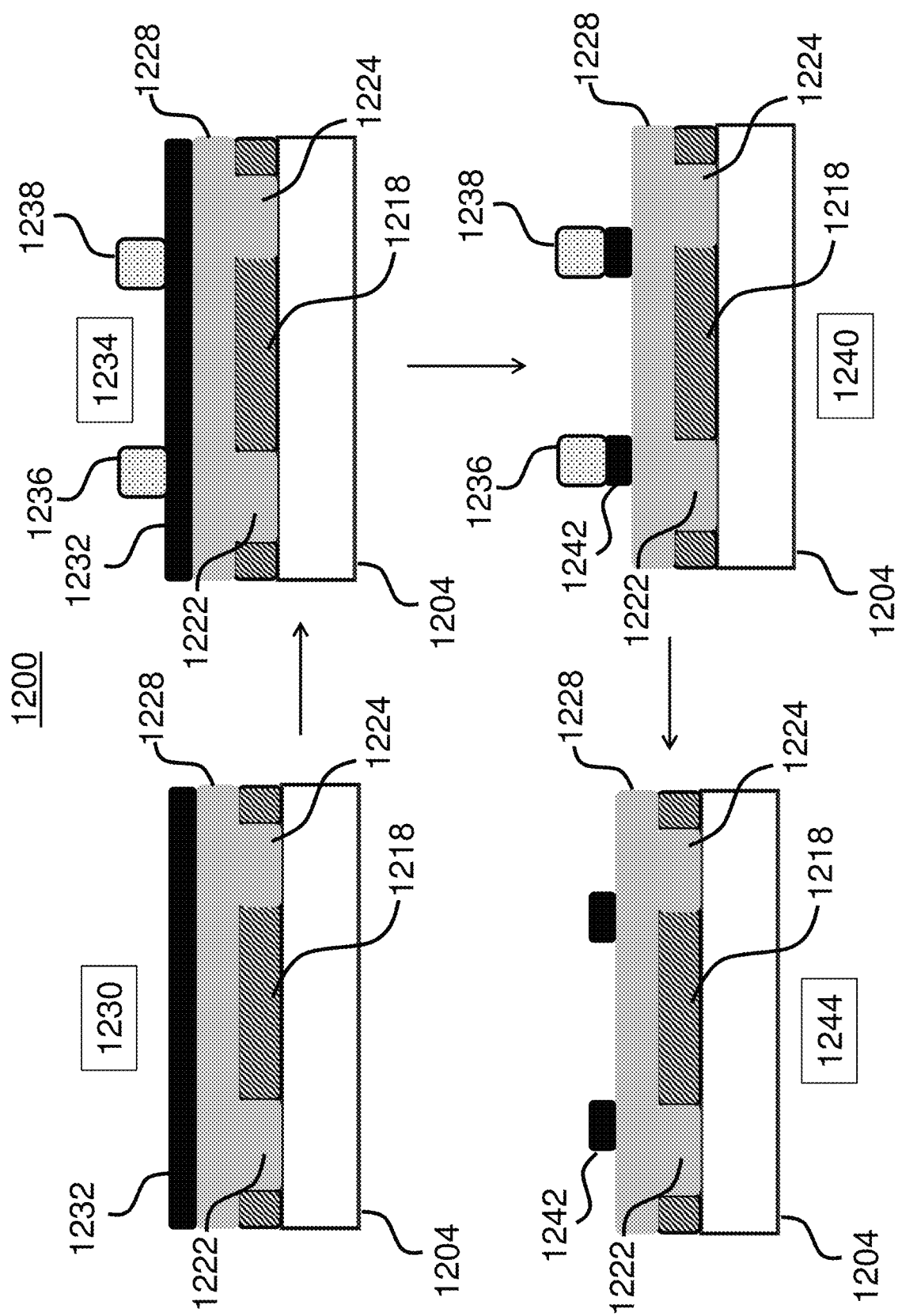
Figure 12D:
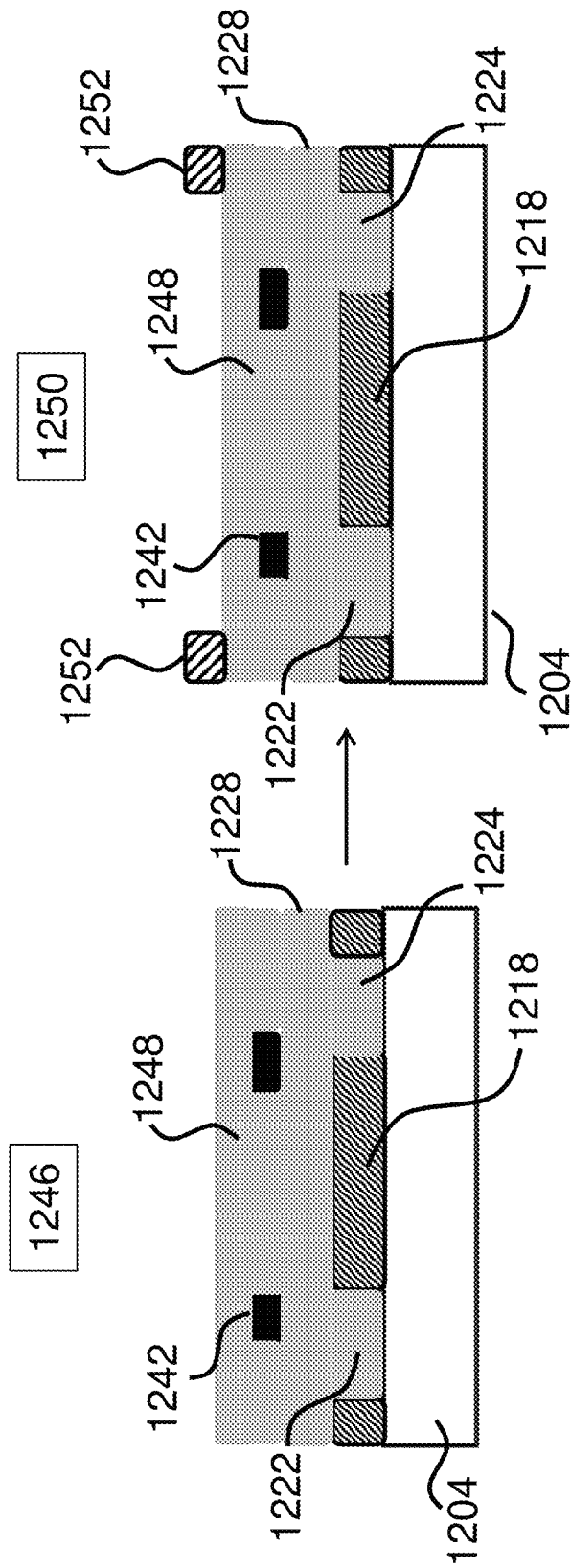
Figure 12E:
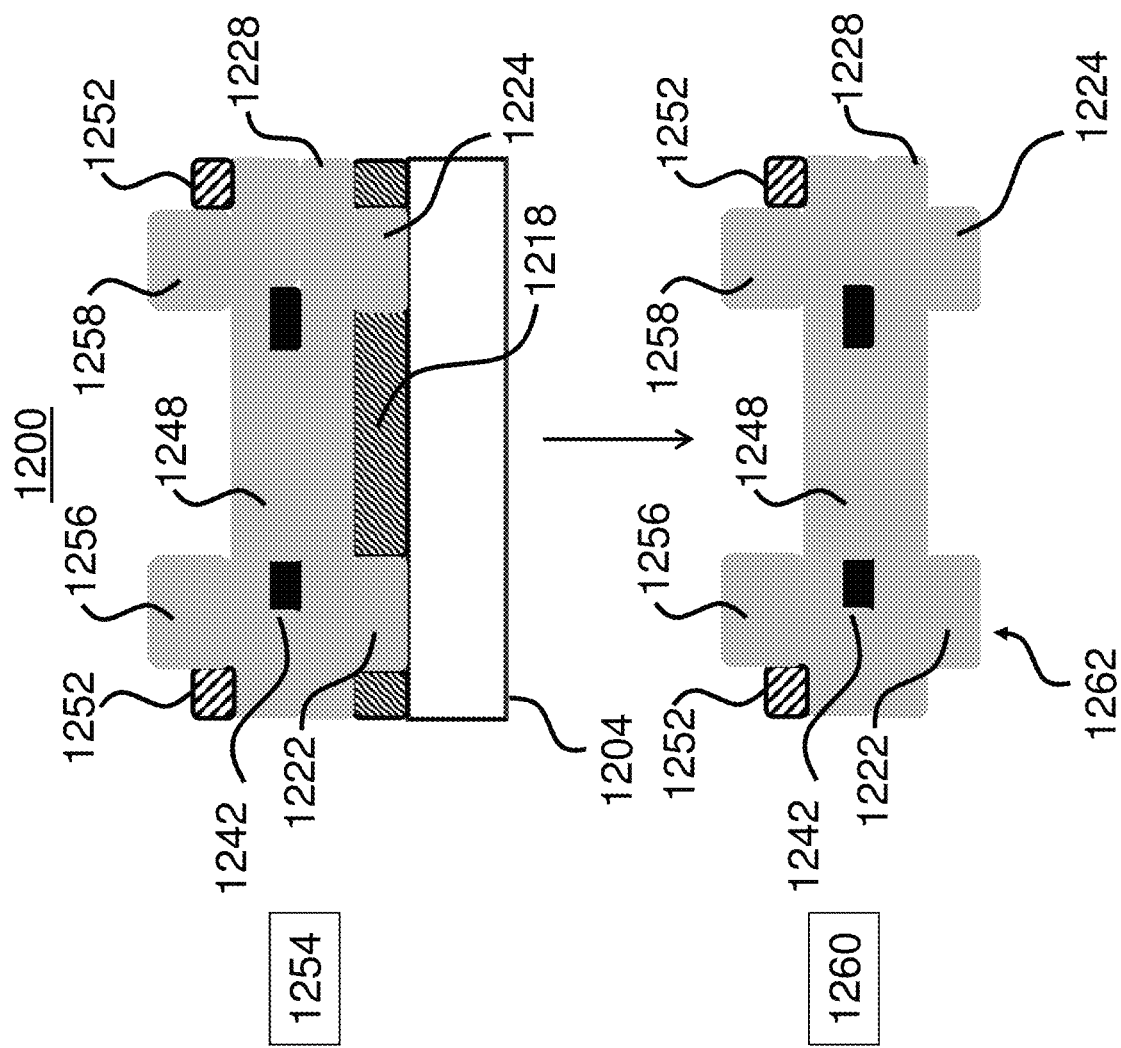

Beginning with FIG. 12A, at block 1202, sacrificial layer 1206 is deposited (e.g., by spin-coating) onto substrate 1204. In some embodiments, substrate 1204 may be a glass substrate. At block 1208, mask 1210 is applied, and sacrificial layer 1206 is exposed with UV light. UV light is applied through mask 1210, allowing UV light segments 1212 and 1214 to pass through and treat sacrificial layer 1206. At block 1216, after development of the structure through standard lithographic development, sacrificial layer 1206 is shaped into shaped sacrificial layer 1218 as a result of the masking of the UV treatment.

Process 1200 continues at block 1220 (FIG. 12B), where the masked holes in shaped sacrificial layer 1218 are filled with a substantially transparent polymer, creating columns 1222 and 1224. At block 1226, substantially transparent polymer layer 1228 is deposited over columns 1222 and 1224, as well as shaped sacrificial layer 1218.

Process 1200 continues at block 1230 (FIG. 12C), where magnetic layer 1232 is deposited over layer 1228. In some embodiments, magnetic layer 1232 includes nickel. In some embodiments, magnetic layer 1232 is deposited by sputtering. At block 1234, an etch-block layer is deposited over magnetic layer 1232, as represented by etch-blocks 1236 and 1238. At block 1240, the unblocked segments of magnetic layer 1232 are etched out, generated shaped magnetic layer 1242. In some embodiments, shaped magnetic layer 1242 may be shaped into a ring shape (with optional asymmetry for indication of orientation) surrounding a center portion of layer 1228 (see, e.g., layer 206 in FIG. 2A). At block 1244, the etch-block layer (as represented by etch-blocks 1236 and 1238) is removed.

Process 1200 continues at block 1246 (FIG. 12D), where substantially transparent polymer layer 1248 is deposited over layers 1228 and 1242 (filling in any holes in layer 1242 created by etch-blocking). At block 1250, substantially non-transparent layer 1252 is deposited and shaped by lithography on top of layer 1248. In some embodiments, layer 1252 is shaped with one or more gear teeth in a ring surrounding magnetic layer 1242 (see, e.g., layer 204 in relation to layers 202 and 206 and center portion 208 of FIG. 2A).

Process 1200 continues at block 1254 (FIG. 12E), where columns 1256 and 1258 are shaped by lithography on top of layer 1248. In some embodiments, columns 1256 and 1258 are made of a substantially transparent polymer. In some embodiments, the columns are positioned as shown in FIGS. 5A & 5B. At block 1260, substrate 1204 is cut into one or more microcarriers of the same shape (i.e., although for simplicity of explanation only one microcarrier is depicted in FIGS. 12A-12E, more than 1 microcarrier may be constructed on substrate 1204 in process 1200). Also at block 1260, the entire structure (i.e., including 1204, 1218, 1222, 1224, 1228, 1242, 1248, 1252, 1256, and 1258) is immersed in a solvent. This solvent treatment dissolves sacrificial layer 1218 and releases microcarrier 1262 from substrate 1204. In some embodiments, microcarrier 1262 may be further modified, for example, by coupling a capture agent to one or both surfaces.

Figure 13A:
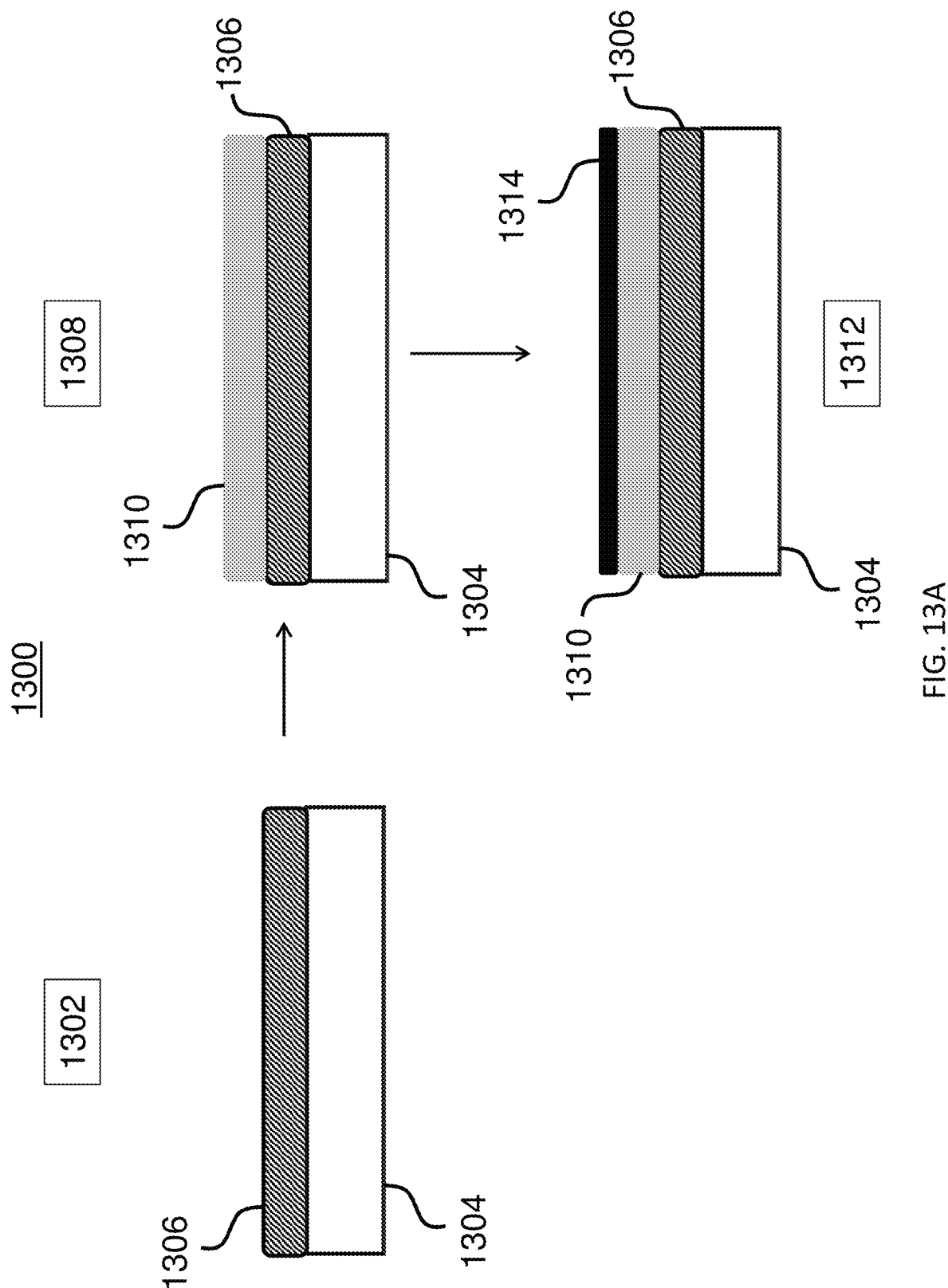
FIGS. 13A-13C show a method for producing an exemplary microcarrier.
Figure 13B:
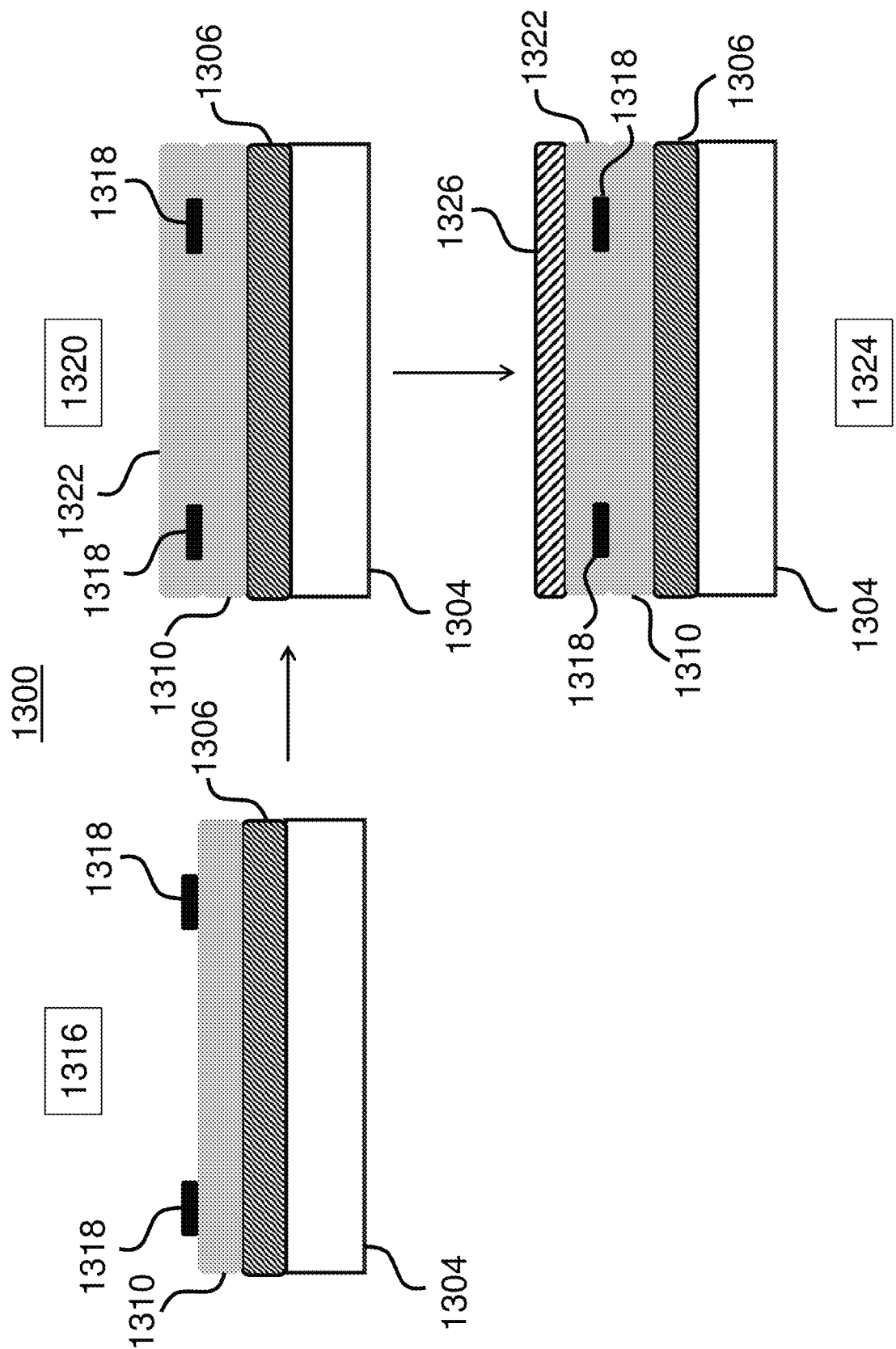
Figure 13C:
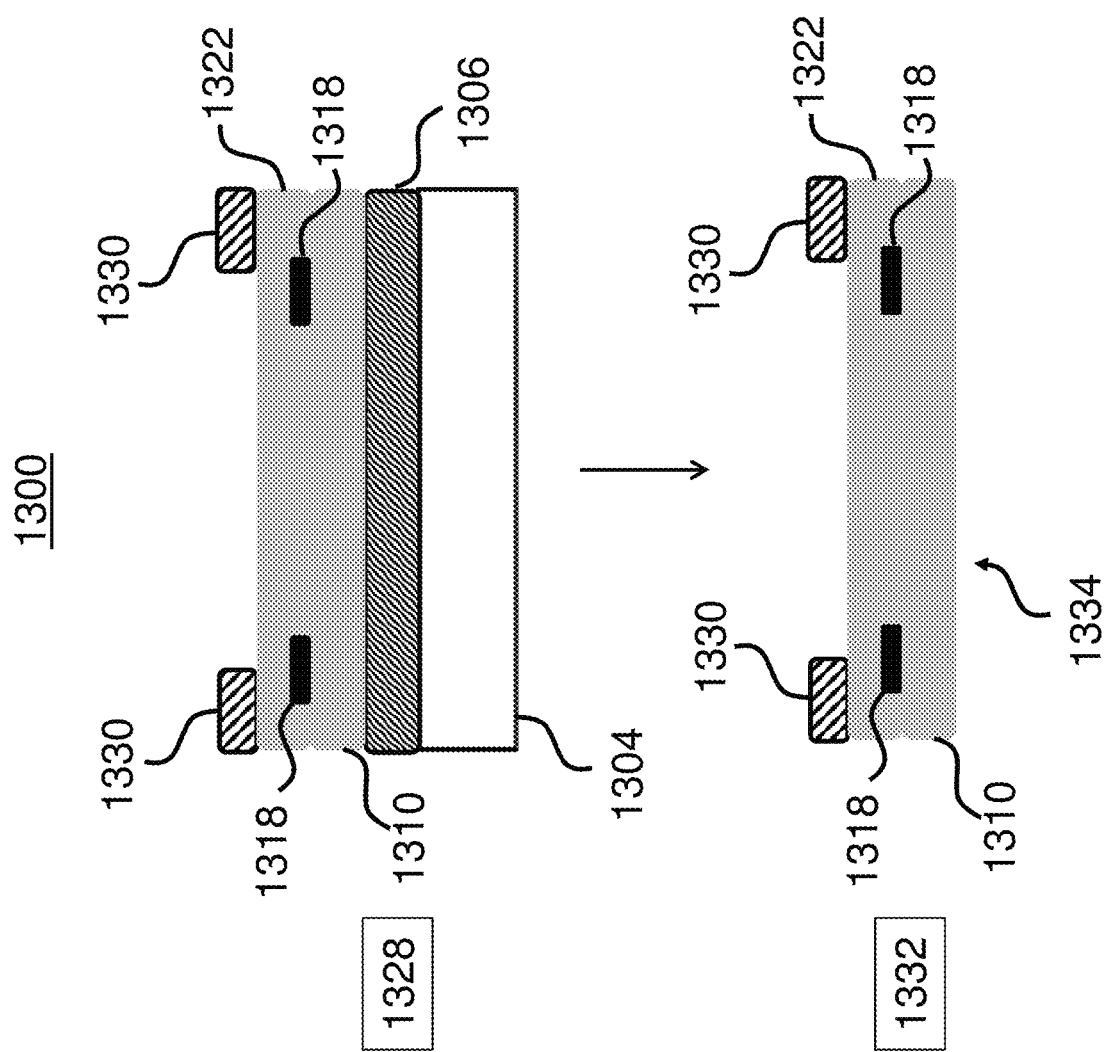

FIGS. 13A-13C illustrate process 1300, an exemplary workflow for generating a different type of multi-layer microcarrier. Beginning with FIG. 13A, at block 1302, sacrificial layer 1306 is deposited on substrate layer 1304. In some embodiments, substrate 1304 is a glass substrate. At block 1308, substantially transparent layer 1310 is deposited over sacrificial layer 1306. At block 1312, magnetic layer 1314 is deposited over layer 1310. In some embodiments, magnetic layer 1314 includes nickel.

Process 1300 continues at block 1316 (FIG. 13B), where magnetic layer 1314 is defined into shaped magnetic layer 1318. In some embodiments, shaped magnetic layer 1318 is defined into a ring shape (with optional asymmetry for indication of orientation) surrounding a center portion of layer 1310 (see, e.g., layer 206 in FIG. 2A). At block 1320, substantially transparent layer 1322 is deposited over layers 1318 and 1310, filling in any holes created by defining shaped layer 1318. At block 1324, substantially non-transparent polymer layer 1326 is deposited over layer 1322.

Process 1300 continues at block 1328 (FIG. 13C), where substantially non-transparent polymer layer 1326 is shaped by lithography into gear-shaped substantially non-transparent polymer layer 1330. In some embodiments, layer 1330 is shaped with one or more gear teeth in a ring surrounding shaped magnetic layer 1318 (see, e.g., layer 204 in relation to layers 202 and 206 and center portion 208 of FIG. 2A). At block 1332, the entire structure (i.e., including 1304, 1306, 1310, 1318, 1322, and 1330) is immersed in a solvent. This solvent treatment dissolves sacrificial layer 1306 and releases microcarrier 1334 from substrate 1304. In some embodiments, microcarrier 1334 may be further modified, for example, by coupling a capture agent to one or both surfaces.

As described supra, in some embodiments, a microcarrier of the present disclosure comprises a magnetic, substantially non-transparent polymer layer that is affixed to the first surface of the substantially transparent polymer layer and can be used, e.g., to generate an analog code of the present disclosure. Exemplary methods for producing such a microcarrier are described in greater detail infra.

In some embodiments, the methods include depositing a substantially transparent polymer layer, wherein the substantially transparent polymer layer has a first surface and a second surface, the first and the second surfaces being parallel to each other; patterning the substantially transparent polymer layer into a microcarrier shape; depositing a magnetic, substantially non-transparent polymer layer on the first surface of the substantially transparent polymer layer; and patterning the magnetic, substantially non-transparent polymer layer to generate a two-dimensional shape representing an analog code.

In some embodiments, a substantially transparent polymer layer of the present disclosure is deposited using spin or spray coating. In some embodiments, a magnetic, substantially non-transparent polymer layer of the present disclosure is deposited using spin or spray coating. A variety of deposition techniques are described herein and known in the art. Any suitable means known in the art for depositing a polymer such as SU-8 may be used.

In some embodiments, the methods include depositing a magnetic, substantially non-transparent polymer layer; patterning the magnetic, substantially non-transparent polymer layer to generate a two-dimensional shape representing an analog code; depositing a substantially transparent polymer layer onto the patterned magnetic, substantially non-transparent polymer layer, wherein the substantially transparent polymer layer has a first surface and a second surface, the first and the second surfaces being parallel to each other; and patterning the substantially transparent polymer layer into a microcarrier shape.

In some embodiments, a probe of the present disclosure may be coupled to a microcarrier of the present disclosure, e.g., a microcarrier described herein and/or a microcarrier produced by any of the methods described herein. Any of the probes described herein may find use in the methods and/or microcarriers of the present disclosure. Exemplary and non-limiting descriptions of techniques for coupling a probe to a microcarrier are provided in section IV.

EXAMPLES

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

Example 1: Multiplex Detection of Colorectal Cancer-Associated Mutations Using Encoded Microcarriers As described above, multiplex screening for cancer-associated DNA mutations represents an attractive technique for early cancer detection. In particular, multiplex screening for colorectal cancer-associated DNA mutations using DNA isolated from a stool sample represents a non-invasive method for early detection. The following Example describes the validation of a microcarrier-based approach for multiplex screening to identify a variety of important DNA mutations associated with colorectal cancer.

Materials and Methods

DNA Sample Preparation

Figure 14:
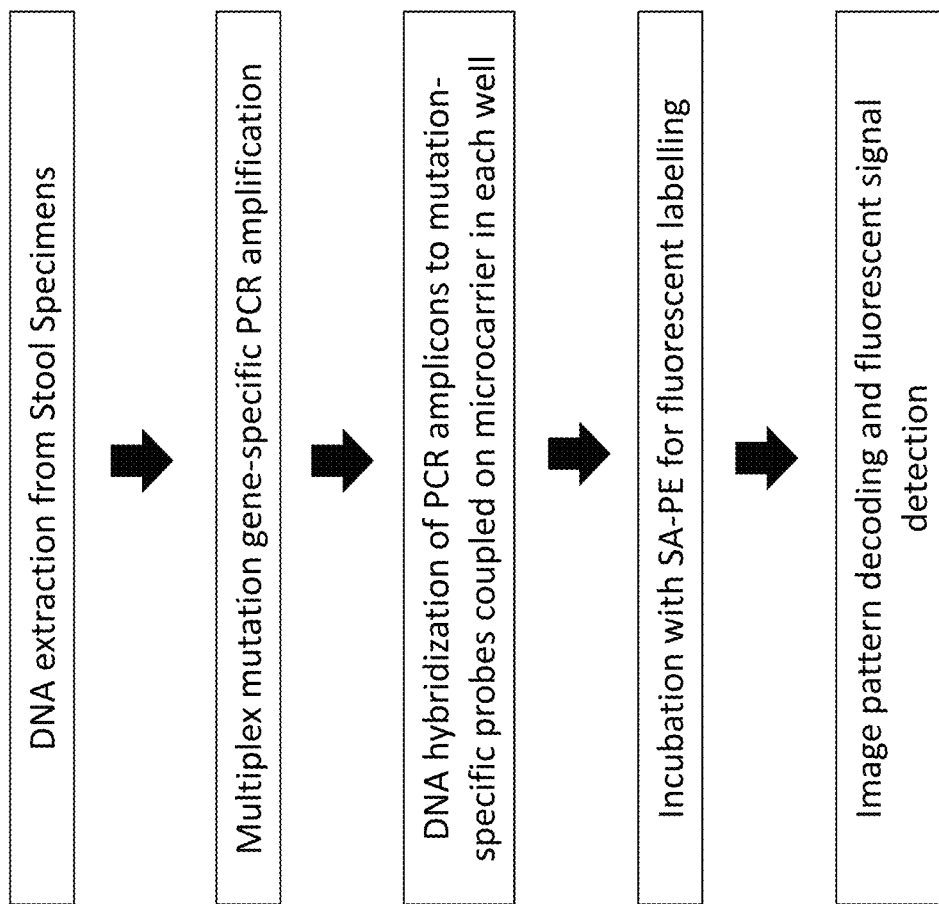
FIG. 14 shows a flowchart illustrating an exemplary method for detecting the presence of DNA mutation(s), in accordance with some embodiments.

A flowchart of the method used to test the detection of mutations using encoded microcarriers is provided in FIG. 14. DNA was isolated from the plasmids described in Table C or K562 cells as described in Table B using standard techniques. DNA was quantified using a NanoDrop™ UV-Vis spectrophotometer (Thermo Scientific) or Qubit® Fluorometer (Thermo Scientific) according to manufacturer's instructions. Concentration of extracted DNA used for all experiments was ≥12.5 ng/µL.

The mutations detected in these experiments are provided in Table A below.

TABLE A

Mutations detected.

| Gene | Exon | Mutation | Amino Acid Change |
|---|---|---|---|
| KRAS | 2 | c.35G > A | G12D |
| | | c.35G > T | G12V |
| | | c.34G > A | G12S |
| | | c.38G > A | G13D |
| BRAF | 15 | c.1799T > A | V600E† |
| | | c.1799_1800TG > AA (Complex) | V600E‡ |
| APC | 15 | 3927-3931delAAAGA | E1309fs*4 |
| | | 4099C > T | Q1367* |
| | | 4348C > T | R1450* |
| | | 4385-4386delAG | S1465fs*3 |
| | | 4666-4667insA | T1556fs*3 |
| CTNNB1 | 3 | 121A > G | T41A |
| | | 122C > T | T41I |
| | | 133T > C | S45P |
| | | 134C > T | S45F |

†Referred to as V600E1 herein.
‡Referred to as V600E2 herein.

For the limit of detection (LOD) testing (results shown in FIGS. 18A & 18B), DNA was extracted from K562 cells for use as "wild type" DNA. DNA with one of various mutations of interest was obtained using plasmids bearing mutated KRAS, BRAF, CTNNB1, or APC sequences. Wild type and mutated DNA were mixed and diluted to achieve a total DNA concentration of 12.5 ng/µL with a ratio of 1% mutated DNA to 99% wild type DNA. Concentration of each DNA sample used for the experiments is shown in Tables B and C below.

TABLE B

Wild-type DNA.

| WT Cell line | WT mutation % | WT DNA Stock conc (ng/µL) | WT DNA 500 ng/µl stock volume | final volume | Tris | WT DNA 100 ng/µl 100 ng/µl volume | final volume | Tris |
|---|---|---|---|---|---|---|---|---|
| K562 | — | 1208 | 207.0 | 500 | 293.0 | 100 | 1000 | 900 |

TABLE C

Mutated DNA.

| | | | | 10% 25 ng | | | 1% 25 ng | | | 1% 12.5 ng | | |
|---|---|---|---|---|---|---|---|---|---|---|---|---|
| Mutated Gene | Mutations/WT Plasmid | 10000 copies stock | TE Buffer | WT DNA (100 ng/µl) | 10% 25 ng Stock | WT DNA (25 ng/µl) | final v (1% 25 ng/µl) | 1% 25 ng Stock | H2O | final v (1% 12.5 ng/µl) |
| KRAS | G12D | 7.25 | 67.75 | 25 | 10 | 90 | 100 | 50 | 50 | 100 |
| | G12V | 7.25 | 67.75 | 25 | 10 | 90 | 100 | 50 | 50 | 100 |

TABLE C-continued

| | | | | | Mutated DNA. | | | | | |
| --- | --- | --- | --- | --- | --- | --- | --- | --- | --- | --- |
| | | | 10% 25 ng | | | 1% 25 ng | | | 1% 12.5 ng | |
| Mutated Gene | Mutations/WT Plasmid | 10000 copies stock | TE Buffer | WT DNA (100 ng/µl) | 10% 25 ng Stock | WT DNA (25 ng/µl) | final v (1% 25 ng/µl) | 1% 25 ng Stock | H2O | final v (1% 12.5 ng/µl) |
| | G12S | 7.25 | 67.75 | 25 | 10 | 90 | 100 | 50 | 50 | 100 |
| | G13D | 7.25 | 67.75 | 25 | 10 | 90 | 100 | 50 | 50 | 100 |
| BRAF | V600E1 | 7.25 | 67.75 | 25 | 10 | 90 | 100 | 50 | 50 | 100 |
| | V600E2 | 7.25 | 67.75 | 25 | 10 | 90 | 100 | 50 | 50 | 100 |
| CTNNB1 | T41A | 7.25 | 67.75 | 25 | 10 | 90 | 100 | 50 | 50 | 100 |
| | T41I | 7.25 | 67.75 | 25 | 10 | 90 | 100 | 50 | 50 | 100 |
| APC | E1309 | 7.25 | 67.75 | 25 | 10 | 90 | 100 | 50 | 50 | 100 |
| | Q1367 | 7.25 | 67.75 | 25 | 10 | 90 | 100 | 50 | 50 | 100 |
| | R1450 | 7.25 | 67.75 | 25 | 10 | 90 | 100 | 50 | 50 | 100 |
| | T1556 | 7.25 | 67.75 | 25 | 10 | 90 | 100 | 50 | 50 | 100 |
| CTNNB1 | S45F | 7.25 | 67.75 | 25 | 10 | 90 | 100 | 50 | 50 | 100 |
| | S45P | 7.25 | 67.75 | 25 | 10 | 90 | 100 | 50 | 50 | 100 |
| APC | S1465 | 7.25 | 67.75 | 25 | 10 | 90 | 100 | 50 | 50 | 100 |

PCR

Figure 15:
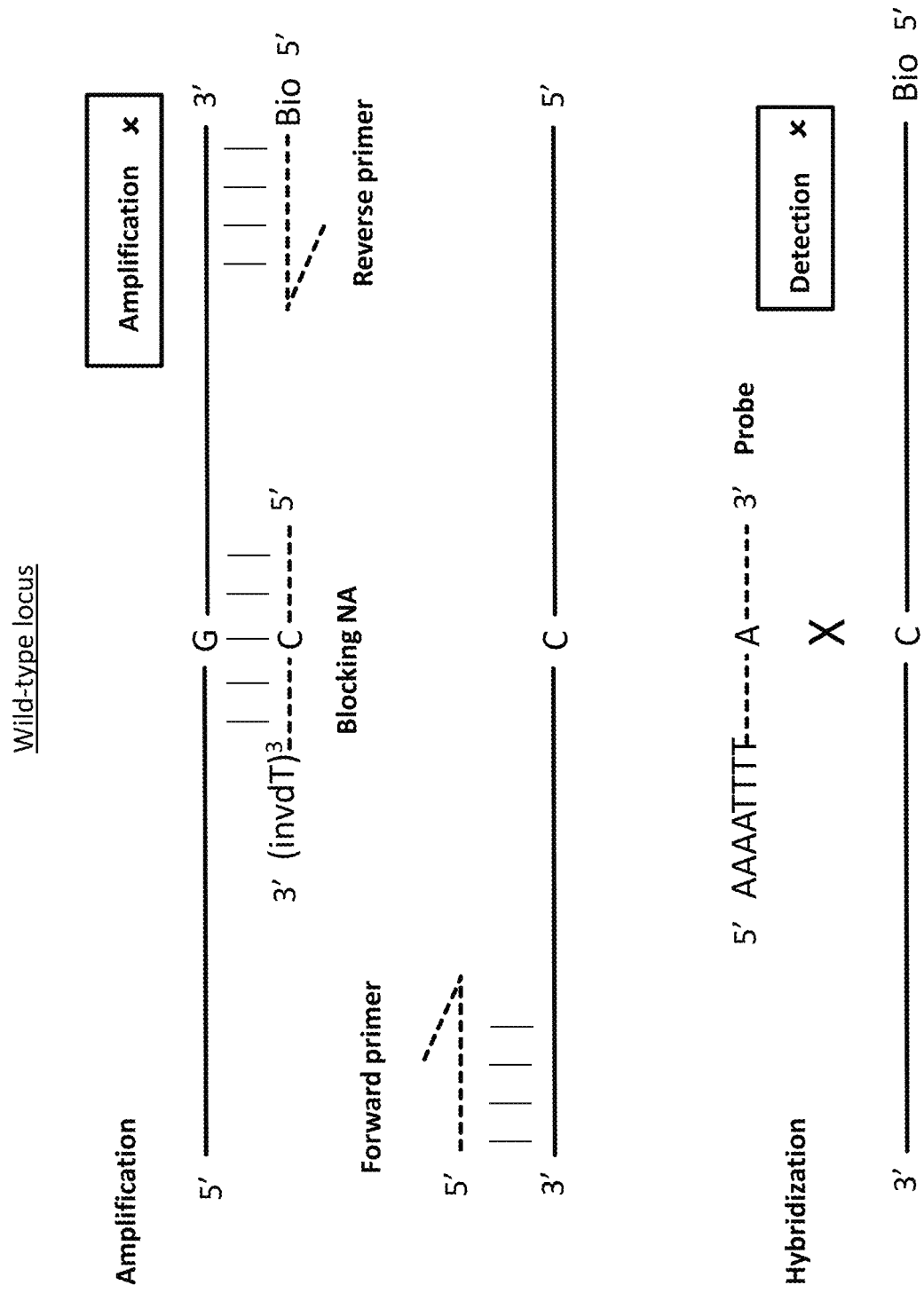
FIGS. 15 & 16 illustrate an exemplary scheme for preferentially amplifying and detecting mutant (FIG. 16) over wild-type (FIG. 15) loci corresponding to a DNA mutation of interest, in accordance with some embodiments. Solid horizontal lines indicate amplified DNA sequences, dashed horizontal lines indicate primer/probe/blocking nucleic acid (NA) sequences, and vertical lines indicate Watson-Crick base pairing.
Figure 16:
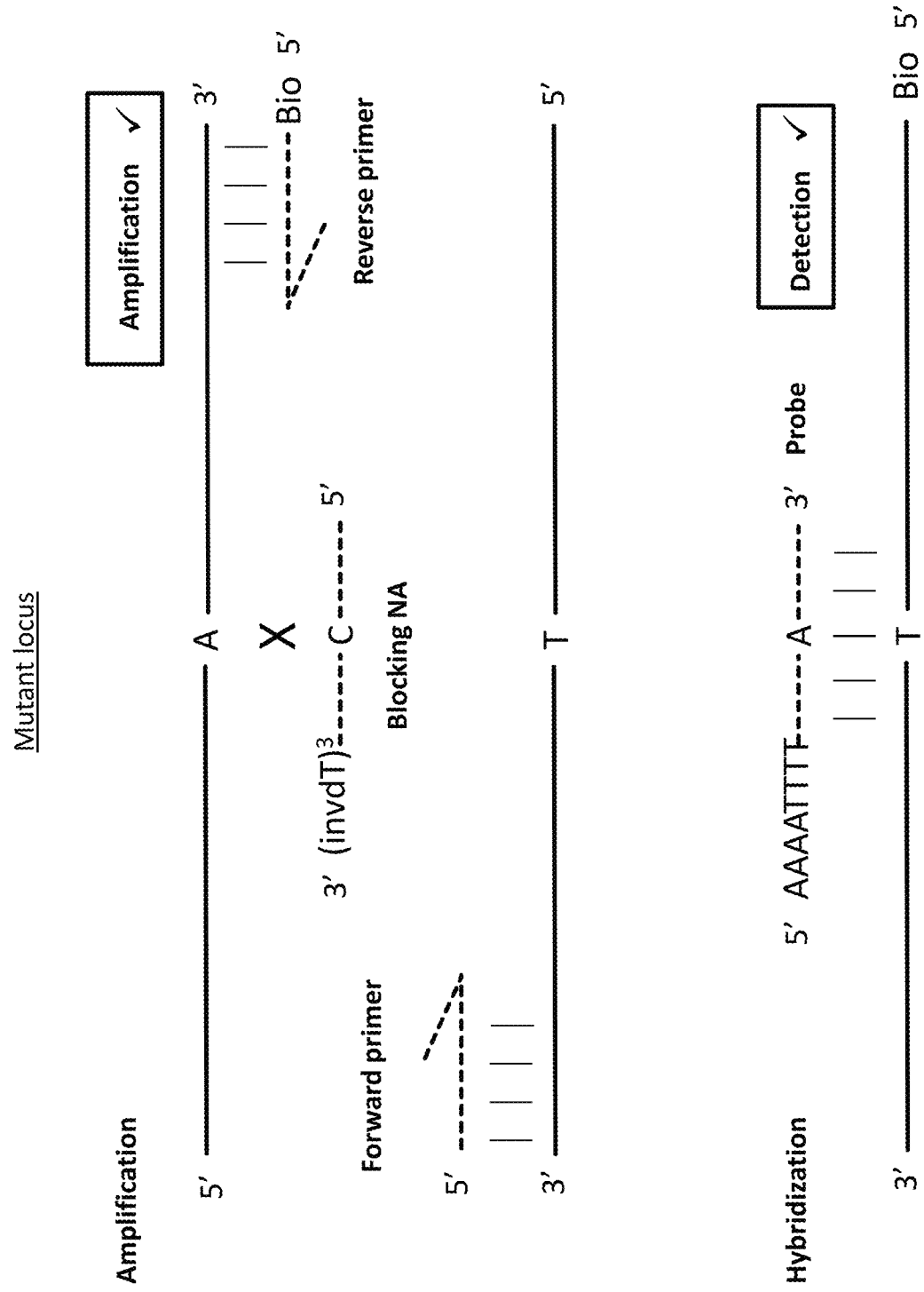

Mutation-enriching PCR was used to selectively amplify polynucleotides having a mutation of interest from the DNA samples prepared above. Locked nucleic acids (LNAs) with 3' inverted dT nucleotides were used to block the amplification of wild-type DNA sequences, thereby enriching for mutations of interest. Briefly, a blocking nucleic acid was included in the PCR reaction to block amplification of the wild-type locus. The blocking nucleic acid hybridized to the sense strand of the wild-type locus and prevented primer extension to amplify from the sense strand, as shown in FIG. 15. LNAs were used because of more stable hybridization, as compared to oligonucleotides with standard nucleic acids. Any copies of the mutant locus present in the sample could be amplified by PCR with no interference from the blocking nucleic acid, since it did not hybridize with the mutant sequence (FIG. 16). The following primer pairs were used: SEQ ID NOs: 1 and 2, 8 and 9, 13 and 14, 18 and 19, 23 and 24, 27 and 28, 31 and 32, 35 and 36, 39 and 40. The following blocking nucleic acids were used: SEQ ID NOs:3, 10, 15, 20, 29, 33, 37, 25, and 41.

Each sample was vortex-mixed, then spun down and kept on ice. PCR reactions were carried out as follows. For each sample, two PCR reactions were performed according to the amounts listed in Tables D and E. Each PCR reaction included 4 µL of 12.5 ng/µL extracted DNA, for a total of 50 ng DNA. Once PCR reaction mixes were generated in PCR tubes, the tubes were mixed by tapping, spun down briefly, and placed in a thermocycler. PCR thermocycle conditions were as described in Table F below. The ramp rate was 1° C./second. PCR reaction 1 included the reagents for detecting the following mutations: KRAS G12D, KRAS G12V, KRAS G12S, KRAS G13D, BRAF V600E1, BRAF V600E2, CTNNB1 T41A, CTNNB1 T41I, APC E1309, APC Q1367, APC R1450, and APC T1556. PCR reaction 2 included the reagents for detecting the following mutations: CTNNB1 S45F, CTNNB1 S45P, and APC S1465.

TABLE D

PCR reaction 1.
PCR Reaction 1

| Material | Vol. (µL) per reaction |
| --- | --- |
| Reaction Mix 1 | 11 |
| Primer Mix 1 | 5 |
| Extracted DNA/PC/NC | 4 |
| Total | 20 |

TABLE E

PCR reaction 2.
PCR Reaction 2

| Material | Vol. (µL) per reaction |
| --- | --- |
| Reaction Mix 2 | 11 |
| Primer Mix 2 | 5 |
| Extracted DNA/PC/NC | 4 |
| Total | 20 |

TABLE F

| PCR cycling conditions. | | |
| --- | --- | --- |
| Temp. (° C.) | Time | Cycles |
| 95 | 10 min | 1 |
| 95 | 20 sec | 40 |
| 70 | 20 sec | |
| 60 | 60 | |
| 4 | Hold | 1 |

*Note:
ramp rate was 1° C./sec.

Hybridization

PCR amplicons were hybridized to the capture agent probe sequences of the microcarriers. The probes were designed to hybridize with the mutant sequence and not the wild-type sequence, thereby allowing the specific detection of the mutant DNA (cf. FIGS. 15 & 16). Combined with the use of blocking nucleic acids that bind the wild-type sequence, this strategy enables the assay to detect mutant DNA even when present at a much lower copy number than the corresponding wild-type locus. The following probes were used: SEQ ID NOs:47-61.

Figure 17:
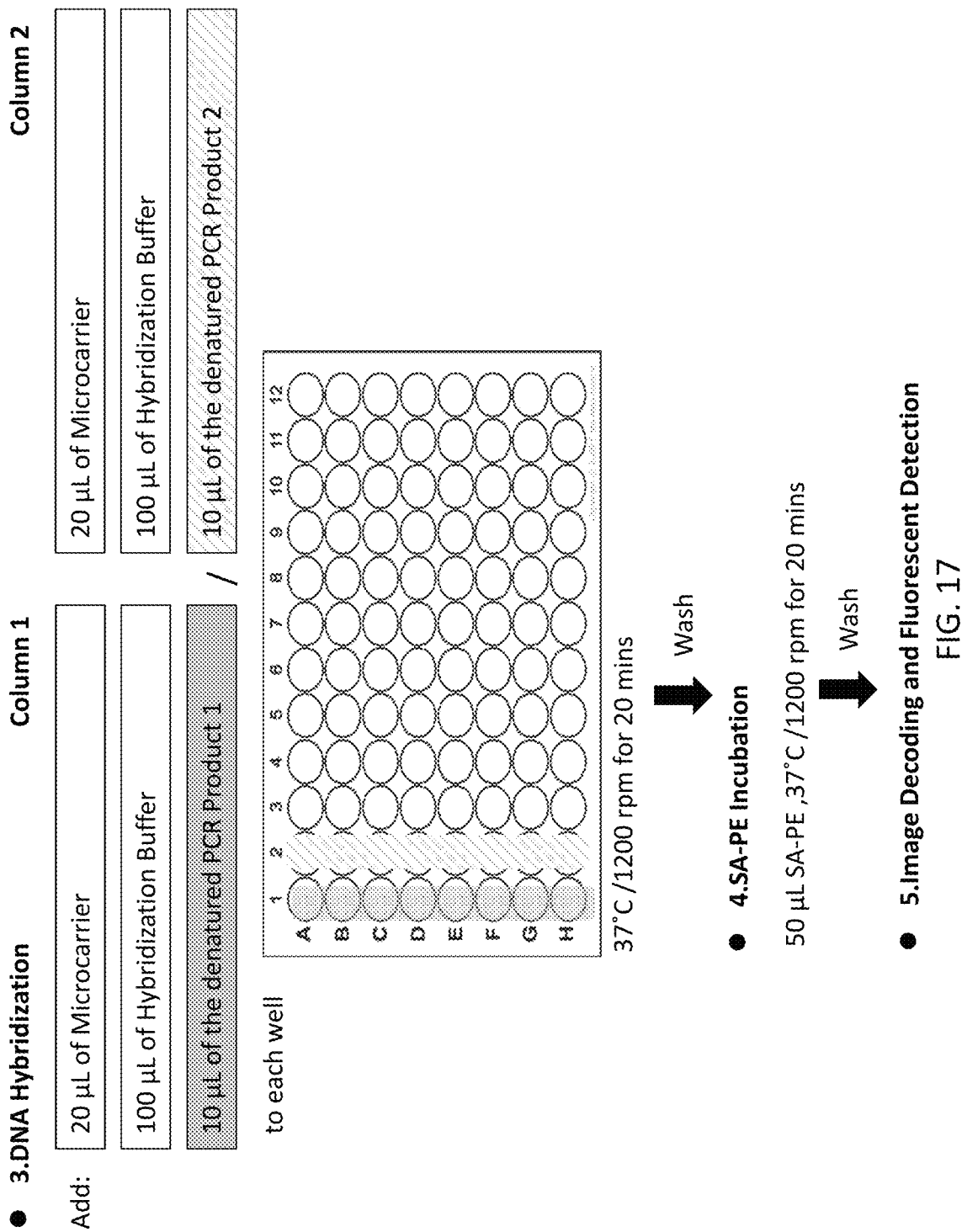
FIG. 17 shows a flowchart illustrating an exemplary protocol for hybridizing amplified DNA, detecting the presence or absence of hybridization of amplified DNA with probe(s) coupled to microcarriers, and detecting analog identifiers of microcarriers, in accordance with some embodiments.

Briefly, encoded microcarriers, each individually specific for a mutation shown in Table A, were pooled into a single well of a 96-well plate. The microcarrier solution was mixed by vortexing for 10 seconds, then 20 μL of microcarrier solution was added to each well of a 96-well plate, as shown in FIG. 17. The stock microcarrier solution was re-vortexed every 4 wells to ensure a homogeneous suspension. 100 μL hybridization buffer (5×SSPE buffer) was added to each well. PCR products from PCR reactions 1 and 2 (see Tables D and E) were spun down and denatured by heating to 95° C. for 5 minutes, then cooled down to 4° C. 10 μL of denatured PCR product 1 or 10 μL of denatured PCR product 2 was added to each well. The assay plate was mixed by shaking at 1200 rpm for 20 minutes at 37° C. Wells were then washed with 1× wash buffer.

For detection, 50 μL of streptavidin-conjugated phycoerythrin (SA-PE) solution was added to each well, and plates were again shaken at 1200 rpm for 10 minutes at 37° C. Wells were then washed again. Each well was then subject to analog image decoding and fluorescent detection.

Results

Microcarriers with probes specific for each of the mutations listed in Table A were used to detect the presence of mutated DNA in the LOD testing assays described above. The results of these experiments are shown in FIG. 18A (primer mix 1) and 18B (primer mix 2). The microcarrier-based assay was validated for each mutation in a pairwise fashion, using one probe and one mutated DNA sequence per assay. The columns indicate which mutated DNA sequence was present in the DNA sample. The rows indicate which probe was coupled to the microcarriers for these assays. For a negative control, "blank" microcarriers with no probe were used. For a positive control, human HLA DNA was amplified and detected using a probe specific for the amplified sequence.

Figure 18B:
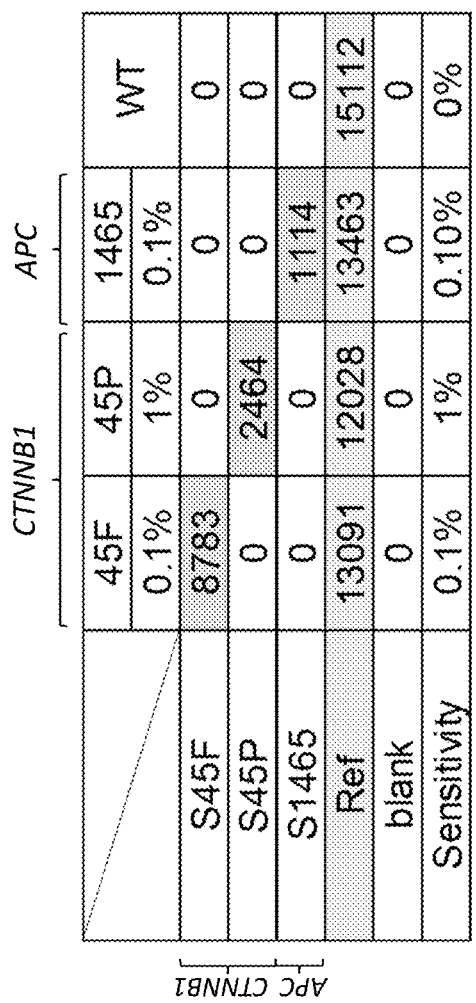

FIGS. 18A & 18B report the fluorescence signal (in arbitrary units, AU) obtained for each experiment. As shown, in nearly all cases in which the mutated DNA sequence and the probe were mismatched, no fluorescence was detected, indicating a lack of hybridization between the probe and DNA (KRAS G12S DNA weakly cross-reacted with both BRAF probes, but yielded much lower fluorescence signal than each respective BRAF DNA sample). In contrast, when each mutated DNA sequence was mixed with the appropriate microcarrier-coupled probe, hybridization was detected by a strong fluorescence signal.

"Sensitivity" as shown in FIGS. 18A & 18B refers to the LOD tested for each mutation. For example, 0.10% sensitivity indicates that 0.1 ng mutated DNA was mixed with 100 ng of wild-type DNA. No signal other than the positive control was detected using wild-type DNA, indicating that the LNA oligonucleotides were effective in blocking wild-type DNA amplification and/or the probe sequences were effective in eliminating hybridization of wild-type DNA.

Detection of APC mutation S1465 was further tested at sensitivity levels of 1.0% and 0.1% (FIG. 18B). Some cross-reactivity was observed among CTNNB1 S45F and S45P mutations and APC mutation S1465. However, when all genes are tested together, the detection of signal for S1465, whether in the presence of absence of signal for S45F and S45P, can indicate the presence of S1465 mutation, given that strong S45F or S45P signal was not observed when using the S1465 probe.

These results demonstrate the sensitive and accurate detection of individual mutations of interest even with wild-type DNA present in amounts greater by orders of magnitude than the mutated sequences of interest. Advantageously, multiplex detection of several mutations in tandem leads to greater confidence and fidelity, since detection of each gene acts as an internal control for all of the other genes. These results suggest a rapid, multiplexed strategy using encoded microcarriers with oligonucleotide probes for the identification of important cancer-associated mutations from human samples.

Example 2: Multiplex Detection of Colorectal Cancer-Associated Mutations from Stool Samples Using Encoded Microcarriers The preceding Example demonstrated the use of encoded microcarriers with oligonucleotide probes for multiplex detection of cancer-associated mutations based on isolated DNA samples. The following Example demonstrates that the efficacy of this approach using DNA extracted from stool samples.

Materials and Methods

For extraction of DNA from stool specimen, 200 mg of each specimen was placed in a tube on ice, and DNA was extracted using the QIAamp® Fast DNA Stool Mini Kit. Briefly, 2 mL InhibitEx® buffer (Qiagen) was added to each sample, then samples were vortexed for 1 minutes or until homogenization. 2 mL of homogenate was pipetted into a microcentrifuge tube and centrifuged at full speed of a microcentrifuge for 1 minute. 600 μL supernatant was added into a new microcentrifuge tube with 25 μL Proteinase K, then 600 μL buffer AL was added and tube was vortexed for 15 seconds. The tubes were then incubated for 10 minutes at 70° C. 600 μL ethanol was added to lysate, then mixed by vortexing. 600 μL lysate was added to a spin column and centrifuged at full speed for 1 minute. Next, 500 μL buffer AW1 was added, and tubes were centrifuged at full speed for 1 minute. 500 μL buffer AW2 was then added, and tubes were centrifuged at full speed for 1 minute. Spin column was then inserted into a new microcentrifuge tube, 200 μL TE buffer was added to elute DNA following 1 minute incubation at room temperature and centrifugation at full speed for 1 minute.

PCR reactions were generated using the DNA isolated above according to the following proportions. Primer mixes were generated as described in Example 1.

TABLE G

PCR reaction 1.
PCR Reaction 1

| Material | Vol. (μL) per reaction |
| --- | --- |
| Reaction Mix 1 | 10 |
| Primer Mix 1 | 10 |
| Extracted DNA/PC/NC | 20 |
| Total | 40 |

TABLE H

PCR reaction 2.
PCR Reaction 2

| Material | Vol. (µL) per reaction |
|---|---|
| Reaction Mix 2 | 10 |
| Primer Mix 2 | 10 |
| Extracted DNA/PC/NC | 20 |
| Total | 40 |

Other PCR conditions (e.g., thermocycling), hybridization conditions, and detection were as described in Example 1. The following primer pairs were used: SEQ ID NOs: 1 and 2, 8 and 9, 13 and 14, 18 and 19, 23 and 24, 27 and 28, 31 and 32, 35 and 36, 39 and 40. The following blocking nucleic acids were used: SEQ ID NOs:3, 10, 15, 20, 29, 33, 37, 25, and 41. The following probes were used: SEQ ID NOs:47, 48, 86, 91, 95, 99, 104, 109, 113, 119, 122, 126, 60, 57, and 61.

Results

Stool specimens from 7 patients were collected before colon cancer surgery. Five individual stool samples (2 g each) representing different regions of the specimen were taken from each patient's specimen (except 4 were taken from patient #5). Each individual stool sample was homogenized separately in 7 mL stabilization buffer (100 mM EDTA, pH 8.0). DNA was extracted as described above. From each sample, 10 ng DNA was used for the assay. Mutation status was detected from each sample, as shown in Table I. Note that no mutations were detected from stools of about 20 healthy patients.

TABLE I

Results of mutation screening from stool samples.

| Sample No. | Results of Detection |
|---|---|
| 01-001 | Wild Type |
| 01-002 | Wild Type |
| 01-003 | Wild Type |
| 01-004 | Wild Type |
| 01-005 | Wild Type |
| 02-001 | CTNNB1 T41A |
| 02-002 | Wild Type |
| 02-003 | Wild Type |
| 02-004 | Wild Type |
| 02-005 | Wild Type |
| 03-001 | KRAS G12V |
| 03-002 | KRAS G12V |
| 03-003 | KRAS G12V |
| 03-004 | Wild Type |
| 03-005 | BRAF V600E1 & APC E1309 |
| 04-001 | Wild Type |
| 04-002 | KRAS G13D |
| 04-003 | KRAS G13D |
| 04-004 | KRAS G13D |
| 04-005 | KRAS G13D |
| 05-001 | BRAF V600E2 & APC R1450 |
| 05-003 | APC R1450 |
| 05-004 | APC R1450 |
| 05-005 | BRAF V600E2 & APC E1309 |
| 06-001 | BRAF V600E2 & APC E1309 |
| 06-002 | BRAF V600E2 |
| 06-003 | BRAF V600E2 |
| 06-004 | Wild Type |
| 06-005 | Wild Type |
| 07-001 | Wild Type |
| 07-002 | BRAF V600E2 & APC E1309 |
| 07-003 | Wild Type |
| 07-004 | Wild Type |
| 07-005 | APC E1309 |

These results demonstrate the successful, multiplex detection of multiple cancer-associated mutations from patient stool samples using the methods described herein. These results further confirm the known heterogeneity of stool specimens, demonstrating that different samples obtained from a single specimen can yield different DNA. Also, as compared with Example 1, the PCR conditions used in Example 2 can be more readily adapted to samples with low DNA concentration. In Example 1, each PCR reaction included 4 µL of 12.5 ng/µL extracted DNA, for a total of 50 ng DNA. In Example 2, each PCR reaction can include 20 µL of 2.5 ng/µL extracted DNA to achieve a total of 50 ng DNA (or 0.5 ng/µL DNA Stock for a total of 10 ng DNA), thereby lessening the starting concentration.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

SEQUENCES

All polypeptide sequences are presented N-terminal to C-terminal unless otherwise noted. All polynucleotide sequences are presented 5' to 3' unless otherwise noted. Italicized nucleotides represent locked nucleotides.

KRAS G12 and G13 forward primer
(SEQ ID NO: 1)
GTACTGGTGGAGTATTTGATAGTG

KRAS G12 and G13 reverse primer
(SEQ ID NO: 2)
ATCGTCAAGGCACTCTTGCCTAC

KRAS G12 and G13 blocker nucleic acid
(SEQ ID NO: 3)
TA*CG*CC*ACC*AGCT*invdTinvdTinvdT KRAS G12D minimal probe
(SEQ ID NO: 4)
GGAGCTGATGG KRAS G12V minimal probe
(SEQ ID NO: 5)
GGAGCTGTTGG KRAS G12S minimal probe
(SEQ ID NO: 6)
TGGAGCTAGTGG KRAS G13D minimal probe
(SEQ ID NO: 7)
TGGAGCTGGTGACGT BRAF V600E forward primer
(SEQ ID NO: 8)
GGACCCACTCCATCGAGATTT BRAF V600E reverse primer
(SEQ ID NO: 9)

-continued
CAGATATATTTCTTCATGAAGACCTCACAGTAA

BRAF V600E1 and V600E2 blocker nucleic acid
(SEQ ID NO: 10)
GAGATTTCACTGTAGCinvdTinvdTinvdT BRAF V600E1 minimal probe
(SEQ ID NO: 11)
TCTAGCTACAGAGAAAT BRAF V600E2 minimal probe
(SEQ ID NO: 12)
GTCTAGCTACAGAAAAAT CTNNB1 T41A and T41I forward primer
(SEQ ID NO: 13)
GGAATCCATTCTGGTGCCACT CTNNB1 T41A and T41I reverse primer
(SEQ ID NO: 14)
AGAAAATCCCTGTTCCCACTCATA CTNNB1 T41A and T41I blocker nucleic acid
(SEQ ID NO: 15)
GCCACTACCACAGCTinvdTinvdTinvdT CTNNB1 T41A minimal probe
(SEQ ID NO: 16)
AGGAGCTGTGGCAG CTNNB1 T41I minimal probe
(SEQ ID NO: 17)
GGAGCTGTGATA CTNNB1 S45F and S45P forward primer
(SEQ ID NO: 18)
GGTGCCACTACCACAGCTCCT CTNNB1 S45F and S45P reverse primer
(SEQ ID NO: 19)
TCTCAAAACTGCATTCTGACTTTCA CTNNB1 S45F and S45P blocker nucleic acid
(SEQ ID NO: 20)
GCTCCTTCTCTGAGTinvdTinvdTinvdT CTNNB1 S45F minimal probe
(SEQ ID NO: 21)
TTTACCACTCAGAAAAG CTNNB1 S45P minimal probe
(SEQ ID NO: 22)
TACCACTCAGAGGAG APC S1465 forward primer
(SEQ ID NO: 23)
TAAAAATAAAGCACCTACTGCTGAAA APC S1465 reverse primer
(SEQ ID NO: 24)
AGCTTGCTTAGGTCCACTCTCTCT APC S1465 blocker nucleic acid
(SEQ ID NO: 25)
CCACTCTCTCTCTTTTCAGCinvdTinvdTinvdT APC S1465 minimal probe
(SEQ ID NO: 26)
ACTGCTGAAAAGAGAGT APC E1309 forward primer
(SEQ ID NO: 27)
TAGGATGTAATCAGACGACACAGGA APC E1309 reverse primer
(SEQ ID NO: 28)
CAGCTGACCTAGTTCCAATCTTTTA APC E1309 blocker nucleic acid
(SEQ ID NO: 29)

-continued
CTTTTCTTTTATTTCTGCinvdTinvdTinvdTinvdT

APC E1309 minimal probe
(SEQ ID NO: 30)
GAAATAAAAGATTGG

APC Q1367 forward primer
(SEQ ID NO: 31)
TCTCCCTCCAAAAGTGGTGCT

APC Q1367 reverse primer
(SEQ ID NO: 32)
TGGCAATCGAACGACTCTCAA

APC Q1367 blocker nucleic acid
(SEQ ID NO: 33)
GTGCTCAGACACCinvdTinvdTinvdT

APC Q1367 minimal probe
(SEQ ID NO: 34)
TTTTGGGTGTCTAAG

APC R1450 forward primer
(SEQ ID NO: 35)
GCAGAAGTAAAACACCTCCACCA

APC R1450 reverse primer
(SEQ ID NO: 36)
GGTGCTTTATTTTTAGGTACTTC

APC R1450 blocker nucleic acid
(SEQ ID NO: 37)
CTTCTCGCTTGGTTinvdTinvdTinvdT

APC R1450 minimal probe
(SEQ ID NO: 38)
CAAACCAAGTGAGAA

APC T1556 forward primer
(SEQ ID NO: 39)
CAGGAAAATGACAATGGGAATG

APC T1556 reverse primer
(SEQ ID NO: 40)
ATCTAATAGGTCCTTTTCAGAATCAATAG

APC T1556 blocker nucleic acid
(SEQ ID NO: 41)
CAATAGTTTTTCTGCCinvdTinvdTinvdT

APC T1556 minimal probe
(SEQ ID NO: 42)
AGAGGCAGAAAAAAACT

HLA forward primer
(SEQ ID NO: 43)
TGAGTGTTACTTCTTCCCACACTC

HLA reverse primer
(SEQ ID NO: 44)
ATTGCTTTTGCGCAATCCCT

HLA minimal probe 1
(SEQ ID NO: 70)
GGAGACGGTCTG

Negative control probe
(SEQ ID NO: 46)
AATATAATATATTAT

KRAS G12D full-length probe
(SEQ ID NO: 47)
TTTTTTTTTTTAAGGAGCTGATGG

KRAS G12V full-length probe
(SEQ ID NO: 48)
TTTTTTTTTTTAAGGAGCTGTTGG

KRAS G12S full-length probe
(SEQ ID NO: 49)

```
KRAS G13D full-length probe
                                    (SEQ ID NO: 50)
TTTTTTTTTTATGGAGCTGGTGACGT BRAF V600E1 full-length probe
                                    (SEQ ID NO: 51)
TTTTTTAATTTCTAGCTACAGAGAAAT BRAF V600E2 full-length probe
                                    (SEQ ID NO: 52)
TTTTTTTATGTCTAGCTACAGAAAAT CTNNB1 T41A full-length probe
                                    (SEQ ID NO: 53)
TTTTTTTTTTTAGGAGCTGTGGCAG CTNNB1 T41I full-length probe
                                    (SEQ ID NO: 54)
TTTTTTTTTTTTGGAGCTGTGATA CTNNB1 S45F full-length probe
                                    (SEQ ID NO: 55)
TTTTTTTTTTTACCACTCAGAAAAG CTNNB1 S45P full-length probe
                                    (SEQ ID NO: 56)
TTTTTTTTTAATACCACTCAGAGGAG APC S1465 full-length probe
                                    (SEQ ID NO: 57)
TTTTTTTTACTGCTGAAAAGAGAGT APC E1309 full-length probe
                                    (SEQ ID NO: 58)
TTTTTTTTTTTTGAAATAAAAGATTGG APC Q1367 full-length probe
                                    (SEQ ID NO: 59)
TTTTTTTTTTTTGGGTGTCTAAG APC R1450 full-length probe
                                    (SEQ ID NO: 60)
TTTTTTTTTACAAACCAAGTGAGAA APC T1556 full-length probe
                                    (SEQ ID NO: 61)
TTTTTTTTTTAGAGGCAGAAAAAACT Human KRAS amino acid sequence
                                    (SEQ ID NO: 62)
MTEYKLVVVGAGGVGKSALTIQLIQNHFVDEYDPTIEDSYRKQVVIDGET
CLLDILDTAGQEEYSAMRDQYMRTGEGFLCVFAINNTKSFEDIHHYREQI
KRVKDSEDVPMVLVGNKCDLPSRTVDTKQAQDLARSYGIPFIETSAKTRQ
GVDDAFYTLVREIRKHKEKMSKDGKKKKKKSKTKCVIM Human BRAF amino acid sequence
                                    (SEQ ID NO: 63)
MAALSGGGGGGAEPGQALFNGDMEPEAGAGAGAAASSAADPAIPEEVWNI
KQMIKLTQEHIEALLDKFGGEHNPPSIYLEAYEEYTSKLDALQQREQQLL
ESLGNGTDFSVSSSASMDTVTSSSSSSLSVLPSSLSVFQNPTDVARSNPK
SPQKPIVRVFLPNKQRTVVPARCGVTVRDSLKKALMMRGLIPECCAVYRI
QDGEKKPIGWDTDISWLTGEELHVEVLENVPLTTHNFVRKTFFTLAFCDF
CRKLLFQGFRCQTCGYKFHQRCSTEVPLMCVNYDQLDLLFVSKFFEHHPI
PQEEASLAETALTSGSSPSAPASDSIGPQILTSPSPSKSIPIPQPFRPAD
EDHRNQFGQRDRSSSAPNVHINTIEPVNIDDLIRDQGFRGDGGSTTGLSA
TPPASLPGSLTNVKALQKSPGPQRERKSSSSSEDRNRMKTLGRRDSSDDW
EIPDGQITVGQRIGSGSFGTVYKGKWHGDVAVKMLNVTAPTPQQLQAFKN
EVGVLRKTRHVNILLFMGYSTKPQLAIVTQWCEGSSLYHHLHIIETKFEM
IKLIDIARQTAQGMDYLHAKSIIHRDLKSNNIFLHEDLTVKIGDFGLATV
KSRWSGSHQFEQLSGSILWMAPEVIRMQDKNPYSFQSDVYAFGIVLYELM
TGQLPYSNINNRDQIIFMVGRGYLSPDLSKVRSNCPKAMKRLMAECLKKK
RDERPLFPQILASIELLARSLPKIHRSASEPSLNRAGFQTEDFSLYACAS
PKTPIQAGGYGAFPVH Human CTNNB1 amino acid sequence
                                    (SEQ ID NO: 64)
MATQADLMELDMAMEPDRKAAVSHWQQQSYLDSGIHSGATTTAPSLSGKG
NPEEEDVDTSQVLYEWEQGFSQSFTQEQVADIDGQYAMTRAQRVRAAMFP
ETLDEGMQIPSTQFDAAHPTNVQRLAEPSQMLKHAVVNLINYQDDAELAT
RAIPELTKLLNDEDQVVVNKAAVMVHQLSKKEASRHAIMRSPQMVSAIVR
TMQNTNDVETARCTAGTLHNLSHHREGLLAIFKSGGIPALVKMLGSPVDS
VLFYAITTLHNLLLHQEGAKMAVRLAGGLQKMVALLNKTNVKFLAITTDC
LQILAYGNQESKLIILASGGPQALVNIMRTYTYEKLLWTTSRVLKVLSVC
SSNKPAIVEAGGMQALGLHLTDPSQRLVQNCLWTLRNLSDAATKQEGMEG
LLGTLVQLLGSDDINVVTCAAGILSNLTCNNYKNKMMVCQVGGIEALVRT
VLRAGDREDITEPAICALRHLTSRHQEAEMAQNAVRLHYGLPVVVKLLHP
PSHWPLIKATVGLIRNLALCPANHAPLREQGAIPRLVQLLVRAHQDTQRR
TSMGGTQQQFVEGVRMEEIVEGCTGALHILARDVHNRIVIRGLNTIPLFV
QLLYSPIENIQRVAAGVLCELAQDKEAAEAIEAEGATAPLTELLHSRNEG
VATYAAAVLFRMSEDKPQDYKKRLSVELTSSLFRTEPMAWNETADLGLDI
GAQGEPLGYRQDDPSYRSFHSGGYGQDALGMDPMMEHEMGGHHPGADYPV
DGLPDLGHAQDLMDGLPPGDSNQLAWFDTDL Human APC amino acid sequence
                                    (SEQ ID NO: 65)
MAAASYDQLLKQVEALKMENSNLRQELEDNSNHLTKLETEASNMKEVLKQ
LQGSIEDEAMASSGQIDLLERLKELNLDSSNFPGVKLRSKMSLRSYGSRE
GSVSSRSGECSPVPMGSFPRRGFVNGSRESTGYLEELEKERSLLLADLDK
EEKEKDWYYAQLQNLTKRIDSLPLTENFSLQTDMTRRQLEYEARQIRVAM
EEQLGTCQDMEKRAQRRIARIQQIEKDILRIRQLLQSQATEAERSSQNKH
ETGSHDAERQNEGQGVGEINMATSGNGQGSTTRMDHETASVLSSSSTHSA
PRRLTSHLGTKVEMVYSLLSMLGTHDKDDMSRTLLAMSSSQDSCISMRQS
GCLPLLIQLLHGNDKDSVLLGNSRGSKEARARASAALHNIIHSQPDDKRG
RREIRVLHLLEQIRAYCETCWEWQEAHEPGMDQDKNPMPAPVEHQICPAV
CVLMKLSFDEEHRHAMNELGGLQAIAELLQVDCEMYGLTNDHYSITLRRY
AGMALTNLTFGDVANKATLCSMKGCMRALVAQLKSESEDLQQVIASVLRN
LSWRADVNSKKTLREVGSVKALMECALEVKKESTLKSVLSALWNLSAHCT
ENKADICAVDGALAFLVGTLTYRSQTNTLAIIESGGGILRNVSSLIATNE
DHRQILRENNCLQTLLQHLKSHSLTIVSNACGTLWNLSARNPKDQEALWD
MGAVSMLKNLIHSKHKMIAMGSAAALRNLMANRPAKYKDANIMSPGSSLP
SLHVRKQKALEAELDAQHLSETFDNIDNLSPKASHRSKQRHKQSLYGDYV
```

FDTNRHDDNRSDNFNTGNMTVLSPYLNTTVLPSSSSSRGSLDSSRSEKDR
SLERERGIGLGNYHPATENPGTSSKRGLQISTTAAQIAKVMEEVSAIHTS
QEDRSSGSTTELHCVTDERNALRRSSAAHTHSNTYNFTKSENSNRTCSMP
YAKLEYKRSSNDSLNSVSSSDGYGKRGQMKPSIESYSEDDESKFCSYGQY
PADLAHKIHSANHMDDNDGELDTPINYSLKYSDEQLNSGRQSPSQNERWA
RPKHIIEDEIKQSEQRQSRNQSTTYPVYTESTDDKHLKFQPHFGQQECVS
PYRSRGANGSETNRVGSNHGINQNVSQSLCQEDDYEDDKPTNYSERYSEE
EQHEEEERPTNYSIKYNEEKRHVDQPIDYSLKYATDIPSSQKQSFSFSKS
SSGQSSKTEHMSSSSENTSTPSSNAKRQNQLHPSSAQSRSGQPQKAATCK
VSSINQETIQTYCVEDTPICFSRCSSLSSLSSAEDEIGCNQTTQEADSAN
TLQIAEIKEKIGTRSAEDPVSEVPAVSQHPRTKSSRLQGSSLSSESARHK
AVEFSSGAKSPSKSGAQTPKSPPEHYVQETPLMFSRCTSVSSLDSFESRS
IASSVQSEPCSGMVSGIISPSDLPDSPGQTMPPSRSKTPPPPPQTAQTKR
EVPKNKAPTAEKRESGPKQAAVNAAVQRVQVLPDADTLLHFATESTPDGF
SCSSSLSALSLDEPFIQKDVELRIMPPVQENDNGNETESEQPKESNENQE
KEAEKTIDSEKDLLDDSDDDDIEILEECIISAMPTKSSRKAKKPAQTASK
LPPPVARKPSQLPVYKLLPSQNRLQPQKHVSFTPGDDMPRVYCVEGTPIN
FSTATSLSDLTIESPPNELAAGEGVRGGAQSGEFEKRDTIPTEGRSTDEA
QGGKTSSVTIPELDDNKAEEGDILAECINSAMPKGKSHKPFRVKKIMDQV
QQQASASSSAPNKNQLDGKKKKPTSPVKPIPQNTEYRTRVRKNADSKNNLN
AERVFSDNKDSKKQNLKNNSKVFNDKLPNNEDRVRGSFAFDSPHHYTPIE
GTPYCFSRNDSLSSLDFDDDDVDLSREKAELRKAKENKESEAKVTSHTEL
TSNQQSANKTQAIAKQPINRGQPKPILQKQSTFPQSSKDIPDRGAATDEK
LQNFAIENTPVCFSHNSSLSSLSDIDQENNNKENEPIKETEPPDSQGEPS
KPQASGYAPKSFHVEDTPVCFSRNSSLSSLSIDSEDDLLQECISSAMPKK
KKPSRLKGDNEKHSPRNMGGILGEDLTLDLKDIQRPDSEHGLSPDSENFD
WKAIQEGANSIVSSLHQAAAAACLSRQASSDSDSILSLKSGISLGSPFHL
TPDQEEKPFTSNKGPRILKPGEKSTLETKKIESESKGIKGGKKVYKSLIT
GKVRSNSEISGQMKQPLQANMPSISRGRTMIHIPGVRNSSSSTSPVSKKG
PPLKTPASKSPSEGQTATTSPRGAKPSVKSELSPVARQTSQIGGSSKAPS
RSGSRDSTPSRPAQQPLSRPIQSPGRNSISPGRNGISPPNKLSQLPRTSS
PSTASTKSSGSGKMSYTSPGRQMSQQNLTKQTGLSKNASSIPRSESASKG
LNQMNNGNGANKKVELSRMSSTKSSGSESDRSERPVLVRQSTFIKEAPSP
TLRRKLEESASFESLSPSSRPASPTRSQAQTPVLSPSLPDMSLSTHSSVQ
AGGWRKLPPNLSPTIEYNDGRPAKRHDIARSHSESPSRLPINRSGTWKRE
HSKHSSSLPRVSTWRRTGSSSSILSASSESSEKAKSEDEKHVNSISGTKQ
SKENQVSAKGTWRKIKENEFSPTNSTSQTVSSGATNGAESKTLIYQMAPA
VSKTEDVWVRIEDCPINNPRSGRSPTGNTPPVIDSVSEKANPNIKDSKDN
QAKQNVGNGSVPMRTVGLENRLNSFIQVDAPDQKGTEIKPGQNNPVPVSE
TNESSIVERTPFSSSSSSKHSSPSGTVAARVTPFNYNPSPRKSSADSTSA
RPSQIPTPVNNNTKKRDSKTDSTESSGTQSPKRHSGSYLVTSV

Human KRAS cDNA sequence
(SEQ ID NO: 66)
TGTGCTCGGAGCTCGATTTTCCTAGGCGGCGGCCGCGGCGGCGGAGGCAG
CAGCGGCGGCGGCAGTGGCGGCGGCGAAGGTGGCGGCGGCTCGGCCAGTA
CTCCCGGCCCCCGCCATTTCGGACTGGGAGCGAGCGCGGCGCAGGCACTG
AAGGCGGCGGCGGGGCCAGAGGCTCAGCGGCTCCCAGGCCTGCTGAAAAT
GACTGAATATAAACTTGTGGTAGTTGGAGCTGGTGGCGTAGGCAAGAGTG
CCTTGACGATACAGCTAATTCAGAATCATTTTGTGGACGAATATGATCCA
ACAATAGAGGATTCCTACAGGAAGCAAGTAGTAATTGATGGAGAAACCTG
TCTCTTGGATATTCTCGACACAGCAGGTCAAGAGGAGTACAGTGCAATGA
GGGACCAGTACATGAGGACTGGGGAGGGCTTTCTTTGTGTATTTGCCATA
AATAATACTAAATCATTTGAAGATATTCACCATTATAGAGAACAAATTAA
AAGAGTTAAGGACTCTGAAGATGTACCTATGGTCCTAGTAGGAAATAAAT
GTGATTTGCCTTCTAGAACAGTAGACACAAAACAGGCTCAGGACTTAGCA
AGAAGTTATGGAATTCCTTTTATTGAAACATCAGCAAAGACAAGACAGAG
AGTGGAGGATGCTTTTTATACATTGGTGAGAGAGATCCGACAATACAGAT
TGAAAAAAATCAGCAAAGAAGAAAAGACTCCTGGCTGTGTGAAAATTAAA
AAATGCATTATAATGTAATCTGGGTGTTGATGATGCCTTCTATACATTAG
TTCGAGAAATTCGAAAACATAAAGAAAAGATGAGCAAAGATGGTAAAAAG
AAGAAAAAG Human BRAF cDNA sequence
(SEQ ID NO: 67)
GTTATAAGATGGCGGCGCTGAGCGGTGGCGGTGGTGGCGGCGCGGAGCCG
GGCCAGGCTCTGTTCAACGGGGACATGGAGCCCGAGGCCGGCGCCGGCGC
CGGCGCCGCGGCCTCTTCGGCTGCGGACCCTGCCATTCCGGAGGAGGTGT
GGAATATCAAACAAATGATTAAGTTGACACAGGAACATATAGAGGCCCTA
TTGGACAAATTTGGTGGGGAGCATAATCCACCATCAATATATCTGGAGGC
CTATGAAGAATACACCAGCAAGCTAGATGCACTCCAACAAAGAGAACAAC
AGTTATTGGAATCTCTGGGGAACGGAACTGATTTTTCTGTTTCTAGCTCT
GCATCAATGGATACCGTTACATCTTCTTCCTCTTCTAGCCTTTCAGTGCT
ACCTTCATCTCTTTCAGTTTTTCAAAATCCCACAGATGTGGCACGGAGCA
ACCCCAAGTCACCACAAAAACCTATCGTTAGAGTCTTCCTGCCCAACAAA
CAGAGGACAGTGGTACCTGCAAGGTGTGGAGTTACAGTCCGAGACAGTCT
AAAGAAAGCACTGATGATGAGAGGTCTAATCCCAGAGTGCTGTGCTGTTT
ACAGAATTCAGGATGGAGAGAAGAAACCAATTGGTTGGGACACTGATATT
TCCTGGCTTACTGGAAGAATTGCATGTGGAAGTGTTGGAGAATGTTCC
ACTTACAACACACAACTTTGTACGAAAAACGTTTTTCACCTTAGCATTTT
GTGACTTTTGTCGAAAGCTGCTTTTCCAGGGTTTCCGCTGTCAAACATGT
GGTTATAAATTTCACCAGCGTTGTAGTACAGAAGTTCCACTGATGTGTGT
TAATTATGACCAACTTGATTTGCTGTTTGTCTCCAAGTTCTTTGAACACC
ACCCAATACCACAGGAAGAGGCGCCTTAGCAGAGACTGCCCTAACATCTG

```
GATCATCCCCTTCCGCACCCGCCTCGGACTCTATTGGGCCCCAAATTCTC
ACCAGTCCGTCTCCTTCAAAATCCATTCCAATTCCACAGCCCTTCCGACC
AGCAGATGAAGATCATCGAAATCAATTGGGCAACGAGACCGATCCTCATC
AGCTCCCAATGTGCATATAAACACAATAGAACCTGTCAATATTGATGACT
TGATTAGAGACCAAGGATTTCGTGGTGATGGAGCCCCTTTGAACCAGCTG
ATGCGCTGTCTTCGGAAATACCAATCCCGGACTCCCAGTCCCTCCTACA
TTCTGTCCCCAGTGAAATAGTGTTTGATTTTGAGCCTGGCCCAGTGTTCA
GAGGATCAACCACAGGTTTGTCTGCTACCCCCCCTGCCTCATTACCTGGC
TCACTAACTAACGTGAAAGCCTTACAGAAATCTCCAGGACCTCAGCGAGA
AAGGAAGTCATCTTCATCCTCAGAAGACAGGAATCGAATGAAAACACTTG
GTAGACGGGACTCGAGTGATGATTGGGAGATTCCTGATGGGCAGATTACA
GTGGGACAAAGAATTGGATCTGGATCATTTGGAACAGTCTACAAGGGAAA
GTGGCATGGTGATGTGGCAGTGAAAATGTTGAATGTGACAGCACCTACAC
CTCAGCAGTTACAAGCCTTCAAAAATGAAGTAGGAGTACTCAGGAAAACA
CGACATGTGAATATCCTACTCTTCATGGGCTATTCCACAAACCACAACTG
GCTATTGTTACCCAGTGGTGTGAGGGCTCCAGCTTGTATCACCATCTCCA
TATCATTGAGACCAAATTTGAGATGATCAAACTTATAGATATTGCACGAC
AGACTGCACAGGGCATGGATTACTTACACGCCAAGTCAATCATCCACAGA
GACCTCAAGAGTAATAATATATTTCTTCATGAAGACCTCACAGTAAAAAT
AGGTGATTTTGGTCTAGCTACAGTGAAATCTCGATGGAGTGGGTCCCATC
AGTTTGAACAGTTGTCTGGATCCATTTTGTGGATGGCACCAGAAGTCATC
AGAATGCAAGATAAAAATCCATACAGCTTTCAGTCAGATGTATATGCATT
TGGAATTGTTCTGTATGAATTGATGACTGGACAGTTACCTTATTCAAACA
TCAACAACAGGGACCAGATAATTTTTATGGTGGGACGAGGATACCTGTCT
CCAGATCTCAGTAAGGTACGGAGTAACTGTCCAAAAGCCATGAAGAGATT
AATGGCAGAGTGCCTCAAAAAGAAAAGAGATGAGAGACCACTCTTTCCCC
AAATTCTCGCCTCTATTGAGCTGCTGGCCCGCTCATTGCCAAAAATTCAC
CGCAGTGCATCAGAACCCTCCTTGAATCGGGCTGGTTTCCAAACAGAGGA
TTTTAGTCTATATGCTTGTGCTTCTCCAAAAACACCCATCCAGGCAGGGG
GATATGGAGAATTTGCAGCCTTCAAGTAGCCACCATCATGGCAGCATCTG
CTCTTATTTCTTAAGTCTTGTGTTCGTACAATTTGTTAACATCAAACAC
AGTTCTGTTCCTCAAATCTTTTTTTAAAGATACAAAATTTCCAATGCATA
AGCTGATGTGGAACAGAATGGAATTTCCCATCCAACAAAGAGGAAAGAA
TGTTTTAGGAACCAGAATTCTCTGCTGCCAGTGTTTCTTCAACAAAAATA
CCACGAGCATACAAGTCTGCCCAGTCCCAGGAAGAAAGAGGAGAGACCCT
GAATTCTGACCTTTTGATGGTCAGGCATGATGGAAAGAAACTGCTGCTAC
AGCTTGGGAGATTTGCTATGGAAAGTCTGCCAGTCAACTTTGCCCTTCTA
ACCACCAGATCAATTTGTGGCTGATCATCTGATGGGCAGTTTCAATCAC
CAAGCATCGTTCTCTTTCCTGTTCTGGAATTTTGTTTTGGAGCTCTTTCC
CCTAGTGACCACCAGTTAGTTTCTGAGGGATGGAACAAAAATGCAGCTTG
CCCTTTCTATGTGGTGCGTGTTCAGGCCTTGACAGATTTTATCAAAAGGA
AACTATTTTATTTAAATGGAGGCTGAGTGGTGAGTAGATGTGTCTTGGTA
TGGAGGAAAAGGGCATGCTGCATCTTCTTCCTGACCTCCGGGGTCTCTGG
CCTTTTGTTTCCTTGCTCACTGAGGGGTCTGTCTAACCAAGCAGGCTAGA
TAGTGCTGGCACACATTGCCTTCTTTCTCATTGGGTCCAGCAATGAAGAT
AAGTGTTTGGGTTTTTTTTTTTCCTCCACAATGTAGCAAATTCTCAGGA
AATACAGTTTATATCTTCCTCCTATGCTCTTCCAGTCACCAACTACTTAT
GCGGCTACTTTGTCCAGGGCACAAAATGCCGTGGCAGTATCTAACTAAAC
CCCCACAAAACTGCTTAATAACAGTTTTGAATGTAGAAATTTAGATAATT
TAAATATAAGGTACAGGTTTTAATTTCTGAGTTTCTTCTTTTCTATTTTT
ATTAAAAGAAAATAATTTTCAGATTTAATTGAATTGGAAAAAAACAATA
CTTCCCACCAGAATTATATATCCTGAAAATTGTATTTTTGTTATATAAAC
AACTTTTAAGAAAGATCATTATCCTTTTCTCTACCTAAATATGAGGAGTC
TTAGCATAATGACAAATATTTATAATTTTTCAATTAATGGTACTTGCTGG
ATCCACACTAACATCTTTGCTAATAATCTCATTGTTTCTTCCAACTGATT
CCTAACACTATATCCCACATCTTCTTTCTAGTCTTTTATCTAGAATATGC
AACCTAAAATAAAAATGGTGGCGTCTCCATTCATTCTCCTTCTTCCTTTT
TTCCCAAGCCTGGTCTTCAAAAGGTTGGGCAATTTGGCAGCTGAATTCCC
AGACAGAGAATAGAGCAATTTTAGGGATATTAGGACTGAGGGAGGGTGTG
GGAAAGCTGTCATCAGTTGTTTTTATAGAAAGAACTGGCATTCATTAAGA
ACCTAAATCTTATCTTTGCACAAATGGAAAATATAACCTAGTTATAGCTT
CCTTTGGCCTTTATTAAAGGGTAATATCAATCACAGTCATAGCAAAGAAA
GCGGATGTATTAATGGCAAATTAATGGAAAACCTCCCTTATCAGGAATCT
AGACTCAGAATTTAGGAACACAAATCAAATCAGACCAACCAAGCTATAGC
CAAGGACTTGAAAGAAATTAAACAAGACCCAGAATAAATCAAGGAATTAG
AAATTGTTATTTAAAAATTTCAGATTGTAATCCAGGCCCTGCTGTCTATA
TTGCAGCCACTAAAAGCTCACTACCATTAGATTTTTGCTAACATACATGT
ATTCAGAAGAAAGCCTATTGAAATTTTCATTGTCTTGTAAAAGGTTGTCC
TAGTAAAATGGAAAAGATCCTTAAGTTATTAATCAGTTTGAAAAGCAAAT
TTGTTTTTAAGTTTTACATCAGCAGGGCAGTGTCTTACAAAATTCAGAAA
TTGCAAAGGTGGAAATAATTCACGCTGATTTGAAGAACATCTTCTGTGCA
ATAATACTGCCTCTCTTGAAAAGCATTGGCTGTTTTTTCTTTTTAAATAT
ATCTCTAGATGCTTTTAAATGTGGCTGTGTTCCCTTTACCAAGATTGGCT
TCAAGTTTCCGCAGGTAGAGAGACCTGGGCTTGAACAAGAGGATGTGTTT
CATGTCCTGCTGAGGAGGTAGAACATGTGCAGCCTGGGTCCGGGACTGCC
TCCGTGGGCAGGGCAGGGCGGTACCATTAGGGAGGAAGCTTAGCATT
TCAGTTTCTTAAACAATATTCAGGGTGATACACTTTTTCTTCCCTTGCAT
TTTAGAATAGGCTGGTATCTCATTTGAACGGGGGAGCAGACTTGATCTCA
AATGAAGCTGTGCCCAGGAGCCAGGCTTAGCATATTGAGATTTTTATAGA
TACCTTAAAAAATAAAATATTTAAACCTCTCTTTTCTTCCTTTTTCTATG
AAATAGGTTTTTTCTCTAGTTTACAAATGACATGAAAATAGGTTTTATTT
```

```
GTGTTTTATCTGCTTTATTTTTTGATGCTTAGACAACAGTTAGACTTACT
GAGCTCCTAAAAAAACGAGGAAGAAGTCCTTATTTGTGAAAAGCACTTTA
TGAGTAATTGTATAGACAGTATGTGGCTGCGTCACTGATCATCTTGTAAG
GGTGTAACAGTCTTGTCTGTAAAGTGGCTGCAGTGCCTTCTGTAGTGTGT
TTTATTTTTGGTAGGGAGAGGTGAAGCCTTCTGAAAAATTTGAGAGCAAC
TACAGAGGATTGTTTGTAACTGTGTAGTATTCCTGATGGACTTTTTTCAT
CGTTAGATCAAGGACCTAGACTTTTGCCACTGAAATAATATTGACCAAAA
AAATAGTTTATAAAAGGGATTTGTGAATAGAAAATTCAGTGTGATCATTT
GTTGTTAATGTGCACCTTAAAAGAAGATTCTGTCTAGCTGTCAAATTCTG
GTTCCCGAATATCTCACCCCTGATTGTATTTGAGATCTAGTAGGGCATAC
TGGGGCATTTTAGAAGATAAAATCCCATACAAATGATATATGCTATATTT
ATGTTGGTGTTGGAGAAGAAAGAGCAGTATATAAAGAAATAATTCAAGAC
TGCAGCACTGTCAACCTGAAACTTTGTAAATATTTCCTAGCTTCTGGTTT
GGTGCGGTGACAGCACTTTCATCACAGGATGTTACCTTGTATTCACCAGG
CGGAGTGCGAGCTGCTGCACATCCTCCTCAGATCTCACCTGTCCCCACTG
TACATCCACCCGCCAGCTGCTTGCAAACCTCATCTCTAGCTTTAGTTCGA
AACCACATTGCAGGGTTCAGGTGACCTCTACAAAAACTACCTCTTCAGA
ATGAGGTAATGAATAGTTATTTATTTTAAAATATGAAAAGTCAGGAGCTC
TAGAACATGACGATGATTTAAGATTTTAACTTTTTTGTGTACTTGTATTT
GAGCACTCTCATTTTGTCCTAAAGGGCATTATACATTTAAGCAGTAATAC
TGTAAAAAATGTGTTGCTCGGAATATCTGAATGTTGTTGAAAGTGGTGC
CAGAACCGGTTTAGGGGTACGTTTCAGAATCTTAACCTTGAGTCAATTGC
ATGAAATTAAATAGCTGTGGTATCACTTCACTAACAGTGATGTAATTTA
ATTTTCAGTAGGCTTGGCATGACAGTACATCCTCATAATGAGTTTGCTGC
AGCTTTGTCACATGCACAGGCATTCATAGAAAGACCACCCAGCTAAGAGG
GTAGAATGATTACTCTTTTTGCAAGATTCTCTTCTTTGTCCAAGTTGGCA
TTGTTAGGCTAGGAATACCAGCACCTTGAGACGAGCAGATTCCAACCATT
AGGCTATAAACACCATAGCCAGAGATGGAAGGTTTACTGTGAGTATGAAC
AGCAAATAGCTTACAGGTCATGAGTTGAAATGGTGTAGGTGAGGCTCTAG
AAAAATACCTTGACAATTTGCCAAATGATCTTACTGTGCCTTCATGATGC
AATAAAAAGCTAACATTTAGCAGAAATCAGTGATTTGTGAAGAGAGCA
GCCACTCTGGTTTAACTCAGCTGTGTTAATAATTTTTAGAGTGCAATTTA
GACTGCATAGGTAAATGCACTAAAGAGTTTATAGCCAAAATCACATTTAA
CAATGAGAAAACACACAGGTAAATTTTCAGTGAACAAAATTATTTTTTA
AAGCACATAATCCCTAGTATAGTCAGATATATTTATCACATAGAGCAACT
AGGTTGCAAATATAGTTCAGTGACATTTCTAGAGAAACTTTTTCTACTCC
CATAGGCTCTTCAAAGCATGGAACTTTTATACAACAGAAATGTTGACAGA
AATTGCTGTAGTTTAGGGTTGAAGTACTGTATGATGGGCAGCAATCATGT
ATTAACTTAGAAGGGGAAATTGAAATATAGGACCGAATTTGGTTTTATCA
GTTTCCAGAGTACTGCTGCCAACCTAGACACTGATTTTTCAGAGTTTGAA
ATGTAAATTTCTTCCCGGGACTTGATTGCACATGAAGCTGGACTGCGTTA
GTCATCCTGTCCCAAAGCGCTGTGGGGGCCAGGGTGGAGGTCTCAAGGCA
TCCTTTATGACCTGGCCATTGGATGTAAAAGAAAACATATTCCATGCTGT
GGTTCTTGTATCTTGTTTCATTCCTCACCATTGAAAGAGAAAGTCCATGT
ATTGTCTCCAGCACATCCTTGAAATGTTATACTGGGATGGATTACTGATG
CCCATCGGTAGTTGAGCCCCAGAAGAGGGTAGTAGCATCTCTGCCTCAGG
TGATGATTTGTAGCTTGGCCAGAGGAGAGCGGAGTCACCAGTATATCTGT
GGTCCATGTTGCTAGCTCTGGTAAAATTAAAAATACTGGTAAGATGTTTG
TTTTATTAGTACACTAGACAGTAAGCTCTGTTTTGTTGTTTTCAAATAAC
CTATTTTCACTTTTGTTTGGGCAAAGACATTTAAATTGAAATTCAATTCT
AATTTTTGTTAATTGTGGAAAGGGTAATTAACAGTTCCTATCAGGTATTT
TTAATGTGGAAAAGGACAGAAACCCAACTCCTAAAATCTTAAATTAAGGT
AACAGTGCTTTAAAAAAAAAAAATGCATGGGGCAATTAGTCGGCAACTCA
ATGAGTGACTAAAGTACTTTTATTTAACATCCACAACTTCAACTGTTAAG
TTTTATTAATTACTAAATCAGCTTTATTAAAATGTTGACATTTATTTAGC
TATTTTGAATAATTATAGTGACTTGACGAGTGTGTATGAGGACACAGCCA
ATGTAAGCCAGTGTATCCATTTTTAGAGGTGCATTTTTTTTAAAGAAT
TCTGTAGATAGAAGTGCTCTGAAAACAACTAAAATATGTTTATTCATGGT
AGTATCAAAAAATGTTTGTACAAACCATCTGCTTCTCCCGGCCAGCCGAG
TTCATTCTCCAGCACCGTGACCGCTGGTTCTCATGTACAGCACATATGCG
GGAGAGTTGGCAGAAAATTTGTGAAGAGATGCCGCAAAGGAAGGGTCTGT
TGACGGGTGGGATTGGGGGTTTTGATGAAGTTGCTTAGTCCTGGTTTTGT
TTTGAAAATTACTGCGTTGCATTTTTGTGTTAAGTTTTTGAACCCACGTG
TGTTTTGGTGGAGTATGAGTTGGAAGTCACTGCAAACTAGCATAAACAAC
AAAGCTCACAGAGTAGGCACAGATGTAGAGAACAGAGACCAAAATGGGT
GAGGTGGCAGTAAATCTAGGATAGGGAAAAATTAATGTGAGGGTGGGAAA
TAAACTGTAATTACCTGAAATCAAATGTAAGAGTGCAATAAGTATGCTTT
TTATTCTAAGCTGTGAACGGTTTTTTTAAGAATCATTCCTTCCTAATACA
TTTGTGTATGTTCCATAGCTGATTAAAACCAGCTATATCAACATATAATG
CCTTTTTATTCATGTTAATGACCAACGTAAGTGGCTAGCCTTTATGTCTT
ATTTATCTTCATGTTATGTTAGTTTACATACAGGGGTGTATGTCTCTGTG
CTGTCCCCTTCTCCTGCCTTCATTTTAAAATGCATCCATGGGTCCTCCGT
GTTTCCTTTGGCCATGCCACATATATAGACTCAGTTTGGCCTTCATGATA
TCGCCTGATTTTTGAGGACTGTATCACAGTGATATGTATTTGTGGTAATC
TCATTTGTTGGTTGTACATCTGATCCTTTCCTCAACATGGCAATTGCTGC
CTTTCCTAAGATAGGATCATACAACTGATCAGGGGATTGAATTTGATCAT
TCATCAACATGTGTCTCTGAATTTTATTCAGTAGTTGTCATTGCTCTTTG
GTTTAGACCAAGAAAAGGAAATCCCCCCTTTTCATGTATTCCTTGGTTT
GAGGACATGACTCCTGTAAGGGAGAGGAAAGGGAGATGCTTCCTGTTTGA
ACTGCAGTGAATTCACGGTTCCTGTTTCACCACTCCAAACCTTATGGCGA
CTCACACACACATTCCTCTTTTCTGTTACTGCCAAAGGTTCGGGTTTAGT
```

```
ACACTTCAGTTCCACTCAAGCATTGAAAAGGTTCTCGTGGAGTCTGGGGC
GTGCCCAGTGAAAAGATGGGGACTTTTTAATTGTCCACAGACCTCTCTAT
ACCTGCTTTGCAAAAATTACAATGGAGTAACTATTTTTAAAGCTTATTTT
TCAATTCATAAAAAAGACATTTATTTTCAGTCAAATGGATGATGTCTCCC
TCTTTTCCCCTATTCTCAATGTTTGCTTGAATCTTTTATTATTTTTTTA
ATTCTCCCCCATACCCACTTCCTGATACTTTGGTTCTCTTTCCTGCTCAG
GTCCCTTCATTTGTACTTTGGAGTTTTTCTCATGTAAATTTGTATAACAG
AAAATATTGTTCAGTTTGGATAGAAAGCATGGAGAATAAAAAAAGATAGC
TGAAATTCAGATTGAAGAAATTTATTTCTGTGTAAAGTTATTTAAAAACT
GTATTATATAAAAGGCAAAAAAAGTTCTATGTACTTGATGTGAATATGCG
AATACTGCTATAATAAAGATTGACTGCATGGAGAAGTC
```

Human CTNNB1 cDNA sequence (SEQ ID NO: 68)

```
AAGTCCCATCAGTCCTGGGGATCGGACCAGTGGACTTTCTCTTAAGATTT
CCTCTTTCATTCTTAAGAATAGAAGTGTTATTATTTTTTTAATGCCCTG
GCTATGTGAGTTTGAATCGAAGCAACTTTAAACCTTAGAGCAACTAAACT
CTAAGTGCAGCGGGTGCGATGCGTCAGTAGGGTGAGCACATAAAAAATCC
ATGTCTTGCACCTGTATTTTAGCGTACTATGCAGGGTATTTGAAGTATAC
CATACAACTGTTTTGAAAATCCAGCGTGGACAATGGCTACTCAAGCTGAT
TTGATGGAGTTGGACATGGCCATGGAACCAGACAGAAAAGCGGCTGTTAG
TCACTGGCAGCAACAGTCTTACCTGGACTCTGGAATCCATTCTGGTGCCA
CTACCACAGCTCCTTCTCTGAGTGGTAAAGGCAATCCTGAGGAAGAGGAT
GTGGATACCTCCCAAGTCCTGTATGAGTGGGAACAGGGATTTTCTCAGTC
CTTCACTCAAGAACAAGTAGCTGATATTGATGGACAGTATGCAATGACTC
GAGCTCAGAGGGTACGAGCTGCTATGTTCCCTGAGACATTAGATGAGGGC
ATGCAGATCCCATCTACACAGTTTGATGCTGCTCATCCCACTAATGTCCA
GCGTTTGGCTGAACCATCACAGATGCTGAAACATGCAGTTGTAAACTTGA
TTAACTATCAAGATGATGCAGAACTTGCCACACGTGCAATCCCTGAACTG
ACAAAACTGCTAAATGACGAGGACCAGGTGGTGGTTAATAAGGCTGCAGT
TATGGTCCATCAGCTTTCTAAAAAGGAAGCTTCCAGACACGCTATCTGCG
TTCTCCTCAGATGGTGTCTGCTATTGTACGTACCATGCAGAATACAAATG
ATGTAGAAACAGCTCGTTGTACCGCTGGGACCTTGCATAACCTTTCCCAT
CATCGTGAGGGCTTACTGGCCATCTTTAAGTCTGGAGGCATTCCTGCCCT
GGTGAAAATGCTTGGTTCACCAGTGGATTCTGTGTTGTTTATGCCATTA
CAACTCTCCACAACCTTTTATTACATCAAGAAGGAGCTAAAATGGCAGTG
CGTTTAGCTGGTGGGCTGCAGAAAATGGTTGCCTTGCTCAACAAAACAAA
TGTTAAATTCTTGGCTATTACGACAGACTGCCTTCAAATTTTAGCTTATG
GCAACCAAGAAAGCAAGCTCATCATACTGGCTAGTGGTGGACCCCAAGCT
TTAGTAAATATAATGAGGACCTATACTTACGAAAAACTACTGTGGACCAC
AAGCAGAGTGCTGAAGGTGCTATCTGTCTGCTCTAGTAATAAGCCGGCTA
TTGTAGAAGCTGGTGGAATGCAAGCTTTAGGACTTCACCTGACAGATCCA
```

```
AGTCAACGTCTTGTTCAGAACTGTCTTTGGACTCTCAGGAATCTTTCAGA
TGCTGCAACTAAACAGGAAGGGATGGAAGGTCTCCTTGGGACTCTTGTTC
AGCTTCTGGGTTCAGATGATATAAATGTGGTCACCTGTGCAGCTGGAATT
CTTTCTAACCTCACTTGCAATAATTATAAGAACAAGATGATGGTCTGCCA
AGTGGGTGGTATAGAGGCTCTTGTGCGTACTGTCCTTCGGGCTGGTGACA
GGGAAGACATCACTGAGCCTGCCATCTGTGCTCTTCGTCATCTGACCAGC
CGACACCAAGAAGCAGAGATGGCCCAGAATGCAGTTCGCCTTCACTATGG
ACTACCAGTTGTGGTTAAGCTCTTACACCCACCATCCCACTGGCCTCTGA
TAAAGGCTACTGTTGGATTGATTCGAAATCTTGCCCTTTGTCCCGCAAAT
CATGCACCTTTGCGTGAGCAGGGTGCCATTCCACGACTAGTTCAGTTGCT
TGTTCGTGCACATCAGGATACCCGCGCCGTACGTCCATGGGTGGGACACA
GCAGCAATTTGTGGAGGGGGTCCGCATGGAAGAAATAGTTGAAGGTTGTA
CCGGAGCCCTTCACATCCTAGCTCGGGATGTTCACAACCGAATTGTTATC
AGAGGACTAAATACCATTCCATTGTTTGTGCAGCTGCTTTATTCTCCCAT
TGAAAACATCCAAAGAGTAGCTGCAGGGGTCCTCTGTGAACTTGCTCAGG
ACAAGGAAGCTGCAGAAGCTATTGAAGCTGAGGGAGCCACAGCTCCTCTG
ACAGAGTTACTTCACTCTAGGAATGAAGGTGTGGCGACATATGCAGCTGC
TGTTTTGTTCCGAATGTCTGAGGACAAGCCACAAGATTACAAGAAACGGC
TTTCAGTTGAGCTGACCAGCTCTCTCTTCAGAACAGAGCCAATGGCTTGG
AATGAGACTGCTGATCTTGGACTTGATATTGGTGCCCAGGGAGAACCCCT
TGGATATCGCCAGGATGATCCTAGCTATCGTTCTTTTCACTCTGGTGGAT
ATGGCCAGGATGCCTTGGGTATGGACCCCATGATGGAACATGAGATGGGT
GGCCACCACCCTGGTGCTGACTATCCAGTTGATGGGCTGCCAGATCTGGG
GCATGCCCAGGACCTCATGGATGGGCTGCCTCCAGGTGACAGCAATCAGC
TGGCCTGGTTTGATACTGACCTGTAAATCATCCTTTAGGAGTAACAATAC
AAATGGATTTTGGGAGTGACTCAAGAAGTGAAGAATGCACAAGAATGGAT
CACAAGATGGAATTTATCAAACCCTAGCCTTGCTTGTTAAATTTTTTTT
TTTTTTTTTAAGAATATCTGTAATGGTACTGACTTTGCTTGCTTTGAAG
TAGCTCTTTTTTTTTTTTTTTTTTTTTTGCAGTAACTGTTTTTTAAG
TCTCTCGTAGTGTTAAGTTATAGTGAATACTGCTACAGCAATTTCTAATT
TTTAAGAATTGAGTAATGGTGTAGAACACTAATTCATAATCACTCTAATT
AATTGTAATCTGAATAAAGTGTAACAATTGTGTAGCCTTTTTGTATAAAA
TAGACAAATAGAAAATGGTCCAATTAGTTTCCTTTTTAATATGCTTAAAA
TAAGCAGGTGGATCTATTTCATGTTTTTGATCAAAAACTATTTGGGATAT
GTATGGGTAGGGTAAATCAGTAAGAGGTGTTATTTGGAACCTTGTTTTGG
ACAGTTTACCAGTTGCCTTTTATCCCAAAGTTGTTGTAACCTGCTGTGAT
ACGATGCTTCAAGAGAAAATGCGGTTATAAAAAATGGTTCAGAATTAAAC
TTTTAATTCATTCGA
```

Human APC cDNA sequence (SEQ ID NO: 69)

```
GTATTGGTGCAGCCCGCCAGGGTGTCACTGGAGACAGAATGGAGGTGCTG
CCGGACTCGGAAATGGGGTCCAAGGGTAGCCAAGGATGGCTGCAGCTTCA
```

```
TATGATCAGTTGTTAAAGCAAGTTGAGGCACTGAAGATGGAGAACTCAAA
TCTTCGACAAGAGCTAGAAGATAATTCCAATCATCTTACAAAACTGGAAA
CTGAGGCATCTAATATGAAGGAAGTACTTAAACAACTACAAGGAAGTATT
GAAGATGAAGCTATGGCTTCTTCTGGACAGATTGATTTATTAGAGCGTCT
TAAAGAGCTTAACTTAGATAGCAGTAATTTCCCTGGAGTAAAACTGCGGT
CAAAAATGTCCCTCCGTTCTTATGGAAGCCGGGAAGGATCTGTATCAAGC
CGTTCTGGAGAGTGCAGTCCTGTTCCTATGGGTTCATTTCCAAGAAGAGG
GTTTGTAAATGGAAGCAGAGAAAGTACTGGATATTTAGAAGAACTTGAGA
AAGAGAGGTCATTGCTTCTTGCTGATCTTGACAAAGAAGAAAAGGAAAAA
GACTGGTATTACGCTCAACTTCAGAATCTCACTAAAAGAATAGATAGTCT
TCCTTTAACTGAAAATTTTTCCTTACAAACAGATATGACCAGAAGGCAAT
TGGAATATGAAGCAAGGCAAATCAGAGTTGCGATGGAAGAACAACTAGGT
ACCTGCCAGGATATGGAAAAACGAGCACAGCGAAGAATAGCCAGAATTCA
GCAAATCGAAAAGGACATACTTCGTATACGACAGCTTTTACAGTCCCAAG
CAACAGAAGCAGAGAGGTCATCTCAGAACAAGCATGAAACCGGCTCACAT
GATGCTGAGCGGCAGAATGAAGGTCAAGGAGTGGGAGAAATCAACATGGC
AACTTCTGGTAATGGTCAGGGTTCAACTACACGAATGGACCATGAAACAG
CCAGTGTTTTGAGTTCTAGTAGCACACACTCTGCACCTCGAAGGCTGACA
AGTCATCTGGGAACCAAGGTGGAAATGGTGTATTCATTGTTGTCAATGCT
TGGTACTCATGATAAGGATGATATGTCGCGAACTTTGCTAGCTATGTCTA
GCTCCCAAGACAGCTGTATATCCATGCGACAGTCTGGATGTCTTCCTCTC
CTCATCCAGCTTTTACATGGCAATGACAAAGACTCTGTATTGTTGGGAAA
TTCCCGGGGCAGTAAAGAGGCTCGGGCCAGGGCCAGTGCAGCACTCCACA
ACATCATTCACTCACAGCCTGATGACAAGAGAGGCAGGCGTGAAATCCGA
GTCCTTCATCTTTTGGAACAGATACGCGCTTACTGTGAAACCTGTTGGGA
GTGGCAGGAAGCTCATGAACCAGGCATGGACCAGGACAAAAATCCAATGC
CAGCTCCTGTTGAACATCAGATCTGTCCTGCTGTGTGTTCTAATGAAA
CTTTCATTTGATGAAGAGCATAGACATGCAATGAATGAACTAGGGGGACT
ACAGGCCATTGCAGAATTATTGCAAGTGGACTGTGAAATGTATGGGCTTA
CTAATGACCACTACAGTATTACACTAAGACGATATGCTGGAATGGCTTTG
ACAAACTTGACTTTTGGAGATGTAGCCAACAAGGCTACGCTATGCTCTAT
GAAAGGCTGCATGAGAGCACTTGTGGCCCAACTAAAATCTGAAGTGAAGA
CTTACGCAGGTTATTGCGAGTGTTTTGAGGAATTTGTCTTGGCGAGCAG
ATGTAAATAGTAAAAAGACGTTGCGAGAAGTTGGAAGTGTGAAAGCATTG
ATGGAATGTGCTTTAGAAGTTAAAAAGGAATCAACCCTCAAAAGCGTATT
GAGTGCCTTATGGAATTTGTCAGCACATTGCACTGAGAATAAAGCTGATA
TATGTGCTGTAGATGGTGCACTTGCATTTTTGGTTGGCACTCTTACTTAC
CGGAGCCAGACAAACACTTTAGCCATTATTGAAAGTGGAGGTGGGATATT
ACGGAATGTGTCCAGCTTGATAGCTACAAATGAGGACCACAGGCAAATCC
TAAGAGAGAACAACTGTCTACAAACTTTATTACAACACTTAAAATCTCAT
```

```
AGTTTGACAATAGTCAGTAATGCATGTGGAACTTTGTGGAATCTCTCAGC
AAGAAATCCTAAAGACCAGGAAGCATTATGGGACATGGGGGCAGTTAGCA
TGCTCAAGAACCTCATTCATTCAAAGCACAAAATGATTGCTATGGGAAGT
GCTGCAGCTTTAAGGAATCTCATGGCAAATAGGCCTGCGAAGTACAAGGA
TGCCAATATTATGTCTCCTGGCTCAAGCTTGCCATCTCTTCATGTTAGGA
AACAAAAGCCCTAGAAGCAGAATTAGATGCTCAGCACTTATCAGAAACT
TTTGACAATATAGACAATTTAAGTCCCAAGGCATCTCATCGTAGTAAGCA
GAGACACAAGCAAAGTCTCTATGGTGATTATGTTTTTGACACCAATCGAC
ATGATGATAATAGGTCAGACAATTTTAATACTGGCAACATGACTGTCCTT
TCACCATATTTGAATACTACAGTGTTACCCAGCTCCTCTTCATCAAGAGG
AAGCTTAGATAGTTCTCGTTCTGAAAAAGATAGAAGTTTGGAGAGAGAAC
GCGGAATTGGTCTAGGCAACTACCATCCAGCAACAGAAAATCCAGGAACT
TCTTCAAAGCGAGGTTTGCAGATCTCCACCACTGCAGCCCAGATTGCCAA
AGTCATGGAAGAAGTGTCAGCCATTCATACCTCTCAGGAAGACAGAAGTT
CTGGGTCTACCACTGAATTACATTGTGTGACAGATGAGAGAAATGCACTT
AGAAGAAGCTCTGCTGCCCATACACATTCAAACACTTACAATTTCACTAA
GTCGGAAAATTCAAATAGGACATGTTCTATGCCTTATGCCAAATTAGAAT
ACAAGAGATCTTCAAATGATAGTTTAAATAGTGTCAGTAGTAGTGATGGT
TATGGTAAAAGAGGTCAAATGAAACCCTCGATTGAATCCTATTCTGAAGA
TGATGAAAGTAAGTTTTGCAGTTATGGTCAATACCCAGCCGACCTAGCCC
ATAAAATACATAGTGCAAATCATATGGATGATAATGATGGAGAACTAGAT
ACACCAATAAATTATAGTCTTAAATATTCAGATGAGCAGTTGAACTCTGG
AAGGCAAAGTCCTTCACAGAATGAAAGATGGGCAAGACCCAAACACATAA
TAGAAGATGAAATAAAACAAAGTGAGCAAAGACAATCAAGGAATCAAAGT
ACAACTTATCCTGTTTATACTGAGAGCACTGATGATAAACACCTCAAGTT
CCAACCACATTTTGGACAGCAGGAATGTGTTTCTCCATACAGGTCACGGG
GAGCCAATGGTTCAGAAACAAATCGAGTGGGTTCTAATCATGGAATTAAT
CAAAATGTAAGCCAGTCTTTGTGTCAAGAAGATGACTATGAAGATGATAA
GCCTACCAATTATAGTGAACGTTACTCTGAAGAAGAACAGCATGAAGAAG
AAGAGAGACCAACAAATTATAGCATAAAATATAATGAAGAGAACGTCAT
GTGGATCAGCCTATTGATTATAGTTTAAAATATGCCACAGATATTCCTTC
ATCACAGAAACAGTCATTTTCATTCTCAAAGAGTTCATCTGGACAAGCAG
TAAAACCGAACATATGTCTTCAAGCAGTGAGAATACGTCCACACCTTCAT
CTAATGCCAAGAGGCAGAATCAGCTCCATCCAAGTTCTGCACAGAGTAGA
AGTGGTCAGCCTCAAAAGGCTGCCACTTGCAAAGTTTCTTCTATTAACCA
AGAAACAATACAGACTTATTGTGTAGAAGATACTCCAATATGTTTTTCAA
GATGTAGTTCATTATCATCTTTGTCATCAGCTGAAGATGAAATAGGATGT
AATCAGACGACACAGGAAGCAGATTCTGCTAATACCCTGCAAATAGCAGA
AATAAAAGAAAGATTGGAACTAGGTCAGCTGAAGATCCTGTGAGCGAAG
TTCCAGCAGTGTCACAGCACCCTAGAACCAAATCCAGCAGACTGCAGGGT
TCTAGTTTATCTTCAGAATCAGCCAGGCACAAAGCTGTTGAATTTTCTTC
```

-continued

```
AGGAGCGAAATCTCCCTCCAAAAGTGGTGCTCAGACACCCAAAAGTCCAC
CTGAACACTATGTTCAGGAGACCCCACTCATGTTTAGCAGATGTACTTCT
GTCAGTTCACTTGATAGTTTTGAGAGTCGTTCGATTGCCAGCTCCGTTCA
GAGTGAACCATGCAGTGGAATGGTAAGTGGCATTATAAGCCCCAGTGATC
TTCCAGATAGCCCTGGACAAACCATGCCACCAAGCAGAAGTAAAACACCT
CCACCACCTCCTCAAACAGCTCAAACCAAGCGAGAAGTACCTAAAAATAA
AGCACCTACTGCTGAAAAGAGAGAGAGTGGACCTAAGCAAGCTGCAGTAA
ATGCTGCAGTTCAGAGGGTCCAGGTTCTTCCAGATGCTGATACTTTATTA
CATTTTGCCACGGAAAGTACTCCAGATGGATTTTCTTGTTCATCCAGCCT
GAGTGCTCTGAGCCTCGATGAGCCATTTATACAGAAAGATGTGGAATTAA
GAATAATGCCTCCAGTTCAGGAAAATGACAATGGGAATGAAACAGAATCA
GAGCAGCCTAAAGAATCAAATGAAAACCAAGAGAAAGAGGCAGAAAAAAC
TATTGATTCTGAAAAGGACCTATTAGATGATTCAGATGATGATGATATTG
AAATACTAGAAGAATGTATTATTTCTGCCATGCCAACAAAGTCATCACGT
AAAGCAAAAAAGCCAGCCCAGACTGCTTCAAAATTACCTCCACCTGTGGC
AAGGAAACCAAGTCAGCTGCCTGTGTACAAACTTCTACCATCACAAAACA
GGTTGCAACCCCAAAAGCATGTTAGTTTTACACCGGGGATGATATGCCA
CGGGTGTATTGTGTTGAAGGGACACCTATAAACTTTTCCACAGCTACATC
TCTAAGTGATCTAACAATCGAATCCCCTCCAAATGAGTTAGCTGCTGGAG
AAGGAGTTAGAGGAGGGGCACAGTCAGGTGAATTTGAAAAACGAGATACC
ATTCCTACAGAAGGCAGAAGTACAGATGAGGCTCAAGGAGGAAAAACCTC
ATCTGTAACCATACCTGAATTGGATGACAATAAAGCAGAGGAAGGTGATA
TTCTTGCAGAATGCATTAATTCTGCTATGCCCAAAGGGAAAAGTCACAAG
CCTTTCCGTGTGAAAAAGATAATGGACCAGGTCCAGCAAGCATCTGCGTC
TTCTTCTGCACCCAACAAAAATCAGTTAGATGGTAAGAAAAAGAAACCAA
CTTCACCAGTAAAACCTATACCACAAAATACTGAATATAGGACACGTGTA
AGAAAAAATGCAGACTCAAAAAATAATTTAAATGCTGAGAGAGTTTTCTC
AGACAACAAAGATTCAAAGAAACAGAATTTGAAAAATAATTCCAAGGTCT
TCAATGATAAGCTCCCAAATAATGAAGATAGAGTCAGAGGAAGTTTTGCT
TTTGATTCACCTCATCATTACACGCCTATTGAAGGAACTCCTTACTGTTT
TTCACGAAATGATTCTTTGAGTTCTCTAGATTTTGATGATGATGATGTTG
ACCTTTCCAGGGAAAAGGCTGAATTAAGAAAGGCAAAAGAAAATAAGGAA
TCAGAGGCTAAAGTTACCAGCCACACAGAACTAACCTCCAACCAACAATC
AGCTAATAAGACACAAGCTATTGCAAAGCAGCCAATAAATCGAGGTCAGC
CTAAACCCATACTTCAGAAACAATCCACTTTTCCCCAGTCATCCAAAGAC
ATACCAGACAGAGGGGCAGCAACTGATGAAAAGTTACAGAATTTTGCTAT
TGAAAATACTCCGGTTTGCTTTTCTCATAATTCCTCTCTGAGTTCTCTCA
GTGACATTGACCAAGAAAACAACAATAAAGAAAATGAACCTATCAAAGAG
ACTGAGCCCCTGACTCACAGGGAGAACCAAGTAAACCTCAAGCATCAGG
CTATGCTCCTAAATCATTTCATGTTGAAGATACCCCAGTTTGTTTCTCAA
```

-continued

```
GAAACAGTTCTCTCAGTTCTCTTAGTATTGACTCTGAAGATGACCTGTTG
CAGGAATGTATAAGCTCCGCAATGCCAAAAAAGAAAAAGCCTTCAAGACT
CAAGGGTGATAATGAAAAACATAGTCCCAGAAATATGGGTGGCATATTAG
GTGAAGATCTGACACTTGATTTGAAAGATATACAGAGACCAGATTCAGAA
CATGGTCTATCCCCTGATTCAGAAAATTTTGATTGGAAAGCTATTCAGGA
AGGTGCAAATTCCATAGTAAGTAGTTTACATCAAGCTGCTGCTGCTGCAT
GTTTATCTAGACAAGCTTCGTCTGATTCAGATTCCATCCTTTCCCTGAAA
TCAGGAATCTCTCTGGGATCACCATTTCATCTTACACCTGATCAAGAAGA
AAAACCCTTTACAAGTAATAAAGGCCCACGAATTCTAAAACCAGGGGAGA
AAAGTACATTGGAAACTAAAAAGATAGAATCTGAAAGTAAAGGAATCAAA
GGAGGAAAAAAGTTTATAAAAGTTTGATTACTGGAAAAGTTCGATCTAA
TTCAGAAATTTCAGGCCAAATGAAACAGCCCCTTCAAGCAAACATGCCTT
CAATCTCTCGAGGCAGGACAATGATTCATATTCCAGGAGTTCGAAATAGC
TCCTCAAGTACAAGTCCTGTTTCTAAAAAAGGCCCACCCCTTAAGACTCC
AGCCTCCAAAAGCCCTAGTGAAGGTCAAACAGCCACCACTTCTCCTAGAG
GAGCCAAGCCATCTGTGAAATCAGAATTAAGCCCTGTTGCCAGGCAGACA
TCCCAAATAGGTGGGTCAAGTAAAGCACCTTCTAGATCAGGATCTAGAGA
TTCGACCCCTTCAAGACCTGCCCAGCAACCATTAAGTAGACCTATACAGT
CTCCTGGCCGAAACTCAATTTCCCCTGGTAGAAATGGAATAAGTCCTCCT
AACAAATTATCTCAACTTCCAAGGACATCATCCCCTAGTACTGCTTCAAC
TAAGTCCTCAGGTTCTGGAAAAATGTCATATACATCTCCAGGTAGACAGA
TGAGCCAACAGAACCTTACCAAACAAACAGGTTTATCCAAGAATGCCAGT
AGTATTCCAAGAAGTGAGTCTGCCTCCAAAGGACTAAATCAGATGAATAA
TGGTAATGGAGCCAATAAAAAGGTAGAACTTTCTAGAATGTCTTCAACTA
AATCAAGTGGAAGTGAATCTGATAGATCAGAAAGACCTGTATTAGTACGC
CAGTCAACTTTCATCAAAGAAGCTCCAAGCCCAACCTTAAGAAGAAAATT
GGAGGAATCTGCTTCATTTGAATCTCTTTCTCCATCATCTAGACCAGCTT
CTCCCACTAGGTCCCAGGCACAAACTCCAGTTTTAAGTCCTTCCCTTCCT
GATATGTCTCTATCCACACATTCGTCTGTTCAGGCTGGTGGATGGCGAAA
ACTCCCACCTAATCTCAGTCCCACTATAGAGTATAATGATGGAAGACCAG
CAAAGCGCCATGATATTGCACGGTCTCATTCTGAAAGTCCTTCTAGATTC
CAATCAATAGGTCAGGAACCTGGAAACGTGAGCACAGCAAACATTCATCA
TCCCTTCCTCGAGTAAGCACTTGGAGAAGAACTGGAAGTTCATCTTCAAT
TCTTTCTGCTTCATCAGAATCCAGTGAAAAGCAAAAGTGAGGATGAAA
AACATGTGAACTCTATTTCAGGAACCAAACAAAGTAAAGAAAACCAAGTA
TCCGCAAAAGGAACATGGAGAAAAATAAAAGAAAATGAATTTTCTCCCAC
AAATAGTACTTCTCAGACCGTTTCCTCAGGTGCTACAAATGGTGCTGAAT
CAAAGACTCTAATTTATCAAATGGCACCTGCTGTTTCTAAAACAGAGGAT
GTTTGGGTGAGAATTGAGGACTGTCCCATTAACAATCCTAGATCTGGAAG
ATCTCCCACAGGTAATACTCCCCCGGTGATTGACAGTGTTTCAGAAAAGG
CAAATCCAAACATTAAAGATTCAAAAGATAATCAGGCAAAACAAAATGTG
```

-continued

GGTAATGGCAGTGTTCCCATGCGTACCGTGGGTTTGGAAAATCGCCTGAA

CTCCTTTATTCAGGTGGATGCCCCTGACCAAAAAGGAACTGAGATAAAAC

CAGGACAAAATAATCCTGTCCCTGTATCAGAGACTAATGAAAGTTCTATA

GTGGAACGTACCCCATTCAGTTCTAGCAGCTCAAGCAAACACAGTTCACC

TAGTGGGACTGTTGCTGCCAGAGTGACTCCTTTTAATTACAACCCAAGCC

CTAGGAAAAGCAGCGCAGATAGCACTTCAGCTCGGCCATCTCAGATCCCA

ACTCCAGTGAATAACAACACAAAGAAGCGAGATTCCAAAACTGACAGCAC

AGAATCCAGTGGAACCCAAAGTCCTAAGCGCCATTCTGGGTCTTACCTTG

TGACATCTGTTTAAAGAGAGGAAGAATGAAACTAAGAAAATTCTATGTT

AATTACAACTGCTATATAGACATTTTGTTTCAAATGAAACTTTAAAAGAC

TGAAAAATTTTGTAAATAGGTTTGATTCTTGTTAGAGGGTTTTTGTTCTG

GAAGCCATATTTGATAGTATACTTTGTCTTCACTGGTCTTATTTTGGGAG

GCACTCTTGATGGTTAGGAAAAAAATAGTAAAGCCAAGTATGTTTGTACA

GTATGTTTTACATGTATTTAAAGTAGCATCCCATCCCAACTTCCTTTAAT

TATTGCTTGTCTTAAAATAATGAACACTACAGATAGAAAATATGATATAT

TGCTGTTATCAATCATTTCTAGATTATAAACTGACTAAACTTACATCAGG

GAAAAATTGGTATTTATGCAAAAAAAAATGTTTTTGTCCTTGTGAGTCCA

TCTAACATCATAATTAATCATGTGGCTGTGAAATTCACAGTAATATGGTT

CCCGATGAACAAGTTTACCCAGCCTGCTTTGCTTTACTGCATGAATGAAA

CTGATGGTTCAATTTCAGAAGTAATGATTAACAGTTATGTGGTCACATGA

TGTGCATAGAGATAGCTACAGTGTAATAATTTACACTATTTTGTGCTCCA

AACAAAACAAAAATCTGTGTAACTGTAAAACATTGAATGAAACTATTTTA

CCTGAACTAGATTTTATCTGAAAGTAGGTAGAATTTTTGCTATGCTGTAA

TTTGTTGTATATTCTGGTATTTGAGGTGAGATGGCTGCTCTTTTATTAAT

GAGACATGAATTGTGTCTCAACAGAAACTAAATGAACATTTCAGAATAAA

TTATTGCTGTATGTAAACTGTTACTGAAATTGGTATTTGTTTGAAGGGTC

TTGTTTCACATTTGTATTAATAATTGTTTAAAATGCCTCTTTTAAAAGCT

TATATAAATTTTTTTCTTCAGCTTCTATGCATTAAGAGTAAAATTCCTCT

TACTGTAATAAAAACAATTGAAGAAGACTGTTGCCACTTAACCATTCCAT

GCGTTGGCACTTATCTATTCCTGAAATTTCTTTTATGTGATTAGCTCATC

TTGATTTTAATATTTTTCCACTTAAACTTTTTTTTCTTACTCCACTGGA

GCTCAGTAAAAGTAAATTCATGTAATAGCAATGCAAGCAGCCTAGCACAG

ACTAAGCATTGAGCATAATAGGCCCACATAATTTCCTCTTTCTTAATATT

ATAGAATTCTGTACTTGAAATTGATTCTTAGACATTGCAGTCTCTTCGAG

GCTTTACAGTGTAAACTGTCTTGCCCCTTCATCTTCTTGTTGCAACTGGG

TCTGACATGAACACTTTTTATCACCCTGTATGTTAGGGCAAGATCTCAGC

AGTGAAGTATAATCAGCACTTTGCCATGCTCAGAAAATTCAAATCACATG

GAACTTTAGAGGTAGATTTAATACGATTAAGATATTCAGAAGTATATTTT

AGAATCCCTGCCTGTTAAGGAAACTTTATTTGTGGTAGGTACAGTTCTGG

GGTACATGTTAAGTGTCCCCTTATACAGTGGAGGGAAGTCTTCCTTCCTG

AAGGAAAATAAACTGACACTTATTAACTAAGATAATTTACTTAATATATC

TTCCCTGATTTGTTTTAAAAGATCAGAGGGTGACTGATGATACATGCATA

CATATTTGTTGAATAAATGAAAATTTATTTTTAGTGATAAGATTCATACA

CTCTGTATTTGGGGAGGGAAAACCTTTTTAAGCATGGTGGGCACTCAGA

TAGGAGTGAATACACCTACCTGGTGCCTTGAAAATCACATCAAGTAGTTA

ATTATCTACCCCTTACCTGTGTTTATAACTTCCAGGTAATGAGAATGATT

TTTTTTAAAGCTAAAATGCCAGTAAATAAAGTGCTATGACTTGAGCTAA

GATATTTGACTCCAATGCCTGTACTGTGTCTACTGCACCACTTTGTAAAC

ACTTCAATTTACTATCTTTGAAATGATTGACCTTTAAATTTTTGCCAAAT

GTTATCTGAAATTGTCTATGAATACCATCTACTTCTGTTGTTTTCCCAGG

CTTCCATAAACAATGGAGATACATGCAAAAAAAAAA

What is claimed is:

1. A method for detecting the presence of DNA mutations in the KRAS, BRAF, CTNNB1, and APC genes, the method comprising:
- (a) isolating DNA from a sample;
- (b) amplifying the isolated DNA by polymerase chain reaction (PCR) using primer pairs specific for the loci of one or more DNA mutations in each of the KRAS, BRAF, CTNNB1, and APC genes;
- (c) hybridizing the amplified DNA with at least four probes, said at least four probes comprising one or more probes specific for a DNA mutation in each of the KRAS, BRAF, CTNNB1, and APC genes, wherein each of said at least four probes is coupled to a microcarrier, wherein each of the microcarriers comprises an identifier corresponding to the probe coupled thereto, and wherein each of the microcarriers comprises:
  - (1) a substantially transparent polymer layer having a first surface and a second surface, the first and the second surfaces being parallel to each other,
  - (2) a substantially non-transparent polymer layer, wherein the substantially non-transparent polymer layer is affixed to the first surface of the substantially transparent polymer layer and encloses a center portion of the substantially transparent polymer layer, and wherein the substantially non-transparent polymer layer comprises a two-dimensional shape representing an analog code, wherein the analog code represents the identifier, and
  - (3) the probe specific for the DNA mutation, wherein the probe is coupled to at least one of the first surface and the second surface of the substantially transparent polymer layer in at least the center portion of the substantially transparent polymer layer;
- (d) detecting presence or absence of hybridization of the amplified DNA with said at least four probes, wherein hybridization between the amplified DNA and one of the probes indicates the presence of the DNA mutation corresponding to the probe;
- (e) detecting the identifiers of the microcarriers; and
- (f) correlating the detected identifiers of the microcarriers with the detected presence or absence of hybridization of the amplified DNA to the corresponding probes of the microcarriers.

2. The method of claim 1, wherein the KRAS, BRAF, CTNNB1, and APC genes are human genes.

3. The method of claim 2, wherein the one or more DNA mutations in the KRAS gene comprise one or more DNA mutations encoding a G12D, G12V, G12S, or G13D mutated KRAS protein.

4. The method of claim 2, wherein the one or more DNA mutations in the BRAF gene comprise one or more DNA mutations encoding a V600E mutated BRAF protein.

5. The method of claim 2, wherein the one or more DNA mutations in the CTNNB1 gene comprise CTNNB1 mutations encoding T41A, T41I, S45F, and S45P mutated CTNNB1 proteins.

6. The method of claim 2, wherein the one or more DNA mutations in the APC gene comprise APC mutations encoding Q1367*, R1450*, E1309 frameshift, S1465 frameshift, and T1556 frameshift mutated APC proteins.

7. The method of claim 1, wherein step (b) comprises amplifying the isolated DNA by PCR in the presence of at least four blocking nucleic acids, wherein each of said at least four blocking nucleic acids hybridizes with a wild-type DNA locus corresponding with one of the DNA mutations in the KRAS, BRAF, CTNNB1, or APC genes and prevents amplification of the wild-type DNA locus.

8. The method of claim 1, wherein each of the primer pairs comprises a primer coupled to a detection reagent.

9. The method of claim 1, wherein the sample is a stool sample.

10. The method of claim 1, wherein each of the microcarriers further comprises an orientation indicator for orienting the analog code of the substantially non-transparent polymer layer.

11. The method of claim 1, wherein the substantially transparent polymer of the substantially transparent polymer layer comprises an epoxy-based polymer.

12. The method of claim 11, wherein the epoxy-based polymer is SU-8.

13. The method of claim 1, wherein each of the microcarriers further comprises a magnetic, substantially non-transparent layer that encloses the center portion of the substantially transparent polymer layer between the substantially non-transparent polymer layer and the center portion of the substantially transparent polymer layer, wherein the magnetic, substantially non-transparent layer is affixed to the first surface or the second surface of the substantially transparent polymer layer.

14. The method of claim 1, wherein each of the microcarriers is less than about 50 µm in thickness.

15. The method of claim 1, wherein the method further comprises:
- amplifying a positive control DNA sequence using a primer pair specific for the positive control DNA sequence;
- hybridizing the amplified positive control gene sequence with a probe specific for the positive control gene sequence, wherein the probe specific for the positive control gene sequence is coupled to a microcarrier with an identifier corresponding to a positive control;
- detecting presence or absence of hybridization of the amplified positive control DNA sequence with the probe specific for the positive control gene sequence; and
- detecting the identifier corresponding to the positive control.

16. The method of claim 15, wherein the positive control DNA sequence comprises a sequence of a human leukocyte antigen gene.

17. The method of claim 1, wherein the method further comprises:
- detecting absence of hybridization of the amplified DNA with a microcarrier having an identifier corresponding to a negative control, wherein the microcarrier with the identifier corresponding to the negative control comprises a probe that does not hybridize with the amplified DNA; and detecting the identifier corresponding to the negative control.

* * * * *